United States Patent
Barany et al.

(10) Patent No.: US 7,358,048 B2
(45) Date of Patent: Apr. 15, 2008

(54) METHOD FOR DETECTION OF PROMOTER METHYLATION STATUS

(75) Inventors: Francis Barany, New York, NY (US); YuWei Cheng, Roosevelt Island, NY (US); Carrie Shawber, Washington, NJ (US)

(73) Assignee: Cornell Research Foundation, Inc., Ithaca, NY (US)

( * ) Notice: Subject to any disclaimer, the term of this patent is extended or adjusted under 35 U.S.C. 154(b) by 364 days.

(21) Appl. No.: 11/049,446

(22) Filed: Feb. 2, 2005

(65) Prior Publication Data

US 2005/0227265 A1    Oct. 13, 2005

Related U.S. Application Data

(60) Provisional application No. 60/543,156, filed on Feb. 10, 2004.

(51) Int. Cl.
*C12Q 1/68* (2006.01)
*C12P 19/34* (2006.01)

(52) U.S. Cl. .......................................... 435/6; 435/91.2

(58) Field of Classification Search ............... None
See application file for complete search history.

(56) References Cited

U.S. PATENT DOCUMENTS 6,017,704 A    1/2000    Herman et al.
6,265,171 B1   7/2001    Herman et al.
6,331,393 B1   12/2001   Laird et al.

FOREIGN PATENT DOCUMENTS

| WO | WO 97/31256 | 8/1997 |
|----|-------------|--------|
| WO | WO 97/45559 | 12/1997 |
| WO | WO 00/56927 | 9/2000 |
| WO | WO 00/56929 | 9/2000 |

OTHER PUBLICATIONS

Eads et al., "MethyLight: A High-Throughput Assay to Measure DNA Methylation," *Nucleic Acids Research* 28(8):e32i-e32vii (2000).

Herman et al., "Methylation-specific PCR: A Novel PCR Assay for Methylation Status of CpG Islands," Proc. Natl. Acad, Sci. USA 93:9821-9826 (1996).

*Primary Examiner*—James Martinell
(74) *Attorney, Agent, or Firm*—Nixon Peabody LLP

(57) ABSTRACT

The present invention relates to the detection of promoter methylation status using a combination of either modification of methylated DNA or restriction endonuclease digestion, multiplex polymerase chain reaction, ligase detection reaction, and a universal array or capillary electrophoresis detection.

82 Claims, 48 Drawing Sheets

Bisulfite/PCR-PCR/LDR/Universal Array

1. Treat DNA with sodium bisulfite to convert unmethylated, but not methylated cytosines into uracils. Only the cytosines present in CpG sites are shown here.

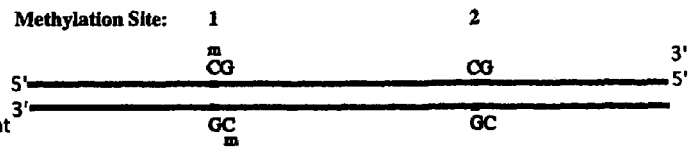

2. The resultant strands are not complementary. PCR amplify one strand using gene-specific/ universal primers and Taq polymerase. ◆

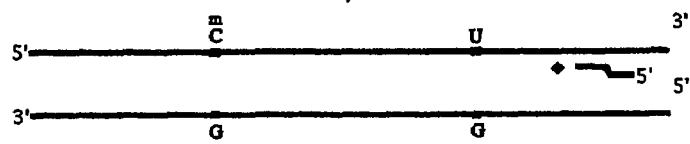

3. PCR amplify the complementary strand of the first PCR synthesis using gene-specific/ universal primers (A) and Taq polymerase. ◆

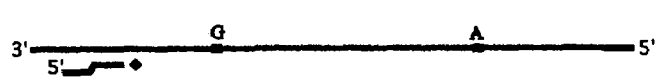

4. PCR ammplify all primary products using universal primers and Taq polymerase. ◆

5. Perform LDR using primers specific for converted unmethylated and methylated sequence, and thermostable ligase. ●

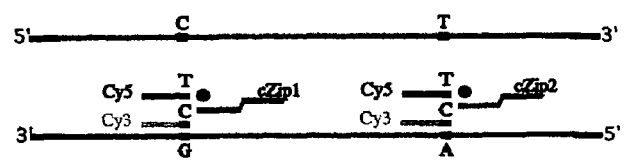

6. Capture fluorescent products on addressable array and score for presence of unmethylated DNA (control) as well as methylated.

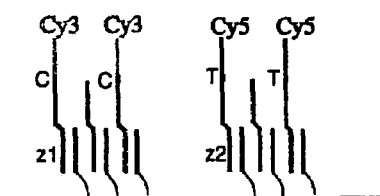

Address Zip1 identifies methylated cytosine in methylation site 1, and address Zip2 identifies unmethylated cytosines in methylation site 2.

Figure 1

Bisulfite/ PCR-PCR/ LDR/ Dual Universal Array

1. Treat DNA with sodium bisulfite to convert unmethylated, but not methylated cytosines into uracils. Only the cytosines present in CpG sites are shown here.

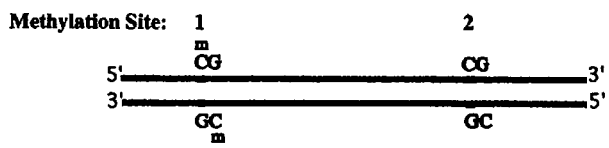

2. The resultant strands are not complementary. PCR amplify one strand using gene-specific/ universal primers and Taq polymerase. ◆

3. PCR amplify the complementary strand of the first PCR synthesis using gene-specific/ universal primers (A) and Taq polymerase. ◆

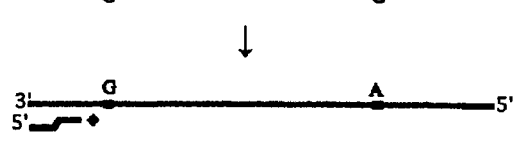

4. PCR ammplify all primary products using universal primers and Taq polymerase. ◆

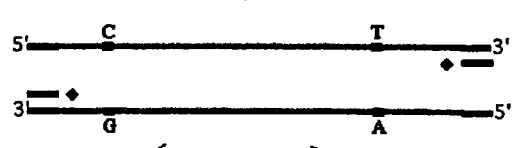

5. Perform LDR using primers specific for either converted unmethylated or methylated sequence, and thermostable ligase. ●

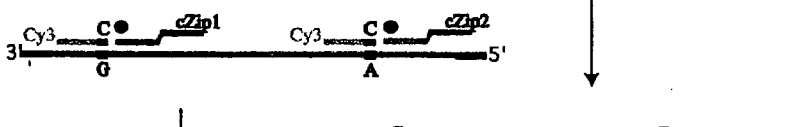

6. Capture fluorescent products on two separated addressable arrays and score for the presence of methylated DNA as well as unmethylated.

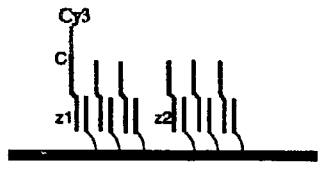 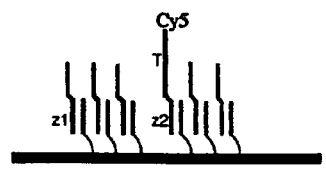

Address Zip1 identifies methylated cytosine in methylation site 1.

Address Zip2 identifies unmethylated cytosine in methylation site 2.

Figure 3

Bisulfite/ PCR-PCR/ LDR/ Capillary Electrophoresis: Nucleotide Analogs

1. Treat DNA with sodium bisulfite to convert unmethylated, but not methylated cytosines into uracils. Only the cytosines present in CpG dinucleotide sites are shown here.

2. The resultant strands are not complementary. PCR amplify one strand using gene-specific/universal primers and Taq polymerase. ◆

3. PCR amplify the complementary strand of the first PCR synthesis using gene-specific/ universal primers (A) and Taq polymerase. ◆

4. PCR ammplify all primary products using universal primers and Taq polymerase. ◆

5. Perform LDR using primers specific for converted unmethylated and methylated sequence, and thermostable ligase. ●

6. Separate fluorescent products using capillary electrophoresis and score for presence of methylated DNA.

Mobility and label identify methylated cytosine in methylation site 2, and unmethylated cytosine in methylation site 6.

Unligated labeled primers

PCR reactions:
1 (includes 4 sets of primers): p15Ex1, p16Ex1, p19Ex1, p21S2
2 (includes 5 sets of primers): p21S1, p27, p53, BRCA1, SNRPN
3 (includes 3 sets of primers): p15Ex1, p21S1, SNRPN
4 (includes 3 sets of primers): p19Ex1, p21S2, p27
5 (includes 3 sets of primers): p16Ex1, p53, BRCA1

PCR reactions#1
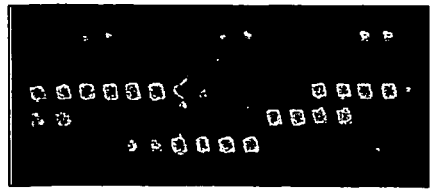
PCR reactions#2
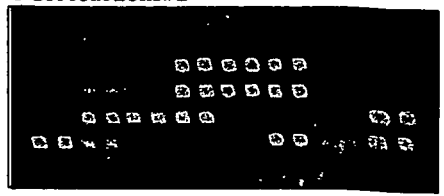
PCR reactions#3
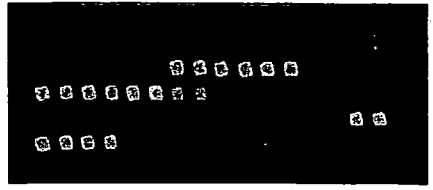
PCR reactions#4
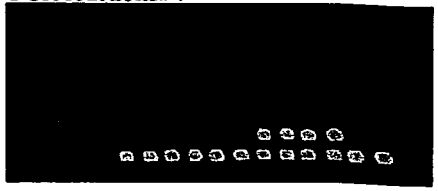
PCR reactions#5
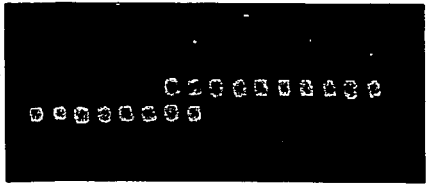
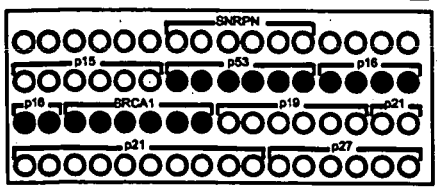
Figure 11

| AMPLICONS #1 | SIZE | AMPLICONS #2 | SIZE | AMPLICONS #3 | SIZE |
|---|---|---|---|---|---|
| p15 Ex1 | 317 | p19 Ex1 | 346 | p16 Ex1 | 363 |
| p21 S1 | 391 | p27 Ex1 | 426 | p53 | 418 |
| APC | 433 | ECAD | 513 | BRCA1 | 459 |

| AMPLICONS #4 | SIZE | AMPLICONS #5 | SIZE | AMPLICON | SIZE |
|---|---|---|---|---|---|
| MGMT | 362 | TIMP3 | 404 | SNRPN | 442 |
| DAPK | 434 | RASSF1 | 474 | | |
| GSTP1 | 507 | RARb | 522 | | |

Hydroquinone and Diethylenetriamine treatment of HTB39 genomic DNA

| AMPLICONS #1 | SIZE | AMPLICONS #2 | SIZE | AMPLICONS #3 | SIZE |
|---|---|---|---|---|---|
| p15 Ex1 | 317 | p21 S2 | 309 | p16 Ex1 | 363 |
| p21 S1 | 391 | p19 Ex1 | 346 | p53 | 418 |
| SNRPN | 442 | p27 Ex1 | 426 | BRCA1 | 459 |

Diethylenetriamine treatment of HTB39 genomic DNA

| AMPLICONS #1 | SIZE | AMPLICONS #2 | SIZE | AMPLICONS #3 | SIZE |
|---|---|---|---|---|---|
| p15 Ex1 | 317 | p21 S2 | 309 | p16 Ex1 | 363 |
| p21 S1 | 391 | p19 Ex1 | 346 | p53 | 418 |
| SNRPN | 442 | p27 Ex1 | 426 | BRCA1 | 459 |

Bisulfite/PCR-PCR/ Ms-PCR-PCR/ LDR/Universal Array

1. Treat DNA with sodium bisulfite to convert unmethylated, but not methylated cytosines into uracils. Only the cytosines present in CpG dinucleotide sites are shown here.

2. The resultant strands are not complementary. PCR amplify one strand using gene-specific/ universal primers (A) and Taq polymerase. ◆

3. PCR amplify the complementary strand of the first PCR synthesis using gene-specific/ universal primers (A) and Taq polymerase. ◆

4. PCR amplify all primary products using universal primers (A) and Taq polymerase. ◆

5. PCR amplify only the converted methylated DNA using methyl-specific/ universal primers (B) and Taq polymerase. ◆

6. PCR amplify all products derived from converted methylated DNA using universal primers (B) and Taq polymerase. ◆

7. Perform LDR using primers specific for originally methylated sequences, and thermostable ligase. ●

8. Capture fluorescent products on addressable array and score for presence of methylated DNA.

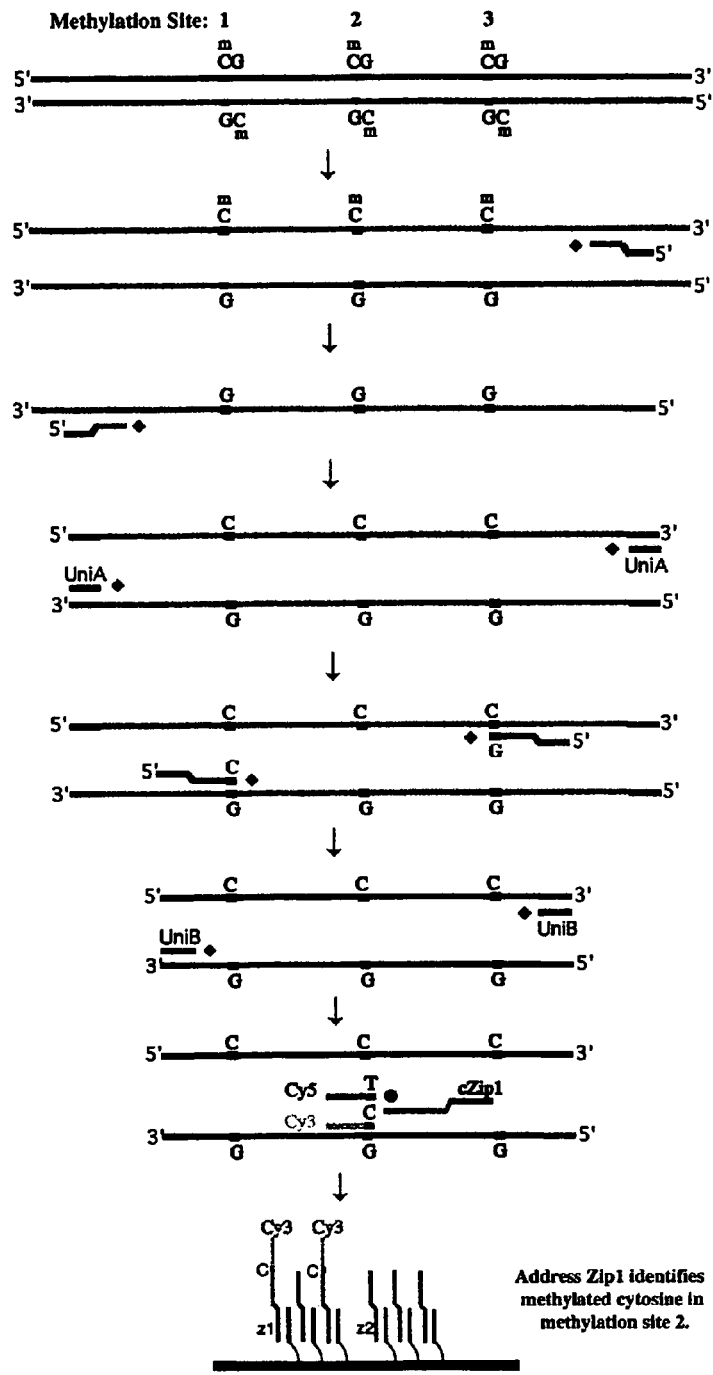

Address Zip1 identifies methylated cytosine in methylation site 2.

Figure 25

Bisulfite/PCR-PCR/ Ms-PCR-PCR/ LDR/ Capillary Electrophoresis: Nucleotide Analogs 1. Treat DNA with sodium bisulfite to convert unmethylated, but not methylated cytosines into uracils. Only the cytosines present in CpG dinucleotide sites are shown here.

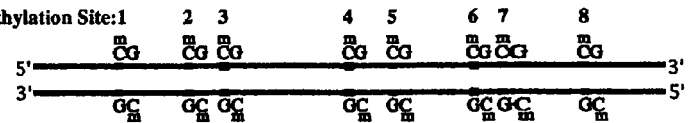

2. The resultant strands are not complementary. PCR amplify one strand using gene-specific/ universal primers (A) and Taq polymerase. ♦

3. PCR amplify the complementary strand of the first PCR synthesis using gene-specific/ universal primers (A) and Taq polymerase. ♦

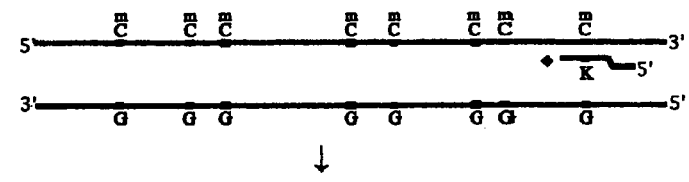

4. PCR amplify all primary products using universal primers (A) and Taq polymerase. ♦

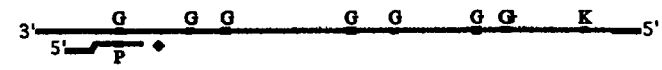

5. PCR amplify only the converted methylated DNA using methyl-specific/ universal primers (B) and Taq polymerase. ♦

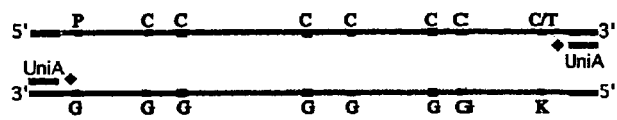

6. PCR amplify all products derived from converted methylated DNA using universal primers (B) and Taq polymerase. ♦

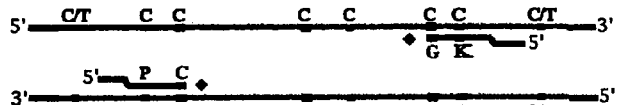

7. Perform LDR using primers specific for originally methylated sequences, and thermostable ligase. ●

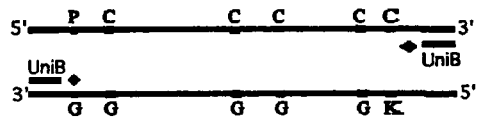

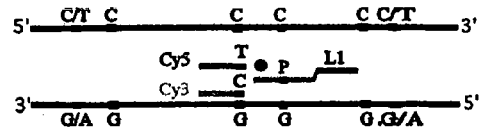

8. Separate fluorescent products using capillary electrophoresis and score for presence of methylated DNA.

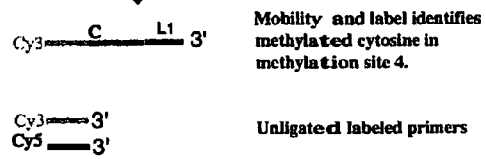

Mobility and label identifies methylated cytosine in methylation site 4.

Unligated labeled primers

Figure 28

Bisulfite/PCR-PCR/ Ms-PCR-PCR/ LDR/Universal Array: Preferential Methylated DNA

1. Treat DNA with sodium bisulfite to convert unmethylated, but not methylated cytosines into uracils. Only the cytosines present in CpG dinucleotide sites are shown here.

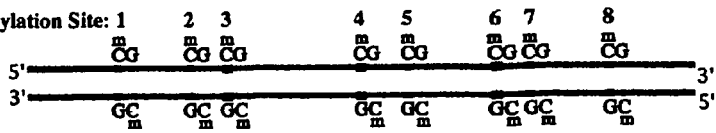

2. The resultant strands are not complementary. PCR amplify one strand using gene-specific/ universal primers (A) and Taq polymerase. ♦

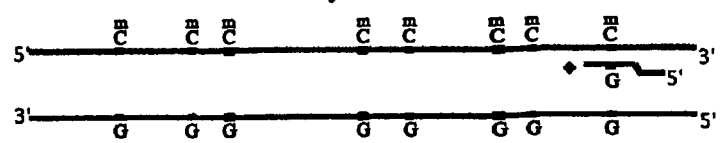

3. PCR amplify the complementary strand of the first PCR synthesis using gene-specific/ universal primers (A) and Taq polymerase. ♦

4. PCR amplify all primary products using universal primers (A) and Taq polymerase. ♦

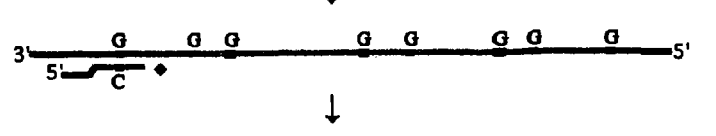

5. PCR amplify only the converted methylated DNA using methyl-specific/ universal primers (B) and Taq polymerase. ♦

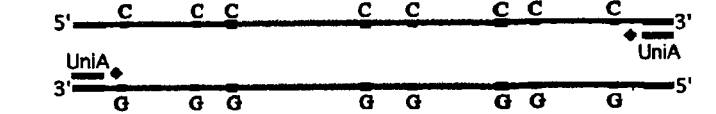

6. PCR amplify all products derived from converted methylated DNA using universal primers (B) and Taq polymerase. ♦

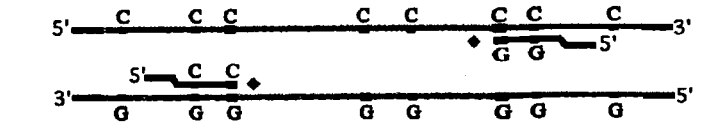

7. Perform LDR using primers specific for originally methylated sequences, and thermostable ligase. ●

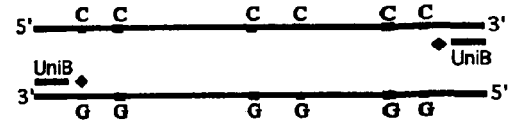

8. Capture fluorescent products on addressable array and score for presence of methylated DNA.

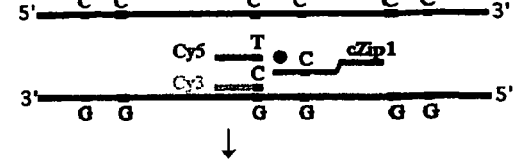

Address Zip1 identifies methylated cytosine in methylation site 4.

Figure 29

The first round of Bisulfite/PCR-PCR/Ms-PCR-PCR/LDR/Universal Array amplification

| AMPLICONS #1 | SIZE | AMPLICONS #2 | SIZE |
|---|---|---|---|
| SNRPN | 442 | BRCA1 | 459 |
| p19 Ex1 | 346 | p16 Ex1 | 363 |

The second round of Bisulfite/PCR-PCR/Ms-PCR-PCR/LDR/Universal Array amplification

| AMPLICONS #1 | SIZE | AMPLICONS #2 | SIZE |
|---|---|---|---|
| SNRPN | 428 | BRCA1 | 433 |
| p19 Ex1 | 332 | p16 Ex1 | 337 |

Bisulfite/ Ms-PCR-PCR/ Ms-PCR-PCR/ LDR/Universal Array

1. Treat DNA with sodium bisulfite to convert unmethylated, but not methylated cytosines into uracils. Only the cytosines present in CpG dinucleotide sites are shown here.

2. The resultant strands are not complementary. PCR amplify one strand using methyl-specific/ universal primers (A) and Taq polymerase. ♦

3. PCR amplify the complementary strand of the first PCR synthesis using gene-specific/ universal primers (A) and Taq polymerase. ♦

4. PCR amplify all primary products using universal primers (A) and Taq polymerase. ♦

5. PCR amplify only the converted methylated DNA using methyl-specific/ universal primers (B) and Taq polymerase. ♦

6. PCR amplify all products derived from converted methylated DNA using universal primers (B) and Taq polymerase. ♦

7. Perform LDR using primers specific for originally methylated sequences, and thermostable ligase. ●

8. Capture fluorescent products on addressable array and score for presence of methylated DNA.

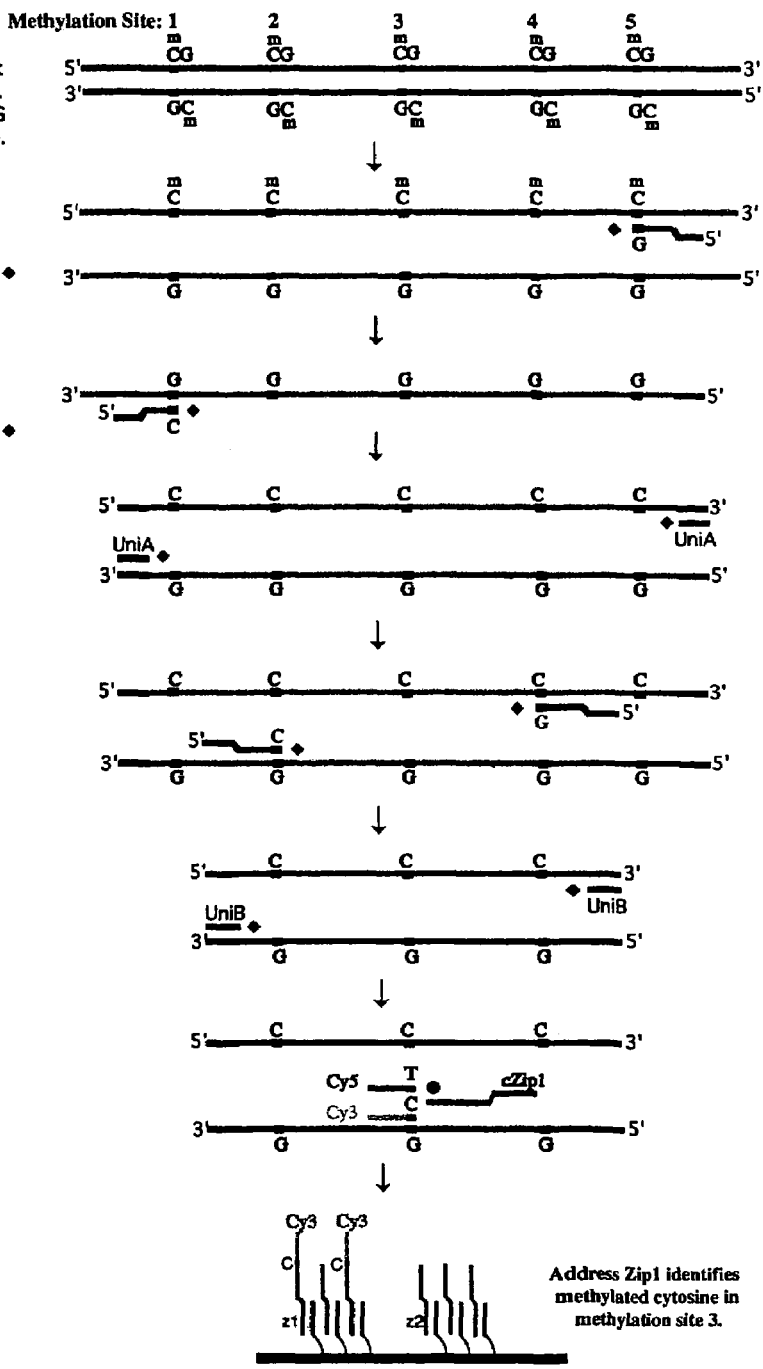

Address Zip1 identifies methylated cytosine in methylation site 3.

Figure 34

Bisulfite/ Ms-PCR-PCR/ Ms-PCR-PCR/ LDR/ Capillary Electrophoresis

1. Treat DNA with sodium bisulfite to convert unmethylated, but not methylated cytosines into uracils. Only the cytosines present in CpG dinucleotide sites are shown here.

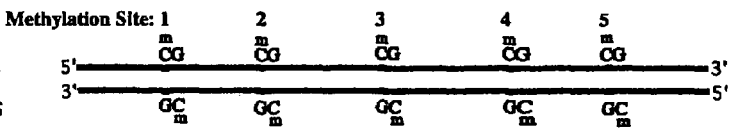

2. The resultant strands are not complementary. PCR amplify one strand using methyl-specific/ universal primers (A) and Taq polymerase. ◆

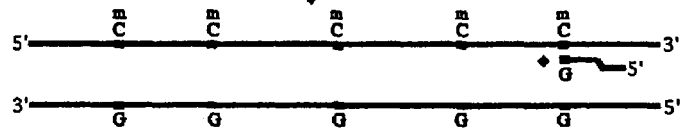

3. PCR amplify the complementary strand of the first PCR synthesis using gene-specific/ universal primers (A) and Taq polymerase. ◆

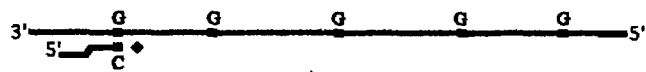

4. PCR amplify all primary products using universal primers (A) and Taq polymerase. ◆

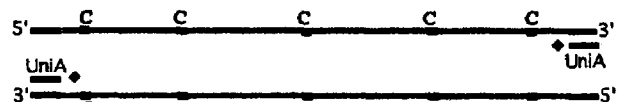

5. PCR amplify only the converted methylated DNA using methyl-specific/ universal primers (B) and Taq polymerase. ◆

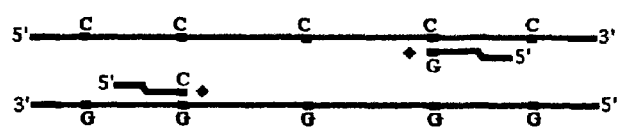

6. PCR amplify all products derived from converted methylated DNA using universal primers (B) and Taq polymerase. ◆

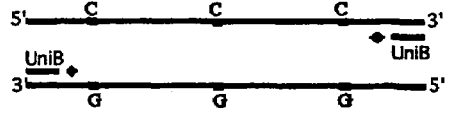

7. Perform LDR using primers specific for originally methylated sequences, and thermostable ligase. ●

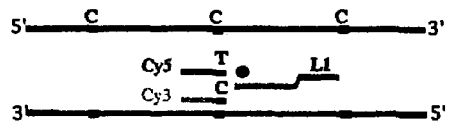

8. Separate fluorescent products using capillary electrophoresis and score for presence of methylated DNA.

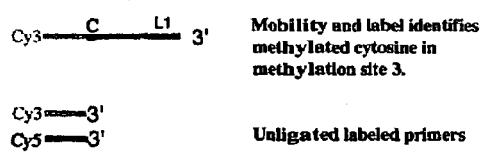

Mobility and label identifies methylated cytosine in methylation site 3.

Unligated labeled primers

Figure 35

Bisulfite/ Ms-PCR-PCR/ Ms-PCR-PCR/ LDR/Universal Array: Nucleotide Analogs

1. Treat DNA with sodium bisulfite to convert unmethylated, but not methylated cytosines into uracils. Only the cytosines present in CpG dinucleotide sites are shown here.

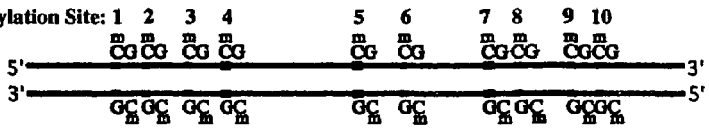

2. The resultant strands are not complementary. PCR amplify one strand using methyl-specific/ universal primers (A) and Taq polymerase. ◆

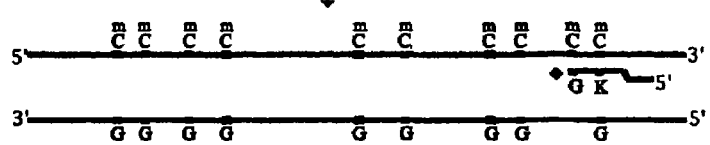

3. PCR amplify the complementary strand of the first PCR synthesis using methyl-specific/ universal primers (A) and Taq polymerase. ◆

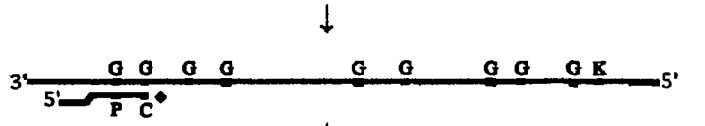

4. PCR amplify all primary products using universal primers (A) and Taq polymerase. ◆

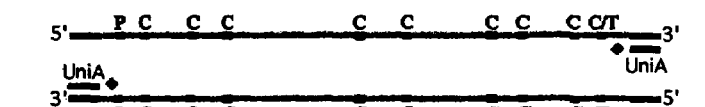

5. PCR amplify only the converted methylated DNA using methyl-specific/ universal primers (B) and Taq polymerase. ◆

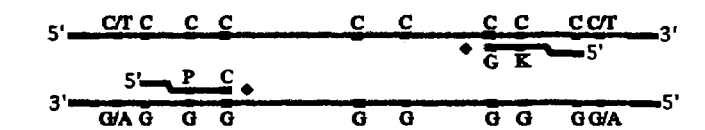

6. PCR amplify all products derived from converted methylated DNA using universal primers (B) and Taq polymerase. ◆

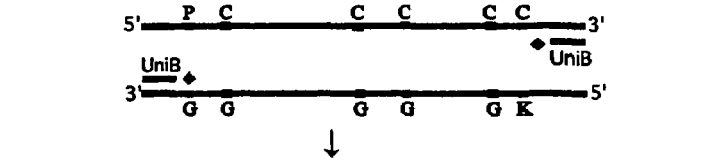

7. Perform LDR using primers specific for originally methylated sequences, and thermostable ligase. ●

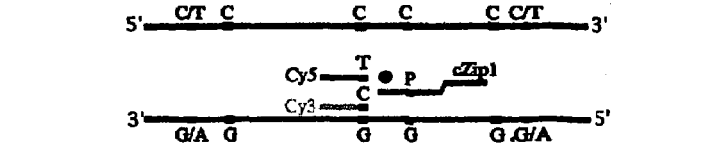

8. Capture fluorescent products on addressable array and score for presence of methylated DNA.

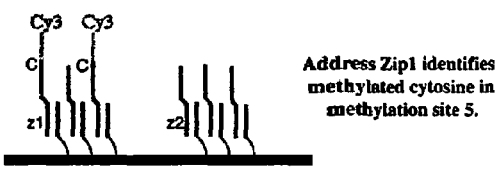

Address Zip1 identifies methylated cytosine in methylation site 5.

Figure 36

Bisulfite/ Ms-PCR-PCR/ Ms-PCR-PCR/ LDR/ Capillary Electrophoresis: Nucleotide Analogs

1. Treat DNA with sodium bisulfite to convert unmethylated, but not methylated cytosines into uracils. Only the cytosines present in CpG dinucleotide sites are shown here.

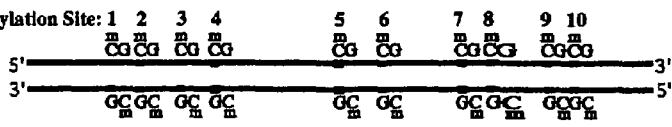

2. The resultant strands are not complementary. PCR amplify one strand using methyl-specific/ universal primers (A) and Taq polymerase. ♦

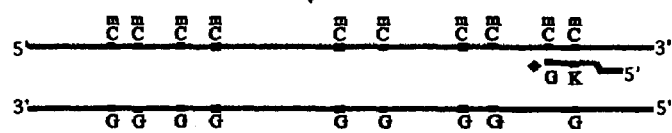

3. PCR amplify the complementary strand of the first PCR synthesis using methyl-specific/ universal primers (A) and Taq polymerase. ♦

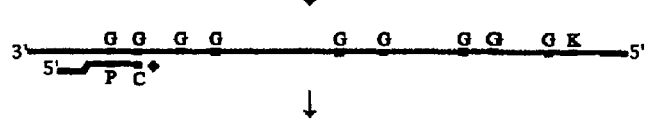

4. PCR amplify all primary products using universal primers (A) and Taq polymerase. ♦

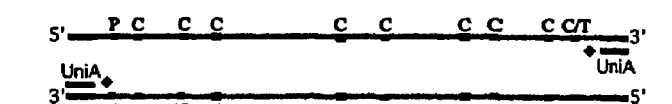

5. PCR amplify only the converted methylated DNA using methyl-specific/ universal primers (B) and Taq polymerase. ♦

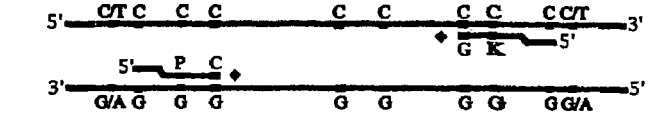

6. PCR amplify all products derived from converted methylated DNA using universal primers (B) and Taq polymerase. ♦

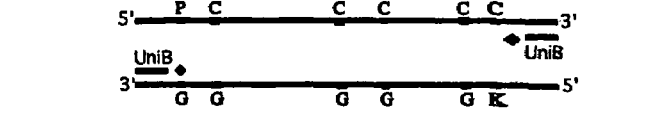

7. Perform LDR using primers specific for originally methylated sequences, and thermostable ligase. ●

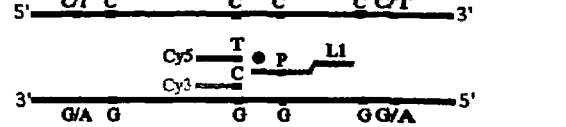

8. Separate fluorescent products using capillary electrophoresis and score for presence of methylated DNA.

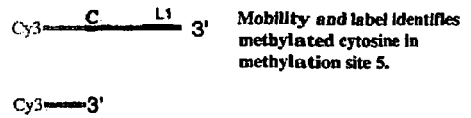

Mobility and label identifies methylated cytosine in methylation site 5.

Unligated labeled primers

Figure 37

Bisulfite/Ms-PCR-PCR/Ms-PCR-PCR/LDR/Capillary Electrophoresis: Preferential Methylated DNA

1. Treat DNA with sodium bisulfite to convert unmethylated, but not methylated cytosines into uracils. Only the cytosines present in CpG dinucleotide sites are shown here.

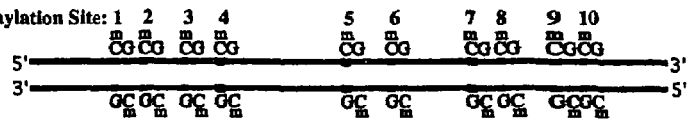

2. The resultant strands are not complementary. PCR amplify one strand using methyl-specific/ universal primers (A) and Taq polymerase. ♦

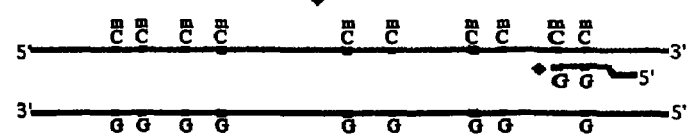

3. PCR amplify the complementary strand of the first PCR synthesis using methyl-specific/ universal primers (A) and Taq polymerase. ♦

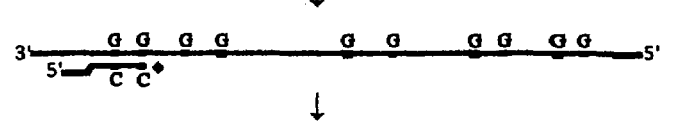

4. PCR amplify all primary products using universal primers (A) and Taq polymerase. ♦

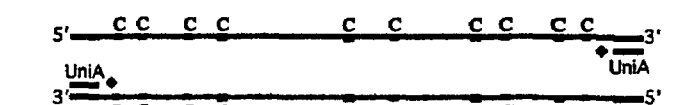

5. PCR amplify only the converted methylated DNA using methyl-specific/ universal primers (B) and Taq polymerase. ♦

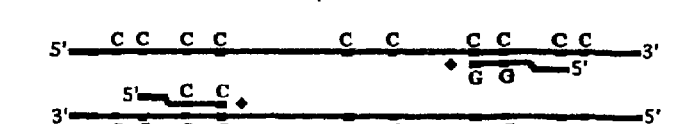

6. PCR amplify all products derived from converted methylated DNA using universal primers (B) and Taq polymerase. ♦

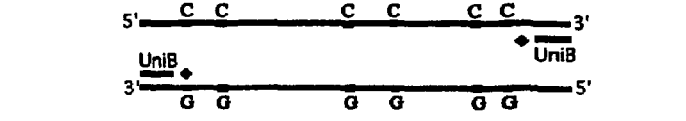

7. Perform LDR using primers specific for originally methylated sequences, and thermostable ligase. ●

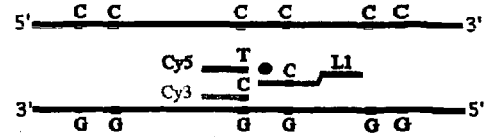

8. Separate fluorescent products using capillary electrophoresis and score for presence of methylated DNA.

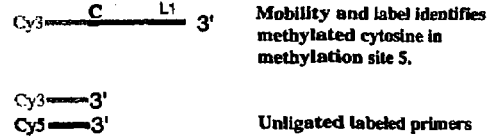

Mobility and label identifies methylated cytosine in methylation site 5.

Unligated labeled primers

Figure 39

BstU1 / Extend / 3' Exo / PCR / LDR / Universal Array
Sensitive determination of methylation status 1. Cleave genomic DNA with BstUI restriction endonuclease. Methylated DNA remains uncut, while majority of unmethylated DNA is cut.

2. Denature DNA, anneal upstream promoter-specific primers, extend with polymerase using α-sdATP and α-sTTP in the presence of BstUI. Hemi-methylated DNA remains uncut, but remaining unmethylated DNA is cut when double stranded.

3. Destroy genomic DNA using 3'->5' exonuclease(s). Extended DNA is resistant to exonucleases.

4. PCR amplify all potential promoter regions using promoter-specific /universal primers and Taq polymerase.

5. PCR amplify all primary products using universal primer and Taq polymerase.

6. Perform LDR using promoter region-specific LDR primers, adjacent primers containing complementary zip code sequences, and thermostable ligase.

7. Capture fluorescent products on addressable array and score for presence at each position to methylated promoter regions.

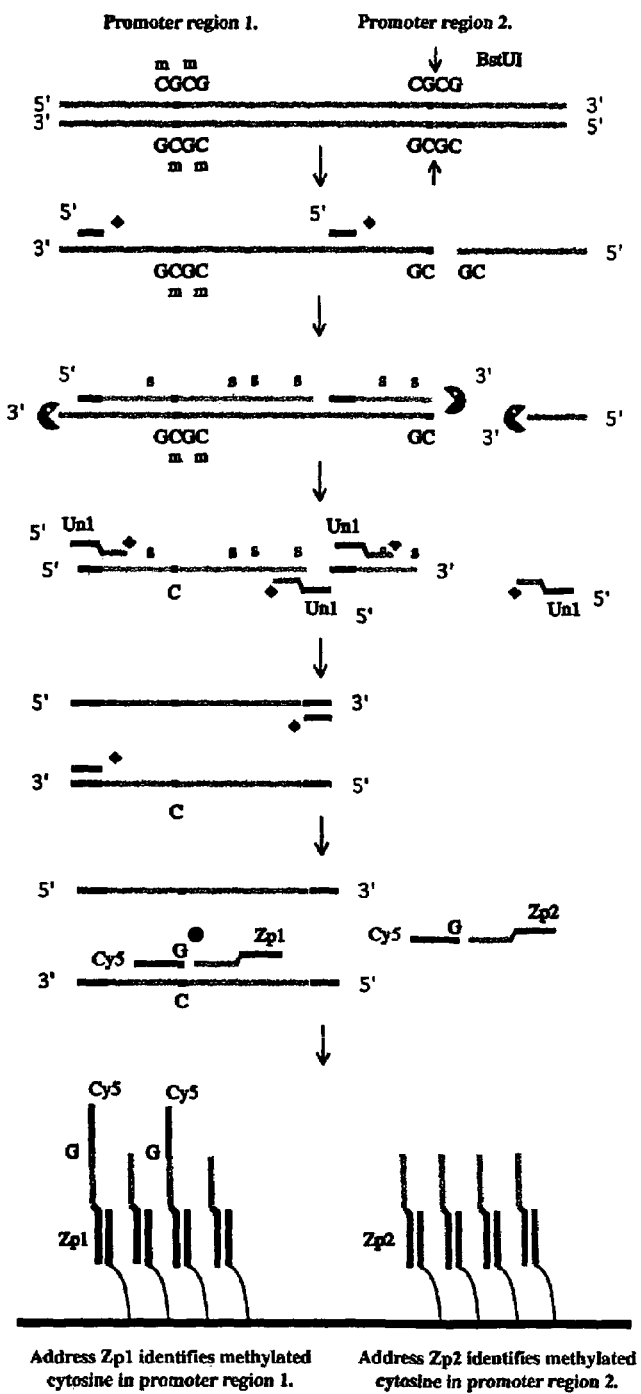

Figure 40

BstU1 / Extend / 3' Exo / PCR / LDR / Capillary Electrophoresis
Sensitive determination of methylation status 1. Cleave genomic DNA with BstUI restriction endonuclease. Methylated DNA remains uncut, while majority of unmethylated DNA is cut.

2. Denature DNA, anneal upstream promoter-specific primers, extend with polymerase using α-sdATP and α-sTTP in the presence of BstUI. Hemi-methylated DNA remains uncut, but remaining unmethylated DNA is cut when double stranded.

3. Destroy genomic DNA using 3'->5' exonuclease(s). Extended DNA is resistant to exonucleases.

4. PCR amplify all potential promoter regions using promoter-specific /universal primers and Taq polymerase.

5. PCR amplify all primary products using universal primer and Taq polymerase.

6. Perform LDR using promoter region-specific LDR primers, adjacent primers containing differnt length tails, and thermostable ligase.

7. Separate fluorescent products using capillary electrophoresis and score for presence at each position to methylated promoter regions.

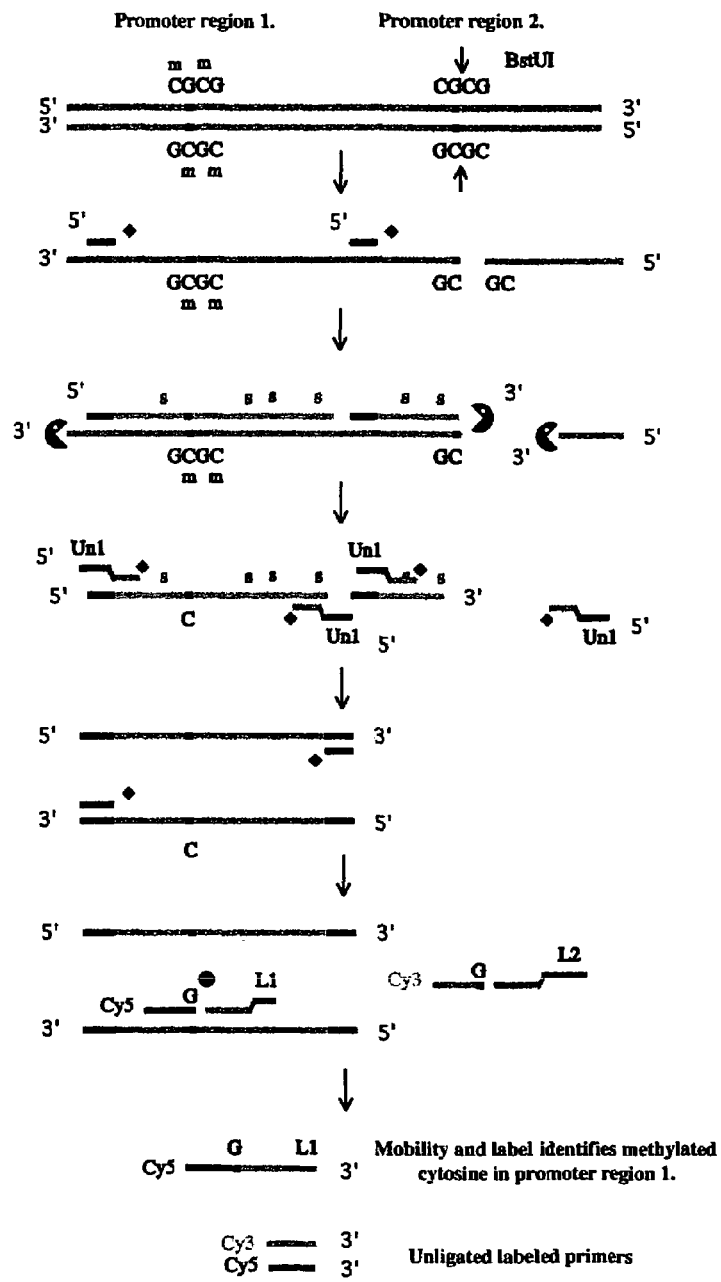

Figure 41

HinP1I / Extend / 3' Exo / PCR / LDR / Universal Array
Sensitive determination of methylation status 1. Cleave genomic DNA with HinP1I restriction endonuclease. Methylated DNA remains uncut, while unmethylated DNA is cut.

2. Denature DNA, anneal upstream promoter-specific primers, extend with polymerase. Recut with HinP1I. Hemi-methylated DNA is nicked, while remaining unmethylated DNA is cut when double stranded. Remove normal dNTPs and extend nicked DNA using α-sdATP and α-sTTP.

3. Destroy genomic DNA using 3'->5' exonuclease(s). Extended DNA is resistant to exonucleases.

4. PCR amplify all potential promoter regions using promoter-specific /universal primers and Taq polymerase. ♦

5. PCR amplify all primary products using universal primer and Taq polymerase. ♦

6. Perform LDR using promoter region-specific LDR primers, adjacent primers containing complementary zip code sequences, and thermostable ligase. ●

7. Capture fluorescent products on addressable array and score for presence at each position to methylated promoter regions.

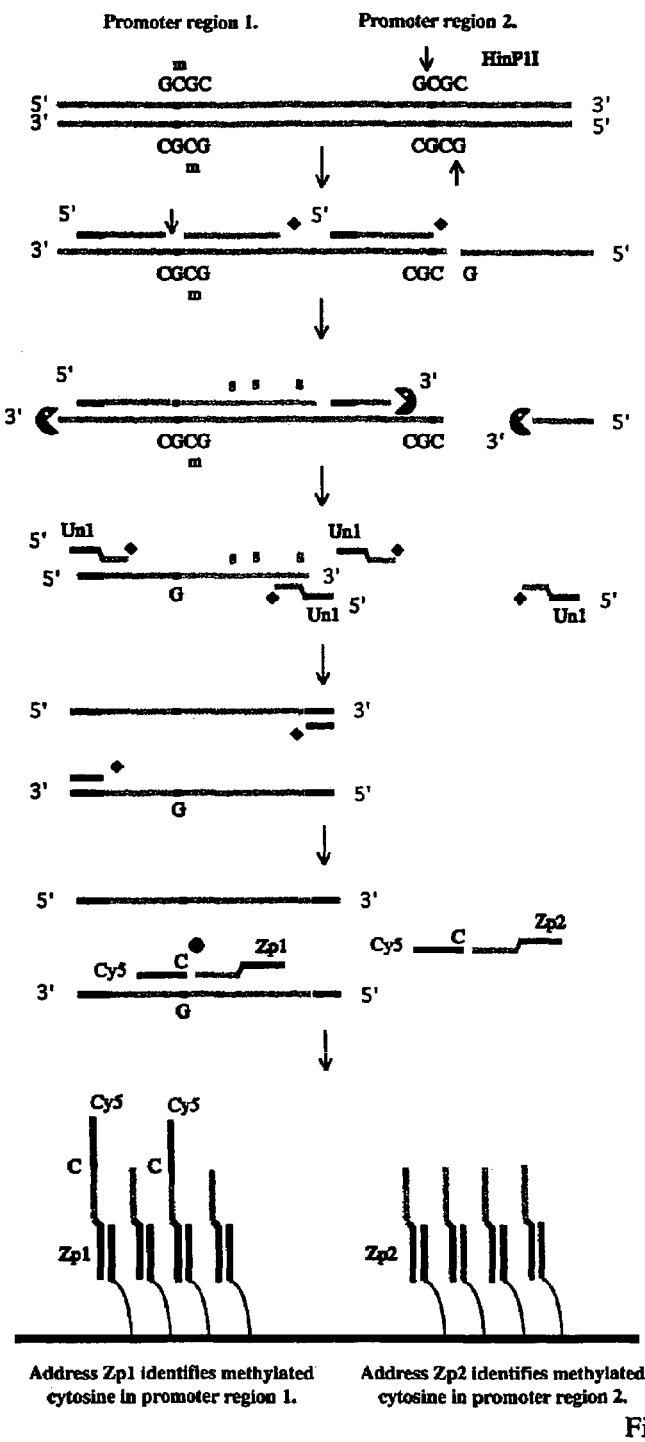

Address Zp1 identifies methylated cytosine in promoter region 1.

Address Zp2 identifies methylated cytosine in promoter region 2.

Figure 42

HinP1I / Extend / 3' Exo / PCR / LDR / Capillary Electrophoresis
Sensitive determination of methylation status 1. Cleave genomic DNA with HinP1I restriction endonuclease. Methylated DNA remains uncut, while unmethylated DNA is cut.

2. Denature DNA, anneal upstream promoter-specific primers, extend with polymerase. Recut with HinP1I. Hemi-methylated DNA is nicked, while remaining unmethylated DNA is cut when double stranded. Remove normal dNTPs and extend nicked DNA using α-sdATP and α-sTTP.

3. Destroy genomic DNA using 3'->5' exonuclease(s). Extended DNA is resistant to exonucleases.

4. PCR amplify all potential promoter regions using promoter-specific /universal primers and Taq polymerase. ◆

5. PCR amplify all primary products using universal primer and Taq polymerase. ◆

6. Perform LDR using promoter region-specific LDR primers, adjacent primers containing differnt length tails, and thermostable ligase. ●

7. Separate fluorescent products using capillary electrophoresis and score for presence at each position to methylated promoter regions.

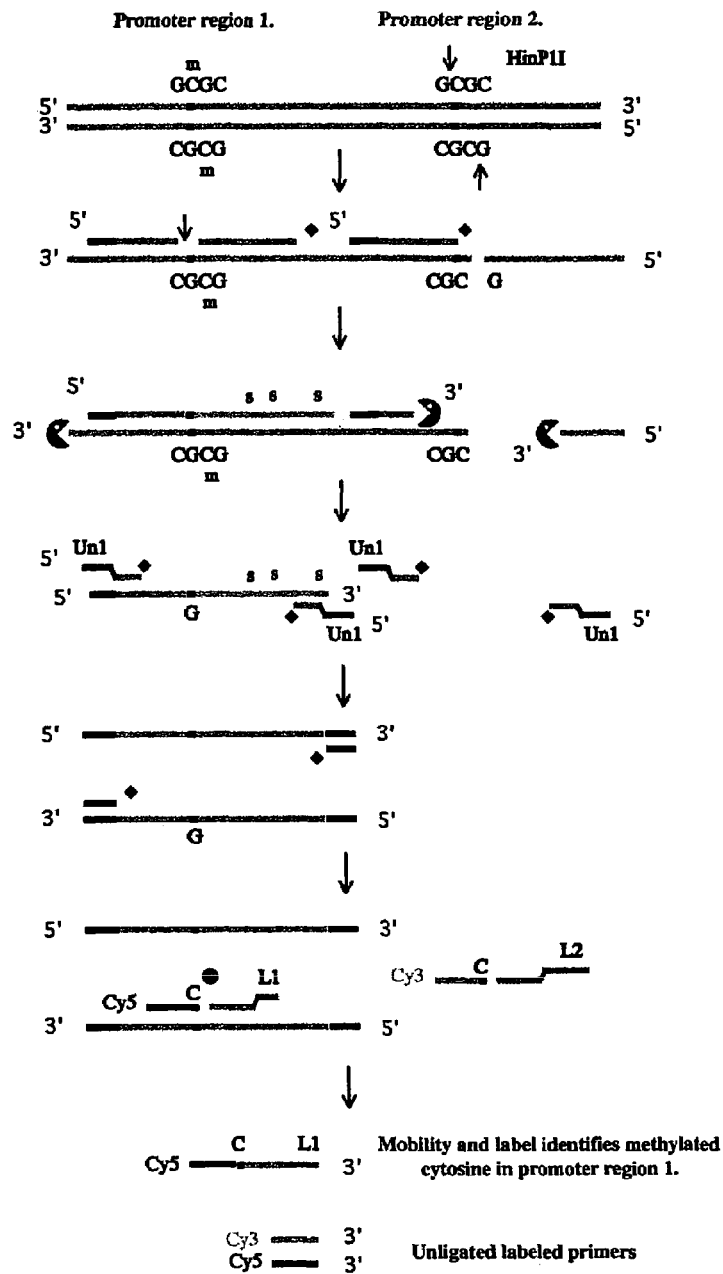

Figure 43

HinP1I / Extend / 5' Exo / PCR / LDR / Universal Array
Sensitive determination of methylation status 1. Cleave genomic DNA with HinP1I restriction endonuclease. Methylated DNA remains uncut, while unmethylated DNA is cut.

2. Denature DNA, anneal upstream promoter-specific primers, extend with Taq polymerase. Recut with HinP1I. Hemi-methylated DNA is nicked, while remaining unmethylated DNA is cut when double stranded. Heat kill HinP1I at 65°C and re-extend nicked DNA.

3. Destroy genomic DNA using 5'->3' lambda exonuclease. Extended DNA is resistant to exonuclease.

4. PCR amplify all potential promoter regions using promoter-specific /universal primers and Taq polymerase.

5. PCR amplify all primary products using universal primer and Taq polymerase.

6. Perform LDR using promoter region-specific LDR primers, adjacent primers containing complementary zip code sequences, and thermostable ligase.

7. Capture fluorescent products on addressable array and score for presence at each position to methylated promoter regions.

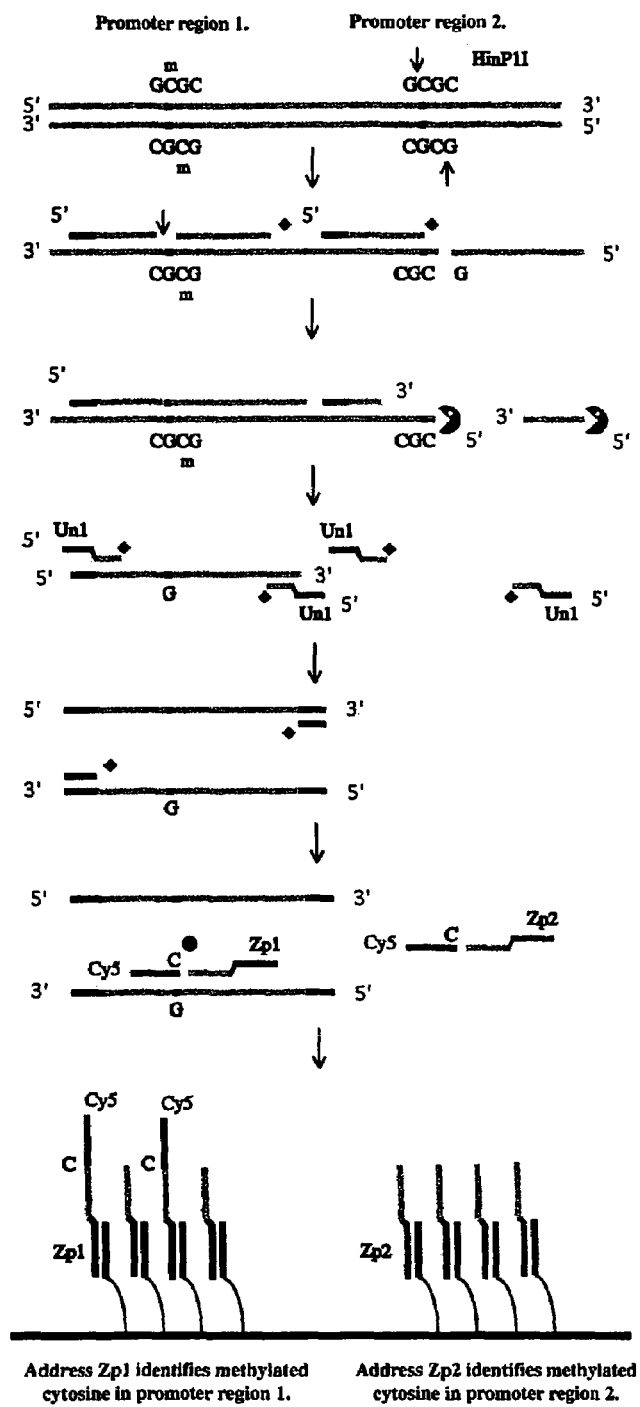

Address Zp1 identifies methylated cytosine in promoter region 1.

Address Zp2 identifies methylated cytosine in promoter region 2.

Figure 44

HinP1I / Extend / 5' Exo / PCR / LDR / Capillary Electrophoresis
Sensitive determination of methylation status 1. Cleave genomic DNA with HinP1I restriction endonuclease. Methylated DNA remains uncut, while unmethylated DNA is cut.

2. Denature DNA, anneal upstream promoter-specific primers, extend with Taq polymerase. Recut with HinP1I. Hemi-methylated DNA is nicked, while remaining unmethylated DNA is cut when double stranded. Heat kill HinP1I at 65°C and re-extend nicked DNA.

3. Destroy genomic DNA using 5'->3' lambda exonuclease. Extended DNA is resistant to exonuclease.

4. PCR amplify all potential promoter regions using promoter-specific /universal primers and Taq polymerase.

5. PCR amplify all primary products using universal primer and Taq polymerase.

6. Perform LDR using promoter region-specific LDR primers, adjacent primers containing differnt length tails, and thermostable ligase.

7. Separate fluorescent products using capillary electrophoresis and score for presence at each position to methylated promoter regions.

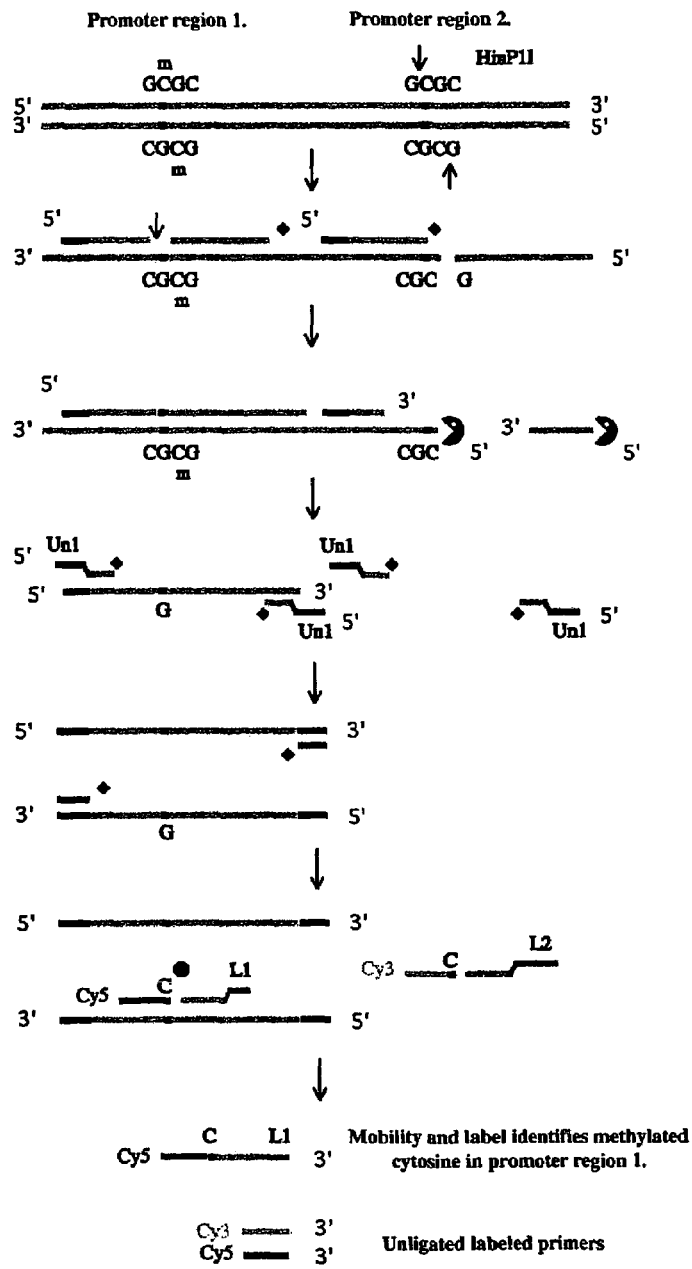

Figure 45

HpaII / Extend / 5' Exo / PCR / LDR / Universal Array
Sensitive determination of methylation status

1. Cleave genomic DNA with HpaII restriction endonuclease. Methylated DNA remains uncut, while unmethylated DNA is cut.

2. Denature DNA, anneal upstream promoter-specific primers, extend with Taq polymerase. Recut with HpaII. Hemi-methylated DNA is not nicked, while remaining unmethylated DNA is cut when double stranded.

3. Destroy genomic DNA using 5'->3' lambda exonuclease. Extended DNA is resistant to exonuclease.

4. PCR amplify all potential promoter regions using promoter-specific /universal primers and Taq polymerase.

5. PCR amplify all primary products using universal primer and Taq polymerase.

6. Perform LDR using promoter region-specific LDR primers, adjacent primers containing complementary zip code sequences, and thermostable ligase.

7. Capture fluorescent products on addressable array and score for presence at each position to methylated promoter regions.

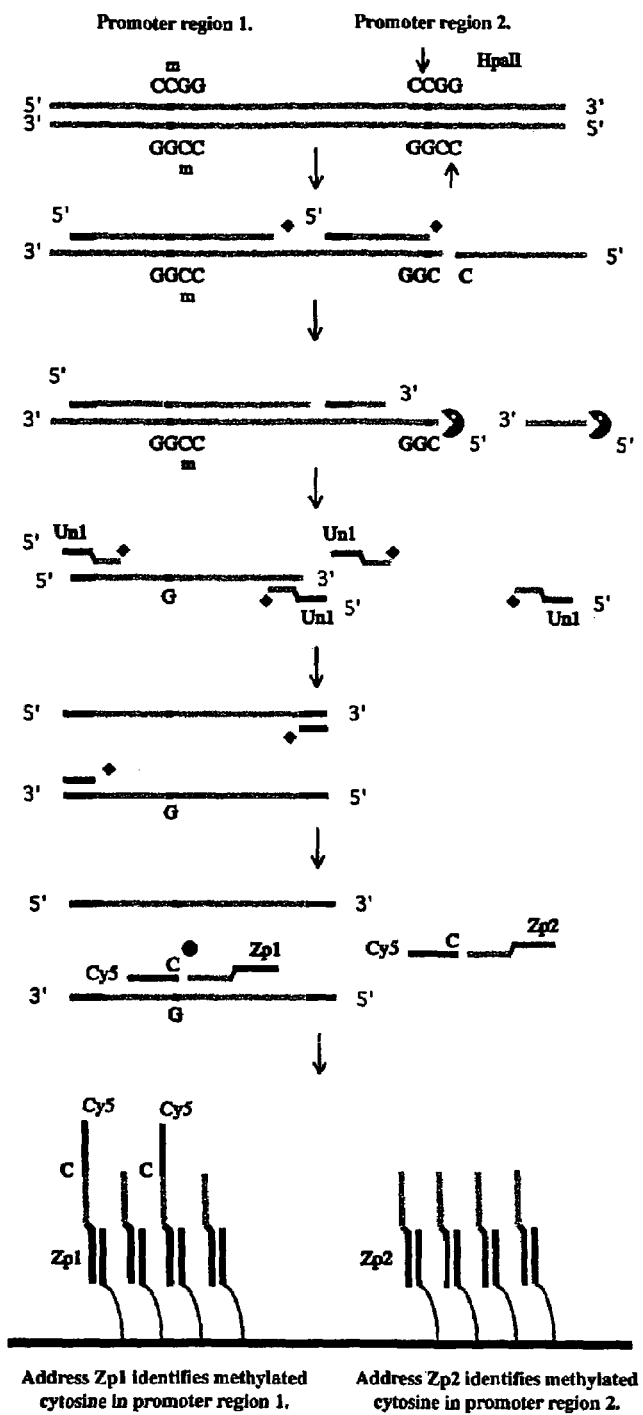

Address Zp1 identifies methylated cytosine in promoter region 1.

Address Zp2 identifies methylated cytosine in promoter region 2.

Figure 46

HpaII / Extend / 5' Exo / PCR / LDR / Capillary Electrophoresis
Sensitive determination of methylation status 1. Cleave genomic DNA with HpaII restriction endonuclease. Methylated DNA remains uncut, while unmethylated DNA is cut.

2. Denature DNA, anneal upstream promoter-specific primers, extend with Taq polymerase. Recut with HpaII. Hemi-methylated DNA is not nicked, while remaining unmethylated DNA is cut when double stranded.

3. Destroy genomic DNA using 5'->3' lambda exonuclease. Extended DNA is resistant to exonuclease.

4. PCR amplify all potential promoter regions using promoter-specific /universal primers and Taq polymerase.

5. PCR amplify all primary products using universal primer and Taq polymerase.

6. Perform LDR using promoter region-specific LDR primers, adjacent primers containing differnt length tails, and thermostable ligase.

7. Separate fluorescent products using capillary electrophoresis and score for presence at each position to methylated promoter regions.

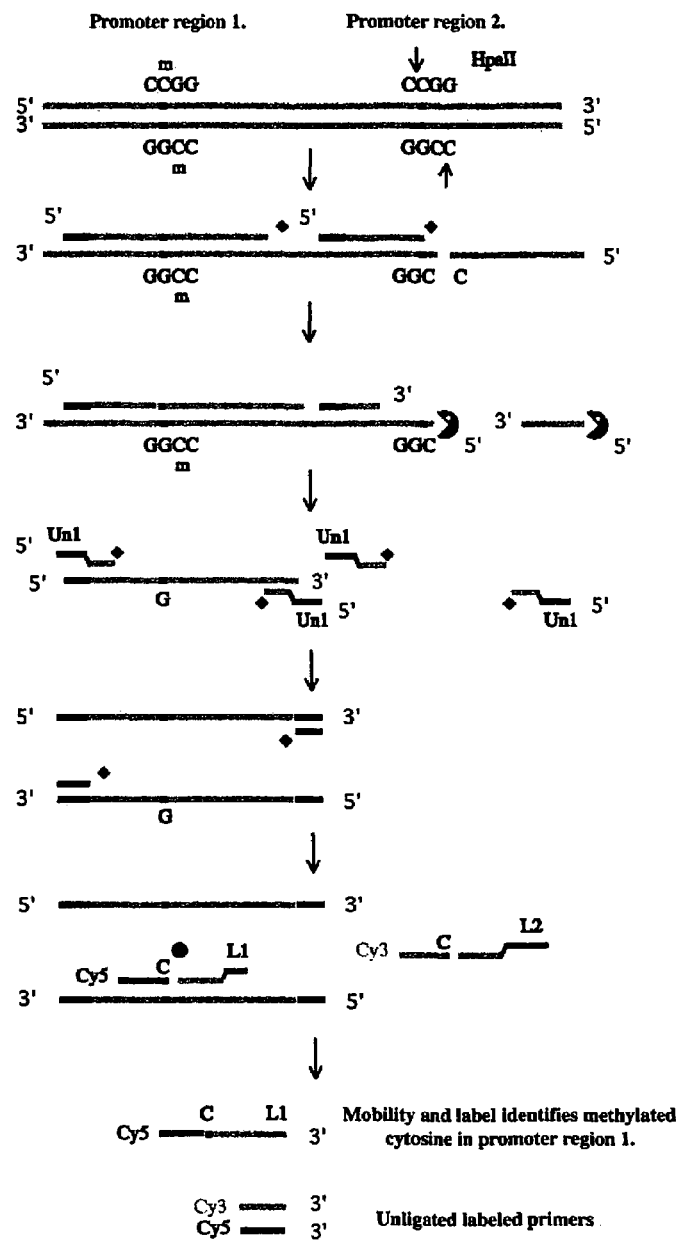

Figure 47

METHOD FOR DETECTION OF PROMOTER METHYLATION STATUS

This application claims benefit of U.S. Provisional Patent Application Ser. No. 60/543,156, filed Feb. 10, 2004.

FIELD OF THE INVENTION

The present invention relates to the detection of promoter methylation status.

BACKGROUND OF THE INVENTION

Cancers contain altered methylation patterns that result in aberrant expression of critical genes. Hypermethylation turns off expression of genes required to regulate normal growth while hypomethylation allows for inappropriate expression of genes that allow cells to proliferate. Aberrant promoter hypermethylation occurs at the 5-position of cytosine within the CpG dinucleotide. Gardiner-Garden, M., et al., *J. Mol. Biol.*, 196(2): 261-82 (1987). It inactivates the expression of critical genes that are involved in tumor suppression, DNA repair, control of tumor metastasis, and invasion. Feinberg, A. P., et al., *Nature*, 301: 89-92 (1983); Jones, P. A., et al., *Nat. Rev. Genet.*, 3(6): 415-28 (2002). There is a great need in both basic and clinical research to identify promoter DNA methylation status with high efficiency and accuracy for diseases diagnoses and prognoses.

Various methods have been developed for the study of promoter DNA methylation status of known genes. Laird P. W., *Nature Review Cancer*, 3: 253-266 (2003). These methods can generally be grouped into two categories: methylation-sensitive restriction endonuclease assays and sodium bisulfite conversion based approaches.

Methylation-Sensitive Restriction Endonuclease Digestion Methods

The enzymatic digestion method traditionally relies on the inability of methylation-sensitive enzymes to cleave restriction sites containing methylated CpG dinucleotides. Genomic DNAs are incubated with the proper restriction endonucleases and the presence and absence of the cleaved DNA fragments can then be identified by Southern hybridization. This method is not only capable of analyzing the methylation status of individual known genomic region, but also allows the global examination of CpG island methylation status. However, the disadvantage is that large quantity of high molecular weight genomic DNA is required to begin with Issa, J. P., et al., *Nature Genetic*, 7(4): 536-40 (1994). This method is suitable for the study where a high percentage of alleles of interest are methylated, such as imprinted genes and X chromosome inactivated genes; this method is not suitable for clinical applications where the quantity and quality of the genomic DNA resource can be a limiting factor.

To circumvent the requirement of large quantity of high molecular weight genomic DNA, a more sensitive approach based on the combination of methylation-sensitive restriction endonuclease digestion and the polymerase chain reaction has also been introduced. Singer-Sam, J., et al., *Nucleic Acids Res.*, 18(3): 687 (1990), Singer-Sam, J., et al., *Mol. Cell. Biol.*, 10(9): 4987-9 (1990). Oligonucleotide polymerase chain reaction ("PCR") primers have been designed flanking the restriction endonuclease site, and PCR amplification is performed after the enzymatic digestion. A methylated restriction endonuclease site results in the presence of the proper PCR product. On the other hand, PCR template can be cleaved by the endonuclease if the restriction site is unmethylated. The credibility of this method depends on the complete digestion of unmethylated DNA by the restriction endonuclease. The problem is exacerbated by the fact that the sample DNA is often limited, and it is difficult to drive endonuclease digestions to completion. Thus, it is sometimes difficult to determine whether PCR amplicons result from incomplete digestion (i.e. false positives) or from those of low abundance methylation sites (i.e. true positives). Restriction enzyme techniques are based on removing the unmethylated DNA, and assuming that PCR amplification of the remaining DNA arises because it was methylated, and consequently the method is susceptible to false positives arising from incomplete removal of unmethylated DNA.

Sodium Bisulfite Based Chemical Conversion Approaches

Chemical conversion of cytosines to uracils using bisulfite can be used to study DNA methylation. 5-methylcytosines are resistant to conversion and deamination only occurs on unmethylated cytosines. Frommer, M., et al., *Proc. Natl. Acad. Sci. USA*, 89(5): 1827-31 (1992). Bisulfite can be quantitatively added to the 5-6 double bonds of cytosine if there is no methyl group on the 5 position. Bisulfite addition renders the cytosine susceptible to hydrolytic deamination; subsequent elimination of the bisulfite results in the formation of uracil. Voss, K. O., et al., *Anal. Chem.*, 70(18): 3818-3823 (1998). One strand of the modified DNA sequences can then be PCR amplified and sequenced. However, due to stromal cell contamination in a typical clinical sample, direct sequencing without cloning the PCR products reduces the sensitivity of the technique. It requires about 25% of the alleles to be methylated for accurate detection. Myohanen, S., et al., *DNA Sequence*, 5: 1-8 (1994).

The development of methylation-specific PCR (MSP) has allowed the sensitive and specific study of low abundance methylation sequences. Herman, J. G., et al., *Proc. Natl. Acad. Sci. USA*, 93(18): 9821-6 (1996). MSP relies upon chemical modification of DNA using bisulfite, the specific designed PCR primers that are complementary to the bisulfite modified DNA template. The MSP specific primers are designed across a CpG rich area within a promoter sequence. Typically, more than three CpG sites have to be included in the oligonucleotide sequences. Two sets of MSP PCR primers are designed, one set of the MSP primers has the sequence to perfectly hybridize to the complementary strand of the bisulfite-treated methylated DNA sequence with methyl-cytosines residing on the CpG sites. The other set of the MSP primers is only designed to perfectly hybridize to the complementary strand of the bisulfite-treated DNA sequence in the absence of methylated cytosine. Consequently, the MSP specific PCR products only results from the DNA template which contains methyl-cytosines.

There are three major difficulties with this approach. The design of MSP primers requires sufficient numbers of methylated cytosines to be present in the primer sequence to ensure the selection capability. It may not be sufficiently sensitive to distinguish partial methylated sequences from fully methylated one. In addition, this assay analyzes one gene at a time, and both sets of MSP primers have different annealing temperatures which may further slowdown its throughput. Finally, bisulfite treatment of DNA often nicks the DNA (i.e. destroys the backbone chain) as it is also converting unmethylated cytosines to uracil. Conditions which assure that all unmethylated cytosines are converted to uracil may also destroy the DNA. Conditions which assure that sufficient DNA remains intact may not assure that all unmethylated cytosines are converted to uracil. Thus, absence of a band may be the consequence of destroying too much of the starting DNA and, consequently, insufficient amplification, leading to a false negative result. Likewise, presence of a band may be the consequence of incomplete conversion of unmethylated cytosine to uracil, allowing for primer binding at an unmethylated site, and leading to a false positive result. Therefore, there is an urgent need to develop a high-throughput assay that can detect methylation status in virtually any gene sequence.

The present invention is directed to meeting this need.

SUMMARY OF THE INVENTION

One aspect of the present invention is directed to a method for identifying, in a sample, one or more target nucleic acid molecules differing from other nucleic acid molecules in the sample by one or more methylated cytosine residues. In this method, a sample potentially containing one or more target nucleic acid molecules is provided and subjected to a bisulfite treatment to convert, in the nucleic acid molecules of the sample, unmethylated cytosine residues, but not methylated cytosine residues, into uracil residues. One or more primary oligonucleotide primer sets are provided. Each set is characterized by (a) a first oligonucleotide primer, having a target-specific portion and a 5' upstream secondary primer-specific portion, wherein the target-specific portion is suitable for hybridization on a first strand of the target nucleic acid molecule in which unmethylated cytosines have been converted to uracil, and (b) a second oligonucleotide primer, having a target-specific portion and a 5' upstream secondary primer-specific portion. The target-specific portion is suitable for hybridization on a polyrnerase extension product of the first strand or on a second strand of the target nucleic acid molecule, either of which have unmethylated cytosines converted to uracil and where the first and second oligonucleotide primers of each set contain the same 5' upstream secondary primer-specific-portion. Also provided is a polymerase. The sample, the primary oligonucleotide primer set, and the polymerase are blended to form a primary polymerase chain reaction mixture. The primary polymerase chain reaction mixture is subjected to two or more polymerase chain reaction cycles comprising a denaturation treatment, where hybridized nucleic acid sequences are separated, a hybridization treatment, where the target-specific portions of the primary oligonucleotide primer sets hybridize to the target nucleic acid molecules with unmethylated cytosines converted to uracil or to extension products of such modified target nucleic acid molecules, and an extension treatment, where the hybridized primary oligonucleotide primers are extended to form primary extension products complementary to the target nucleic acid molecules with unmethylated cytosines converted to uracil. Also provided is a secondary oligonucleotide primer set characterized by (a) a first secondary primer containing the 5' upstream portion of the first oligonucleotide primer of the primary oligonucleotide primer set, and (b) a second secondary primer containing the 5' upstream portion of the second oligonucleotide primer of the primary oligonucleotide primer set. The primary extension products, the secondary oligonucleotide primer set, and the polymerase are blended to form a secondary polymerase chain reaction mixture. The secondary polymerase chain reaction mixture is subjected to two or more polymerase chain reaction cycles comprising a denaturation treatment, where hybridized nucleic acid sequences are separated, a hybridization treatment, where the secondary oligonucleotide primers hybridize to the primary extension products, and an extension treatment, where the hybridized secondary oligonucleotide primers are extended to form secondary extension products complementary to the primary extension products. Also provided are a plurality of oligonucleotide probe sets, each set characterized by (a) a first oligonucleotide probe, having a secondary extension product-specific portion and a detectable reporter label, and (b) a second oligonucleotide probe, having a secondary extension product-specific portion. The oligonucleotide probes in a particular set are suitable for ligation together when hybridized on a complementary secondary extension product, but have a mismatch which interferes with such ligation when hybridized to any other nucleic acid molecule present in the sample. A ligase is provided, and the secondary extension products, the plurality of oligonucleotide probe sets, and the ligase are blended to form a ligase detection reaction mixture. The ligase detection reaction ("LDR") mixture is subjected to one or more ligase detection reaction cycles comprising a denaturation treatment, where any hybridized oligonucleotides are separated from the secondary extension product, and a hybridization treatment, where the oligonucleotide probe sets hybridize in a base-specific manner to their respective secondary extension products, if present, and ligate to one another to form a ligation product containing (a) the detectable reporter label and (b) the secondary extension product-specific portions connected together. The oligonucleotide probe sets may hybridize to nucleic acid molecules but do not ligate together due to a presence of one or more mismatches and individually separate during the denaturation treatment. The reporter labels of the ligation products are detected, thereby indicating the presence of two or more methylated cytosine bases in the target nucleotide sequences in the sample.

Another aspect of the present invention relates to a method for identifying one or more target nucleic acids in a sample, differing by one or more methylated cytosine residues. In accordance with this aspect of the present invention, a sample potentially containing one or more target nucleic acid molecules is provided and subjected to a bisulfite treatment to convert, in the nucleic acid molecules of the sample, unmethylated cytosine residues, but not methylated cytosine residues, into uracil residues. One or more primary oligonucleotide primer sets are provided, each set characterized by (a) a first oligonucleotide primer, having a target-specific portion and a 5' upstream secondary primer-specific portion, where the target-specific portion is suitable for hybridization on a first strand of the target nucleic acid molecule in which unmethylated cytosines have been converted to uracil, and (b) a second oligonucleotide primer, having a target-specific portion and a 5' upstream secondary primer-specific portion, where the target-specific portion is suitable for hybridization on a polymerase extension product of the first strand or on a second strand of the target nucleic acid molecule, either of which having unmethylated cytosines converted to uracil. The first and second oligonucleotide primers of each set contain the same 5' upstream secondary primer-specific-portion. Also provided is a polymerase. The sample, the primary oligonucleotide primer set, and the polymerase are blended to form a primary polymerase chain reaction mixture. The primary polymerase chain reaction mixture is subjected to two or more polymerase chain reaction cycles comprising a denaturation treatment, where hybridized nucleic acid sequences are separated, a hybridization treatment, where the target-specific portions of the primary oligonucleotide primer sets hybridize to the target nucleic acid molecules with unmethylated cytosines converted to uracil or to extension products of such modified target nucleic acid molecules, and an extension treatment, where the hybridized primary oligonucleotide primers are extended to form primary extension products complementary to the target nucleic acid molecules with unmethylated cytosines converted to uracil. Also provided is a secondary oligonucleotide primer set characterized by (a) a first secondary primer containing the 5' upstream portion of the first oligonucleotide primer of the primary oligonucleotide primer set, and (b) a second secondary primer containing the 5' upstream portion of the second oligonucleotide primer of the primary oligonucleotide primer set. The primary extension products, the secondary oligonucleotide primer set, and the polymerase are blended to form a secondary polymerase chain reaction mixture. The secondary polymerase chain reaction mixture is subjected to two or more polymerase chain reaction cycles comprising a denaturation treatment, where hybridized nucleic acid sequences are separated, a hybridization treatment, where the secondary oligonucleotide primers hybridize to the primary extension products, and an extension treatment, where the hybridized secondary oligonucleotide primers are extended to form secondary extension products complementary to the primary extension products. One or more tertiary oligonucleotide primer sets are provided, each set characterized by (a) a first oligonucleotide primer, having a target-specific portion and a 5' upstream quaternary primer-specific portion, where the target-specific portion is suitable for and preferentially hybridizes to the secondary extension products that arise when the target nucleic acid molecule is methylated in the region of hybridization, and (b) a second oligonucleotide primer, having a target-specific portion and a 5' upstream quaternary primer-specific portion, where the target-specific portion is suitable for and preferentially hybridizes to the secondary extension products that arise when the target nucleic acid molecule is methylated in the region of hybridization, to permit formation of a polymerase chain reaction product, but have a mismatch which interferes with formation of such a polymerase chain reaction product when hybridized to any other nucleic acid molecule present in the sample. The secondary polymerase chain reaction mixture, the tertiary oligonucleotide primers, and the polymerase are blended to form a tertiary polymerase chain reaction mixture. The tertiary polymerase chain reaction mixture to two or more polymerase chain reaction cycles comprising a denaturation treatment, where hybridized nucleic acid sequences are separated, a hybridization treatment, where the target-specific portions of the tertiary oligonucleotide primers hybridize to the secondary extension products, and an extension treatment, where the hybridized tertiary oligonucleotide primers are extended to form tertiary extension products complementary to the target nucleic acid molecule to which a tertiary oligonucleotide primer is hybridized. A quaternary oligonucleotide primer set is provided which is characterized by (a) a first quaternary oligonucleotide primer containing the same sequence as the 5' upstream quaternary primer-specific portion of a first oligonucleotide primer of the tertiary oligonucleotide primer set, and (b) a second quaternary oligonucleotide primer containing the same sequence as the 5' upstream quaternary primer-specific portion of a second oligonucleotide primer of the tertiary oligonucleotide primer set, where a set of quaternary oligonucleotide primers may be used to amplify all of the tertiary extension products. The tertiary extension products, the quaternary oligonucleotide primers, and the polymerase are blended to form a quaternary polymerase chain reaction mixture. The quaternary polymerase chain reaction mixture is subjected to two or more polymerase chain reaction cycles comprising a denaturation treatment, where hybridized nucleic acid sequences are separated, a hybridization treatment, where the quaternary oligonucleotide primers hybridize to the tertiary extension products, and an extension treatment, where the hybridized quaternary oligonucleotide primers are extended to form quaternary extension products complementary to the tertiary extension products. A plurality of oligonucleotide probe sets are provided with each set characterized by (a) a first oligonucleotide probe, having a quaternary extension product-specific portion and a detectable reporter label, and (b) a second oligonucleotide probe, having a quaternary extension product-specific portion, where the oligonucleotide probes in a particular set are suitable for ligation together when hybridized on a complementary quaternary extension product, but have a mismatch which interferes with such ligation when hybridized to any other nucleic acid molecule present in the sample. A ligase is provided, and the quaternary extension products, the plurality of oligonucleotide probe sets, and the ligase are blended to form a ligase detection reaction mixture. The ligase detection reaction mixture is subjected to one or more ligase detection reaction cycles comprising a denaturation treatment, where any hybridized oligonucleotides are separated from the quaternary extension product, and a hybridization treatment, where the oligonucleotide probe sets hybridize in a base-specific manner to their respective quaternary extension products, if present, and ligate to one another to form a ligation product containing (a) the detectable reporter label and (b) the quaternary extension product-specific portions connected together. The oligonucleotide probe sets may hybridize to nucleic acid molecules but do not ligate together due to a presence of one or more mismatches and individually separate during the denaturation treatment. The reporter labels of the ligation products are detected, thereby indicating the presence of two or more methylated cytosine bases in the target nucleotide sequences in the sample.

Another aspect of the present invention is directed to a method for identifying, in sample, one or more target nucleic acid molecules differing by one or more methylated cytosine residues. In carrying out this method, a sample potentially containing one or more target nucleic acid molecules and a restriction endonuclease that cleaves the one or more target nucleic acid moldules at an unmethylated cytosine residue, does not cleave the one or more target nucleic acid molecules at a methylated cytosine residue on both strands, and does not nick a heteroduplex comprising one strand containing a methylated cytosine residue and one strand containing an unmethylated cytosine residue, are provided. The sample, and the restriction endonuclease are blended to form a primary restriction endonuclease reaction mixture. The restriction endonuclease reaction mixture is subjected to enzymatic digestion conditions effective to cut the majority of the one or more target nucleic acid molecules at an unmethylated cytosine residue while leaving the one or more target nucleic acid molecules at a methylated cytosine residue intact. In accordance with this aspect of the present invention, the following are provided: a plurality of primary oligonucleotide primers having a target-specific portion suitable for hybridization on one strand of a target nucleic acid molecule upstream of one or more restriction sites; one or more nucleotide analogues and additional nucleotides that may be incorporated into a polymerase extension product, does not interfere with cleavage of heteroduplexed extension products by the restriction endonuclease, and renders the extension product resistant to exonucleolytic digestion; and a polymerase. The restriction endonuclease reaction mixture, the primary oligonucleotide primers, the one or more nucleotide analogues and additional nucleotides, and the polymerase are blended to form a primary extension reaction mixture. The primary extension reaction mixture is subjected to a primary extension reaction comprising a denaturation treatment, where hybridized nucleic acid molecules are separated, a hybridization treatment, where the target-specific portions of the primary oligonucleotide primers hybridize to the target nucleic acid molecules, and an extension treatment where the hybridized primary oligonucleotide primers are extended to form primary extension products, containing nucleotide analogues and additional nucleotides, which is complementary to the target nucleic acid molecule to which the primary oligonucleotide primers are hybridized. The extension reaction mixture and the restriction endonuclease are blended to form an extension/restriction reaction mixture. The extension/restriction reaction mixture is subjected to enzymatic digestion conditions effective to cut both strands of the residual unmethylated nucleic acid molecules resulting from extension of primary oligonucleotide primers on unmethylated target nucleic acid molecules during the primary extension reaction, while neither nicking nor cutting either strand of hemi-methylated target nucleic acid molecule resulting from extension of primary oligonucleotide primers on methylated target nucleic acid molecules during the primary extension reaction. An exonuclease is also provided, and the extension/restriction reaction mixture, and the exonuclease are blended to form an exonuclease reaction mixture. The exonuclease reaction mixture is subjected to enzymatic digestion under conditions effective to digest target nucleic acid molecules but not primary extension products resulting from primary oligonucleotide primers hybridized and extended on methylated target nucleic acid molecules. A group of secondary oligonucleotide primer sets are provided with each set characterized by (a) a first secondary oligonucleotide primer, having a target-specific portion and a 5' upstream tertiary primer-specific portion, and (b) a second secondary oligonucleotide primer, having a target-specific portion and a 5' upstream tertiary primer-specific portion. The first oligonucleotide primers of each set contain the same 5' upstream tertiary primer-specific portion, and the second oligonucleotide primers of each set contain the same 5' upstream tertiary primer-specific portion, where the secondary oligonucleotide primers in a particular set are suitable for hybridization on complementary strands of a corresponding target nucleic acid molecules. The exonuclease reaction mixture, the secondary oligonucleotide primers, and the polymerase are blended to form a secondary polymerase chain reaction mixture. The secondary polymerase chain reaction mixture is subjected to two or more polymerase chain reaction cycles comprising a denaturation treatment, where hybridized nucleic acid molecules are separated, a hybridization treatment, where the target-specific portions of the secondary oligonucleotide primers hybridize to the target nucleic acid molecules or to extension products of the target nucleic acid molecules, and an extension treatment, where the hybridized secondary oligonucleotide primers are extended to form secondary extension products complementary to the target nucleic acid molecules to which the secondary oligonucleotide primer is hybridized. A tertiary oligonucleotide primer set is provided which is characterized by (a) a first tertiary primer containing the same sequence as the 5' upstream portion of a first secondary oligonucleotide primer, and (b) a second tertiary primer containing the same sequence as the 5' upstream portion of the second secondary oligonucleotide primer from the same secondary oligonucleotide primer set as the first secondary oligonucleotide primer contained by the first tertiary primer, wherein a set of tertiary oligonucleotide primers may be used to amplify all of the secondary extension products. The secondary extension products, the tertiary oligonucleotide primers, and the polymerase are blended to form a tertiary polymerase chain reaction mixture. The tertiary polymerase chain reaction mixture is subjected to two or more polymerase chain reaction cycles comprising a denaturation treatment, where hybridized nucleic acid molecules are separated, a hybridization treatment, where the tertiary oligonucleotide primers hybridize to the secondary extension products, an extension treatment, where the hybridized tertiary oligonucleotide primers are extended to form tertiary extension products complementary to the secondary extension products. A plurality of oligonucleotide probe sets are provided with each set characterized by (a) a first oligonucleotide probe, having a tertiary extension product-specific portion and a detectable reporter label, and (b) a second oligonucleotide probe, having a tertiary extension product-specific portion. The oligonucleotide probes in a particular set are suitable for ligation together when hybridized on a complementary tertiary extension product, but have a mismatch which interferes with such ligation when hybridized to any other nucleic acid molecule present in the sample. A ligase is provided, and the tertiary extension products, the plurality of oligonucleotide probe sets, and the ligase are blended to form a ligase detection reaction mixture. The ligase detection reaction mixture is subjected to one or more ligase detection reaction cycles comprising a denaturation treatment, where any hybridized oligonucleotides are separated from the tertiary extension product, and a hybridization treatment, where the oligonucleotide probe sets hybridize in a base-specific manner to their respective tertiary extension products, if present, and ligate to one another to form a ligation product containing (a) the detectable reporter label and (b) the tertiary extension product-specific portions connected together. The oligonucleotide probe sets may hybridize to nucleic acid molecules other than their respective complementary tertiary extension products but do not ligate together due to a presence of one or more mismatches and individually separate during the denaturation treatment. The reporter labels of the ligation products are detected, thereby indicating the presence of methylated cytosine bases in the target nucleic acid molecules in the sample.

Another aspect of the present invention relates to a method for identifying one or more target nucleic acid molecules differing by one or more methylated cytosine residues. In accordance with this method, a sample potentially containing one or more target nucleic acid molecules and a restriction endonuclease that cleaves the one or more target nucleic acid at an unmethylated cytosine residue and does not cleave the one or more target nucleic acid at a methylated cytosine residue on both strands, but does nick a heteroduplex comprising of one strand containing a methylated cytosine residue and one strand containing unmethylated cytosine residue, are provided. The sample and the restriction endonuclease are blended to form a primary restriction endonuclease reaction mixture. The restriction endonuclease reaction mixture is subjected to an enzymatic digestion procedure under conditions effective to cut the majority of the unmethylated cytosine residues while leaving the methylated cytosine residues intact. The following are provided: a plurality of primary oligonucleotide primers having a target-specific portion suitable for hybridization on one strand of the target nucleic acid molecule upstream of one or analogue(s); and one or more nucleotide analogues and additional nucleotides that may be incorporated by a polymerase into an extension product, and does not interfere with cleavage of the heteroduplexed extension product by the restriction endonuclease, but which renders the extension product resistant to exonucleolytic digestion. The restriction endonuclease reaction mixture, the primary oligonucleotide primers, the one or more nucleotide analogues and additional nucleotides, and the polymerase are blended to form a primary extension reaction mixture. The primary extension reaction mixture is subjected to a primary extension reaction comprising a denaturation treatment, where hybridized nucleic acid sequences are separated, a hybridization treatment, where the target-specific portions of the primary oligonucleotide primers hybridize to the target nucleic acid molecule, and an extension treatment, where the hybridized primary oligonucleotide primers are extended to form primary extension products complementary to the target nucleic acid molecule to which the primary oligonucleotide primers are hybridized. The primary extension reaction mixture, the one or more nucleotide analogues and additional nucleotides, and the restriction endonuclease are blended to form a restriction/extension reaction mixture. The restriction/extension reaction mixture is subjected to a restriction/extension cycle comprising a enzymatic digestion phase under conditions effective to cut both strands of the residual unmethylated cytosine residues resulting from extension of the primary oligonucleotide primers on unmethylated cytosine residues of target nucleic acid molecules, while nicking the unmethylated strand of hemi-methylated target nucleic acid molecules resulting from extension of primary oligonucleotide primers on methylated cytosine residues of target nucleic acid molecules, followed by an incubation effective to inactivate the restriction endonuclease but not denature the nicked primary extension products from their target nucleic acid molecules. The nicked primary extension products re-extend at the nick, generating extension products, containing nucleotide analogues and additional nucleotides, which are complementary to the target nucleic acid molecules to which the primary oligonucleotide primers are hybridized. An exonuclease is provided, and the restriction/extension reaction mixture and the exonuclease blended to form an exonuclease reaction mixture. The exonuclease reaction mixture is subjected to a enzymatic digestion process under conditions effective to digest target nucleic acid molecule but not the extension product containing nucleotide analogues resulting from oligonucleotide extension primers hybridized to and extended on methylated cytosine residues of target nucleic acid molecules. A group of secondary oligonucleotide primer sets are provided with each set characterized by (a) a first secondary oligonucleotide primer, having a target-specific portion and a 5' upstream tertiary primer-specific portion, and (b) a second secondary oligonucleotide primer, having a target-specific portion and a 5' upstream tertiary primer-specific portion, where the first oligonucleotide primers of each set contain the same 5' upstream tertiary primer-specific portion and the second oligonucleotide primers of each set in the group contain the same 5' upstream tertiary primer-specific portion. The exonuclease reaction mixture, the secondary oligonucleotide primers, and the polymerase are blended to form a secondary polymerase chain reaction mixture. The secondary polymerase chain reaction mixture is subjected to two or more polymerase chain reaction cycles comprising a denaturation treatment, where hybridized nucleic acid sequences are separated, a hybridization treatment, where the target-specific portions of the secondary oligonucleotide primers hybridize to the target nucleic acid molecules in the exonuclease reaction mixture or to extension products thereof, and an extension treatment, where the hybridized secondary oligonucleotide primers are extended to form secondary extension products complementary to the target nucleic acid molecule sequence to which the secondary oligonucleotide primer is hybridized. A tertiary oligonucleotide primer set is provided which is characterized by (a) a first tertiary primer containing the same sequence as the 5' upstream portion of a first secondary oligonucleotide primer, and (b) a second secondary primer containing the same sequence as the 5' upstream portion of a second secondary primary oligonucleotide primer from the same secondary oligonucleotide primer set as the 5' upstream portion of the first secondary oligonucleotide primer contained by the first tertiary primer. The set of tertiary oligonucleotide primers may be used to amplify all of the secondary extension products in the group. The secondary extension products, the tertiary oligonucleotide primers, and the polymerase are blended to form a tertiary polymerase chain reaction mixture. The tertiary polymerase chain reaction mixture is subjected to two or more polymerase chain reaction cycles comprising a denaturation treatment, where hybridized nucleic acid sequences are separated, a hybridization treatment, where the tertiary oligonucleotide primers hybridize to the secondary extension products, an extension treatment, where the hybridized tertiary oligonucleotide primers are extended to form tertiary extension products complementary to the secondary extension products. A plurality of oligonucleotide probe sets are provided with each set characterized by (a) a first oligonucleotide probe, having a tertiary extension product-specific portion and a detectable reporter label, and (b) a second oligonucleotide probe, having a tertiary extension product-specific portion. The oligonucleotide probes in a particular set are suitable for ligation together when hybridized on a complementary tertiary extension product, but have a mismatch which interferes with such ligation when hybridized to any other nucleic acid molecule present. A ligase is provided, and the tertiary extension products, the plurality of oligonucleotide probe sets, and the ligase are blended to form a ligase detection reaction mixture. The ligase detection reaction mixture is subjected to one or more ligase detection reaction cycles comprising a denaturation treatment, where any hybridized oligonucleotides are separated from the tertiary extension product, and a hybridization treatment, where the oligonucleotide probe sets hybridize in a base-specific manner to their respective tertiary extension products, if present, and ligate to one another to form a ligation product containing (a) the detectable reporter label and (b) the tertiary extension product-specific portions connected together. The oligonucleotide probe sets may hybridize to target nucleic acid molecules other than their respective complementary tertiary extension products but do not ligate together due to a presence of one or more mismatches and individually separate during the denaturation treatment. The reporter labels of the ligation product are detected, thereby indicating the presence of methylated cytosine bases in the target nucleic acid molecule in the sample.

A further embodiment of the present invention relates to a method for identifying one or more target nucleic acid molecules differing by one or more methylated cytosine residues. This method involves providing a sample potentially containing one or more target nucleic acid molecules with a plurality of sequence differences. A restriction endonuclease that cleaves unmethylated cytosine residues in the target nucleic acid molecules and does not cleave target nucleic acid molecules which are methylated on both strands. The sample and the restriction endonuclease are blended to form a primary restriction endonuclease reaction mixture. The restriction endonuclease reaction mixture is subjected to an enzymatic digestion processs under conditions effective to cut the majority of unmethylated cytosine residues in the target nucleic acid molecules while leaving the methylated cytosine residues in the target nucleic acid molecules intact. A plurality of primary oligonucleotide primers are provided which have either a non-phosphorylated end, a blocked 5' end, or internal nucleotide or backbone analogue(s) that confer resistance to digestion by exonuclease(s). The primary oligonucleotide primers have a target-specific portion suitable for hybridization on one strand of the target nucleic acid molecules upstream of one or more restriction sites. The following are provided: a polymerase and one or more nucleotide analogues and additional nucleotides that may be incorporated by a polymerase into an extension product, and does not interfere with cleavage of the heteroduplexed extension product by the restriction endonuclease, but which renders the extension product resistant to exonucleolytic digestion. The restriction endonuclease reaction mixture, the primary oligonucleotide primers, the one or more nucleotide analogues and additional nucleotides, and the polymerase are blended to form a primary extension reaction mixture. The primary extension reaction mixture is subjected to an extension reaction comprising a denaturation treatment, where hybridized nucleic acid molecules are separated, a hybridization treatment, where the target-specific portions of the primary oligonucleotide primers hybridize to the target nucleic acid molecules, and an extension treatment, where the hybridized primary oligonucleotide primers are extended to form primary extension products complementary to the target nucleic acid molecule to which the primary oligonucleotide primers are hybridized. The primary extension reaction mixture and the restriction endonuclease are blended to form a restriction/extension reaction mixture. The restriction/extension reaction mixture is subjected to a restriction/extension cycle comprising an incubation phase sufficient to cut both strands of residual unmethylated cytosine residues in the target nucleic acid molecules arising from extension of secondary oligonucleotide primers on unmethylated cytosine residues in the target nucleic acid molecules, while either nicking or not cleaving the unmethylated strand of hemi-methylated target nucleic acid molecule arising from extension of oligonucleotide primers on a methylated target nucleic acid molecule. This is followed by an incubation sufficient to inactivate the restriction endonuclease but not denature the nicked extension products from their target sequences, where the nicked secondary extension products re-extend at the nick generating extension products complementary to the target nucleic acid molecule to which the primary oligonucleotide primers are hybridized. An exonuclease is provided, and the restriction/extension reaction mixture and the exonuclease are blended to form an exonuclease reaction mixture. The exonuclease reaction mixture is subjected to enzymatic digestion conditions effective to digest target nucleic acid molecules but not extension products arising from the primary oligonucleotide primers hybridized and extended on methylated target nucleic acid molecules. A set of secondary oligonucleotide primers are provided with each set characterized by (a) a first secondary oligonucleotide primer, having a target-specific portion and a 5' upstream tertiary primer-specific portion, and (b) a second secondary oligonucleotide primer, having a target-specific portion and a 5' upstream secondary primer-specific portion. The first secondary oligonucleotide primers of each set contain the same 5' upstream tertiary primer-specific portion and the second secondary oligonucleotide primers of each set contain the same 5' upstream tertiary primer-specific portion. The exonuclease reaction mixture, the secondary oligonucleotide primers, and the polymerase are blended to form a secondary polymerase chain reaction mixture. The secondary polymerase chain reaction mixture is subjected to two or more polymerase chain reaction cycles comprising a denaturation treatment, where hybridized nucleic acid molecules are separated, a hybridization treatment, where the target-specific portions of the secondary oligonucleotide primers hybridize to treated target nucleic acid molecules or to extension products of the target nucleic acid molecules, and an extension treatment, where the hybridized secondary oligonucleotide primers are extended to form secondary extension products complementary to the target nucleic acid molecule to which the secondary oligonucleotide primers is hybridized. A tertiary oligonucleotide primer set is provided which is characterized by (a) a first tertiary primer containing the same sequence as the 5' upstream portion of a first secondary oligonucleotide primer, and (b) a second tertiary primer containing the same sequence as the 5' upstream portion of a second secondary oligonucleotide primer from the same secondary oligonucleotide primer set as the first secondary oligonucleotide primer contained by the first tertiary oligonucleotide primer. A set of tertiary oligonucleotide primers may be used to amplify all of the secondary extension products. The secondary extension products, the tertiary oligonucleotide primers, and the polymerase are blended to form a tertiary polymerase chain reaction mixture. The tertiary polymerase chain reaction mixture is subjected to two or more polymerase chain reaction cycles comprising a denaturation treatment, where hybridized nucleic acid molecules are separated, a hybridization treatment, where the tertiary oligonucleotide primers hybridize to the secondary extension products, an extension treatment, where the hybridized tertiary oligonucleotide primers are extended to form tertiary extension products complementary to the secondary extension products. A plurality of oligonucleotide probe sets are provided with each set characterized by (a) a first oligonucleotide probe, having a tertiary extension product-specific portion and a detectable reporter label, and (b) a second oligonucleotide probe, having a tertiary extension product-specific portion, where the oligonucleotide probes in a particular set are suitable for ligation together when hybridized on a complementary tertiary extension product, but have a mismatch which interferes with such ligation when hybridized to any other nucleic acid molecule present in the sample. A ligase is provided, and the tertiary extension products, the plurality of oligonucleotide probe sets, and the ligase are blended to form a ligase detection reaction mixture. The ligase detection reaction mixture is subjected to one or more ligase detection reaction cycles comprising a denaturation treatment, where any hybridized oligonucleotides are separated from the tertiary extension product, and a hybridization treatment, where the oligonucleotide probe sets hybridize in a base-specific manner to their respective tertiary extension products, if present, and ligate to one another to form a ligation product containing (a) the detectable reporter label and (b) the tertiary extension product-specific portions connected together, where the oligonucleotide probe sets may hybridize to nucleic acid molecules other than their respective complementary tertiary extension products but do not ligate together due to a presence of one or more mismatches and individually separate during the denaturation treatment. The reporter labels of the ligation product are detected, thereby indicating the presence of methylated cytosine bases in the target nucleic acid molecules in the sample.

The present application describes a robust assay to determine the methylation status of candidate genes involved in human cancer, for disease characterization and diagnostic tool development. The current techniques for detection of such variation can be divided into two categories: 1) detection of the known gene promoter methylation status (also known as candidate gene approach) and 2) detection of unknown gene, namely the detection of global methylation status of a cell. This application focuses on the identification of known gene promoter methylation status.

Analysis of methylation status is useful in cancer detection for a number of reasons. Firstly, expression of genes required to regulate normal growth is silenced in many human cancers. Jones, P. A., et al., *Nature Review Genetics*, 3: 415-428 (2002), which is hereby incorporated by reference in its entirety. Secondly, Esteller et al. recently examined over 600 specimens from 15 major tumor types and found that each tumor type has a unique and gene-specific promoter methylation profile. Esteller, M., et al., *Cancer Res.*, 61(8): 3225-9 (2001), which is hereby incorporated by reference in its entirety. Thirdly, in contrast to methods for the detection of other DNA molecular markers, technologies for accurate high-throughput promoter methylation profiling are still under development. A robust assay is necessary for translating basic science research into clinical applications. Finally, the combination of promoter methylation profiles with other molecular marker approaches is likely to provide a more precise "molecular signature" of diseases for accurate diagnosis and prognosis. Laird P. W., *Nature Review Cancer*, 3: 253-266 (2003), which is hereby incorporated by reference in its entirety. Thus, there is an urgent need for accurately determining methylation status, with the aim to improve cancer prevention, reduce mortality, and enable accurate identification of patients for whom curative resection would be beneficial.

BRIEF DESCRIPTION OF THE DRAWINGS

FIG. 1 is a schematic diagram, illustrating the procedure for high-throughput detection of promoter methylation status with the combination of bisulfite treatment, multiplex PCR, multiplex LDR, and universal array approaches. The different fluorescently labeled (Cy3 and Cy5) LDR products are captured on the same addressable array.

FIG. 3 is a schematic diagram, illustrating the procedure for high-throughput detection of promoter methylation status with the combination of bisulfite treatment, multiplex PCR, multiplex LDR, and universal array approaches. The different fluorescently labeled (Cy3 and Cy5) LDR products are captured on separate addressable arrays.

FIG. 5 is a schematic diagram, illustrating the procedure for high-throughput detection of promoter methylation status with the combination of bisulfite treatment, multiplex PCR, multiplex LDR, and capillary electrophoresis approaches. Nucleotide analogs dK and dP are introduced in the multiplex PCR primer and LDR probe designs (at methylation sites 1, 3, 7, and 8). These analog-containing oligonucleotide primers/probes have the capability of hybridizing to DNA sequences regardless whether the templates are fully or partially methylated.

FIG. 9 is a schematic diagram, illustrating the procedure for high-throughput detection of promoter methylation status with the combination of bisulfite treatment, multiplex PCR, multiplex LDR and capillary electrophoresis approaches. Nucleotides A and T are used in the multiplex PCR primers and LDR probes. The hybridization of such primers/probes with their DNA template results in the A:T Watson-Crick base pairings on un-methylated sequences, yet G:T wobble base pairings of methylated sequences occur. Thus, the designs of these primers/probes take the advantage of preferentially hybridizing to un-methylated DNA sequences occur. As shown in this diagram, for example, the methylation sites 1, 3, 7, and 8 contribute to the preferential enrichment of the final signal of un-methylated cytosines at methylation sites 2 and 6.

FIG. 11 shows the results of multiplex LDR using the corresponding multiplex PCR DNA products (shown in FIG. 10) as templates. The fluorescently labeled LDR products (Cy5, false color green) were displayed on universal arrays and designed to detect unmethylated cytosines in the DNA sequences in this experiment. The presence of the Cy5 signals among the individual multiplex products demonstrates the existence of unmethylated cytosines in the tumor suppressor promoter regions of normal human lymphocyte genomic DNAs.

FIG. 12A is the LDR results of normal human lymphocyte genomic DNAs in the presence (right panel) and absence (left panel) of in vitro methylation using SssI methylase. In FIGS. 12B-C, the methylation profiles of two colorectal cancer cell line genomic DNAs were analyzed. Among the eight genes that were analyzed in cell line SW1116, Cy3 signal is only present on the p16 promoter region. This indicates that only the p16 promoter was hypermethylated. The presence of Cy3 signal on both p16 and p19 promoters in cell line DLD-1 indicates that both of these promoters are hypermethylated.

FIG. 25 is a schematic diagram illustrating the Bisulfite/PCR-PCR/MS-PCR-PCR/LDR/Universal Array procedure for high-throughput detection of promoter methylation status of low abundance methylation alleles in a given sample. This procedure consists of bisulfite treatment of genomic DNA, multiplex PCR with gene specific/universal primers (A), methylation specific ("MS") multiplex PCR with methyl-specific/universal primers (B), multiplex LDR, and universal array approaches. The methyl-specific/universal PCR primer has the discriminating 3'OH base pairing to the cytosine of CpG dinucleotides (or pairing the guanine if it is on the opposite DNA strand) to ensure the selection of methylated alleles.

FIG. 28 is a schematic diagram illustrating the Bisulfite/PCR-PCR/MS-PCR-PCR/LDR/capillary electrophoresis procedure for high-throughput detection of promoter methylation status of low abundance methylation alleles in a given sample. This procedure consists of bisulfite treatment of genomic DNA, multiplex PCR with gene specific/universal primer (A), methylation specific multiplex PCR with methyl-specific/universal primers (B), multiplex LDR, and capillary electrophoresis approaches. The methyl-specific/universal PCR primer has the discriminating 3'OH base pairing to the cytosine of CpG dinucleotides (or pairing the guanine if it is on the opposite DNA strand) to ensure the selection of methylated alleles. Nucleotide analogs dK and dP are introduced in the multiplex PCR (both gene-specific and methyl-specific primers) and LDR probe designs. These analog-containing oligonucleotide probes have the capability of hybridizing to DNA sequences regardless whether the templates are fully or partially methylated. Notice that in this approach, as shown in the diagram, the identification of a methylated cytosine at methylation site 4 requires methylated cytosines at sites 3 and 6.

FIG. 29 is a schematic diagram illustrating the Bisulfite/PCR-PCR/MS-PCR-PCR/LDR/Universal Array procedure for high-throughput detection of promoter methylation status of low abundance methylation alleles in a given sample. This procedure consists of bisulfite treatment of genomic DNA, multiplex PCR with gene specific/universal primers (A), methylation specific multiplex PCR with methyl-specific/universal primers (B), multiplex LDR, and universal array approaches. The methyl-specific/universal PCR primer has the discriminating 3'OH base pairing to the cytosine of CpG dinucleotides (or pairing the guanine if it is on the opposite DNA strand) to ensure the selection of methylated alleles. Nucleotides G and C are used in the designs of multiplex PCR (both gene-specific and methyl-specific) and LDR probes. The hybridization of such probes with their DNA template results in the C:G Watson-Crick base pairings on methylated sequences, yet G:T wobble base pairings and C:A mismatches on un-methylated sequences occur. The designs of these probes have the advantage of preferentially selecting fully methylated DNA sequences. Notice that in this approach, as shown in this figure, the identification of a methylated cytosine at methylation site 4 requires methylated cytosines at sites 3 and 6. Further, the methylated cytosines at methylation sites 1, 2, 5, 7, and 8 provide additional selective power for methylated alleles since these positions are located in the middle of oligonucleotide probes.

FIG. 34 is a schematic diagram illustrating the Bisulfite/Ms-PCR-PCR/MS-PCR-PCR/LDR/Universal Array procedure for high-throughput detection of promoter methylation status of low abundance methylation alleles in a given sample. This procedure consists of bisulfite treatment of genomic DNA, multiplex PCR with methyl-specific/universal primers (A), methylation specific multiplex PCR with methyl-specific/universal primers (B), multiplex LDR, and universal array approaches. The methyl-specific/universal PCR primer has the discriminating 3'OH base pairing to the cytosine of CpG dinucleotides (or pairing the guanine if it is on the opposite DNA strand) to ensure the selection of methylated alleles. Notice that the identification of a methylated cytosine at methylation site 3 requires methylated cytosines at methylation sites 1, 2, 4, and 5.

FIG. 35 is a schematic diagram illustrating the Bisulfite/MS-PCR-PCR/MS-PCR-PCR/LDR/capillary electrophoresis procedure for high-throughput detection of promoter methylation status of low abundance methylation alleles in a given sample. This procedure consists of bisulfite treatment of genomic DNA, multiplex PCR with methyl-specific/universal primers (A), methylation specific multiplex PCR with methyl-specific/universal primers (B), multiplex LDR, and capillary electrophoresis approaches. The methyl-specific/universal PCR primer has the discriminating 3'OH base pairing to the cytosine of CpG dinucleotides (or pairing the guanine if it is on the opposite DNA strand) to ensure the selection of methylated alleles. Note that the identification of a methylated cytosine at methylation site 3 requires methylated cytosines at methylation sites 1, 2, 4, and 5.

FIG. 36 is a schematic diagram illustrating the Bisulfite/MS-PCR-PCR/MS-PCR-PCR/LDR/Universal Array procedure for high-throughput detection of promoter methylation status of low abundance methylation alleles in a given sample. This procedure consists of bisulfite treatment of genomic DNA, multiplex PCR with methyl-specific/universal primers (A), methylation specific multiplex PCR with methyl-specific/universal primers (B), multiplex LDR, and universal array approaches. The methyl-specific/universal PCR primer has the discriminating 3'OH base pairing to the cytosine of CpG dinucleotides (or pairing the guanine if it is on the opposite DNA strand) to ensure the selection of methylated alleles. Nucleotide analogs dK and dP are introduced in the multiplex PCR (methylation sites 1, 3, 8, and 10) and LDR probe designs (methylation site 6). These analog-containing oligonucleotide probes have the capability of hybridizing to DNA sequences regardless whether the templates are fully or partially methylated. Notice that the identification of a methylated cytosine at methylation site 5 requires the methylated cytosines at sites 2, 4, 7, and 9.

FIG. 37 is a schematic diagram illustrating the Bisulfite/MS-PCR-PCR/MS-PCR-PCR/LDR/capillary electrophoresis procedure for high-throughput detection of promoter methylation status of low abundance methylation alleles in a given sample. This procedure consists of bisulfite treatment of genomic DNA, multiplex PCR with methyl-specific/universal primers (A), methylation specific multiplex PCR with methyl-specific/universal primers (B), multiplex LDR, and capillary electrophoresis approaches. The methyl-specific/universal PCR primer has the discriminating 3'OH base pairing to the cytosine of CpG dinucleotides (or pairing the guanine if it is on the opposite DNA strand) to ensure the selection of methylated alleles. Nucleotide analogs dK and dP are introduced in the multiplex PCR (methylation sites 1, 3, 8, and 10) and LDR probe designs (methylation site 6). These analog-containing oligonucleotide probes have the capability of hybridizing to DNA sequences regardless whether the templates are fully or partially methylated. Notice that the identification of a methylated cytosine at methylation site 5 requires the methylated cytosines at sites 2, 4, 7, and 9.

FIG. 39 is a schematic diagram illustrating the Bisulfite/ MS-PCR-PCR/MS-PCR-PCR/LDR/capillary electrophoresis procedure for high-throughput detection of promoter methylation status of low abundance methylation alleles in a given sample. This procedure consists of bisulfite treatment of genomic DNA, multiplex PCR with methyl-specific/universal primers (A), methylation specific multiplex PCR with methyl-specific/universal primers (B), multiplex LDR, and capillary electrophoresis approaches. The methyl-specific/universal PCR primer has the discriminating 3'OH base pairing to the cytosine of CpG dinucleotides (or pairing the guanine if it is on the opposite DNA strand) to ensure the selection of methylated alleles. Nucleotides G and C are used in the multiplex PCR primers and LDR probes (methylation sites 1, 3, 6, 8, and 10). The hybridization of such probes with their DNA template results in the C:G Watson-Crick base pairings on methylated sequences, yet G:T wobble base pairings and C:A mismatches on un-methylated sequences occur. The designs of these primers/probes have the advantage of preferentially selecting fully methylated DNA sequences. Notice that the identification of a methylated cytosine at methylation site 5 requires the methylated cytosines at sites 2, 4, 7, and 9. Further, the methylated cytosines at methylation sites 1, 3, 6, 8, and 10 provide additional selective power for methylated alleles since these positions are located in the middle of oligonucleotide probes.

FIG. 40 is a schematic diagram illustrating the BstWX Extend/3' Exo/PCR/LDR/Universal Array procedure for high-throughput detection of promoter methylation status of low abundance methylation alleles in a given sample. This procedure consists of digestion of genomic DNA with BstUI restriction endonuclease, DNA denaturation, the synthesis of a new DNA strand bearing the thio-phosphodiester bond in the presence of BstUI, destroying DNA using 3'→5' exonuclease, multiplex PCR amplification of the candidate promoter regions, multiplex LDR, and universal array approaches. Notice that the methylated DNA remains uncut under BstUI digestion. The DNA strand containing thio-phosphodiester bonds is resistant to exonuclease digestion and, thus, is amplified for the subsequent LDR detection.

FIG. 41 is a schematic diagram illustrating the capillary electrophoresis version of the BstUI/Extend/3' Exo/PCR/ LDR/Capillary Electrophoresis procedure for high-throughput detection of promoter methylation status of low abundance methylation alleles in a given sample. This procedure consists of digestion of genomic DNA with BstU1 restriction endonuclease, DNA denaturation, the synthesis of a new DNA strand bearing the thio-phosphodiester bond in the presence of BstU1, destroying DNA using 3'->5' exonuclease, multiplex PCR amplification of the candidate promoter regions, multiplex LDR, and capillary electrophoresis separation of the LDR products. Notice that the methylated DNA remains uncut under BstUI digestion. The DNA strand containing thio-phosphodiester bonds is resistant to exonucleases digestion and, thus, is amplified for the subsequent LDR detection.

FIG. 42 is a schematic diagram illustrating the HinP1I/ Extend/3' Exo/PCR/LDR/Universal Array procedure for high-throughput detection of promoter methylation status of low abundance methylation alleles in a given sample. This procedure consists of digestion of genomic DNA with HinP1 I restriction endonuclease, DNA denaturation, the synthesis of a new DNA strand bearing the thio-phosphodiester bond, destroying DNA using 3'→5' exonuclease, multiplex PCR amplification of the candidate promoter regions, multiplex LDR, and universal array approaches. Notice that after the new DNA strand extension, DNA is recut by HinP1 I. This restriction step further digests the remaining unmethylated DNA and the hemi-methylated DNA can also be nicked by HinP1 I. This step will drastically reduce the false-positive selection of the methylated alleles.

FIG. 43 is a schematic diagram illustrating the capillary electrophoresis version of the HinP1 I/Extend/3' Exo/PCR/ LDR/Capillary Electrophoresis procedure for high-throughput detection of promoter methylation status of low abundance methylation alleles in a given sample. This procedure consists of digestion of genomic DNA with HinP1 I restriction endonuclease, DNA denaturation, the synthesis of a new DNA strand bearing the thio-phosphodiester bond, destroying DNA using 3'→5' exonuclease, multiplex PCR amplification of the candidate promoter regions, multiplex LDR, and capillary electrophoresis separation of the LDR products. Note that after the new DNA strand extension, DNA is recut by HinP1 I. This restriction step further digests the remaining unmethylated DNA and the hemi-methylated DNA can also be nicked by HinP1 I. This step Will drastically reduce the false-positive selection of the methylated alleles.

FIG. 44 is a schematic diagram illustrating the HinP1 I/Extend/5' Exo/PCR/LDR/Universal Array procedure for high-throughput detection of promoter methylation status of low abundance methylation alleles in a given sample. This procedure consists of digestion of genomic DNA with HinP1 I restriction endonuclease, DNA denaturation, the synthesis of a new DNA strand with exonuclease resistant 5' end, destroying DNA using 5'→3' exonuclease, multiplex PCR amplification of the candidate promoter regions, multiplex LDR, and universal array approaches. Notice that after the new DNA strand extension, DNA is recut by HinP1 I. This restriction step further digests the remaining unmethylated DNA and the hemi-methylated DNA can also be nicked by HinP1 I. This step will drastically reduce the false-positive signal results from the methylated alleles. The primer used for new strand extension has an exonuclease resistant 5' end. With the use of a 5'→3' exonuclease in the procedure, this design eliminates the need for thio-phosphate incorporation during strand extension.

FIG. 45 is a schematic diagram illustrating the capillary electrophoresis version of HinP1 I/Extend/5' Exo/PCR/LDR/Capillary Electrophoresis procedure for high-throughput detection of promoter methylation status of low abundance methylation alleles in a given sample. This procedure consists of digestion of genomic DNA with HinP1 I restriction endonuclease, DNA denaturation, the synthesis of a new DNA strand with exonuclease resistant 5' end, destroying DNA using 5'→3' exonuclease, multiplex PCR amplification of the candidate promoter regions, multiplex LDR, and capillary electrophoresis separation of the LDR products. Note that after the new DNA strand extension, DNA is recut by HinP1 I. This restriction step further digests the remaining unmethylated DNA and the hemi-methylated DNA can also be nicked by HinP1 I. This step will drastically reduce the false-positive signal results from the methylated alleles. The primer used for new strand extension has an exonuclease resistant 5' end. With the use of a 5'→3' exonuclease in the procedure, this design eliminates the need for thio-phosphate incorporation during strand extension.

FIG. 46 is a schematic diagram illustrating the HpaII/Extend/5' Exo/PCR/LDR/Universal Array procedure for high-throughput detection of promoter methylation status of low abundance methylation alleles in a given sample. This procedure consists of digestion of genomic DNA with HpaII restriction endonuclease, DNA denaturation, the synthesis of a new DNA strand with exonuclease resistant 5' end, destroying DNA using 5'→3' exonuclease, multiplex PCR amplification of the candidate promoter regions, multiplex LDR, and universal array approaches. Note that after the new DNA strand extension, DNA is recut by HpaII. This recut step further digests the remaining unmethylated DNA. This step will drastically reduce the false-positive signal results from the methylated alleles. The primer used for new strand extension has an exonuclease resistant 5' end. With the use of a 5'→3' exonuclease in the procedure, this design eliminates the need for thio-phosphate incorporation during strand extension.

FIG. 47 is a schematic diagram illustrating the capillary electrophoresis version of HpaII/Extend/5' Exo/PCR/LDR/Capillary Electrophoresis procedure for high-throughput detection of promoter methylation status of low abundance methylation alleles in a given sample. This procedure consists of digestion of genomic DNA with HpaII restriction endonuclease, DNA denaturation, the synthesis of a new DNA strand with exonuclease resistant 5' end, destroying DNA using 5'→3' exonuclease, multiplex PCR amplification of the candidate promoter regions, multiplex LDR, and capillary electrophoresis separation of the LDR products. Notice that after the new DNA strand extension, DNA is recut by HpaII. This recut step further digests the remaining unmethylated DNA. This step will drastically reduce the false-positive signal results from the methylated alleles. The primer used for new strand extension has an exonuclease resistant 5' end. With the use of a 5'→3' exonuclease in the procedure, this design eliminates the need for thio-phosphate incorporation during strand extension.

DETAILED DESCRIPTION OF THE INVENTION

Figure 2:
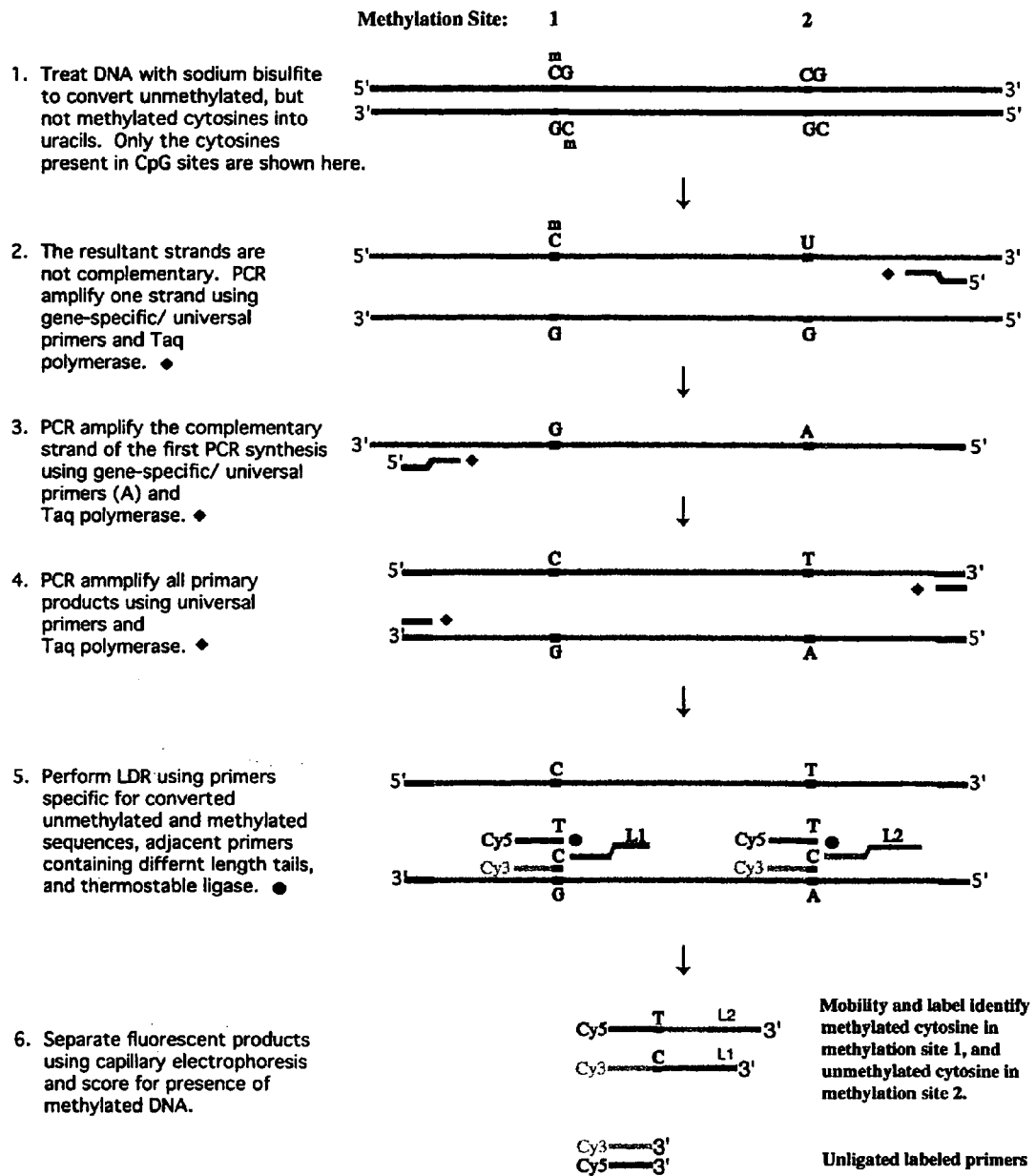
FIG. 2 is a schematic diagram illustrating the procedure for high-throughput detection of promoter methylation status with the combination of bisulfite treatment, multiplex PCR, multiplex LDR, and capillary electrophoresis approaches. The fluorescent labeled (Cy3 and Cy5) LDR products are separated using capillary electrophoresis and scored for presence of methylated DNA.

Detecting DNA Methylation Status Using Bisulfite Treatment

One aspect of the present invention is directed to a method for identifying, in a sample, one or more target nucleic acid molecules differing from other nucleic acid molecules in the sample by one or more methylated cytosine residues. In this method, a sample potentially containing one or more target nucleic acid molecules is provided and subjected to a bisulfite treatment to convert, in the nucleic acid molecules of the sample, unmethylated cytosine residues, but not methylated cytosine residues, into uracil residues. One or more primary oligonucleotide primer sets are provided. Each set is characterized by (a) a first oligonucleotide primer, having a target-specific portion and a 5' upstream secondary primer-specific portion, wherein the target-specific portion is suitable for hybridization on a first strand of the target nucleic acid molecule in which unmethylated cytosines have been converted to uracil, and (b) a second oligonucleotide primer, having a target-specific portion and a 5' upstream secondary primer-specific portion. The target-specific portion is suitable for hybridization on a polymerase extension product of the first strand or on a second strand of the target nucleic acid molecule, either of which have unmethylated cytosines converted to uracil and where the first and second oligonucleotide primers of each set contain the same 5' upstream secondary primer-specific-portion. Also provided is a polymerase, and the sample, the primary oligonucleotide primer set, and the polymerase are blended to form a primary polymerase chain reaction mixture. The primary polymerase chain reaction mixture is subjected to two or more polymerase chain reaction cycles comprising a denaturation treatment, where hybridized nucleic acid sequences are separated, a hybridization treatment, where the target-specific portions of the primary oligonucleotide primer sets hybridize to the target nucleic acid molecules with unmethylated cytosines converted to uracil or to extension products of such modified target nucleic acid molecules, and an extension treatment, where the hybridized primary oligonucleotide primers are extended to form primary extension products complementary to the target nucleic acid molecules with unmethylated cytosines converted to uracil. Also provided is a secondary oligonucleotide primer set characterized by (a) a first secondary primer containing the 5' upstream portion of the first oligonucleotide primer of the primary oligonucleotide primer set, and (b) a second secondary primer containing the 5' upstream portion of the second oligonucleotide primer of the primary oligonucleotide primer set. The primary extension products, the secondary oligonucleotide primer set, and the polymerase are blended to form a secondary polymerase chain reaction mixture. The secondary polymerase chain reaction mixture is subjected to two or more polymerase chain reaction cycles comprising a denaturation treatment, where hybridized nucleic acid sequences are separated, a hybridization treatment, where the secondary oligonucleotide primers hybridize to the primary extension products, and an extension treatment, where the hybridized secondary oligonucleotide primers are extended to form secondary extension products complementary to the primary extension products. Also provided are a plurality of oligonucleotide probe sets, each set characterized by (a) a first oligonucleotide probe, having a secondary extension product-specific portion and a detectable reporter label, and (b) a second oligonucleotide probe, having a secondary extension product-specific portion. The oligonucleotide probes in a particular set are suitable for ligation together when hybridized on a complementary secondary extension product, but have a mismatch which interferes with such ligation when hybridized to any other nucleic acid molecule present in the sample. A ligase is provided, and the secondary extension products, the plurality of oligonucleotide probe sets, and the ligase are blended to form a ligase detection reaction mixture. The ligase detection reaction mixture is subjected to one or more ligase detection reaction cycles comprising a denaturation treatment, where any hybridized oligonucleotides are separated from the secondary extension product, and a hybridization treatment, where the oligonucleotide probe sets hybridize in a base-specific manner to their respective secondary extension products, if present, and ligate to one another to form a ligation product containing (a) the detectable reporter label and (b) the secondary extension product-specific portions connected together. The oligonucleotide probe sets may hybridize to nucleic acid molecules but do not ligate together due to a presence of one or more mismatches and individually separate during the denaturation treatment. The reporter labels of the ligation products are detected, thereby indicating the presence of two or more methylated cytosine bases in the target nucleotide sequences in the sample.

This aspect of the present invention is directed to a method for identifying methylated and unmethylated cytosines differing by the 5-methyl group.

FIGS. 1-9 are schematic drawings illustrating the process of the present invention. Initial step 1 of the present invention is the preparation of sodium bisulfite modified genomic DNAs. In the preferred embodiment, genomic DNA is incubated with bisulfite and hydroquinone solution for 15-20 hours, more preferably 16 hours, in a DNA thermal cycler (Perkin Elmer Cetus) with the cycles of 50° C. for 20 minutes followed by a denaturing step of 85° C. for 15 seconds. This cycle can be repeated up to 45 times. The bisulfite-treated DNA can be desalted with Wizard DNA clean-up kit (Promega, Madison, Wis.), or, alternatively, it can be desalted using MICROCON centrifugal filter devices (Millipore, Bedford, Mass.). This eliminates bisulfite and fragmented small pieces of nucleic acid molecules and concentrates the bisulfite-treated sample. The desalted DNA is ethanol precipitated and the DNA pellet is resuspended in deionized $H_2O$ or proper buffer until PCR amplification.

In steps 2 and 3 of the process of the present invention, as shown in FIGS. 1-9, the bisulfite-treated genomic DNA is amplified using two PCR primers designed with a Tm around 70° C. to hybridize to the complementary sequence of each of the interested bisulfite-modified promoter region. Bisulfite modifies DNA asymmetrically, such that the two strands are now no longer complementary to each other. Thus, one of the PCR primers has a specific 3' portion that is complementary to DNA that has undergone bisulfite treatment. Since native cytosine has been converted to a uracil, the PCR primer should have an "A" base opposite the uracil. The resultant PCR primers are usually longer than standard PCR primers since they are now AT rich. When this PCR primer extends across the DNA, polymerase makes a copy of the uracil containing DNA, incorporating an A opposite T, an A opposite U, a T opposite A, a C opposite G, and a G opposite 5-methyl C as well as residual native C that did not undergo deamination during the bisulfite treatment. The resultant strand is not the same as the opposite strand of bisulfite treated genomic DNA. Consequently, the second PCR primer is designed to be complementary to the extension product of the first bisulfite-treated strand of genomic DNA.

In carrying out this aspect of the present invention, nucleotide analogues designated dP and dK are used in the primer syntheses. In this method, the nucleotide analogues are incorporated in either the PCR primers, the LDR probes, or both. Those nucleotide positions that specifically base pair to cytosine of CpG dinucleotides are synthesized with the dK analogue. Those nucleotide positions that specifically base pair to the nucleotides complementary to the cytosine of CpG dinucleotides are synthesized with the dP analogue. The pyrimidine derivative dP, when introduced into oligonucleotide primers, base pair with either A or G, while the purine derivative dK base pairs with either C or T. These analog-containing oligonucleotide primers will hybridize with similar efficiency to DNA sequences containing bisulfite-treated CpG dinucleotides, or the complement of such sequence regardless of whether that initial CpG dinucleotide was fully methylated, partially methylated, or un-methylated.

Suitable nucleotide analogues include 2-dimethylaminomethyleneamino-6-methyoxyaminopurine (dK), 6H,8H-3,4-dihydro-pyrimido[4,5-c][1,2]oxazin-7-one (dP), 3-nitropyrrole, 5-nitroindole, and inosine.

Another aspect of the present invention is the use of diethylenetriamine as a catalyst for sodium bisulfite modification. Komiyama, M., et al., *Tetrahedron Letters*, 35: 8185-8188 (1994), which is hereby incorporated by reference in its entirety. This method comprises a DNA sample potentially containing the methylated as well as native (unmethylated) cytosines in the promoter sequences and sodium bisulfite treatment to convert unmethylated cytosines into uracils. The bisulfite treatment is catalyzed by diethylenetriamine (instead of hydroquinone) and the bisulfite solution is pre-equilibrated with argon gas to eliminate the dissolving oxygen before adding the catalyst. The reaction mixture is then incubated under cycling conditions to periodically dissociate both strands of genomic DNA to maximize the bisulfite modification efficiency. Suitable cycling conditions involve incubating at 50° C. for 20 minutes, incubating at 85° C. is seconds, and repeating this cycle 45 times.

Figure 4:
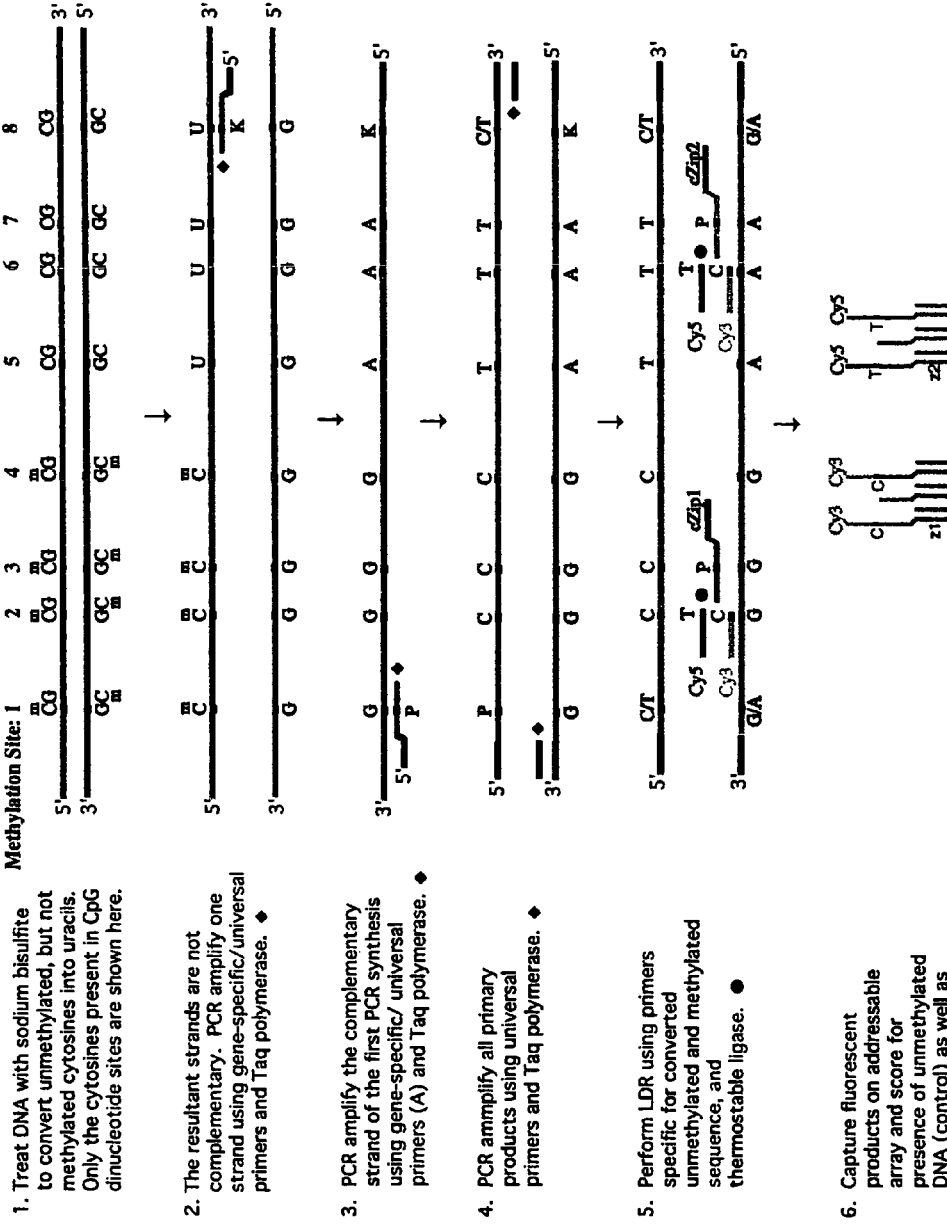
FIG. 4 is a schematic diagram, illustrating the procedure for high-throughput detection of promoter methylation status with the combination of bisulfite treatment, multiplex PCR, multiplex LDR, and universal array approaches. Nucleotide analogs dK and dP are introduced in the multiplex PCR primer and LDR probe designis (at methylation sites 1, 3, 7, and 8). These analog-containing oligonucleotide primer/probes have the capability of hybridizing to DNA sequences regardless of whether the templates are fully partially or un-methylated.

A cytosine within a CpG dinucleotide can be converted into uracil (if unmethylated) or remaines as cytosine (if methylated) when the target DNA is treated with bisulfite. Nucleotide analogs dK and dP are used in the PCR primers syntheses as depicted in FIGS. 4 and 5 so they will hybridize with similar efficiency to DNA sequences containing bisulfite treated CpG dinucleotides, regardless of whether that initial CpG dinucleotide was fully methylated, partially methylated, or un-methylated. The pyrimidine derivative dP, when introduced into oligonucleotide primers (at methylation site 1), base pairs with either A or G, while the purine derivative dK (at methylation site 8) base pairs with either C or T. Table 1 shows the gene-specific PCR primer sequences used in the Bisulfite/PCR-PCR procedure. As shown in Table 1, those nucleotide positions in the PCR primers that specifically base pair to cytosine of CpG dinucleotides are synthesized with the dK analogue. Those nucleotide positions that specifically base pair to the nucleotides complementary to the cytosine of CpG dinucleotides are synthesized with the dP analogue.

TABLE 1

| Primers | Sequence (5' to 3') | Amount in PCR |
|---|---|---|
| p15 Ex1 FP (B2) | CGCTGCCAACTACCGCACATCCTTTACCKACTAACTCC CCACTCTAC (SEQ ID NO: 1) | 1.25 pmol |
| p15 Ex1 RP (B2) | CGCTGCCAACTACCGCACATCTTTTTTTTTTTAGGAG ATTTGGGTTTAG (SEQ ID NO: 2) | 1.25 pmol |
| p21 S1 FP (B2) | CGCTGCCAACTACCGCACATCCCTCCTAAAAAATACCA ACTCATTCTC (SEQ ID NO: 3) | 2.5 pmol |
| p21 S1 RP (B2) | CGCTGCCAACTACCGCACATCTGATTTPGGTAGTTGTT TATATTTAGTTG (SEQ ID NO: 4) | 2.5 pmol |
| SNRPNb FP (B2) | CGCTGCCAACTACCGCACATCGTTGGGATTTTTGTATT GPGGTAAATAAG (SEQ ID NO: 5) | 5 pmol |
| SNRPN RP (B2) | CGCTGCCAACTACCGCACATCCCAATACKAACKAACAA AATACCATC (SEQ ID NO: 6) | 5 pmol |
| p21 S2b FP (B2) | CGCTGCCAACTACCGCACATCKACAAACAACAAAAAAC CCCKAAC (SEQ ID NO: 7) | 1.25 pmol |
| p21 S2 RP (B2) | CGCTGCCAACTACCGCACATCGPGTGATTAGGGATTTT TGTATTTG (SEQ ID NO: 8) | 1.25 pmol |
| p19 Ex1b FP (B2) | CGCTGCCAACTACCGCACATCCCCAATCTACAATTAAA AAAACAAAAATAAC (SEQ ID NO: 9) | 2.5 pmol |
| p19 Ex1 RP (B2) | CGCTGCCAACTACCGCACATCGGTTTTTTTTATTTGGT TTTTTAGGAAG (SEQ ID NO: 10) | 2.5 pmol |
| p27 Ex1 FP (B2) | CGCTGCCAACTACCGCACATCACCACCCTCTCCKCTTA CCTAATC (SEQ ID NO: 11) | 5 pmol |
| p27 Ex1 RP (B2) | CGCTGCCAACTACCGCACATCATPGGGTPGAAGAGGTT TTTGTAG (SEQ ID NO: 12) | 5 pmol |
| p16 Ex1b FP (B2) | CGCTGCCAACTACCGCACATCKAAAAAAACTCTTCCKC CAACAC (SEQ ID NO: 13) | 1.25 pmol |
| p16 Ex1b RP (B2) | CGCTGCCAACTACCGCACATCPGTTPGTTATTTTTGT TTTPGTTGTAG (SEQ ID NO: 14) | 1.25 pmol |
| p53b FP (B2) | CGCTGCCAACTACCGCACATCTTTGGTTTGTAGAATTT TTTATTTAAAATGTTAG (SEQ ID NO: 15) | 2.5 pmol |
| p53 RP (B2) | CGCTGCCAACTACCGCACATCTCAAATTCAATCAAAAA CTTACCCAATC (SEQ ID NO: 16) | 2.5 pmol |
| BRCA1 FP (B2) | CGCTGCCAACTACCGCACATCGAGATTTTTATTAGGGP GGAAAGAGTG (SEQ ID NO: 17) | 5 pmol |
| BRCA1 RP (B2) | CGCTGCCAACTACCGCACATCCCKTCCAAAAAATCTCA ACKAACTC (SEQ ID NO: 18) | 5 pmol |

Figure 6:
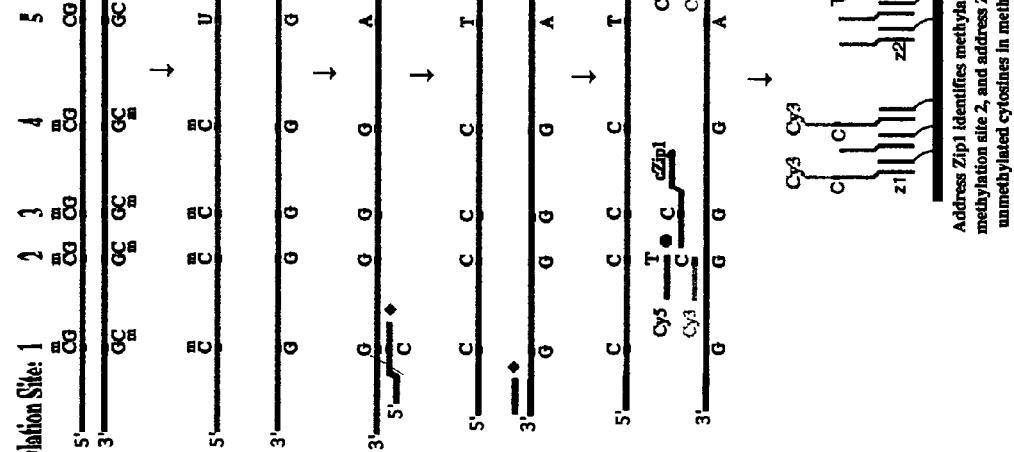
FIG. 6 is a schematic diagram, illustrating the procedure for high-throughput detection of promoter methylation status with the combination of bisulfite treatment, multiplex PCR, multiplex LDR, and universal array approaches. Nucleotides G and C are used in the multiplex PCR primers and LDR probes. The hybridization of such primers/probes with their DNA template results in the C:G Watson-Crick base pairings on methylated genomic sequences, yet G:T wobble base pairings and C:A mismatches occur on un-methylated sequences. Thus, the designs of these primers/probes take the advantage of preferentially hybridizing to methylated DNA sequences. As shown in this diagram, for example, the methylation sites 1, 3, 7, and 8 contribute to the preferential enrichment of the final signal of methylated cytosines at methylation sites 2 and 6.
Figure 7:
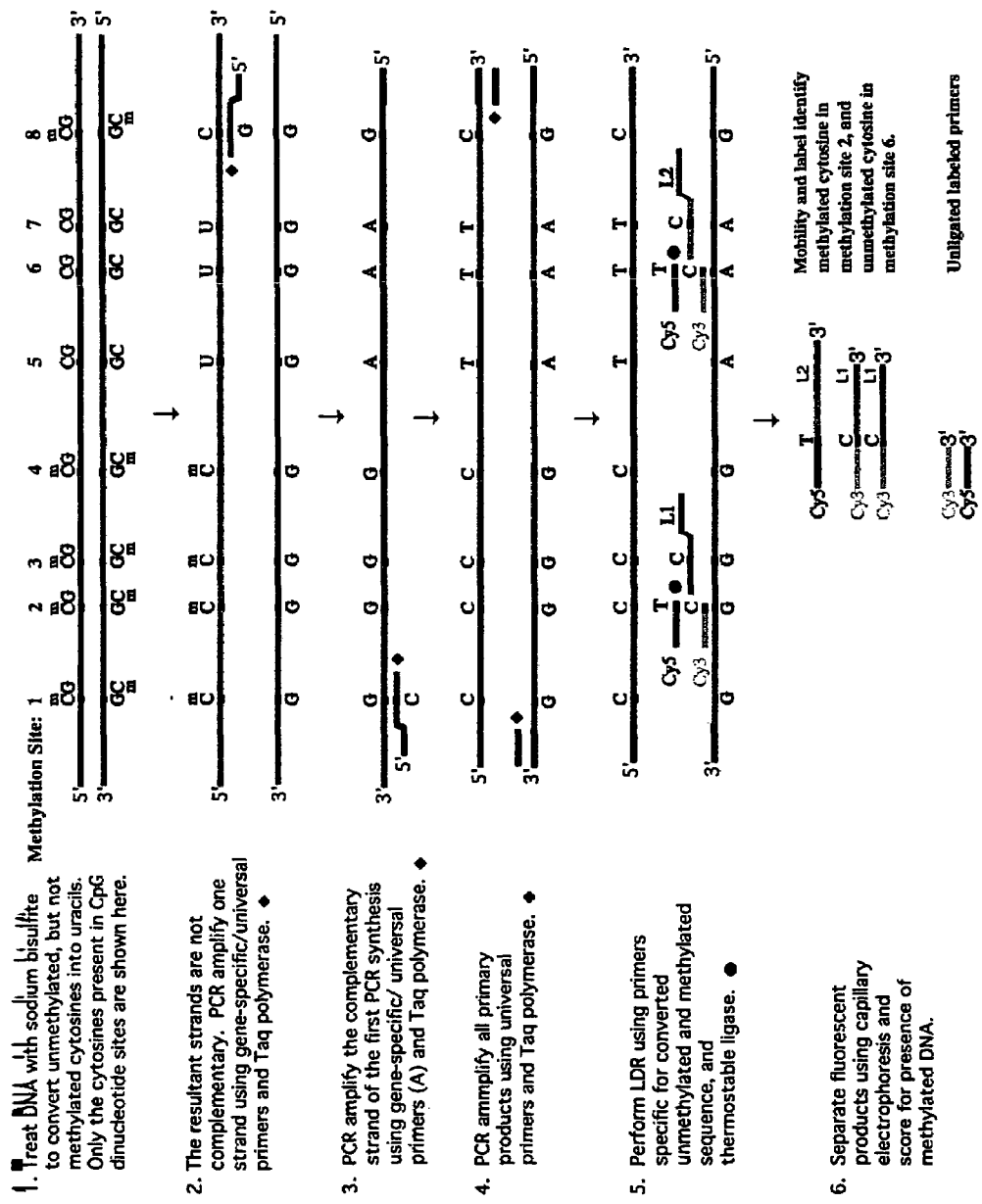
FIG. 7 is a schematic diagram, illustrating the procedure for high-throughput detection of promoter methylation status with the combination of bisulfite treatment, multiplex PCR, multiplex LDR, and capillary electrophoresis approaches. Nucleotides G and C are used in the multiplex PCR primers and LDR probes. The hybridization of such primers/probes with their DNA template results in the C:G Watson-Crick base pairings on methylated sequences, yet G:T wobble base pairings and C:A mismatches occur on un-methylated sequences. Thus, the designs of these primers/probes take the advantage of preferentially hybridizing to methylated DNA sequences. As shown in this diagram, for example, the methylation sites 1, 3, 7, and 8 contribute to the preferential enrichment of the final signal of methylated cytosines at methylation sites 2 and 6.

Alternatively, those nucleotide positions of primers where dK and dP can be incorporated (see methylation sites 1 and 8 in FIGS. 4 and 5) are substituted by nucleotides dG and dC, respectively, to make the PCR amplification preferential for methylated alleles. An example of dG is 2'-deoxyGuanosine, and an example of dC is 2'-deoxyCytidine. As shown in FIGS. 6 and 7, the substituted nucleotide dG (at methylation site 8) in the PCR primer can form either Watson-Crick base pair to C (if it is methylated) or wobble base pair to U (if it is unmethylated) of the bisulfite-treated DNA template. The substituted nucleotide dC (at methylation site 1) in the reverse PCR primer can form either a Watson-Crick base pair to G (if it is methylated) or mismatch pairing to A (if it is unmethylated) of the extension product of the first PCR primer. Note that primers designed in this way (see Table 2) provide additional selective power for methylated alleles since these positions are located in the middle of oligonucleotide primers (sites 1 and 8).

Table 2 shows more of the gene-specific PCR primer sequences used in the Bisulfite/PCR-PCR procedure. Note that nucleotide analogs dK and dP were replaced with G and T, respectively, in the primer syntheses.

TABLE 2

| Primers | Sequence (5' to 3') | Amount in PCR |
|---|---|---|
| Group 1 | | |
| p15 Ex1 FP (B2)/G | CGCTGCCAACTACCGCACATCCTTTACCGACTAACTC CCCACTCTAC (SEQ ID NO: 19) | 1.25 pmol |
| p15 Ex1 RP (B2) | CGCTGCCAACTACCGCACATCTTTTTTTTTTTTAGGA GATTTGGGTTTAG (SEQ ID NO: 20) | 1.25 pmol |
| p21 S1 FP (B2) | CGCTGCCAACTACCGCACATCCCTCCTAAAAAATACC AACTCATTCTC (SEQ ID NO: 21) | 2.5 pmol |
| p21 S1 RP (B2)/T | CGCTGCCAACTACCGCACATCTGATTTTGGTAGTTGT TTATATTTTAGTTG (SEQ ID NO: 22) | 2.5 pmol |
| APC FP (B2) | CGCTGCCAACTACCGCACATCACGAACTACACCAATA CAACCACATATC (SEQ ID NO: 23) | 5 pmol |
| APC RP (B2) | CGCTGCCAACTACCGCACATCTATTGTTTTTTTGTGT TGTAAAAATTATAGTAATT (SEQ ID NO: 24) | 5 pmol |
| SNRPNb FP (B2) | CGCTGCCAACTACCGCACATCGTTGGGATTTTTGTAT TGTGGTAAATAAG (SEQ ID NO: 25) | 2.5 pmol |
| SNRPN RP (B2) | CGCTGCCAACTACCGCACATCCCAATACGAACGAACA AAATACCATC (SEQ ID NO: 26) | 2.5 pmol |
| Group 2 | | |
| p19 Ex1b FP (B2) | CGCTGCCAACTACCGCACATCCCCAATCTACAATTAA AAAACAAAAATAAC (SEQ ID NO: 27) | 2.5 pmol |
| p19 Ex1 RP (B2) | CGCTGCCAACTACCGCACATCGGTTTTTTTTATTTGG TTTTTTAGGAAG (SEQ ID NO:28) | 2.5 pmol |
| p27 Ex1 FP (B2)/G | CGCTGCCAACTACCGCACATCACCACCCTCTCCGCTT ACCTAATC (SEQ ID NO: 29) | 2.5 pmol |
| p27 Ex1 RP (B2)/T | CGCTGCCAACTACCGCACATCATTGGGTTGAAGAGGT TTTTGTAG (SEQ ID NO:30) | 2.5 pmol |
| ECAD FPc (B2) | CGCTGCCAACTACCGCACATCTCACCTACCGACCACA ACCAATC (SEQ ID NO: 31) | 5 pmol |
| ECAD RPc (B2) | CGCTGCCAACTACCGCACATCTTATTGTTTTTGTTCG TTTCGATTTG (SEQ ID NO: 32) | 5 pmol |
| Group 3 | | |
| p16 Ex1b FP (B2) | CGCTGCCAACTACCGCACATCGAAAAAAACTCTTCCG CCAACAC (SEQ ID NO: 33) | 1.25 pmol |
| p16 Ex1b RP (B2) | CGCTGCCAACTACCGCACATCTGTTTGTTATTTTTTG TTTTTGTTGTAG (SEQ ID NO: 34) | 1.25 pmol |
| p53b FP (B2) | CGCTGCCAACTACCGCACATCTTTGGTTTGTAGAATT TTTTATTTTAAAATGTTAG (SEQ ID NO: 35) | 2.5 pmol |
| p53 RP (B2) | CGCTGCCAACTACCGCACATCTCAAATTCAATCAAAA ACTTACCCAATC (SEQ ID NO: 36) | 2.5 pmol |
| BRCA1 FP (B2)/T | CGCTGCCAACTACCGCACATCGAGATTTTTATTAGGG TGGAAAGAGTG (SEQ ID NO: 37) | 5 pmol |
| BRCA1 RP (B2)/G | CGCTGCCAACTACCGCACATCCCGTCCAAAAAATCTC AACGAACTC (SEQ ID NO: 38) | 5 pmol |
| Group 4 | | |
| MGMT FP (B2) | CGCTGCCAACTACCGCACATCCCGACCCTAATCCTCC GACAAC (SEQ ID NO: 39) | 1.25 pmol |
| MGMT RP (B2) | CGCTGCCAACTACCGCACATCTTTGATTAGGGGAGTG GTTTTAG ((SEQ ID NO: 40) | 1.25 pmol |
| DAPK FPa (B2) | CGCTGCCAACTACCGCACATCGCGCCCTAACTAAAAA AACAAAAAC (SEQ ID NO: 41) | 2.5 pmol |

TABLE 2-continued

| Primers | Sequence (5' to 3') | Amount in PCR |
|---|---|---|
| DAPK RP (B2) | CGCTGCCAACTACCGCACATCCGTTAGTTCGTTTGTA GGGTTTTTATTG ((SEQ ID NO: 42) | 2.5 pmol |
| GSTP1 FP (B2) | CGCTGCCAACTACCGCACATCCGAATTAACCCCATAC TAAAAACTCTAAAC (SEQ ID NO: 43) | 5 pmol |
| GSTP1 RP (B2) | CGCTGCCAACTACCGCACATCTGTTTTGTGAAGTGGG TGTGTAAG (SEQ ID NO: 44) | 5 pmol |
| Group 5 | | |
| TIMP3 FPa (B2) | CGCTGCCAACTACCGCACATCCCGCTCTACCCCGCTA CCTAA (SEQ ID NO: 45) | 5 pmol |
| TIMP3 RPa (B2) | CGCTGCCAACTACCGCACATCGTTGGTTTTGGTTTGG GTTAGAGATA (SEQ ID NO: 46) | 5 pmol |
| RASSF1 FPa (B2) | CGCTGCCAACTACCGCACATCCGACGACTACGCTACC CCTTAACTAC (SEQ ID NO: 47) | 5 pmol |
| RASSF1 RP (B2) | CGCTGCCAACTACCGCACATCTTTTCGTCGTTTAGTT TGGATTTTG (SEQ ID NO: 48) | 5 pmol |
| RARb FP (B2) | CGCTGCCAACTACCGCACATCTCCCAAATTCTCCTTC CAAATAAATAC (SEQ ID NO: 49) | 1.25 pmol |
| RARb RP (B2) | CGCTGCCAACTACCGCACATCTTGGTTTTTTTTTTGT TTATTTTAAAAGT (SEQ ID NO: 50) | 1.25 pmol |
| UniB2 | CGCTGCCAACTACCGCACATC (SEQ ID NO: 51) | |

Figure 8:
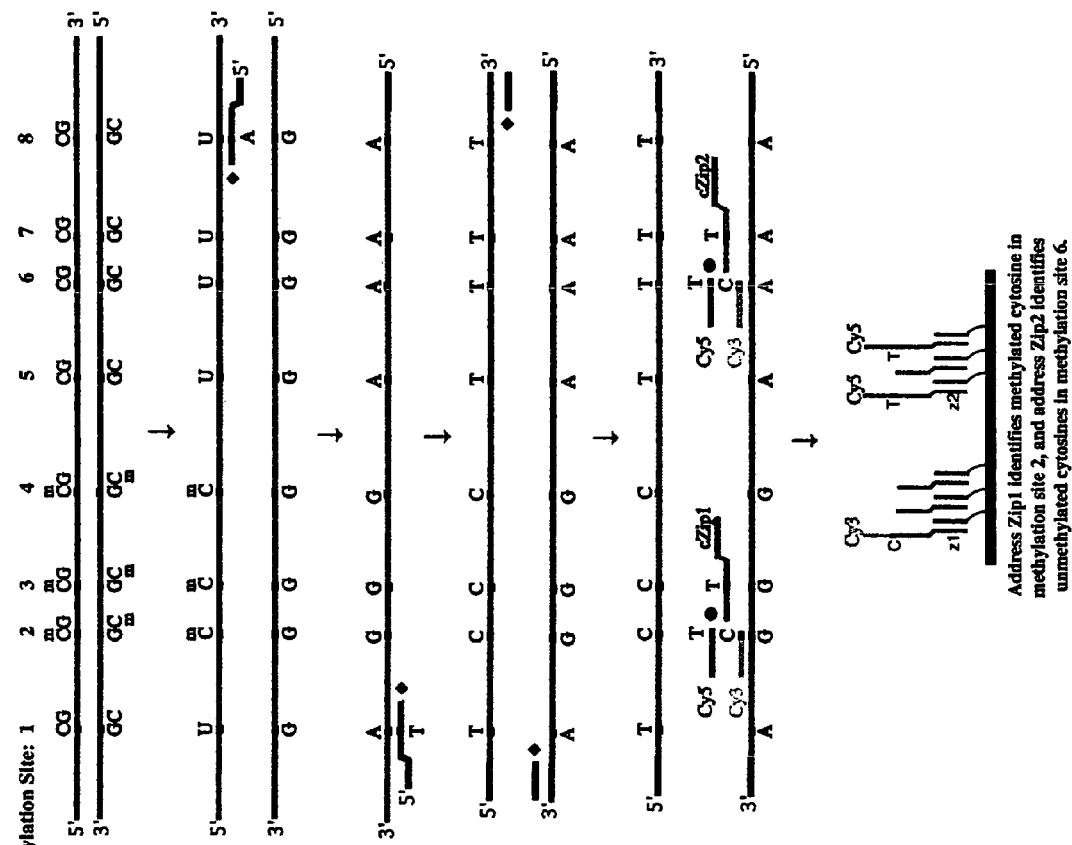
FIG. 8 is a schematic diagram, illustrating the procedure for high-throughput detection of promoter methylation status with the combination of bisulfite treatment, multiplex PCR, multiplex LDR, and universal array approaches. Nucleotides A and T are used in the multiplex PCR primers and LDR probes. The hybridization of such primers/probes with their DNA template results in the A:T Watson-Crick base pairings on un-methylated sequences, yet G:T wobble base pairings of methylated sequences occur. Thus, the designs of these primers/probes take the advantage of preferentially hybridizing to un-methylated DNA sequences occur. As shown in this diagram, for example, the methylation sites 1, 3, 7, and 8 contribute to the preferential enrichment of the final signal of un-methylated cytosines at methylation sites 2 and 6.
Figure 9:
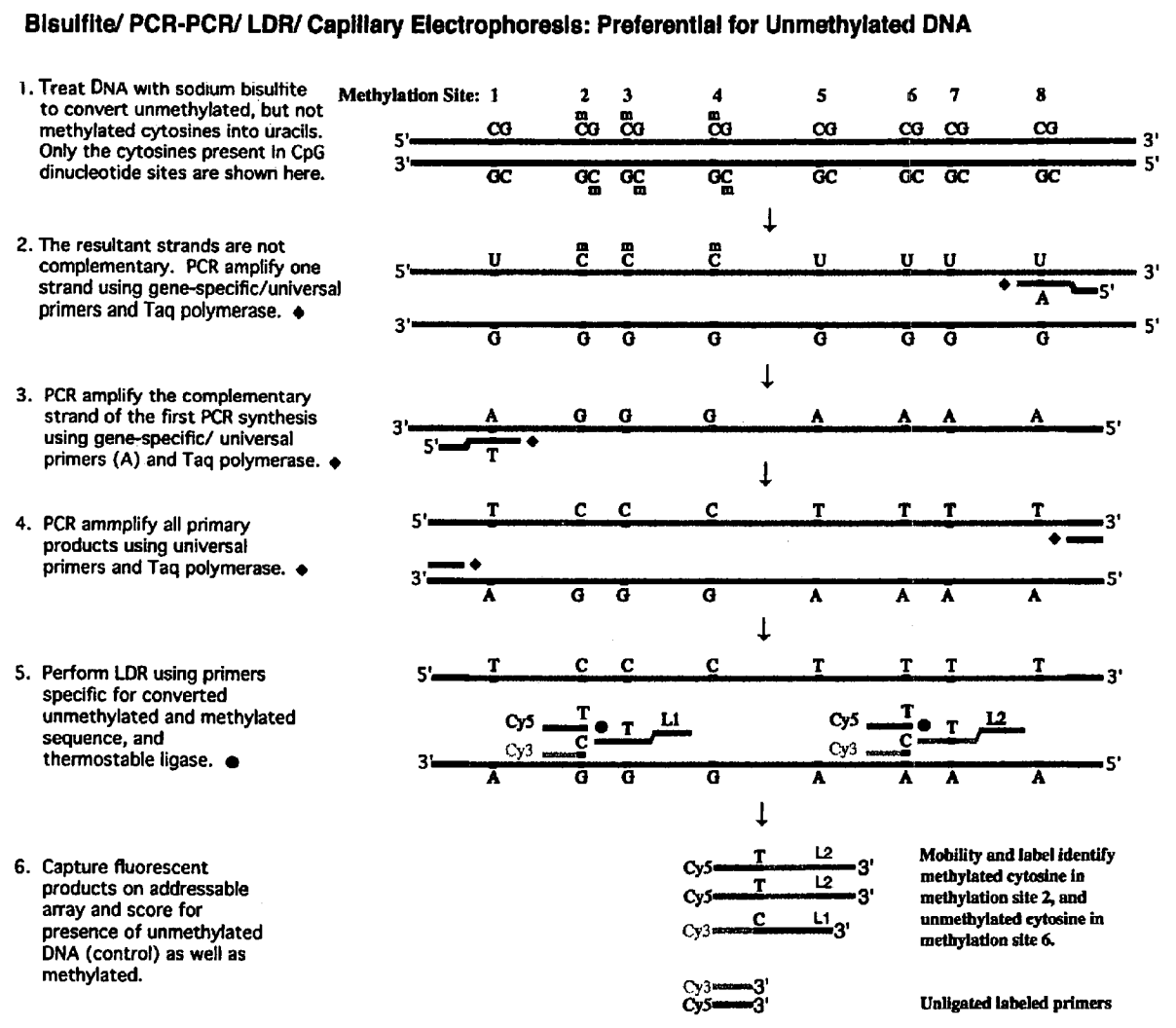

Furthermore, those nucleotide positions of primers where dK and dP can be incorporated (see methylation sites 1 and 8 in FIGS. 4 and 5) are substituted by nucleotides dA and dT, respectively, to make the PCR amplification preferential for unmethylated alleles. An example of dA is 2'-deoxyAdenosine, and an example of dT is 2'-deoxyThymidine. As shown in FIGS. 8 and 9, the substituted nucleotide dA (at methylation site 8) in the PCR primer can form either a Watson-Crick base pair to U/T (if it is unmethylated) or a mismatch base pair to C (if it is methylated) of the bisulfite-treated DNA template. The substituted nucleotide dT (at methylation site 1) in the reverse PCR primer can form either a Watson-Crick base pair to A (if it is unmethylated) or a wobble base pair to G (if it is methylated) of the extension product of the first PCR primer. Note that primers designed in this fashion provide additional selective power for unmethylated alleles since these positions are located in the middle of oligonucleotide primers (sites 1 and 8).

Each of the PCR primers consists of a gene-specific 3' portion and an upstream universal sequence. The amplification is performed in a multiplex format to increase the assay throughput. The PCR primers are designed in the promoter region that can give the optimal PCR amplification, regardless the number of CpG dinucleotide sites present in that region. At least 3 or more promoter regions can be multiplex amplified in one PCR reaction.

The polymerase used for PCR amplification is either a native or recombinant thermostable polymerase such as Thermus aquaticus, Thermus thermophilus, Pyrococcus furious, or Thermotoga maritime. The polymerase chain reaction process is fully described in H. Erlich, et. al., "Recent Advances in the Polymerase Chain Reaction," Science 252: 1643-50 (1991); M. Innis, et. al., PCR Protocols: A Guide to Methods and Applications, Academic Press: New York (1990); and R. Saiki, et. al., "Primer-directed Enzymatic Amplification of DNA with a Thermostable DNA Polymerase," Science 239: 487-91 (1988), which are hereby incorporated by reference.

In carrying out this procedure, the target nucleic acid, when present in the form of a double stranded DNA molecule is denatured to separate the strands. This is achieved by heating to a temperature of 80-105° C. Polymerase chain reaction primers are then added and allowed to hybridize to the strands, typically at a temperature of 20-85° C. A thermostable polymerase (e.g., Thermus aquaticus polymerase) is also added, and the temperature is then adjusted to 50-85° C. to extend the primer along the length of the nucleic acid to which the primer is hybridized. After the extension phase of the polymerase chain reaction, the resulting double stranded molecule is heated to a temperature of 80-105° C. to denature the molecule and to separate the strands. These hybridization, extension, and denaturation steps may be repeated a number of times to amplify the target nucleic acid to an appropriate level.

In step 4 of the present invention, as shown in FIGS. 1-9, all of the desired promoter regions are simultaneously amplified with a universal PCR primer. The universal sequence has been appended to the 5' portion of each gene-specific PCR primer. In this round of PCR amplification, the annealing temperature of PCR reaction is preferably 5° C. lower than the prior PCR conditions used to carry out gene-specific amplification. This lower annealing temperature ensures all of the first round full length PCR products are amplified at similar efficiency. Proteinase K (QIAGEN, Valencia, Calif.) is added at the end of the second round multiplex PCR reaction to inactivate the remaining thermostable polymerase. Before pooling the PCR products for further LDR analysis, the presence of the correct PCR fragments is verified by gel or capillary electrophoresis. The universal primer may have a fluorescent reporter to facilitate identification of PCR products on an automated capillary or gel DNA sequencing machine, such as an ABI 3730 or 377.

In the preferred embodiment, the same universal primer is used on both the upstream and downstream primers of each PCR primer pair. This design facilitates multiplexed PCR amplification. Regular multiplexed PCR often fails to amplify all desired products. For "n" primer pairs, there are $2n^2+n$ possible classes of PCR amplicons. Thus, as the number of primer pairs increases, the number of potentially false amplicons is squared, including a rapidly increasing probability of forming primer dimers. Once primer dimers form, they will generally amplify faster than the desired amplicon, leading to amplicon dropout and a false negative result.

Bisulfite-treated DNA is particularly prone to giving false amplicons. A 16 base region of genomic DNA has a frequency of about 1 in 4 billion bases and is thus unique in the genome. In contrast, when such a 16mer is treated with bisulfite, on average, 4 of the bases will be converted from C to T. Thus, the 16 bases will have about half of the bases as T, in other words, the bisulfite-treated sequence will appear once every 16.7 million bases or 179 times in the genome (=3 billion/16.7 million). To attempt to get around this difficulty, primers are made longer and, when possible, in regions where the number of changes is optimal for the particular assay. Nevertheless, until the present invention, multiplex PCR amplification of bisulfite-treated DNA has been exceedingly difficult if not impossible.

By using either identical or greater than 80% identical universal sequence on the 5' portion of both the forward and reverse PCR primers in the second PCR step, spurious amplifications from primer dimers are eliminated. Since the 5' and 3' portion of each strand of an amplicon are complementary to each other, an undesired primer dimer will form a panhandle structure upon denaturation/renaturation. This inhibits binding of a universal primer, and, thus, the primer dimmer does not amplify efficiently. While authentic amplicons also have the same universal sequence on both ends, these are far enough apart such that primer hybridization effectively competes against intramolecular (panhandle) hybridization. In the preferred embodiment, the PCR primers are designed so their 3' ends are between 150 and 500 bp apart. The concentration of the initial PCR primers may be adjusted to assist in obtaining approximately equal amplification of all the PCR amplicons.

Alternatively, the universal primers may be designed such that they contain some sequence differences (but still retain greater than 80% sequence identity), either at the 3' end, the 5' end, internally, or a combination of the above. By using two universal primers that are slightly different, smaller fragments may be more easily amplified as the two universal primers are less likely to form a panhandle, but primer dimers still do not amplify as the proximity and overall similarity in sequences still favors panhandle formation (and consequently inhibition of amplification).

Multiplexed PCR amplification will occasionally yield additional unanticipated amplicons. However, by using LDR to score methylation status of a particular amplicon, false PCR products are not detected and, consequently, do not interfere with the proper interpretation of the results.

The next step (step 5 as depicted in the process of FIGS. 1-9) is to carry out an LDR procedure to interrogate the methylation status of the cytosines reside in the CpG dinucleotides. Nine gene-specific LDR probes (six discriminating probes and three common probes) are designed for each of the three CpG dinucleotide sites in the promoter region of interest (see e.g., Table 3, 4, and 5).

The ligase detection reaction process, in accordance with the present invention, is described generally in WO 90/17239 to Barany et al., F. Barany et al., "Cloning, Overexpression and Nucleotide Sequence of a Thermostable DNA Ligase-encoding Gene," *Gene*, 109:1-11 (1991), and F. Barany, "Genetic Disease Detection and DNA Amplification Using Cloned Thermostable Ligase," *Proc. Natl. Acad. Sci. USA*. 88:189-193 (1991), the disclosures of which are hereby incorporated by reference in their entirety. In accordance with the present invention, the ligase detection reaction can use 2 sets of complementary oligonucleotides. This is known as the ligase chain reaction which is described in the 3 immediately preceding references, which are hereby incorporated by reference in their entirety. Alternatively, the ligase detection reaction can involve a single cycle which is also known as the oligonucleotide ligation assay. See Landegren, et al., "A Ligase-Mediated Gene Detection Technique," *Science* 241:1077-80 (1988); Landegren, et al., "DNA Diagnostics—Molecular Techniques and Automation," *Science* 242:229-37 (1988); and U.S. Pat. No. 4,988,617 to Landegren, et al.

During the ligase detection reaction phase of the process, the denaturation treatment is carried out at a temperature of 80-105° C., while hybridization takes place at 50-85° C. Each cycle comprises a denaturation treatment and a thermal hybridization treatment which in total is from about one to five minutes long. Typically, the ligation detection reaction involves repeatedly denaturing and hybridizing for 2 to 50 cycles. The total time for the ligase detection reaction phase of the process is 1 to 250 minutes.

The oligonucleotide probe sets can be in the form of ribonucleotides, deoxynucleotides, modified ribonucleotides, modified deoxyribonucleotides, peptide nucleotide analogues, modified peptide nucleic acid analogues, modified phosphate-sugar-backbone oligonucleotides, nucleotide analogs, and mixtures thereof.

In one variation, the oligonucleotides of the oligonucleotide probe sets each have a hybridization or melting temperature (i.e. $T_m$) of 66-70° C. These oligonucleotides are 20-28 nucleotides long.

It may be desirable to destroy chemically or enzymatically unconverted LDR oligonucleotide probes that contain addressable nucleotide array-specific portions after the ligase detection reaction process is completed. Such unconverted probes will otherwise compete with ligation products for hybridization to other nucleic acid molecules during downstream processing. Destruction can be accomplished by utilizing an exonuclease, such as exonuclease III (L-H Guo and R. Wu, *Methods in Enzymology* 100:60-96 (1985), which is hereby incorporated by reference in its entirety) in combination with LDR probes that are blocked at the ends and not involved with ligation of probes to one another. The blocking moiety could be a reporter group or a phosphorothioate group. T. T. Nikiforow, et al., "The Use of Phosphorothioate Primers and Exonuclease Hydrolysis for the Preparation of Single-stranded PCR Products and their Detection by Solid-phase Hybridization," *PCR Methods and Applications*, 3:p.285-291 (1994), which is hereby incorporated by reference in its entirety. After the LDR process, unligated probes are selectively destroyed by incubation of the reaction mixture with the exonuclease. The ligated probes are protected due to the elimination of free 3' ends which are required for initiation of the exonuclease reaction. This approach results in an increase in the signal-to-noise ratio, especially where the LDR reaction forms only a small amount of product. Since unligated oligonucleotides compete for hybridization to other nucleic acid molecules in downstream processing, such competition with the ligated oligonucleotides lowers the signal. An additional advantage of this approach is that unhybridized label-containing sequences are degraded and, therefore, are less able to cause a target-independent background signal, because they can be removed more easily by washing.

Table 3 shows examples of LDR probe sequences used to interrogate the methylated cytosines in the CpG dinucleotides of an individual promoter region. The Cy3 labeled LDR probes are ending with C at the very 3' end. The corresponded zip address of each common probe (probe where zip code-complement attaches) is indicated in the parenthesis. Notice that nucleotide analogs dK and dP were used in the syntheses of these probes.

TABLE 3

| Primers | Sequence (5' to 3') |
|---|---|
| SNRPN 484C | Cy3-AGGTAGGTTGGPGPGTATGTTTAGGC (SEQ ID NO: 52) |
| SNRPN 558C | Cy3-GAGPGGTPGTPGGAGATGTTTGAC (SEQ ID NO: 53) |
| SNRPN 646C | Cy3-GTGGTTTTTTTTAAGAGATAGTTTGGGGAGC (SEQ ID NO: 54) |
| SNRPN 484Mcom (Zip 4) | pGGGGATGTGTGPGAAGTTTGTPGTTGATGGCCGTGCTGGGGAC AAGTCAA-Bk (SEQ ID NO: 55) |
| SNRPN 558Mcom (Zip 5) | pGTATTTGTTTGAGGAGPGGTTAGTGAPGPGTTGCAACGGGCTG GTCAACGTCAA-Bk (SEQ ID NO: 56) |
| SNRPN 646Mcom (Zip 6) | pGGTTATTTTATTTATTAGATATTTTAAGTTTTTAGGATTTGG AGTATTGCATCATGGGGGAAAGCTTCGTCAA-Bk (SEQ ID NO: 57) |
| p15 Ex1 299C | Cy3-GGAPGTAGTPGAGTTTAAAGTPGTTTTGGTC (SEQ ID NO: 58) |
| p15 Ex1 366C | Cy3-TTTTTGGPGTTTAAGAATTAGPGGGC (SEQ ID NO: 59) |
| p15 Ex1 430C | Cy3-GTPGTTTTTTTGPGGTTTGGGGTTTC (SEQ ID NO: 60) |
| p15 Ex1 299Mcom (Zip 9) | pGTAGGGTGPGGAPGPGTPGPGGCATCGTCCCTTTCGATGGGAT CAA-Bk (SEQ ID NO: 61) |
| p15 Ex1 366Mcom (Zip 10) | pGPGTTTGGATTGTTTTTGGGAAAAAGPGCAAGGCACGTCCCAG ACGCATCAA-Bk (SEQ ID NO: 62) |
| p15 Ex1 430Mcom (Zip 11) | pGTGTAGTGGTPGAGPGGTPGGTPGGCACGGGAGCTGACGACGT GTCAA-Bk (SEQ ID NO: 63) |
| p16 Ex1 351C | Cy3-TTGTTTTTTTTTTTTPGTAGTPGTPGAGC (SEQ ID NO: 64) |
| p16 Ex1 438C | Cy3-GGTPGPGGTPGTGGTTAGTTAGTTAGTC (SEQ ID NO: 65) |
| p16 Ex1 520C | Cy3-ATPGGTTTTPGATPGTAATTATTPGGTGC (SEQ ID NO: 66) |
| p16 Ex1 351Mcom (Zip 15) | pGTAPGPGGTTPGTTTTATTTTTGGTGATTAGCTGGCTGGCAC GCACCAGAATCA-Bk (SEQ ID NO:67) |
| p16 Ex1 438Mcom (Zip 16) | pGAAGGTTTTATGTTGTTTTPGTPGTPGGTTGGCTCCGTCAGA AAGCGACAATCA-Bk (SEQ ID NO: 68) |
| p16 Ex1 520Mcom (Zip 17) | pGTTGGGTAGPGTTTTPGTTTTAGTAGPGTTACGAGGGATACC CGCAAACGATCA-Bk (SEQ ID NO: 69) |
| p19 Ex1 606C | Cy3-TTAGGTPGAGTTPGGTAGTPGTTGC (SEQ ID NO: 70) |
| p19 Ex1 673C | Cy3-PGGGTPGTAPGPGPGTPGAATTC (SEQ ID NO: 71) |
| p19 Ex1 761C | Cy3-GTAPGAGGGTTATAGPGGPGGGC (SEQ ID NO: 72) |
| p19 Ex1 606Mcom (Zip 21) | pGTPGTTTTTGGTATTAGAGGTGAGTAGPGTTATTTTGTCCGT CCATGGCAAGCGTGATCA-Bk (SEQ ID NO: 73) |
| p19 Ex1 673Mcom (Zip 22) | pGGAGGGTTATTAAGAATTTGPGTATTATGTTTTPGTGGCTGCA CCCGTTGAGGCACATCA-Bk (SEQ ID NO: 74) |

TABLE 3-continued

| Primers | Sequence (5' to 3') |
|---|---|
| p19 Ex1 761Mcom (Zip 23) | pGTTTTTGGPGTTGTTTATTTTTTPGTGAGTPTCAACATCGGCT AACGGTCCATCA-Bk (SEQ ID NO: 75) |
| p21 S1 2968C | Cy3-TTTTTTAGTTTTTPGTTTGPGTTGGTG<u>C</u> (SEQ ID NO: 76) |
| p21 S1 3036C | Cy3-TTAGTTGAGTTTGGTPGAGTTTTAGTAGGTTAGT<u>C</u> (SEQ ID NO: 77) |
| p21 S1 3142C | Cy3-GGTTPGTTTTAAGGAGGPGGGATT<u>C</u> (SEQ ID NO: 78) |
| p21 S1 2968Mcom (Zip 24) | pGTTGGATATATTTTTTTAPGAAGTGAGTTATAAATTTGGTTCG CACGCAGTCCTCCTCCGTATCA-Bk (SEQ ID NO: 79) |
| p21 S1 3036Mcom (Zip 25) | pGGTTTPGGAATTTPGCGTGTTGTAGGGGCTCGCAGGCTGGCTC ATCCTAA-Bk (SEQ ID NO: 80) |
| p21 S1 3142Mcom (Zip 26) | pGPGTTPGGTTTATPGPGTPGTTPGGCGCATGAGGGGAAACGAC GAGATT-Bk (SEQ ID NO: 81) |
| p21 S2 3379C | Cy3-TATTPGPGAATAPGTATTTTPGPGGATA<u>C</u> (SEQ ID NO: 82) |
| p21 S2 3459C | Cy3-TPGTGTGPGTAAGTPGAGPGPGTAT<u>C</u> (SEQ ID NO: 83) |
| p21 S2 3514C | Cy3-TTTTPGTTTPGGGGTTTTPGGTATATTT<u>C</u> (SEQ ID NO: 84) |
| p21 S2 3379Mcom (Zip 27) | pGTAGGGATATAPGPGGGTAPGTTGGTTPGCACCGTGAACGAC AGTTGCGATT-Bk (SEQ ID NO: 85) |
| p21 S2 3459Mcom (Zip 28) | pGATTTAPGTTPGTTATTTATTTGTPGTAGAAATATTTGTGCGC AGGTCGCTGCGTGTCCTGATT-Bk (SEQ ID NO: 86) |
| p21 S2 3514Mcom (Zip 29) | pGATTTTPGTTATTPGPGTATTTAGAGATATPGTGTCGCAAAGC AGACACAGGGTCGATT-Bk (SEQ ID NO: 87) |
| p27 Ex1 575C | Cy3-GTTAAAAGATATAGATTTPGAPGAGTTAPGGTT<u>C</u> (SEQ ID NO: 88) |
| p27 Ex1 644C | Cy3-AAAATPGAATAAAATAAAGPGTTTTTAPGTAGTT<u>C</u> (SEQ ID NO: 89) |
| p27 Ex1 770C | Cy3-GGGTGTTTPGTTTGTTTGGPGTTTATT<u>C</u> (SEQ ID NO: 90) |
| p27 Ex1 575Mcom (Zip 30) | pGAGTTTTAGGAGPGPGTAGGGGTTGPCATCGCACTTCGCTTTG GCTGATT-Bk (SEQ ID NO: 91) |
| p27 Ex1 644Mcom (Zip 31) | pGAATTTTTTTPGGAAGTTTAGPGATTGTTTTPGTTGCGGGAAC TCACGAGGTCGTAT-Bk (SEQ ID NO: 92) |
| p27 Ex1 770Mcom (Zip 32) | pGTTTTAGGTTAGGGTTTTPGTTAGATATTPGTAPGTTTGCACG GCTCGATAGGTCAAGCTTT-Bk (SEQ ID NO: 93) |
| p53 498C | Cy3-TAGGPGGATTATTTGTTTTTATTTGTTATGG<u>C</u> (SEQ ID NO: 94) |
| p53 577C | Cy3-GGGTTTTTTTTTTTATGTGTTTAAGATTGG<u>C</u> (SEQ ID NO: 95) |
| p53 661C | Cy3-TGGGTTTPGGGGATATTTTGPGTT<u>C</u> (SEQ ID NO: 96) |
| p53 498Mcom (Zip 12) | pGATTGTTTAGTTTTGTGTTAGGAGTTTPGTAGGGGAGACGCAC CGCAACAGGCTGTCAA-Bk (SEQ ID NO: 97) |
| p53 577Mcom (Zip 13) | pGTTAAAAGTTTTGAGTTTTTTAAAAGTTTAGAGTTATCGTTTA GGCATCGCTGCAAGTACCGCACTCAA-Bk (SEQ ID NO: 98) |
| p53 661Mcom (Zip 14) | pGGGTTGGGAGPGTGTTTTTTAPGAPGGGGCTGGGACGTGCAGAC CGTTCAA-Bk (SEQ ID NO: 99) |

TABLE 3-continued

| Primers | Sequence (5' to 3') |
|---|---|
| BRCA1 839C | Cy3-ATTTTGATTTTPGTATAGTAATTATTGTGATGTAAT AAGTC (SEQ ID NO: 100) |
| BRCA1 963C | Cy3-GGGGGTAGATTGGGTGGTTAATTTAGAGTTTC (SEQ ID NO: 101) |
| BRCA1 1068C | Cy3-TAGPGGTAGTTTTTTGGTTTTPGTGGTAAC (SEQ ID NO: 102) |
| BRCA1 839Mcom (Zip 18) | pGTAATTGGAAGAGTAGAGGTTAGAGGGTAGGTATTTTATGGGG GAGGCTGCTGTCCTTTCGATCA-Bk (SEQ ID NO: 103) |
| BRCA1 963Mcom (Zip 19) | pGAGAGAPGTTTGGTTTTTTTTGTTTTTTTTATTTTTTGACAGC GTGTTCGTTGCTTGCATCA-Bk (SEQ ID NO: 104) |
| BRCA1 1068Mcom (Zip 20) | pGGAAAAGPGPGGGAATTATAGATAAATTAAAATTGATGGCGAT GGTCCACTCGCAATCA-Bk (SEQ ID NO: 105) |

Table 4 shows examples of the LDR probe sequences used to interrogate the unmethylated cytosines in the CpG dinucleotides of an individual promoter region. The Cy5 labeled LDR probes are ending with A at the very 3' end. The corresponding zip address of each common probe (probe where zip code-complement attaches) is indicated in the parenthesis. Note that nucleotide analogs dK and dP were used in the syntheses of these primers.

TABLE 4

| Primers | Sequence (5' to 3') |
|---|---|
| SNRPN 484A | Cy5-KACAAACTTCKCACACATCCCCA (SEQ ID NO: 106) |
| SNRPN 558A | Cy5-ACTAACCKCTCCTCAAACAAATACA (SEQ ID NO: 107) |
| SNRPN 646A | Cy5-TAAAAACTTAAAATATCTAATAAATAAAAATAACCA (SEQ ID NO: 108) |
| SNRPN 484Com (Zip 4) | pCCTAAACATACKCKCCAACCTACCTCTAATGGCCGTGCTGGGGAC AAGTCAA-BK (SEQ ID NO: 109) |
| SNRPN 558Com (Zip 5) | pTCAAACATCTCCKACKACCKCTCCATTGCAACGGGCTGGTCAACG TCAA-BK (SEQ ID NO: 110) |
| SNRPN 646Com (Zip 6) | pCTCCCCAAACTATCTCTTAAAAAAAACCACCKACATCATGGGGGA AAGCTTCGTCAA-BK (SEQ ID NO: 111) |
| p15Ex1 299A | Cy5-TCCKCKACKCKTCCKCACCCTACA (SEQ ID NO: 112) |
| p15Ex1 366A | Cy5-CCAAAAACAATCCAAACKCA (SEQ ID NO: 113) |
| p15Ex1 430A | Cy5-ACCKCTCKACCACTACACA (SEQ ID NO: 114) |
| p15Ex1 299Com (Zip 9) | pACCAAAACKACTTTAAACTCKACTACKTCCKCCATCGTCCCTTTC GATGGGATCAA-BK (SEQ ID NO: 115) |
| p15Ex1 366Com (Zip 10) | pCCCKCTAATTCTTAAACKCCAAAACAAGGCACGTCCCAGACGCAT CAAG-Bk (SEQ ID NO: 116) |
| p15Ex1 430Com (Zip 11) | pAAACCCCAAACCKCAAAAAAAGCACGGGAGCTGACGACGTGTCAA G-Bk (SEQ ID NO: 117) |
| p16 Ex1 351A | Cy5-AAATAAAACKAACCKCKTACA (SEQ ID NO: 118) |
| p16 Ex1 438A | Cy5-CCKTCKACKAAAAACAACATAAAACCTTCA (SEQ ID NO: 119) |
| p16 Ex1d 520A | Cy5-CKCTACTAAAAACKAAAACKCTACCCAACA (SEQ ID NO: 120) |
| p16 Ex1c 351Com (Zip 15) | pCTCKACKACTACKAAAAAAAAAAAAACAAAGCTGGCTGGCACGCA CCAGAATCA-Bk (SEQ ID NO: 121) |
| p16 Ex1 438Com (Zip 16) | pACTAACTAACTAACCACKACCKCKACCKAAATCGGCTCCGTCAGA AAGCGACAATCAG-Bk (SEQ ID NO: 122) |

TABLE 4-continued

| Primers | Sequence (5' to 3') |
| --- | --- |
| p16 Ex1c 520Com (Zip 17) | pCACCKAATAATTACKATCKAAAACCKATCCACGAGGGATACCCGCAAACGATCA-Bk (SEQ ID NO: 123) |
| p19 Ex1 606A | Cy5-CACCTCTAATACCAAAAAACKACA (SEQ ID NO: 124) |
| p19 Ex1 673A | Cy5-ACATAATACKCAAATTCTTAATAACCCTCCA (SEQ ID NO: 125) |
| p19 Ex1d 761A | Cy5-CTCACKAAAAAATAAACAACKCCAAAAACA (SEQ ID NO: 126) |
| p19 Ex1 606Com (Zip 21) | pCAACKACTACCKAACTCKACCCTAAGTCCGTCCATGGCAAGCGTGATCA-BK (SEQ ID NO: 127) |
| p19 Ex1 673Com (Zip 22) | pAATTCKACKCKCKTACKACCCKCCKCGGCTGCACCCGTTGAGGCACATCA-BK (SEQ ID NO: 128) |
| p19 Ex1c 761Com (Zip 23) | pCCCKCCKCTATAACCCTCKTACTTCAACATCGGCTAACGGTCCATCA-BK (SEQ ID NO: 129) |
| p21 S1 2968A | Cy5-CACTTCKTAAAAAAATATATCCAACA (SEQ ID NO: 130) |
| p21 S1 3037A | Cy5-TACAACACKCKAAATTCCKAAACCA (SEQ ID NO: 131) |
| p21 S1b 3142A | Cy5-AACKACKCKATAAACCKAACKCA (SEQ ID NO: 132) |
| p21 S1c 2968Com (Zip 24) | pCACCAACKCAAACKAAAAACTAAAAAAAACGCACGCAGTCCTCCTCCGTATCA-Bk (SEQ ID NO: 133) |
| p21 S1 3037Com (Zip 25) | pACTAACCTACTAAAACTCKACCAAACTCAACTAACTCKGGCTCGCAGGCTGGCTCATCCTAA-Bk (SEQ ID NO: 134) |
| p21 S1b 3142Com (Zip 26) | pAATCCCKCCTCCTTAAAACKAACCCKCGCATGAGGGGAAACGACGAGATTG-Bk (SEQ ID NO: 135) |
| p21 S2 3379A | Cy5-ACCAAACKTACCCKCKTATATCCCTACA (SEQ ID NO: 136) |
| p21 S2b 3459A | Cy5-CTACKACAAATAAATAACKAACKTAAATCA (SEQ ID NO: 137) |
| p21 S2b 3514A | Cy5-CTCTAAATACKCKAATAACKAAAATCA (SEQ ID NO: 138) |
| p21 S2 3379Com (Zip 27) | pTATCCKCKAAAATACKTATTCKCKAATATATACGCACCGTGAACGACAGTTGCGATT-Bk (SEQ ID NO: 139) |
| p21 S2c 3459Com (Zip 28) | pATACKCKCTCKACTTACKCACACKATACGCAGGTCGCTGCGTGTCCTGATTG-BK (SEQ ID NO: 140) |
| p21 S2c 3514Com (Zip 29) | pAAATATACCKAAAACCCCKAAACKAAAAACCGCAAAGCAGACACAGGGTCGATTG-BK (SEQ ID NO: 141) |
| p27 Ex1 575A | Cy5-CTACKCKCTCCTAAAACTCA (SEQ ID NO: 142) |
| p27 Ex1 644A | Cy5-KCTAAACTTCCKAAAAAAATTCA (SEQ ID NO: 143) |
| p27 Ex1 770A | Cy5-AACKAAAACCCTAACCTAAAACA ((SEQ ID NO: 144) |
| p27 Ex1 575Com (Zip 30) | pAACCKTAACTCKTCKAAATCTATATCTTTCATCGCACTTCGCTTTGGCTGATTG-BK (SEQ ID NO: 145) |
| p27 Ex1 644Com (Zip 31) | pAACTACKTAAAAACKCTTTATTTTATTCKATTTGCGGGAACTCACGAGGTCGTATG-BK (SEQ ID NO: 146) |
| p27 Ex1 770Com (Zip 32) | pAATAAACKCCAAACAAACKAAACACGCACGGCTCGATAGGTCAAGCTTT-BK (SEQ ID NO: 147) |
| p53 498A | Cy5-CTACKAAACTCCTAACACAAAACTAAACAATCA (SEQ ID NO: 148) |
| p53 577A | Cy5-CTCTAAACTTTTAAAAAACTCAAAACTTTTAACA (SEQ ID NO: 149) |
| p53 661A | Cy5-CKTAAAAAACACKCTCCCAACCCA (SEQ ID NO: 150) |

TABLE 4-continued

| Primers | Sequence (5' to 3') |
|---|---|
| p53 498Com (Zip12) | pCCATAACAAATAAAAACAAATAATCCKCCACCAGACGCACCGCAA CAGGCTGTCAAG-BK (SEQ ID NO: 151) |
| p53 577Com (Zip 13) | pCCAATCTTAAACACATAAAAAAAAAAAACCCAATCATCGCTGCAA GTACCGCACTCAAG-BK (SEQ ID NO: 152) |
| p53 661Com (Zip 14) | pAACKCAAAATATCCCCKAAACCCAACGGCTGGGACGTGCAGACCG TTCAA-Bk (SEQ ID NO: 153) |
| BRCA1 839A | Cy5-CTACCCTCTAACCTCTACTCTTCCAATTACA (SEQ ID NO: 154) |
| BRCA1 963A | Cy5-AAAACAAAAAAAACCAAACKTCTCTCA (SEQ ID NO: 155) |
| BRCA1 1068A | Cy5-ATCTATAATTCCCKCKCTTTTCCA (SEQ ID NO: 156) |
| BRCA1 839Com (Zip 18) | pACTTATTACATCACAATAATTACTATACKAAAATCAAAATCKCGG GAGGCTGCTGTCCTTTCGATCA-BK (SEQ ID NO: 157) |
| BRCA1 963Com (Zip 19) | pAAACTCTAAATTAACCACCCAATCTACCCCCKAAACAGCGTGTTC GTTGCTTGCATCA-BK (SEQ ID NO: 158) |
| BRCA1 1068Com (Zip 20) | pTTACCACKAAAACCAAAAAACTACCKCATGGCGATGGTCCACTCG CAATCA-BK (SEQ ID NO: 159) |

Table 5 shows examples of the LDR probe sequences used to interrogate the methylation status of cytosines in the CpG dinucleotides of an individual promoter region. The Cy5 labeled LDR probes detect unmethylated cytosines and ending with T at the very 3' end. The Cy3 labeled LDR probes detect methylated cytosines and ending with C at the very 3' end. The corresponded zip address of each common probe (probes where zip code-complement attaches) is indicated in the parenthesis. Note that nucleotide analogs dK and dP were not used in the probe syntheses.

TABLE 5

| Primers | Sequence (5' to 3') |
|---|---|
| APC | |
| APC 559T | Cy5-TTTTTGGTATTTTGTGTTAATTTTTTGTTTGT (SEQ ID NO: 160) |
| APC 719T | Cy5-TGTGTTTTATTGTGGAGTGTGGGTT (SEQ ID NO: 161) |
| APC 783T | Cy5-GATGTGGATTAGGGTGTTTTTATTTTT (SEQ ID NO: 162) |
| APC 559C | Cy3-TTTCGGTATTTTGTGTTAATTTTTTGTTTGC (SEQ ID NO: 163) |
| APC 719C | Cy3-TGTGTTTTATTGCGGAGTGCGGGTC (SEQ ID NO: 164) |
| APC 783C | Cy3-GATGCGGATTAGGGCGTTTTTTATTTTC (SEQ ID NO: 165) |
| (cZip 27) APC 559Mcom | pGGATTTTTTTCGATTTTTATTATGCGTGTTAATTGTGCACCGTGAAC GACAGTTGCGATT-BK (SEQ ID NO: 166) |
| (cZip 28) APC 719Mcom | pGGGAAGTGGAGAGAGAAGTAGTTGTGTAATTTGCGCAGGTCGCTGCGT GTCCTGATT-BK (SEQ ID NO: 167) |
| (cZip 29) APC 783Mcom | pGTGGGAGTTTGTTGATTGGTTGGGCGCAAAGCAGACACAGGGTCGAT T-BK (SEQ ID NO: 168) |
| DAPK | |
| DAPK 300T | Cy5-GTTTTTTGTTTAAAAGGCGGTAAGGAGTT (SEQ ID NO: 169) |
| DAPK 380T | Cy5-TTTTGTTTTTTTTGTGGAGGGGATTT (SEQ ID NO: 170) |
| DAPK 500T | Cy5-TTTTCGGTGTTGGTGTTTATGGTT (SEQ ID NO: 171) |
| DAPK 300C | Cy3-GTTTTTCGTTTAAAAGGCGGTAAGGAGTC (SEQ ID NO: 172) |
| DAPK 380C | Cy3-TTTTGTTTTTTTCGCGGAGGGGATTC (SEQ ID NO: 173) |

TABLE 5-continued

| Primers | Sequence (5' to 3') |
| --- | --- |
| DAPK 500C | Cy3-TTTTCGGCGTTGGCGTTTATGGTC (SEQ ID NO: 174) |
| (cZip 33) DAPK 300Mcom | pGAGAGGTTGTTTCGGAGTGTGAGGAGGATACGATTTCGACTCAAGCGGCTCTTT-BK (SEQ ID NO: 175) |
| (cZip 34) DAPK 380Mcom | pGGTAATTCGTAGCGGTAGGGTTTGGGGTCGCAATGGTAGGTGAGCAAGCAGA-BK (SEQ ID NO: 176) |
| (cZip 35) DAPK 500Mcom | pGGTTTTCGATAGCGTTTCGGAGGGATCGTCCCCGTTACCTAGGCGATCAGA-BK (SEQ ID NO: 177) |
| ECAD | |
| ECAD 190T | Cy5-TTAGGAGTTTGAGGTTGTAGTGAGTTGTGATT (SEQ ID NO: 178) |
| ECAD 359T | Cy5-GTTGGGATTTGAATTTAGTGGAATTAGAATT (SEQ ID NO: 179) |
| ECAD 429T | Cy5-GAGGGTTATTGTGTTTATGTGAGGTT (SEQ ID NO: 180) |
| ECAD 190C | Cy3-TTAGGAGTTCGAGGTTGTAGTGAGTTGTGATC (SEQ ID NO: 181) |
| ECAD 359C | Cy3-GTTGGGATTCGAATTTAGTGGAATTAGAATC (SEQ ID NO: 182) |
| ECAD 429C | Cy3-GAGGGTTATCGCGTTTATGCGAGGTC (SEQ ID NO: 183) |
| (cZip 36) ECAD 190Mcom | pGTATTATTGTATTTTAGTTTGGGTGAAAGAGTGAGTTTTATTTTTAAATGGGTCCACAGTACCGCTGCAGA-BK (SEQ ID NO: 184) |
| (cZip 37) ECAD 359Mcom | pGTGTAGGTTTTATAATTTATTTAGATTTTAGTAATTTTAGGTTAGAGGGTCCGTGGGAGATTAGGTGGCTCAGA-BK (SEQ ID NO: 185) |
| (cZip 38) ECAD 429Mcom | pGGGTGGGCGGGTCGTTAGTTTCGGGGAATGGAGGTGGGAACGAGACA-BK (SEQ ID NO: 186) |
| GSTP1 | |
| GSTP 925T | Cy5-TTTAGGGAATTTTTTTTGTGATGTTTT (SEQ ID NO: 187) |
| GSTP 1028T | Cy5-GATTTGGGAAAGAGGGAAAGGTTTTTTT (SEQ ID NO: 188) |
| GSTP 1144T | Cy5-GGGAGTTTGTGGGATTTTTTAGAAGAGT (SEQ ID NO: 189) |
| GSTP 925C | Cy3-TTTAGGGAATTTTTTTCGCGATGTTTC (SEQ ID NO: 190) |
| GSTP 1028C | Cy3-GATTTGGGAAAGAGGGAAAGGTTTTTTC (SEQ ID NO: 191) |
| GSTP 1144C | Cy3-GGAGTTCGCGGGATTTTTAGAAGAGC (SEQ ID NO: 192) |
| (cZip 39) GSTP 925Mcom | pGGCGCGTTAGTTCGTTGCGTATATTTCGCGTGGCTGACTCGCTGCGATGACA-BK (SEQ ID NO: 193) |
| (cZip 40) GSTP 1028Mcom | pGGTTAGTTGTGTGGTGATTTTGGTTGCGCACCATCAGGTTAGGGACA-BK (SEQ ID NO: 194) |
| (cZip 41) GSTP 1144Mcom | pGGTCGGCGTCGTGATTTAGTATTGGGGCACCGATATGGAGACCGCACACA-BK (SEQ ID NO: 195) |
| MGMT | |
| MGMT 180T | Cy5-TGGGTTTAGTGTAGTTGTTTTGAGTAGGATT (SEQ ID NO: 196) |
| MGMT 237T | Cy5-GATTTTTGTGTGTTTTTAGGATTATTT (SEQ ID NO: 197) |
| MGMT 346T | Cy5-AGTTTTAGGTGGAAGTTGGGAAGGT (SEQ ID NO: 198) |
| MGMT 180C | Cy3-CGGGTTTAGCGTAGTCGTTTCGAGTAGGATC (SEQ ID NO: 199) |
| MGMT 237C | Cy3-GATTTTCGCGCGTTTTTAGGATTATTC (SEQ ID NO: 200) |
| MGMT 346C | Cy3-GTTTTAGGCGGAAGTTGGGAAGGC (SEQ ID NO: 201) |
| (cZip 42) MGMT 180Mcom | pGGGATTTTTATTAAGCGGGCGTCGTTTCATCGACAAGGTAACGCGTGGACA-BK (SEQ ID NO: 202) |

TABLE 5-continued

| Primers | Sequence (5' to 3') |
|---|---|
| (cZip 43) MGMT 237Mcom | pGGGTACGTGGTAGGTCGTTTGTACGTTCGTGAGCGCAAGGTCAGAGCACGACA-BK (SEQ ID NO: 203) |
| (cZip 44) MGMT 346Mcom | pGTTGTTTGGTTTGTATTGGTTGAAGGGAAGCCGCAGCACGATTCCGTGACA-BK (SEQ ID NO: 204) |
| RARb | |
| RARb 127T | Cy5-GAAAGAAAATGTTGGTTTGTGTGTTT (SEQ ID NO: 205) |
| RARb 244T | Cy5-ATGTTAGATTAGTTGGGTTATTTGAAGGTTAGTAGTTT (SEQ ID NO: 206) |
| RARb 411T | Cy5-ATGTGAGTTGTTTGAGGATTGGGATGTT (SEQ ID NO: 207) |
| RARb 127C | Cy3-GAAAGAAAACGTCGGTTTGTGCGTTC (SEQ ID NO: 208) |
| RARb 244C | Cy3-ATGTTAGATTAGTTGGGTTATTTGAAGGTTAGTAGTTC (SEQ ID NO: 209) |
| RARb 411C | Cy3-ATGCGAGTTGTTTGAGGATTGGGATGTC (SEQ ID NO: 210) |
| (cZip 45) RARb 127Mcom | pGTTGTTTGTTTTTTTGGTTGTTTGTTTTTGTAGGGTGAGAAGCGTCCAAGCCAGAACGA-BK (SEQ ID NO: 211) |
| (cZip 46) RARb 244Mcom | pGGGTAGGGTTTATTGAAAGTTTATTTGTATATATTAGGTAACATCCAAGGTCCGACACGCAACGA-BK (SEQ ID NO: 212) |
| (cZip 47) RARb 411Mcom | pGAGAATGTGAGTGATTTGAGTAGGGTTTCGACGATTCGCATCAACGCAAG-BK (SEQ ID NO: 213) |
| RASSF1 | |
| RASSF1 423T | Cy5-GGTTTGTGTTTGTTAGTGTTTAAAGTTAGT (SEQ ID NO: 214) |
| RASSF1 518T | Cy5-GGTGTGTTGGGAAGGGTTGTATTT (SEQ ID NO: 215) |
| RASSF1 593T | Cy5-TGTGTAATTTTATATGGTAGTTGGTTTTTGGTT (SEQ ID NO: 216) |
| RASSF1 423C | Cy3-GTTCGCGTTTGTTAGCGTTTAAAGTTAGC (SEQ ID NO: 217) |
| RASSF1 518C | Cy3-GGCGCGTTGGGAAGGGTCGTATTC (SEQ ID NO: 218) |
| RASSF1 593C | Cy3-CGTGTAATTTTATACGGTAGTTGGTTTTTGGTC (SEQ ID NO: 219) |
| (cZip 48) RASSF1 423Mcom | pGAAGTACGGGTTTAATCGGGTTATGTCGGGAACGGGGAAGGTTGAGCGTGACAG-BK (SEQ ID NO: 220) |
| (cZip 49) RASSF1 518Mcom | pGGTTGGAGCGTGTTAACGCGTTGCGCACTGCACACGAAACGGCACACAG-BK (SEQ ID NO: 221) |
| (cZip 50) RASSF1 593Mcom | pGTGGTTATCGTTTTTAGTTCGCGGGGTTTACCGACATCCTGGGATTGCATGG-BK (SEQ ID NO: 222) |
| TIMP3 | |
| TIMP3 288T | Cy5-GGTTAGGGTGTAGATGAGAAGGGGTAT (SEQ ID NO: 223) |
| TIMP3 363T | Cy5-GTGTGTTTTAGTTTATTTATTTGTGTGTTTAT (SEQ ID NO: 224) |
| TIMP3 456T | Cy5-TTTGGTTTTGTTTTTTTTGGAGGGTT (SEQ ID NO: 225) |
| TIMP3 288C | Cy3-GGTTAGGGCGTAGACGAGAAGGGGTAC (SEQ ID NO: 226) |
| TIMP3 363C | Cy3-GCGCGTTTTAGTTTATTTATTCGCGTGTTTAC (SEQ ID NO: 227) |
| TIMP3 456C | Cy3-TTCGGTTTCGTTTTTTTTTGGAGGGTC (SEQ ID NO: 228) |
| (cZip 51) TIMP3 288Mcom | pGAGGGTTTTGTTTTGAGGATTTAGTGGACTCCGCATTGCCAGAGCTGATGG-BK (SEQ ID NO: 229) |
| (cZip 52) TIMP3 363Mcom | pGGTGGTATTATTTTTTATAAGGATTTGAATGATTTGCGATGGCTTCCTTACCCAGATTCG-BK (SEQ ID NO: 230) |

TABLE 5-continued

| Primers | Sequence (5' to 3') |
|---|---|
| (cZip 53) TIMP3 456Mcom | pGATGAGGTAATGTGGTTTTGTTATTGGTTTGACGCATTCGATGGACAG GACATTCG-BK (SEQ ID NO: 231) |

Each of the discriminating probes contains a label on the 5' end (such as a fluorescent label) and the 3' nucleotide discriminates the methylation status of a given cytosine. The useful labels include chromophores, fluorescent moieties, enzymes, antigens, heavy metals, magnetic probes, infrared dyes, phosphorescent groups, radioactive materials, chemiluminescent moieties, and electrochemical detecting moieties.

In this aspect of the present invention, the second oligonucleotide probe of each set has an addressable array-specific portion. A solid support is provided with different capture oligonucleotides immobilized at different particular sites, where the capture oligonucleotides have nucleotide sequences complementary to the addressable array-specific portions. After being subjecting to one or more ligase detection reaction cycles, the ligase detection reaction mixture is contacted with the solid support under conditions effective to hybridize the ligation product sequences to the capture oligonucleotides in a base-specific manner (i.e. at a temperature of 45-90° C. for a period of up to 60 minutes).

Hybridization may be accelerated by adding volume exclusion or chaotropic agents. When an array consists of dozens to hundreds of addresses, it is important that the correct ligation products have an opportunity to hybridize to the appropriate address. This may be achieved by the thermal motion of oligonucleotides at the high temperatures used, by mechanical movement of the fluid in contact with the array surface, or by moving the oligonucleotides across the array by electric fields. After hybridization, the array is washed sequentially with a low stringency wash buffer and then a high stringency wash buffer.

It is important to select capture oligonucleotide probes and addressable array-specific portions which will hybridize in a stable fashion. This requires that the oligonucleotide probe sets and the capture oligonucleotides be configured so that the oligonucleotide sets hybridize to the target nucleic acid molecules at a temperature less than that which the capture oligonucleotides hybridize to the addressable array-specific portions. Unless the oligonucleotides are designed in this fashion, false positive signals may result due to capture of adjacent unreacted oligonucleotides from the same oligonucleotide set which are hybridized to the target.

The solid support can be made from a wide variety of materials. The substrate may be biological, nonbiological, organic, inorganic, or a combination of any of these, existing as particles, strands, precipitates, gels, sheets, tubing, spheres, containers, capillaries, pads, slices, films, plates, slides, discs, membranes, etc. The substrate may have any convenient shape, such as a disc, square, circle, etc. The substrate is preferably flat but may take on a variety of alternative surface configurations. For example, the substrate may contain raised or depressed regions on which the synthesis takes place. The substrate and its surface preferably form a rigid support on which to carry out the reactions described herein. The substrate and its surface is also chosen to provide appropriate light-absorbing characteristics. For instance, the substrate may be a polymerized Langmuir Blodgett film, functionalized glass, Si, Ge, GaAs, GaP, $SiO_2$, $SiN_4$, modified silicon, or any one of a wide variety of gels or polymers such as (poly)tetrafluoroethylene, (poly)vinylidenedifluoride, polystyrene, polycarbonate, polyethylene, polypropylene, polyvinyl chloride, poly(methyl acrylate), poly(methyl methacrylate), or combinations thereof. Other substrate materials will be readily apparent to those of ordinary skill in the art upon review of this disclosure. In a preferred embodiment, the substrate is flat glass or single-crystal silicon.

A variety of commercially-available materials, which include suitably modified glass, plastic, or carbohydrate surfaces or a variety of membranes, can be used. Depending on the material, surface functional groups (e.g., silanol, hydroxyl, carboxyl, amino) may be present from the outset (perhaps as part of the coating polymer), or will require a separate procedure (e.g., plasma amination, chromic acid oxidation, treatment with a functionalized side chain alkyltrichlorosilane) for introduction of the functional group.

The surface of the functionalized substrate is preferably provided with a layer of linker molecules, although it will be understood that the linker molecules are not required elements of the invention. The linker molecules are preferably of sufficient length to permit polymers in a completed substrate to interact freely with molecules exposed to the substrate. The linker molecules should be 6-50 atoms long to provide sufficient exposure. The linker molecules may be, for example, aryl acetylene, ethylene glycol oligomers containing 2-10 monomer units, diamines, diacids, amino acids, or combinations thereof.

Further details regarding solid supports, functional groups, and linkers are set forth in U.S. patent application Ser. No. 08/794,851 to Barany et. al., and WO 97/31256 to Barany et. al., which are hereby incorporated by reference in their entirety. Techniques for improving the performance of addressable arrays is set forth in U.S. Pat. No. 6,506,594 to Barany et. al., which is hereby incorporated by reference in its entirety.

As a result, the addressable array-specific portions are captured on the solid support at the site with the complementary capture oligonucleotide. The presence of ligation product sequences captured using the addressable array-specific portions and immobilized to the solid support at particular sites indicates the presence of one or more target nucleotide sequences in the sample. This embodiment of the present invention is shown in FIGS. 1, 3, 4, 6, and 8. In FIGS. 1 and 3, the results show that the sample contains a nucleic acid with a methylated cytosine at methylation site 1 and an unmethylated cytosine at methylation site 2. On the other hand, FIGS. 4, 6, and 8 depict the results achieved when the sample contains a nucleic acid with a methylated cytosine at methylation site 2 and an unmethylated cytosine at methylation site 6.

Alternatively, the LDR probes may be designed such that the products have different mobility when separated by gel or capillary electrophoresis, and products are separated and distinguished by their unique fluorescent label and their size or electrophoretic mobility (See e.g., FIGS. 2, 5, 7, and 9). Day, D., et al., *Genomics,* 29:152-162 (1995), Belgrader, et al., *Genome Science and Technology,* 1:77-87 (1996); and Day, D. J., et al., *Human Molecular Genetics,* 5:2039-2048 (1996), which are hereby incorporated by reference in their entirety. In FIG. 2, the results show that the sample contains a nucleic acid with a methylated cytosine at methylation site 1 and an unmethylated cytosine at methylation site 2. On the other hand, FIGS. 5, 7, and 9 depict the results achieved when the sample contains a nucleic acid with a methylated cytosine at methylation site 2 and an unmethylated cytosine at methylation site 6.

The ligase used in this invention is a thermostable ligase, such as *Thermus thermophilus, Thermus species* AK16D, *Thermus aquaticus, Pyrococcus furiosus,* or *Thermotoga maritima.* The thermostable ligase may be derived from *Thermus thermophilus* or it can be prepared recombinantly. Procedures for such isolation as well as the recombinant production of *Thermus thermophilus* ligase as well as *Thermus aquaticus* ligase are disclosed in WO 90/17239 to Barany et. al., and F. Barany, et al., "Cloning, Expression and Nucleotide Sequence of a Thermostable DNA-Ligase Encoding Gene," *Gene* 109: 1-11 (1991), M. Takahashi, et al., "Thermophillic DNA Ligase," *J. Biol. Chem.* 259: 10041-47 (1984), Tong, J., et al. *Nucleic Acids Research* 27:788-794 (1999), which are hereby incorporated by reference. Some of these references contain complete sequence information for this ligase as well as the encoding DNA. Other suitable ligases include, without limitation, *E. coli* ligase, T4 ligase, *Thermus* sp. AK16 ligase (WO 00/26381 to Barany et al., which is hereby incorporated by reference), *Aquifex aeolicus* ligase, *Thermotoga maritima* ligase, and *Pyrococcus* ligase. The ligation detection reaction mixture may include a carrier DNA, such as salmon sperm DNA.

The method of the present invention is used to distinguish a presence of low abundance methylated target nucleic acid molecule in the sample from a presence of a majority of unmethylated target nucleic acid molecule in the sample. This may involve situations where the presence of low abundance methylated target nucleic acid molecule in the sample may be distinguished in the presence of a 10 to 100-fold excess, preferably 10 to 1,000-fold excess, more preferably 100 to 10,000-fold excess, and most preferably 10,000 to 100,000-excess of unmethylated target nucleic acid molecules, in the sample.

To ensure the scoring accuracy of a methylated promoter region, six additional LDR probes were designed (three discriminating probes and three common probes, shown in Table 6) to interrogate the methylation status of three additional CpG sites in the same PCR product.

Table 6 shows additional LDR probe sequences used to interrogate the methylated cytosines in the CpG dinucleotides of an individual promoter region. The Cy3 labeled LDR probes detect methylated cytosines and ending with C at the very 3' end. The corresponded zip address of each common probe (probe where zip code-complement attaches) is indicated in the parenthesis. Note that nucleotide analogs dK and dP were not used in the probe syntheses.

TABLE 6

| Primers | Sequence (5' to 3') |
|---|---|
| APC 570C | Cy3-TGTTAATTTTTTGTTTTGCGGATTTTTTC (SEQ ID NO: 232) |
| APC 645C | Cy3-GGGATTGGGGTCGTGAGGGTATATTTTC (SEQ ID NO: 233) |
| APC760C | Cy3-AGAGAGAAGTAGTTGTGTAATTCGTTGGATGC (SEQ ID NO: 234) |
| (cZip 27) APC 570Mcom | pGATTTTTTATTATGCGTGTTAATTGTTATTAATTTTTTGTTTGGCAC CGTGAACGACAGTTGCGATT-BK (SEQ ID NO: 235) |
| (cZip28) APC 645Mcom | pGAGGGGTACGGGGTTAGGGTTAGGTAGGTTCGCAGGTCGCTGCGTGTC CTGATT-BK (SEQ ID NO: 236) |
| (cZip29) APC 760Mcom | pGGATTAGGGCGTTTTTTATTTTCGTCGGGCGCAAAGCAGACACAGGGT CGATT-BK (SEQ ID NO: 237) |
| DAPK | |
| DAPK 313C | Cy3-AGGCGGTAAGGAGTCGAGAGGTTGTTTC (SEQ ID NO: 238) |
| DAPK 429Cb | Cy3-GGTCGGCGTTTGGGAGGGATTTGC (SEQ ID NO: 239) |
| DAPK 507C | Cy3-GCGTTGGCGTTTATGGTCGGTTTTC (SEQ ID NO: 240) |
| (cZip 57) DAPK 313Mcom | pGGAGTGTGAGGAGGATAGTCGGATCGAGAAGCAAGCCAAGGTATGGCT TTGC-BK (SEQ ID NO: 241) |
| (cZip 58) DAPK 429Mcom | pGTTTTTTATTTATTTTTAGTTGTGTTTTCGTCGTCGTTTTCGGCTGT TCGTAGGCAAGAGGT-BK (SEQ ID NO: 242) |
| (cZip 59) DAPK 507Mcom | pGATAGCGTTTCGGAGGGATCGGGGTAGGGCACATGGGCACTTGCAGG T-BK (SEQ ID NO: 243) |
| ECAD | |
| ECAD 378C | Cy3-GGGGTTAGAGGATCGTTTGAGTTTAGGAGTTC (SEQ ID NO: 244) |
| ECAD 548C | Cy3-GTTATCGGCGGGGTTGGGATTC (SEQ ID NO: 245) |

TABLE 6-continued

| Primers | Sequence (5' to 3') |
|---|---|
| ECAD 647C | Cy3-GTTTATGCGAGGTCGGGTGGGC (SEQ ID NO: 246) |
| (cZip 60) ECAD 378Mcom | pGAGGTTGTAGTGAGTTGTGATCGTATTATTGTATTTTAGTTTGTTCGG GGAGTCCGGTCCAGATCCT-BK (SEQ ID NO: 247) |
| (cZip 61) ECAD 548Mcom | pGAATTTAGTGGAATTAGAATCGTGTAGGTTTTATAATTTATTTAGGCT CGTGTGTAGCTGCCGTTCCT-BK (SEQ ID NO: 248) |
| (cZip 62) ECAD 647Mcom | pGGGTCGTTAGTTTCGTTTTGGGGAGGGGTCAAGCGCTGAGGTGGTCCA TC-BK (SEQ ID NO: 249) |
| GSTP1 | |
| GSTP 938C | Cy3-CGCGATGTTTCGGCGCGTTAGTTC (SEQ ID NO: 250) |
| GSTP 1063C | Cy3-GGCGATTTCGGGGATTTTAGGGC (SEQ ID NO: 251) |
| GSTP 1203C | Cy3-GCGGGGCGGGATTATTTTTATAAGGTTC (SEQ ID NO: 252) |
| (cZip 39) GSTP 938MCom | pGTTGCGTATATTTCGTTGCGGTTTTTTTTTTGCGTGGCTGACTCGCTG CGATGACA-BK (SEQ ID NO: 253) |
| (cZip 40) GSTP 1063MCom | pGTTTTTTTGCGGTCGACGTTCGGGTTGCGCACCATCAGGTTAGGGAC A-BK (SEQ ID NO: 254) |
| (cZip 41) GSTP 1203MCom | pGGAGGTCGCGAGGTTTTCGTTGGAGCACCGATATGGAGACCGCAGAC A-BK (SEQ ID NO: 255) |
| MGMT | |
| MGMT 196C | Cy3-GTTTCGAGTAGGATCGGGATTTTTATTAAGC (SEQ ID NO: 256) |
| MGMT 253C | Cy3-TTTTTAGGATTATTCGGGTACGTGGTAGGTC (SEQ ID NO: 257) |
| MGMT 331C | Cy3-CGGGTTATTTGGTAAATTAAGGTATAGAGTTTTAGGC (SEQ ID NO: 258) |
| (cZip 42) MGMT 196MCom | pGGGCGTCGTTTTACGATTTTCGCGCATCGACAAGGTAACGCGTGGAC A-BK (SEQ ID NO: 259) |
| (cZip 43) MGMT 253MCom | pGTTTGTACGTTCGCGGATTATTTTTGTGATAGGTGAGCGCAAGGTCAG AGCACGACA-BK (SEQ ID NO: 260) |
| (cZip 44) MGMT 331MCom | pGGAAGTTGGGAAGGCGTCGTTCGGAAGCCGCAGCACGATTCCGTGAC A-BK (SEQ ID NO: 261) |
| RARb | |
| RARb 123C | Cy3-AATAGGAAAGAAAACGTCGGTTTGTGC (SEQ ID NO: 262) |
| RARb 258C | Cy3-TATTTGAAGGTTAGTAGTTCGGGTAGGGTTTATC (SEQ ID NO: 263) |
| RARb 450C | Cy3-AGCGATTCGAGTAGGGTTTGTTTGGGTATC (SEQ ID NO: 264) |
| (cZip 45) RARb 123Mcom | pGTTCGTTGTTTGTTTTTTTGGTTGTTTGTTTTTGTGAGAAGCGTCCAA GCCAGAACGA-BK (SEQ ID NO: 265) |
| (cZip 46) RARb 258Mcom | pGAAAGTTTATTCGTATATATTAGGTAATTTAATTTTTTATTTGTGTG CATCCAAGGTCCGACACGCAACGA-BK (SEQ ID NO: 266) |
| (cZip 47) RARb 450Mcom | pGTCGGGGTAGGATTCGGAACGTATTCGTTCGACGATTCGCATCAACGC AAG-BK (SEQ ID NO: 267) |
| RASSF1 | |
| RASSF1 410C | Cy3-TTTCGTTCGGTTCGCGTTTGTTAGC (SEQ ID NO: 268) |
| RASSF1 512C | Cy3-TTGGGCGCGTTGGGAAGGGTC (SEQ ID NO: 269) |
| RASSF1 602C | Cy3-ATACGGTAGTTGGTTTTTGGTCGTGGTTATC (SEQ ID NO: 270) |
| (cZip 48) RASSF1 410Mcom | pGTTTAAAGTTAGCGAAGTACGGGTTTAATCGGGTAACGGGGAAGGTTG AGCGTGACAG-BK (SEQ ID NO: 271) |
| (cZip 49) RASSF1 512Mcom | pGTATTCGGTTGGAGCGTGTTAACGCGTCACTGCACACGAAACGGCACA CAG-BK (SEQ ID NO: 272) |

TABLE 6-continued

| Primers | Sequence (5' to 3') |
|---|---|
| cZip 50) RASSF1 602Mcom | pGTTTTTAGTTCGCGGGGTTCGTTACGTATTACCGACATCCTGGGATTG CATGG-BK (SEQ ID NO: 273) |
| TIMP3 | |
| TIMP3 297C | Cy3-GTAGACGAGAAGGGGTACGAGGGTTTC (SEQ ID NO: 274) |
| TIMP3 437C | Cy3-TTTCGTTTCGTTATTTTTTGTTTTCGGTTTC (SEQ ID NO: 275) |
| TIMP3 494C | Cy3-CGGTTTTGTTATTGGTTTGAGGGGGC (SEQ ID NO: 276) |
| (cZip 54) TIMP3 297Mcom | pGTTTCGAGGATTTAGCGGTAAGTATCGGTTTCGGGCTACGACGCATGT AAACGTTCG-BK (SEQ ID NO: 277) |
| (cZip 55) TIMP3 437Mcom | pGTTTTTTTTTTGGAGGGTCGATGAGGTAATGCGTCCCAAGTTGCGGCT CACTTTCG-BK (SEQ ID NO: 278) |
| (cZip 56) TIMP3 494Mcom | pGGGTTTTAATAGTTCGAGGCGGGGTTTTCGTGCGCACACTCACTGTCC TTCG-BK (SEQ ID NO: 279) |
| p16 Ex1 | |
| p16 Ex1 364C | Cy3-CGTCGTTCGTTGTTTGTTTTTTTTTTTC (SEQ ID NO: 280) |
| p16 Ex1 456C | Cy3-TTATTCGATTTCGGGTCGCGGTC (SEQ ID NO: 281) |
| p16 Ex1 525C | Cy3-TATTTGGATCGGTTTTCGATCGTAATTATTC (SEQ ID NO: 282) |
| (cZip 15) p16Ex1 364Mcom | pGTAGTCGTCGAGCGTACGCGGTTCGTGCTGGCTGGCACGCACCAGAAT CA-BK (SEQ ID NO: 283) |
| (cZip 16) p16Ex1 456Mcom | pGTGGTTAGTTAGTTAGTCGAAGGTTTTATGTTGTTTTCGGGCTCCGT CAGAAAGCGACAATCA-BK (SEQ ID NO: 284) |
| (cZip 17) p16Ex1 525Mcom | pGGTGCGTTGGGTAGCGTTTTCGTTTTTACGAGGGATACCCGCAAACGA TCA-BK (SEQ ID NO: 285) |
| p19 Ex1 | |
| p19 Ex1 618C | Cy3-ATGTTTTCGTCGTTTTTAGGGTCGAGTTC (SEQ ID NO: 286) |
| p19 Ex1 714C | Cy3-TTTCGTGAGTCGCGGGATGTGAATTAC (SEQ ID NO: 287) |
| p19 Ex1 780C | Cy3-GTTGTTGTTTTAGACGTTGGTTTTTTAGTAGTATTAGTAC (SEQ ID NO: 288) |
| (cZip 21) p19Ex1 618Mcom | pGGTAGTCGTTGCGTCGTTTTTTGGTATTAGAGTCCGTCCATGGCAAGC GTGATCA-BK (SEQ ID NO: 289) |
| (cZip 22) p19Ex1 714Mcom | pGAAAATTTTTATTCGCGGCGGGTCGTGGCTGCACCCGTTGAGGCACAT CA-BK (SEQ ID NO: 290) |
| (cZip 23) p19Ex1 780Mcom | pGAGGGTTATAGCGGCGGGCGTTTTTCAACATCGGCTAACGGTCCATC A-BK (SEQ ID NO: 291) |

Therefore, the method of the present invention has the capability to use LDR to analyze the methylation status of total six CpG sites for a given PCR fragment. To avoid the LDR probes overlapping each other, these additional LDR probes are pooled and the LDR reactions are done in a separate tube. Therefore, two independent LDR reactions are performed to detect the methylation status of six CpG dinucleotide sites with a given PCR amplified promoter region.

The process of the present invention is capable of distinguishing methylated cytosines from unmethylated ones after bisulfite treatment. This distinction can be made in tumor suppressor genes, cell cycle regulators, DNA mismatch repair genes, genes involved in carcinogenesis, and aging. Such genes include, but are not limited to 14-3-3 Sigma, ABL1 (P1), ABO, APC, AR (Androgen Receptor), BLT1 (Leukotriene B4 Receptor), BRCA1, CALCA (Calcitonin), CASP8 (CASPASE 8), Caveolin 1, CD44, CDH1, CFTR, GNAL, COX2, CSPG2 (Versican), CX26 (Connexin 26), Cyclin A1, DAPK1, DBCCR1, DCIS-1, ECAD (E-cadherin), Endothelin Receptor B, EPHA3, EPO (Erythropoietin), ER (Estrogen Receptor), FHIT, GALNR2, GATA-3, COL9A1, GPC3 (Glypican 3), GST-pi, H19, H-Cadherin (CDH 13), HIC1, hMLH 1, HOXAS, IGF2 (Insulin-Like Growth Factor II), IRF7, KAI1, LKB1, LRP-2 (Megalin), MDGI (Mammary-derived growth inhibitor), MDR1, MDR3 (PGY3), MGMT (O6 methyl guanine methyl transferase), MINT, MT1a (metallothionein 1), MYOD1, N33, NEP (Neutral Endopeptidase 24.1)/CALLA, NF-L (light-neurofilament-encoding gene), NIS (sodium-iodide symporter gene), P15 (CDKN2B), P16 (CDKN2A), P19 (ARF), P21 (CIP1), P27(KIP1), p53, p57 KIP2, p73, PAX6, PgR (Progesterone Receptor), POU3F1, RAR-Beta2, RASSF1, RB1 (Retinoblastoma), RPA2 (replication protein A2), SIM2, TERT, TESTIN, TGFBR1, THBS1 (Thrombospondin-1), TIMP3, TLS3 (T-Plastin), TMEFF2, Urokinase (uPA), VHL (Von-Hippell Lindau), WT1, ZO2 (Zona Occludens 2). See the following web site for list of gene promoter regions which are methylated in various diseases: http://www3.mdanderson.org/leukemia/methylation/

Another aspect of the present invention is the ability to quantify the degree of methylation at a given region for a biological sample. Since the present invention teaches both PCR and LDR probe design which does not bias amplification or detection of methylation status, independent of methylation status of neighboring CpG dinucleotides (i.e. by using nucleotide analogues or degenerate bases within the primer designs), it is possible to quantify methylation status at a given site. For example, a tumor sample is composed of both tumor cells and normal infiltrating cells. Further, the tumor may be heterogeneous, where some portions have invaded into neighboring tissue. Different genes may have undergone methylation silencing during progression of the tumor, and the degree or progression of that silencing may be clinically relevant. Methylation status may be assayed by two related approaches. In the first, the ratio of LDR product arising from methylated to unmethylated DNA (Cy3-sample/Cy5-sample) is determined at each position. This is calibrated against known mixtures of methylated and unmethylated DNA, or synthetic substrates corresponding to the sequence resulting from PCR amplification of methylated and unmethylated DNA, respectively. In the second approach, the ratio of ratios of LDR product arising from methylated to unmethylated DNA of tumor to normal (Cy3-tumor/Cy5-tumor)/(Cy3-normal/Cy5-normal) is determined at each position. This provides an internal control at every position.

The foregoing has focused on tumor progression arising from hypermethylation of genes such as tumor suppressor genes. Tumors may also progress due to hypomethylation, resulting in activation of imprinted growth factor genes, or activation of latent or ancient viral genes (FIGS. 18-21). In each of these embodiments, the process of the present invention is described as above with references to FIGS. 1-9. However, in each case, the results with either normal v. abnormal samples or maternal imprinting v. loss of maternal imprinting are compared. Cui, M., et al., *Science,* 299:1753-1755 (2003), Cui, M., et al., *Cancer Research,* 62: 6442-6446 (2002), which are hereby incorporated by reference in their entirety. In such cases the normal DNA is either hemi-methylated or completely methylated. To determine if hypomethylation has taken place, the ratio of ratios of LDR products arising from unmethylated to methylated DNA of tumor to normal (Cy3-normal/Cy5-normal)/(Cy3-tumor/Cy5-tumor) is determined at each position. If the DNA is completely methylated, low abundance unmethylated DNA may also be detected by using probes biased for preferentially amplifying and detecting unmethylated DNA.

Another aspect of the present invention relates to a method for identifying one or more target nucleic acids in a sample, differing by one or more methlylated cytosine residues. in accordance with this aspect of the present invention, a sample potentially containing one or more target nucleic acid molecules is provided and subjected to a bisulfite treatment to convert, in the nucleic acid molecules of the sample, unmethylated cytosine residues, but not methylated cytosine residues, into uracil residues. One or more primary oligonucleotide primer sets are provided, each set characterized by (a) a first oligonucleotide primer, having a target-specific portion and a 5' upstream secondary primer-specific portion, where the target-specific portion is suitable for hybridization on a first strand of the target nucleic acid molecule in which unmethylated cytosines have been converted to uracil, and (b) a second oligonucleotide primer, having a target-specific portion and a 5' upstream secondary primer-specific portion, where the target-specific portion is suitable for hybridization on a polymerase extension product of the first strand or on a second strand of the target nucleic acid molecule, either of which having unmethylated cytosines converted to uracil. The first and second oligonucleotide primers of each set contain the same 5' upstream secondary primer-specific-portion. Also provided is a polymerase. The sample, the primary oligonucleotide primer set, and the polymerase are blended to form a primary polymerase chain reaction mixture. The primary polymerase chain reaction mixture is subjected to two or more polymerase chain reaction cycles comprising a denaturation treatment, where hybridized nucleic acid sequences are separated, a hybridization treatment, where the target-specific portions of the primary oligonucleotide primer sets hybridize to the target nucleic acid molecules with unmethylated cytosines converted to uracil or to extension products of such modified target nucleic acid molecules, and an extension treatment, where the hybridized primary oligonucleotide primers are extended to form primary extension products complementary to the target nucleic acid molecules with unmethylated cytosines converted to uracil. Also provided is a secondary oligonucleotide primer set characterized by (a) a first secondary primer containing the 5' upstream portion of the first oligonucleotide primer of the primary oligonucleotide primer set, and (b) a second secondary primer containing the 5' upstream portion of the second oligonucleotide primer of the primary oligonucleotide primer set. The primary extension products, the secondary oligonucleotide primer set, and the polymerase are blended to form a secondary polymerase chain reaction mixture. The secondary polymerase chain reaction mixture is subjected to two or more polymerase chain reaction cycles comprising a denaturation treatment, where hybridized nucleic acid sequences are separated, a hybridization treatment, where the secondary oligonucleotide primers hybridize to the primary extension products, and an extension treatment, where the hybridized secondary oligonucleotide primers are extended to form secondary extension products complementary to the primary extension products. One or more tertiary oligonucleotide primer sets are provided, each set characterized by (a) a first oligonucleotide primer, having a target-specific portion and a 5' upstream quaternary primer-specific portion, where the target-specific portion is suitable for and preferentially hybridizes to the secondary extension products that arise when the target nucleic acid molecule is methylated in the region of hybridization, and (b) a second oligonucleotide primer, having a target-specific portion and a 5' upstream quaternary primer-specific portion, where the target-specific portion is suitable for and preferentially hybridizes to the secondary extension products that arise when the target nucleic acid molecule is methylated in the region of hybridization, to permit formation of a polymerase chain reaction product, but have a mismatch which interferes with formation of such a polymerase chain reaction product when hybridized to any other nucleic acid molecule present in the sample. The secondary polymerase chain reaction mixture, the tertiary oligonucleotide primers, and the polymerase are blended to form a tertiary polymerase chain reaction mixture. The tertiary polymerase chain reaction mixture to two or more polymerase chain reaction cycles comprising a denaturation treatment, where hybridized nucleic acid sequences are separated, a hybridization treatment, where the target-specific portions of the tertiary oligonucleotide primers hybridize to the secondary extension products, and an extension treatment, where the hybridized tertiary oligonucleotide primers are extended to form tertiary extension products complementary to the target nucleic acid molecule to which a tertiary oligonucleotide primer is hybridized. A quaternary oligonucleotide primer set is provided which is characterized by (a) a first quaternary oligonucleotide primer containing the same sequence as the 5' upstream quaternary primer-specific portion of a first oligonucleotide primer of the tertiary oligonucleotide primer set, and (b) a second quaternary oligonucleotide primer containing the same sequence as the 5' upstream quaternary primer-specific portion of a second oligonucleotide primer of the tertiary oligonucleotide primer set, where a set of quaternary oligonucleotide primers may be used to amplify all of the tertiary extension products. The tertiary extension products, the quaternary oligonucleotide primers, and the polymerase are blended to form a quaternary polymerase chain reaction mixture. The quaternary polymerase chain reaction mixture is subjected to two or more polymerase chain reaction cycles comprising a denaturation treatment, where hybridized nucleic acid sequences are separated, a hybridization treatment, where the quaternary oligonucleotide primers hybridize to the tertiary extension products, and an extension treatment, where the hybridized quaternary oligonucleotide primers are extended to form quaternary extension products complementary to the tertiary extension products. A plurality of oligonucleotide probe sets are provided with each set characterized by (a) a first oligonucleotide probe, having a quaternary extension product-specific portion and a detectable reporter label, and (b) a second oligonucleotide probe, having a quarternary extension product-specific portion, where the oligonucleotide probes in a particular set are suitable for ligation together when hybridized on a complementary quarternary extension product, but have a mismatch which interferes with such ligation when hybridized to any other nucleic acid molecule present in the sample. A ligase is provided, and the quarternary extension products, the plurality of oligonucleotide probe sets, and the ligase are blended to form a ligase detection reaction mixture. The ligase detection reaction mixture is subjected to one or more ligase detection reaction cycles comprising a denaturation treatment, where any hybridized oligonucleotides are separated from the quarternary extension product, and a hybridization treatment, where the oligonucleotide probe sets hybridize in a base-specific manner to their respective quarternary extension products, if present, and ligate to one another to form a ligation product containing (a) the detectable reporter label and (b) the quarternary extension product-specific portions connected together. The oligonucleotide probe sets may hybridize to nucleic acid molecules but do not ligate together due to a presence of one or more mismatches and individually separate during the denaturation treatment. The reporter labels of the ligation products are detected, thereby indicating the presence of two or more methylated cytosine bases in the target nucleotide sequences in the sample.

FIGS. 25-30 are schematic drawings illustrating the process of the present invention. This scheme has the benefit of retaining the multiplex capability for high-throughput analysis of all the promoter regions. In this embodiment of the process of the present invention, steps 1-4 and 7-8, as depicted in FIGS. 25-30, are substantially the same as steps 1-4 and 5-6, respectively in the embodiment shown in FIGS. 1-9.

The first step of the present invention, as shown in FIGS. 25-30, is the preparation of sodium bisulfite modified genomic DNAs. In the preferred embodiment, genomic DNA is incubated with bisulfite and hydroquinone solution for 15-20 hours, more preferably 16 hours, in a DNA thermal cycler (Perkin Elmer Cetus, Boston, Mass.) with the cycles of 50° C. for 20 minutes followed by a denaturing step of 85° C. for 15 seconds. The bisulfite treated DNA can be desalted with MICROCON centrifugal filter devices (Millipore, Bedford, Mass.) or, alternatively, Wizard DNA clean-up kit (Promega, Madison, Wis.) can be used. The desalted DNA is ethanol precipitated and the DNA pellet is resuspended in deionized $H_2O$ or proper buffer for further PCR amplification.

In the second step, a primary non-selective PCR prior to a nested and selective methylation-specific PCR amplification are employed. Two PCR primers are designed with Tm around 70° C. to hybridize to the complementary sequence of each of the interested bisulfite modified promoter region. Each of the PCR primer consists of a gene-specific 3' portion and an upstream first universal sequence. The amplification is done in a multiplex format to increase the assay throughput. The PCR primers are designed in the promoter region that can give the optimal PCR amplification, regardless of the number of CpG dinucleotide sites present in that region. At least 3 or more promoter regions can be multiplex amplified in one PCR reaction.

In the preferred embodiment, the same first universal primer is used on both the upstream and downstream primers of each PCR primer pair. By using the same universal primer on both sides of the amplicon in the second PCR step, spurious amplifications from primer dimers are eliminated. If a primer dimer accidentally forms, it creates a panhandle structure upon denaturation/renaturation, and this inhibits binding of a first universal primer, and thus does not amplify. While authentic amplicons also have the same universal sequence on both ends, these are far enough apart such that primer hybridization effectively competes against internal (panhandle) hybridization. In the preferred embodiment, the PCR primers are designed so their 3' ends are between 150 and 500 bp apart. The concentration of the initial PCR primers may be adjusted to assist in obtaining approximately equal amplifications of all the PCR amplicons. Further, by using LDR to score methylation status of a particular amplicon, false PCR products are not detected and, consequently, do not interfere with the proper interpretation of the results.

Figure 27:
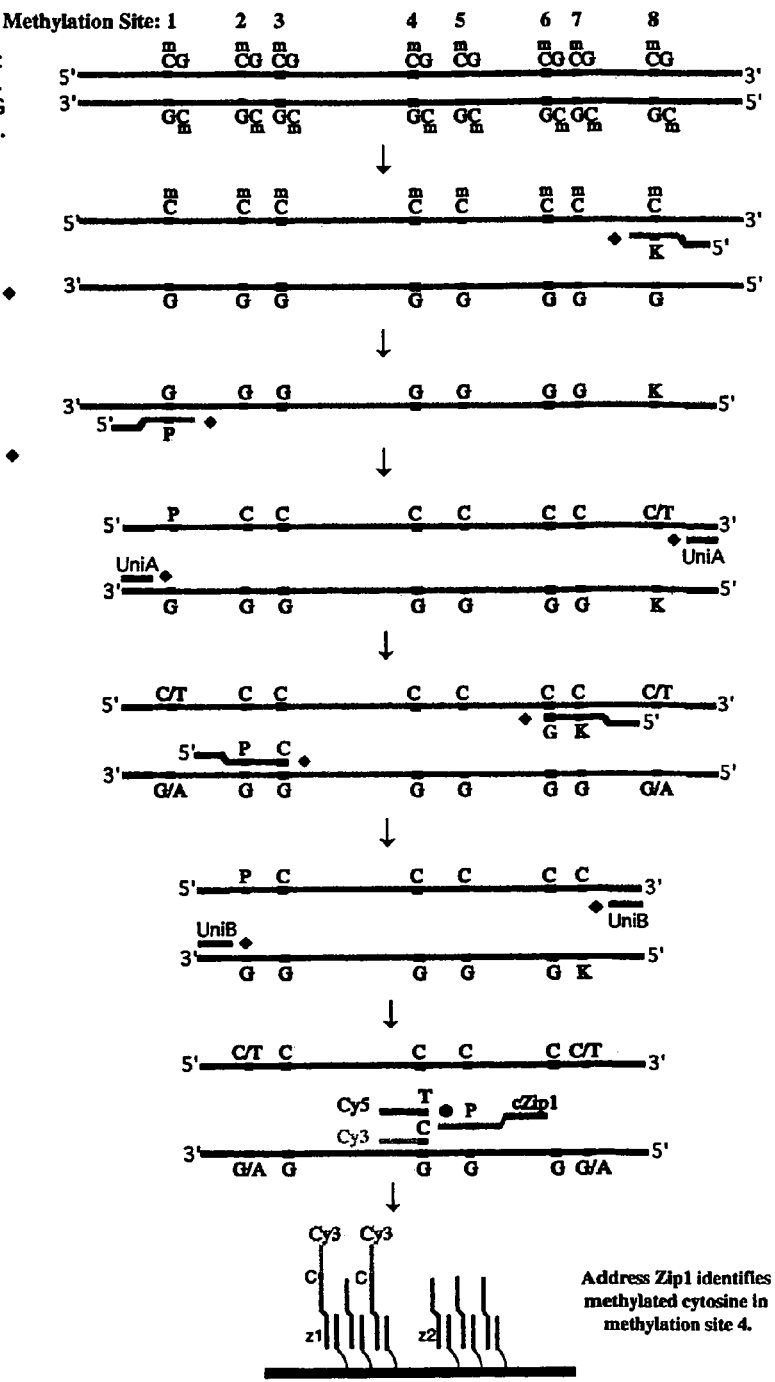
FIG. 27 is a schematic diagram illustrating the Bisulfite/PCR-PCR/MS-PCR-PCR/LDR/Universal Array procedure for high-throughput detection of promoter methylation status of low abundance methylation alleles in a given sample. This procedure consists of bisulfite treatment of genomic DNA, multiplex PCR with gene specific/universal primers (A), methylation specific multiplex PCR with methyl-specific/universal primers (B), multiplex LDR, and universal array approaches. The methyl-specific/universal PCR primer has the discriminating 3'OH base pairing to the cytosine of CpG dinucleotides (or pairing the guanine if it is on the opposite DNA strand) to ensure the selection of methylated alleles. Nucleotide analogs dK and dP are introduced in the multiplex PCR (both gene-specific and methyl-specific primers) and LDR probe designs. These analog-containing oligonucleotide primers have the capability of hybridizing to DNA sequences regardless whether the templates are fully or partially methylated. Notice that in this approach, as shown in this figure, the identification of a methylated cytosine at methylation site 4 requires methylated cytosines at sites 3 and 6.

Nucleotide analogs dK and dP are used in the PCR and LDR probe syntheses as depicted in FIGS. 27 and 28 that will hybridize with similar efficiency to DNA sequences containing bisulfite treated CpG dinucleotides, regardless of whether that initial CpG dinucleotide was fully methylated, partially methylated, or un-methylated,. The pyrimidine derivative dP, when introduced into oligonucleotide primers (at methylation sites 1, 2, and 5), base pair with either A or G, while the purine derivative dK (at methylation sites 7 and 8) base pairs with either C or T. Those nucleotide positions in the PCR primers that specifically base pair to cytosine of CpG dinucleotides are synthesized with the dK analogue. Those nucleotide positions that specifically base pair to the nucleotides complementary to the cytosine of CpG dinucleotides are synthesized with the dP analogue. Note that the identification of a methylated cytosine at methylation site 4 requires methylated cytosines at methylation sites 3 and 6.

Figure 30:
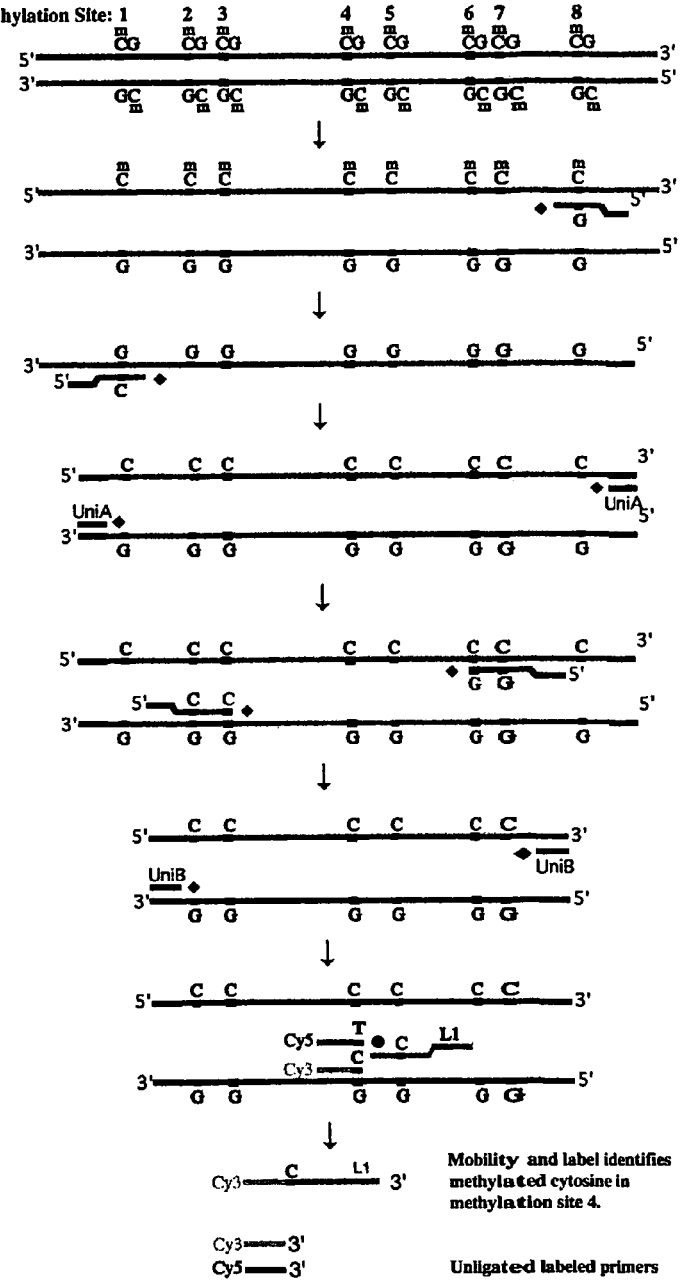
FIG. 30 is a schematic diagram illustrating the Bisulfite/PCR-PCR/MS-PCR-PCR/LDR/capillary electrophoresis procedure for high-throughput detection of promoter methylation status of low abundance methylation alleles in a given sample. This procedure consists of bisulfite treatment of genomic DNA, multiplex PCR with gene specific/universal primers (A), methylation specific multiplex PCR with methyl-specific/universal primers (B), multiplex LDR, and capillary electrophoresis approaches. The methyl-specific/universal PCR primer has the discriminating 3'OH base pairing to the cytosine of CpG dinucleotides (or pairing the guanine if it is on the opposite DNA strand) to ensure the selection of methylated alleles. Nucleotides G and C are used in the designs of multiplex PCR (both gene-specific and methyl-specific) and LDR probes. The hybridization of such probes with their DNA template results in the C:G Watson-Crick base pairings on methylated sequences, yet G:T wobble base pairings and C:A mismatches on unmethylated sequences occur. The designs of these probes have the advantage of preferentially selecting fully methylated DNA sequences. Notice that in this approach, as shown in the diagram, the identification of a methylated cytosine at methylation site 4 requires methylated cytosines at sites 3 and 6. Further, the methylated cytosines at methylation sites 1, 2, 5, 7, and 8 provide additional selective power for methylated alleles since these positions are located in the middle of oligonucleotide probes.

Alternatively, those nucleotide positions of primers where dK and dP can be incorporated (see methylation sites 1, 2, 5, 7, and 8 in FIGS. 27 and 28) are substituted by nucleotides dG and dC, respectively, to make the PCR amplification preferential for methylated alleles. As shown in FIGS. 29 and 30, the substituted nucleotide dG (at methylation sites 7 and 8) in the PCR primer can form either a Watson-Crick base pair to C (if it is methylated) or a wobble base pair to U (if it is unmethylated) of the bisulfite treated DNA template. The substituted nucleotide dC (at methylation sites 1 and 2) in the reverse PCR primer can form either a Watson-Crick base pair to G (if it is methylated) or mismatch pairing to A (if it is unmethylated) of the extension product of the first PCR primer. Note that the identification of a methylated cytosine at methylation site 4 requires methylated cytosines at methylation sites 3 and 6. Primers designed in this way provide additional selective power for methylated alleles since these positions are located in the middle of oligonucleotide primers (sites 1, 2, 5, 7, and 8).

Steps 5 and 6, as depicted in FIGS. 25-30, show a methylation-specific ("MS") PCR amplification step and a second universal PCR amplification step using different universal primers than in the first universal PCR amplification step, respectively.

The methylation-specific PCR primers hybridize to regions containing one or more CpG dinucleotides. Furthermore the 3' nucleotide of each primer was designed to end on a cytosine of a CpG dinucleotide. Thus, the methyl-specific PCR primer is suitable for hybridization on the complementary strands of the target PCR products that arise from originally methylated target DNA that was treated to convert unmethylated cytosines into uracils, but are not suitable for hybridization on the complementary strands of the target PCR products that arise from originally unmethylated target DNA that was treated to convert unmethylated cytosines into uracils. This ensures enrichment of the originally methylated alleles during this methyl-specific PCR amplification. Each of the PCR primers consists of a gene-specific 3' portion and a second upstream universal sequence.

After methylation-specific PCR amplification (i.e. step 5 shown in FIGS. 25-30), all target regions are simultaneously amplified with a second universal primer, as shown in step 6 of FIGS. 25-30. In step 6, the annealing temperature of the universal PCR reaction is lower than that used for methylation-specific PCR amplification. This ensures that all of the full length PCT products are amplified at a similar efficiency. Proteinase K (Qiagen, Valencia, Calif.) may be added at the end of the second round of multiplex PCR to inactivate any remaining thermostable polymerase.

In the embodiment of FIGS. 25-30, the subsequent LDR procedure is carried out in a manner as described above with reference to the embodiment of FIGS. 1-9.

In contrast to Methylation Specific PCR (MSP)-based methods, the bisulfite/PCR/LDR approaches circumvent the issues of incomplete bisulfite conversion (C to U deamination is not 100% efficient) and the potential primer extension of unmethylated DNA by extension of a G:U mismatch. The requirement of scoring methylation at 3 to 6 CpG sites per promoter using LDR allows the assay to retain its exquisite specificity. Note that this assay requires methylation at a total of (at least) 5 sites within the promoter region; at least two sites that are covered by the methyl specific PCR primers, and three sites covered by the methyl specific LDR probes.

Another variation of this method is to use MS-PCR/PCR in the first PCR amplification (in steps 2 and 3) following bisulfite treatment, as depicted in FIGS. 34-39. This early MS-PCR/PCR procedure is carried out in substantially the same manner as described above with reference to the MS-PCR/PCR procedure depicted in FIGS. 25-30. As noted above, this initial MS-PCR/PCR procedure may result in some amplification of unmethylated DNA; however, the second MS-PCR/PCR and subsequent LDR detection steps will insure that only authentic methylated promoter sequences are scored positive. Since this approach incorporates two rounds of selection for methylated sequences, the sensitivity may approach 1 in $10^6$ DNA molecules or better and, thus, may be ideal for detection of circulating tumor cells in bodily fluids such as urine or blood.

Detecting DNA Methylation Status Using Methyl Sensitive Restriction Endonucleases.

Another aspect of the present invention is directed to a method for identifying, in sample, one or more target nucleic acid molecules differing by one or more methylated cytosine residues. In carrying out this method, a sample potentially containing one or more target nucleic acid molecules and a restriction endonuclease that cleaves the one or more target nucleic acid moldules at an unmethylated cytosine residue, does not cleave the one or more target nucleic acid molecules at a methylated cytosine residue on both strands, and does not nick a heteroduplex comprising one strand containing a methylated cytosine residue and one strand containing an unmethylated cytosine residue, are provided. The sample, and the restriction endonuclease are blended to form a primary restriction endonuclease reaction mixture. The restriction endonuclease reaction mixture is subjected to enzymatic digestion conditions effective to cut the majority of the one or more target nucleic acid molecules at an unmethylated cytosine residue while leaving the one or more target nucleic acid molecules at a methylated cytosine residue intact. In accordance with this aspect of the present invention, the following are provided: a plurality of primary oligonucleotide primers having a target-specific portion suitable for hybridization on one strand of a target nucleic acid molecule upstream of one or more restriction sites; one or more nucleotide analogues and additional nucleotides that may be incorporated into a polymerase extension product, does not interfere with cleavage of heteroduplexed extension products by the restriction endonuclease, and renders the extension product resistant to exonucleolytic digestion; and a polymerase. The restriction endonuclease reaction mixture, the primary oligonucleotide primers, the one or more nucleotide analogues and additional nucleotides, and the polymerase are blended to form a primary extension reaction mixture. The primary extension reaction mixture is subjected to a primary extension reaction comprising a denaturation treatment, where hybridized nucleic acid molecules are separated, a hybridization treatment, where the target-specific portions of the primary oligonucleotide primers hybridize to the target nucleic acid molecules, and an extension treatment where the hybridized primary oligonucleotide primers are extended to form primary extension products, containing nucleotide analogues and additional nucleotides, which is complementary to the target nucleic acid molecule to which the primary oligonucleotide primers are hybridized. The extension reaction mixture and the restriction endonuclease are blended to form an extension/restriction reaction mixture. The extension/restriction reaction mixture is subjected to enzymatic digestion conditions effective to cut both strands of the residual unmethylated nucleic acid molecules resulting from extension of primary oligonucleotide primers on unmethylated target nucleic acid molecules during the primary extension reaction, while neither nicking nor cutting either strand of hemi-methylated target nucleic acid molecule resulting from extension of primary oligonucleotide primers on methylated target nucleic acid molecules during the primary extension reaction. An exonuclease is also provided, and the extension/restriction reaction mixture, and the exonuclease are blended to form an exonuclease reaction mixture. The exonuclease reaction mixture is subjected to enzymatic digestion under conditions effective to digest target nucleic acid molecules but not primary extension products resulting from primary oligonucleotide primers hybridized and extended on methylated target nucleic acid molecules. A group of secondary oligonucleotide primer sets are provided with each set characterized by (a) a first secondary oligonucleotide primer, having a target-specific portion and a 5' upstream tertiary primer-specific portion, and (b) a second secondary oligonucleotide primer, having a target-specific portion and a 5' upstream tertiary primer-specific portion. The first oligonucleotide primers of each set contain the same 5' upstream tertiary primer-specific portion, and the second oligonucleotide primers of each set contain the same 5' upstream tertiary primer-specific portion, where the secondary oligonucleotide primers in a particular set are suitable for hybridization on complementary strands of a corresponding target nucleic acid molecules. The exonuclease reaction mixture, the secondary oligonucleotide primers, and the polymerase are blended to form a secondary polymerase chain reaction mixture. The secondary polymerase chain reaction mixture is subjected to two or more polymerase chain reaction cycles comprising a denaturation treatment, where hybridized nucleic acid molecules are separated, a hybridization treatment, where the target-specific portions of the secondary oligonucleotide primers hybridize to the target nucleic acid molecules or to extension products of the target nucleic acid molecules, and an extension treatment, where the hybridized secondary oligonucleotide primers are extended to form secondary extension products complementary to the target nucleic acid molecules to which the secondary oligonucleotide primer is hybridized. A tertiary oligonucleotide primer set is provided which is characterized by (a) a first tertiary primer containing the same sequence as the 5' upstream portion of a first secondary oligonucleotide primer, and (b) a second tertiary primer containing the same sequence as the 5' upstream portion of the second secondary oligonucleotide primer from the same secondary oligonucleotide primer set as the first secondary oligonucleotide primer contained by the first tertiary primer, wherein a set of tertiary oligonucleotide primers may be used to amplify all of the secondary extension products. The secondary extension products, the tertiary oligonucleotide primers, and the polymerase are blended to form a tertiary polymerase chain reaction mixture. The tertiary polymerase chain reaction mixture is subjected to two or more polymerase chain reaction cycles comprising a denaturation treatment, where hybridized nucleic acid molecules are separated, a hybridization treatment, where the tertiary oligonucleotide primers hybridize to the secondary extension products, an extension treatment, where the hybridized tertiary oligonucleotide primers are extended to form tertiary extension products complementary to the secondary extension products. A plurality of oligonucleotide probe sets are provided with each set characterized by (a) a first oligonucleotide probe, having a tertiary extension product-specific portion and a detectable reporter label, and (b) a second oligonucleotide probe, having a tertiary extension product-specific portion. The oligonucleotide probes in a particular set are suitable for ligation together when hybridized on a complementary tertiary extension product, but have a mismatch which interferes with such ligation when hybridized to any other nucleic acid molecule present in the sample. A ligase is provided, and the tertiary extension products, the plurality of oligonucleotide probe sets, and the ligase are blended to form a ligase detection reaction mixture. The ligase detection reaction mixture is subjected to one or more ligase detection reaction cycles comprising a denaturation treatment, where any hybridized oligonucleotides are separated from the tertiary extension product, and a hybridization treatment, where the oligonucleotide probe sets hybridize in a base-specific manner to their respective tertiary extension products, if present, and ligate to one another to form a ligation product containing (a) the detectable reporter label and (b) the tertiary extension product-specific portions connected together. The oligonucleotide probe sets may hybridize to nucleic acid moleucules other than their respective complementary tertiary extension products but do not ligate together due to a presence of one or more mismatches and individually separate during the denaturation treatment. The reporter labels of the ligation products are detected, thereby indicating the presence of methylated cytosine bases in the target nucleic acid molecules in the sample.

As mentioned supra, methylation patterns have been inferred by using PCR primers that flank a methylation sensitive restriction endonuclease site. PCR amplification is performed after enzymatic digestion, and if the site was methylated (i.e. resistant), the proper PCR product is amplified. The credibility of this method depends on the complete digestion of unmethylated DNA by the restriction endonuclease. The problem is exacerbated by the fact that the sample DNA is often limited, it is difficult to drive endonuclease digestions to completion, and DNA samples often contain a small percentage of denatured DNA (i.e. single stranded) that is not cleaved but is a substrate for amplification. Thus, it is sometimes difficult to determine whether PCR amplicons result from incomplete digestion (i.e. false positives) or from those of low abundance methylation sites (i.e. true positives). Restriction enzyme techniques are based on removing the unmethylated DNA, and assuming that PCR amplification of the remaining DNA arises because it was methylated. Consequently, the above method utilizing bisulfite treatment is susceptible to false positives arising from incomplete removal of unmethylated DNA.

The present invention introduces a new approach to using methylation sensitive restriction endonucleases for a highly sensitive determination of methylation status.

The first approach takes advantage of a unique property of the methylation sensitive restriction endonuclease BstUI. As shown in step 1 of FIGS. 40-41, BstUI recognizes the sequence CGCG which is methylated at both CpG sites in promoter regions. However, when the substrate contains one double methylated strand and one unrethylated strand, the BstUI endonuclease cannot nick the unmethylated strand.

In step 2, the DNA subjected to BstUI restriction endonuclease treatment is denatured and, then, upstream promoter-specific primers are annealed to the denatured DNA. The annealed primers are then extended with polymerase using α-sdATP and α-sTTP in the presence of the BstUI restriction endonuclease. Hemi-methylated DNA remains uncut, while the remaining unmethylated DNA is cut when double stranded.

As shown in step 3 of FIGS. 40 and 41, genomic DNA is then destroyed using 3'→5" exonucleases. However, polymerase-extended DNA is resistant to exonucleases.

Following exonuclease digestion, all PCR extension products are PCR amplified using promoter-specific/universal primers and Taq polymerase, as shown in step 4 of FIGS. 40-41. This step is substantially the same as described supra with reference to step 3 of the embodiment shown in FIGS. 1-9.

Next the products of step 4 are PCR amplified using universal primers and Taq polymerase, as shown in step 5 of FIGS. 40-41. This step is substantially the same as described supra with reference to step 4 of the embodiment shown in FIGS. 1-9.

Steps 6-7, as depicted in FIGS. 40-41, involve LDR with detection on an addressable array (FIG. 40) or on a gel (See FIG. 41) as described above.

A unique zip-code oligonucleotide sequence can be covalently linked to individual address on the universal array. Each address on the universal array can capture a unique ligase detection reaction product by hybridizing to the complementary zip-code that is attached to each unlabeled common oligonucleotide LDR probe. The presence of methyl cytosine can thus be identified based upon the particular fluorescence label attached to the LDR probe, and hybridized to a given address on the array. See FIG. 40.

Alternatively, the LDR probes may be designed such that the products have different mobility when separated by gel or capillary electrophoresis, and products identified by their unique fluorescent label and mobility (See FIG. 41).

In the preferred embodiment, nucleotide analogues protect the extended primer from digestion by 3'→5' exonucleases such as exonuclease I and exonuclease III. In an alternate approach, the extension primer has a non-phosphorylated or blocked 5' end, or contains analogue(s) that confer exonuclease resistance, and genomic DNA is degraded by digestion with by 5'→3' exonucleases such as lambda exonuclease. Both approaches may be used simultaneously to confer even greater sensitivity in detecting low abundance methylated DNA.

The advantage of this scheme is that a primer hybridized to genomic DNA will be extend through a BstUI site only if that site is methylated. This creates an extension strand resistant to exonucleases. Any residual unmethylated genomic DNA that survives the initial restriction selection will be cleaved on both strands when extended with the specific extension primers. Genomic DNA that did not have any primer extension is degraded by subsequent addition of exonucleases. Thus, this method provides an exceedingly sensitive assay for detecting the presence of a minority fraction of DNA that is methylated at specific regions.

Another aspect of the present invention relates to a method for identifying one or more target nucleic acid molecules differing by one or more methylated cytosine residues. In accordance with this method, a sample potentially containing one or more target nucleic acid molecules and a restriction endonuclease that cleaves the one or more target nucleic acid at an unmethylated cytosine residue and does not cleave the one or more target nucleic acid at a methylated cytosine residue on both strands, but does nick a heteroduplex comprising of one strand containing a methylated cytosine residue and one strand containing unmethylated cytosine residue, are provided. The sample and the restriction endonuclease are blended to form a primary restriction endonuclease reaction mixture. The restriction endonuclease reaction mixture is subjected to an enzymatic digestion procedure under conditions effective to cut the majority of the unmethylated cytosine residues while leaving the methylated cytosine residues intact. The following are provided: a plurality of primary oligonucleotide primers having a target-specific portion suitable for hybridization on one strand of the target nucleic acid molecule upstream of one or more restriction sites are provided; a polymerase which can incorporate nucleotide analogue(s); and one or more nucleotide analogues and additional nucleotides that may be incorporated by a polymerase into an extension product, and does not interfere with cleavage of the heteroduplexed extension product by the restriction endonuclease, but which renders the extension product resistant to exonucleolytic digestion. The restriction endonuclease reaction mixture, the primary oligonucleotide primers, the one or more nucleotide analogues and additional nucleotides, and the polymerase are blended to form a primary extension reaction mixture. The primary extension reaction mixture is subjected to a primary extension reaction comprising a denaturation treatment, where hybridized nucleic acid sequences are separated, a hybridization treatment, where the target-specific portions of the primary oligonucleotide primers hybridize to the target nucleic acid molecule, and an extension treatment, where the hybridized primary oligonucleotide primers are extended to form primary extension products complementary to the target nucleic acid molecule to which the primary oligonucleotide primers are hybridized. The primary extension reaction mixture, the one or more nucleotide analogues and additional nucleotides, and the restriction endonuclease are blended to form a restriction/extension reaction mixture. The restriction/extension reaction mixture is subjected to a restriction/extension cycle comprising an enzymatic digestion phase under conditions effective to cut both strands of the residual unmethylated cytosine residues resulting from extension of the primary oligonucleotide primers on unmethylated cytosine residues of target nucleic acid molecules, while nicking the unmethylated strand of hemi-methylated target nucleic acid molecules resulting from extension of primary oligonucleotide primers on methylated cytosine residues of target nucleic acid molecules, followed by an incubation effective to inactivate the restriction endonuclease but not denature the nicked primary extension products from their target nucleic acid molecules. The nicked primary extension products re-extend at the nick, generating extension products, containing nucleotide analogues and additional nucleotides, which are complementary to the target nucleic acid molecules to which the primary oligonucleotide primers are hybridized. An exonuclease is provided, and the restriction/extension reaction mixture and the exonuclease blended to form an exonuclease reaction mixture. The exonuclease reaction mixture is subjected to a enzymatic digestion process under conditions effective to digest target nucleic acid molecules but not the extension products containing nucleotide analogues resulting from oligonucleotide extension primers hybridized to and extended on methylated cytosine residues of target nucleic acid molecules. A group of secondary oligonucleotide primer sets are provided with each set characterized by (a) a first secondary oligonucleotide primer, having a target-specific portion and a 5' upstream tertiary primer-specific portion, and (b) a second secondary oligonucleotide primer, having a target-specific portion and a 5' upstream tertiary primer-specific portion, where the first oligonucleotide primers of each set contain the same 5' upstream tertiary primer-specific portion and the second oligonucleotide primers of each set in the group contain the same 5' upstream tertiary primer-specific portion. The exonuclease reaction mixture, the secondary oligonucleotide primers, and the polymerase are blended to form a secondary polymerase chain reaction mixture. The secondary polymerase chain reaction mixture is subjected to two or more polymerase chain reaction cycles comprising a denaturation treatment, where hybridized nucleic acid sequences are separated, a hybridization treatment, where the target-specific portions of the secondary oligonucleotide primers hybridize to the target nucleic acid molecules in the exonuclease reaction mixture or to extension products thereof, and an extension treatment, where the hybridized secondary oligonucleotide primers are extended to form secondary extension products complementary to the target nucleic acid molecule sequence to which the secondary oligonucleotide primer is hybridized. A tertiary oligonucleotide primer set is provided which is characterized by (a) a first tertiary primer containing the same sequence as the 5' upstream portion of a first secondary oligonucleotide primer, and (b) a second secondary primer containing the same sequence as the 5' upstream portion of a second secondary primary oligonucleotide primer from the same secondary oligonucleotide primer set as the 5' upstream portion of the first secondary oligonucleotide primer contained by the first tertiary primer. The set of tertiary oligonucleotide primers may be used to amplify all of the secondary extension products in the group. The secondary extension products, the tertiary oligonucleotide primers, and the polymerase are blended to form a tertiary polymerase chain reaction mixture. The tertiary polymerase chain reaction mixture is subjected to two or more polymerase chain reaction cycles comprising a denaturation treatment, where hybridized nucleic acid sequences are separated, a hybridization treatment, where the tertiary oligonucleotide primers hybridize to the secondary extension products, an extension treatment, where the hybridized tertiary oligonucleotide primers are extended to form tertiary extension products complementary to the secondary extension products. A plurality of oligonucleotide probe sets are provided with each set characterized by (a) a first oligonucleotide probe, having a tertiary extension product-specific portion and a detectable reporter label, and (b) a second oligonucleotide probe, having a tertiary extension product-specific portion. The oligonucleotide probes in a particular set are suitable for ligation together when hybridized on a complementary tertiary extension product, but have a mismatch which interferes with such ligation when hybridized to any other nucleic acid molecule present. A ligase is provided, and the tertiary extension products, the plurality of oligonucleotide probe sets, and the ligase are blended to form a ligase detection reaction mixture. The ligase detection reaction mixture is subjected to one or more ligase detection reaction cycles comprising a denaturation treatment, where any hybridized oligonucleotides are separated from the tertiary extension product, and a hybridization treatment, where the oligonucleotide probe sets hybridize in a base-specific manner to their respective tertiary extension products, if present, and ligate to one another to form a ligation product containing (a) the detectable reporter label and (b) the tertiary extension product-specific portions connected together. The oligonucleotide probe sets may hybridize to target nucleic acid molecules other than their respective complementary tertiary extension products but do not ligate together due to a presence of one or more mismatches and individually separate during the denaturation treatment. The reporter labels of the ligation product are detected, thereby indicating the presence of methylated cytosine bases in the target nucleic acid molecule in the sample.

A further embodiment of the present invention relates to a method for identifying one or more target nucleic acid molecules differing by one or more methylated cytosine residues. This method involves providing a sample potentially containing one or more target nucleic acid molecules with a plurality of sequence differences. A restriction endonuclease that cleaves unmethylated cytosine residues in the target nucleic acid molecules and does not cleave target nucleic acid molecules which are methylated on both strands. The sample and the restriction endonuclease are blended to form a primary restriction endonuclease reaction mixture. The restriction endonuclease reaction mixture is subjected to an enzymatic digestion processs under conditions effective to cut the majority of unmethylated cytosine residues in the target nucleic acid molecules while leaving the methylated cytosine residues in the target nucleic acid molecules intact. A plurality of primary oligonucleotide primers are provided which have either a non-phosphorylated end, a blocked 5' end, or internal nucleotide or backbone analogue(s) that confer resistance to digestion by exonuclease(s). The primary oligonucleotide primers have a target-specific portion suitable for hybridization on one strand of the target nucleic acid molecules upstream of one or more restriction sites. The following are provided: a polymerase and one or more nucleotide analogues and additional nucleotides that may be incorporated by a polymerase into an extension product, and does not interfere with cleavage of the heteroduplexed extension product by the restriction endonuclease, but which renders the extension product resistant to exonucleolytic digestion. The restriction endonuclease reaction mixture, the primary oligonucleotide primers, the one or more nucleotide analogues and additional nucleotides, and the polymerase are blended to form an primary extension reaction mixture. The primary extension reaction mixture is subjected to an extension reaction comprising a denaturation treatment, where hybridized nucleic acid molecules are separated, a hybridization treatment, where the target-specific portions of the primary oligonucleotide primers hybridize to the target nucleic acid molecules, and an extension treatment, where the hybridized primary oligonucleotide primers are extended to form primary extension products complementary to the target nucleic acid molecule to which the primary oligonucleotide primers are hybridized. The primary extension reaction mixture and the restriction endonuclease are blended to form a restriction/extension reaction mixture. The restriction/extension reaction mixture is subjected to a restriction/extension cycle comprising an incubation phase sufficient to cut both strands of residual unmethylated cytosine residues in the target nucleic acid molecules arising from extension of secondary oligonucleotide primers on unmethylated cytosine residues in the target nucleic acid molecules, while either nicking or not cleaving the unmethylated strand of hemi-methylated target nucleic acid molecule arising from extension of oligonucleotide primers on a methylated target nucleic acid molecule. This is followed by an incubation sufficient to inactivate the restriction endonuclease but not denature the nicked extension products from their target sequences, where the nicked secondary extension products re-extend at the nick generating extension products complementary to the target nucleic acid molecule to which the primary oligonucleotide primers are hybridized. An exonuclease is provided, and the restriction/extension reaction mixture and the exonuclease are blended to form an exonuclease reaction mixture. The exonuclease reaction mixture is subjected to enzymatic digestion conditions effective to digest target nucleic acid molecules but not extension products arising from the primary oligonucleotide primers hybridized and extended on methylated target nucleic acid molecules. A set of secondary oligonucleotide primers are provided with each set characterized by (a) a first secondary oligonucleotide primer, having a target-specific portion and a 5' upstream tertiary primer-specific portion, and (b) a second secondary oligonucleotide primer, having a target-specific portion and a 5' upstream secondary primer-specific portion. The first secondary oligonucleotide primers of each set contain the same 5' upstream tertiary primer-specific portion and the second secondary oligonucleotide primers of each set contain the same 5' upstream tertiary primer-specific portion. The exonuclease reaction mixture, the secondary oligonucleotide primers, and the polymerase are blended to form a secondary polymerase chain reaction mixture. The secondary polymerase chain reaction mixture is subjected to two or more polymerase chain reaction cycles comprising a denaturation treatment, where hybridized nucleic acid molecules are separated, a hybridization treatment, where the target-specific portions of the secondary oligonucleotide primers hybridize to treated target nucleic acid molecules or to extension products of the target nucleic acid molecules, and an extension treatment, where the hybridized secondary oligonucleotide primers are extended to form secondary extension products complementary to the target nucleic acid molecule to which the secondary oligonucleotide primers is hybridized. A tertiary oligonucleotide primer set is provided which is characterized by (a) a first tertiary primer containing the same sequence as the 5' upstream portion of a first secondary oligonucleotide primer, and (b) a second tertiary primer containing the same sequence as the 5' upstream portion of a second secondary oligonucleotide primer from the same secondary oligonucleotide primer set as the first secondary oligonucleotide primer contained by the first tertiary oligonucleotide primer. A set of tertiary oligonucleotide primers may be used to amplify all of the secondary extension products. The secondary extension products, the tertiary oligonucleotide primers, and the polymerase are blended to form a tertiary polymerase chain reaction mixture. The tertiary polymerase chain reaction mixture is subjected to two or more polymerase chain reaction cycles comprising a denaturation treatment, where hybridized nucleic acid molecules are separated, a hybridization treatment, where the tertiary oligonucleotide primers hybridize to the secondary extension products, an extension treatment, where the hybridized tertiary oligonucleotide primers are extended to form tertiary extension products complementary to the secondary extension products. A plurality of oligonucleotide probe sets are provided with each set characterized by (a) a first oligonucleotide probe, having a tertiary extension product-specific portion and a detectable reporter label, and (b) a second oligonucleotide probe, having a tertiary extension product-specific portion, where the oligonucleotide probes in a particular set are suitable for ligation together when hybridized on a complementary tertiary extension product, but have a mismatch which interferes with such ligation when hybridized to any other nucleic acid molecule present in the sample. A ligase is provided, and the tertiary extension products, the plurality of oligonucleotide probe sets, and the ligase are blended to form a ligase detection reaction mixture. The ligase detection reaction mixture is subjected to one or more ligase detection reaction cycles comprising a denaturation treatment, where any hybridized oligonucleotides are separated from the tertiary extension product, and a hybridization treatment, where the oligonucleotide probe sets hybridize in a base-specific manner to their respective tertiary extension products, if present, and ligate to one another to form a ligation product containing (a) the detectable reporter label and (b) the tertiary extension product-specific portions connected together, where the oligonucleotide probe sets may hybridize to nucleic acid molecules other than their respective complementary tertiary extension products but do not ligate together due to a presence of one or more mismatches and individually separate during the denaturation treatment. The reporter labels of the ligation product are detected, thereby indicating the presence of methylated cytosine bases in the target nucleic acid molecules in the sample.

This approach takes advantage of the ability of methylation sensitive restriction endonucleases, such as HinP1I, HhaI (recognition sequence: GCGC), TaqI (recognize sequence: TCGA), or AciI (recognition sequence: CCGC) to nick the unmethylated strand of a homoduplex under appropriate buffer conditions (see FIGS. 42-45). The concept is to nick and extend hemimethylated substrates, while cleaving unmethylated substrates. The extended strands are resistant to exonuclease digestion and are subsequently amplified and detected by LDR.

As shown in step 1 of FIGS. 42-45, the methylation sensitive restriction endonuclease Hinp1I recognizes the sequence GCGC which is methylated at the CpG sites in the promoter regions and is used to cleave genomic DNA. Methylated DNA remains uncut, while unmethylated DNA is cut.

In step 2, the DNA subjected to Hinp1I restriction endonuclease treatment is denatured and, then, upstream promoter-specific primers are annealed to the denatured DNA. The annealed primers are then extended with polymerase. The extension product is then recut with HinP1 I restriction endonuclease. This causes hemi-methylated DNA to be nicked, while the remaining unmethylated DNA is cut when double stranded. Next normal dNTPs are removed and the nicked DNA is extended using α-sdATP and α-sTTP.

As shown in step 3 of FIGS. 42-43 or FIGS. 44-45, respectively, genomic DNA is then destroyed using 3'→5' exonucleases or 5'→3' exonucleases. However, polymerase-extended DNA is resistant to exonucleases. This step is carried out in substantially the same manner as corresponding step 3 depicted in FIGS. 40-41.

Following exonuclease digestion, all PCR extension products are PCR amplified using promoter-specific/universal primers and Taq polymerase, as shown in step 4 of FIGS. 42-45. This step is substantially the same as described supra with reference to step 3 of the embodiment shown in FIGS. 1-9.

Next, the products of step 4 are PCR amplified using universal primers and Taq polymerase, as shown in step 5 of FIGS. 42-45. This step is substantially the same as described supra with reference to step 4 of the embodiment shown in FIGS. 1-9.

Steps 6-7, as depicted in FIGS. 42-45, involve LDR with detection on an addressable array (FIGS. 42 and 44) or on a gel (See FIGS. 43 and 45) as described above.

A universal array to capture the ligase detection reaction products. A unique zip-code oligonucleotide sequence has been covalently linked to individual address on the universal array. Each address on the universal array can capture a unique ligase detection reaction product by hybridizing to the complementary zip-code that is attached to each unlabeled common oligonucleotide LDR probe. The presence of methyl cytosine can thus be identified based upon the particular fluorescence label attached to the LDR probe, and hybridized to a given address on the array. See FIGS. 42 and 44.

Alternatively, the LDR probes may be designed such that the products have different mobility when separated by gel or capillary electrophoresis, and products identified by their unique fluorescent label and mobility (FIGS. 43 and 45).

The embodiment of FIGS. 46-47 are substantially the same as that of FIGS. 44-45, except that in the latter embodiment, the methylation sensitive restriction endonuclease Hinp1I is utilized, while the former embodiment employs the HpaII methylation sensitive restriction endonuclease.

As shown in step 1 of FIGS. 46-47, the methylation sensitive restriction endonuclease HpaII recognizes the sequence CCGG which is methylated at the CpG sites in the promoter regions and is used to cleave genomic DNA. Methylated DNA remains uncut, while unmethylated DNA is cut.

In step 2, the DNA subjected to HpaII restriction endonuclease treatment is denatured and, then, upstream promoter-specific primers are annealed to the denatured DNA. The annealed primers are then extended with polymerase. The extension product is then recut with HpaII restriction endonuclease. This causes hemi-methylated DNA to not be nicked, while the remaining unmethylated DNA is cut when double stranded.

As shown in step 3 of FIGS. 46-47, genomic DNA is then destroyed using 5'→3' exonucleases. However, polymerase-extended DNA is resistant to exonucleases. This step is carried out in substantially the same manner as corresponding step 3 depicted in FIGS. 40-41.

Following exonuclease digestion, all PCR extension products are PCR amplified using promoter-specific/universal primers and Taq polymerase, as shown in step 4 of FIGS. 46-47. This step is substantially the same as described supra with reference to step 3 of the embodiment shown in FIGS. 1-9.

Next, the products of step 4 are PCR amplified using universal primers and Taq polymerase, as shown in step 5 of FIGS. 46-47. This step is substantially the same as described supra with reference to step 4 of the embodiment shown in FIGS. 1-9.

Steps 6-7, as depicted in FIGS. 46-47, involve LDR with detection on an addressable array (FIG. 46) or on a gel (See FIG. 47) as described above.

In the preferred embodiment, nucleotide analogues protect the extended primer from digestion by 3'→5' exonucleases such as exonuclease I and exonuclease III (as shown in FIGS. 42-43). In an alternate approach, the extension primer has a non-phosphorylated or blocked 5' end, or contains analogue(s) that confer exonuclease resistance, and genomic DNA degraded by digestion with 5'→3' exonucleases such as lambda exonucleases (as illustrated in FIGS. 44, 45, 46, and 47). Both approaches may be used simultaneously to confer even greater sensitivity in detecting low abundance methylated DNA.

The advantage of this scheme is that after forming initial extension products to genomic DNA the methylation sensitive restriction endonuclease site will be nicked only if that site is hemi-methylated. This allows for polymerase to create an extension product off the nicked strand that is resistant to exonucleases. Any residual unmethylated genomic DNA that survived the initial restriction selection will be cleaved on both strands and, consequently, is not extended (other than filling in a 5' overhang if one is generated). Genomic DNA that did not have any primer extension is degraded by subsequent addition of exonucleases. Unlike other restriction endonuclease assays, this method provides a positive selection for the presence of a methylated strand. The exonuclease resistant extension product only forms when the restriction endonuclease nicks a hemi-methylated substrate. Thus, this method provides an exceedingly sensitive assay for detecting the presence of a minority fraction of DNA that is methylated at specific regions.

EXAMPLES

Example 1

Reagents and Media

All routine chemical reagents were purchased from Sigma Chemicals (St. Louis, Mo.) or Fisher Scientific (Fair Lawn, N.J.). Deoxynucleotides were purchased from Applied Biosystems (Foster City, Calif.). SuperPure Plus columns were purchased from Biosearch Technologies Inc (Novato, Calif.). Deoxyoligonucleotides were ordered from Integrated DNA Technologies Inc. Phosphoramidites for primer syntheses were purchased from Glen Research (Sterling, Va.). PCR buffer and AmpiTaq Gold were purchased from Applied Biosystems (Foster City, Calif.). Human genomic DNA was purchased from Roche (Indianapolis, Ind.). SssI methylase was purchased from NewEngland BioLabs (Beverly, Mass.). Proteinase K was purchased from QIAGEN (Valencia, Calif.).

A 20 μl ligase detection reaction (LDR) contains 20 mM Tris pH 7.6, 10 MM $MgCl_2$, 100 mM KCl, 10 mM DTT, 0.5 mM NAD, 25 mM Tth ligase, 250 fmol LDR probes and pooled multiplex PCR products. Tth ligase storage buffer contains 10 mM Tris pH 8.5, 1 mM EDTA, 1 mM DTT, 200 mg/ml BSA, 50% glycerol. Tth ligase dilution buffer contains 15 mM Tris pH 7.6, 7.5 MM $MgCl_2$, 0.15 mg/ml BSA.

Example 2

Sodium Bisulfite Treatment of Genomic DNAs

Sodium bisulfite has been widely use to distinguish 5-methylcytosine from cytosine. Bisulfite converts cytosine into uracil via deamination reaction while leaving 5-methylcytosine unchanged. Genomic DNAs extracted from tumor cell lines and colon tumor samples were used in this study. Typically, 2 μg genomic DNA in a volume of 40 μl was incubated with 0.2N NaOH at 37° C. for 10 minutes. 30 μl freshly made 10 mM hydroquinone and 520 μl of freshly made 3M sodium bisulfite were then added. 3M sodium bisulfite was made with 1.88 g sodium bisulfite (Sigma Chemicals, ACS grade) dissolved in a final total 5 μl deionized $H_2O$ with final pH 5.0. This mixture was then incubated for 16 hours in a DNA thermal cycler (Perkin Elmer Cetus) with the cycles of 50° C. for 20 minutes followed by a denaturing step of 85° C. for 15 seconds. The bisulfite-treated DNAs can be desalted using MICROCON centrifugal filter devices (Millipore, Bedford, Mass.) or, alternatively, were cleaned with Wizard DNA clean-up kit (Promega, Madison, Wis.). The eluted DNAs were incubated with one-tenth volume of 3N NaOH at room temperature for 5 minutes before ethanol precipitation. The DNA pellet was then resuspended in 20 μl deionized $H_2O$ and stored at 4° C. until PCR amplification.

Example 3

Multiplex PCR Amplification

The promoter regions of cancer genes are amplified in a multiplex fashion to increase the throughput. A schematic diagram of this procedure is shown in FIG. 1. The multiplex PCR of the present invention has two stages, namely a gene-specific amplification (stage one) and an universal amplification (stage two). Three promoter regions were simultaneously amplified in one PCR reaction. The current protocol was designed to do parallel analysis at 16 promoter regions. The PCR primers (as shown in Table 1) were grouped as follows to minimize the nonspecific amplification and primer dimers during the multiplex PCR. Group 1: p15, p21, and APC. Group 2: p19, p27, and ECAD. Group 3: p16, p53, and BRCA1. Group 4: MGMT, DAPK, and GSTP1. Group 5: TIMP3, RASSF1, and RARβ. SNRPN gene was used as an internal positive control.

The gene-specific PCR primers were designed such that the 3' sequence contains a gene-specific region and an universal sequence attached to the 5' end. The gene specific primers were designed in the promoter regions where there are as few CpG sites as possible. For those primers that were inevitably including CpG dinucleotides, the initial design was to employ analog K for the potential hybridization of either nucleotide C or T, and use nucleotide analog P for the potential hybridization of nucleotide G or A. The sequences of such nucleotide analog primers were shown in Table 1. To reduce the cost of primer synthesis, some PCR primers were designed without nucleotide analogs and using nucleotides G to replace K (purine derivative) and T to replace P (pyrimidine derivative), respectively (Table 1). This type of primer design favors pairing to DNA that was initially methylated, although it also allows the mismatch pairing of G/T when the original DNA was unmethylated at that site. The ethidium bromide staining intensity of PCR amplicons separated by the agarose gel electrophoresis, demonstrated that this primer design was as robust as using analogs-containing primers.

At the first stage, the multiplex PCR reaction mixture (12.5 μl) consisted of 1.5 μl bisulfite modified DNA, 400 μM of each dNTP, 1× AmpliTaq Gold PCR buffer, 4 mM $MgCl_2$, and 1.25 U AmpliTaq Gold polymerase. The gene-specific PCR primer concentrations were listed in the Table 1. Minimal oil was added to each reaction before thermal cycling. The PCR procedure included a pre-denaturation step at 95° C. for 10 minutes, 15 cycles of three-step amplification with each cycle consisting of denaturation at 94° C. for 30 second, annealing at 60° C. for 1 minute, and extension at 72° C. for 1 minute. A final extension step was at 72° C. for 5 minutes.

The second stage of multiplex PCR amplification primed from the universal sequences (UniA) located at the extreme 5' end of the gene-specific primers. The second stage PCR reaction mixture (12.5 μl) consisted of 400 μM of each dNTP, 1× AmpliTaq Gold PCR buffer, 4 mM $MgCl_2$, 12.5 pmol universal primer B (UniB) and 1.25 U AmpliTaq Gold polymerase. The UniB PCR primer sequence is listed in the Table 1. The 12.5 μl reaction mixtures were added through the minimal oil to the finished first stage PCR reactions. The PCR procedure included a pre-denaturation step at 95° C. for 10 minutes, 30 cycles of three-step amplification with each cycle consisting of denaturation at 94° C. for 30 second, annealing at 55° C. for 1 minute, and extension at 72° C. for 1 minute. A final extension step was at 72° C. for 5 minutes.

After the two-stage PCR reaction, 1.25 μl Qiagen Proteinase K (approximately 20 mg/ml) was added to the total 25 μl reaction. The Proteinase K digestion condition consisted of 70° C. for 10 minutes and 90° C. for 15 minutes.

Example 4

Methylation Enrichment PCR Amplification

To increase the detection sensitivity of the Bisulfite/PCR/PCR/LDR/Universal Array assay, a nested Bisulfite/PCR-PCR/MS-PCR-PCR approach has been devised to substitute the original Bisulfite/PCR/PCR method. This new approach, Bisulfite/PCR-PCR/Ms-PCR-PCR/LDR/Universal Array, has the potential advantage to detect the methylation status of trace circulating tumor cells in blood or bodily fluid (e.g. sputum). There were two major multiplex PCR stages in the procedure, namely the Bisulfite/PCR-PCR amplification (stage one) and MS-PCR-PCR amplification (stage two). In the current study, two promoter regions were simultaneously amplified in one PCR reaction. The PCR primers (as shown in Table 2) were grouped as follows to minimize the nonspecific amplification and primer dimers during the multiplex PCR. Group 1: p19 and SNRPN. Group 2: p16 and BRCA1. SNRPN and BRCA1 genes were used as internal positive and negative controls, respectively.

The stage one Bisulfite/PCR-PCR amplification included a gene-specific amplification followed by an universal amplification. The gene-specific primers were designed based on the criteria indicated in the Example 3.

At the gene-specific amplification stage, the multiplex PCR reaction mixture (12.5 μl) consisted of 1.5 μl bisulfite modified DNA, 400 μM of each dNTP, 1× AmpliTaq Gold PCR buffer, 4 mM $MgCl_2$, and 1.25 U AmpliTaq Gold polymerase. The gene-specific PCR primer concentrations were listed in the Table 2. Minimal oil was added to each reaction before thermal cycling. The PCR procedure included a pre-denaturation step at 95° C. for 10 minutes, 15 cycles of three-step amplification with each cycle consisting of denaturation at 94° C. for 30 second, annealing at 60° C. for 1 minute, and extension at 72° C. for 1 minute. A final extension step was at 72° C. for 5 minutes.

The universal PCR amplification primed from the universal sequences located at the extreme 5' end of the gene-specific primers. The second sub-stage PCR reaction mixture (12.5 μl) consisted of 400 μM of each dNTP, 1× AmpliTaq Gold PCR buffer, 4 mM $MgCl_2$, 12.5 pmol universal primer A (UniA), and 1.25 U AmpliTaq Gold polymerase. The UniB PCR primer sequence is listed in the Table 1. The 12.5 μl reaction mixtures were added through the minimal oil to the finished first sub-stage PCR reactions. The PCR procedure included a pre-denaturation step at 95° C. for 10 minutes, 30 cycles of three-step amplification with each cycle consisting of denaturation at 94° C. for 30 second, annealing at 55° C. for 1 minute, and extension at 72° C. for 1 minute. A final extension step was at 72° C. for 5 minutes.

The stage two Ms-PCR-PCR amplification included a methylation-enrichment, gene-specific amplification followed by an universal amplification with a primer different than the one used in stage one. The methylation-enrichment, gene-specific PCR primers were designed further inward from the gene-specific primers shown in the Example 3. CpG dinucleotides were not excluded in the primer design, furthermore; the 5' most nucleotide of each primer was ended on the cytosine of a CpG dinucleotide to ensure the enrichment of PCR amplification on the hypermethylated promoter sequences.

At the methylation-enrichment, gene-specific amplification sub-stage, the multiplex PCR reaction mixture (12.5 μl) consisted of 1.5 μl bisulfite modified DNA, 400 μM of each dNTP, 1× AmpliTaq Gold PCR buffer, 4 mM $MgCl_2$, and 1.25 U AmpliTaq Gold polymerase. 1 µl of diluted stage one PCR amplicon (1:50 dilution) was used as the PCR template. The methylation-enrichment, gene-specific PCR primer sequences and concentrations were listed in the Table 2. Minimal oil was added to each reaction before thermal cycling. The PCR procedure included a pre-denaturation step at 95° C. for 10 minutes, 15 cycles of three-step amplification with each cycle consisting of denaturation at 94° C. for 30 second, annealing at 60° C. for 1 minute, and extension at 72° C. for 1 minute. A final extension step was at 72° C. for 5 minutes.

The universal PCR amplification primed from the universal sequences (UniB) located at the extreme 5' end of the methylation-enrichment, gene-specific primers. The second sub-stage PCR reaction mixture (12.5 µl) consisted of 400 µM of each dNTP, 1× AmpliTaq Gold PCR buffer, 4 mM $MgCl_2$, 12.5 pmol universal primer B (UniB), and 1.25 U AmpliTaq Gold polymerase. The UniB PCR primer sequence is listed in the Table 2. The 12.5 µl reaction mixtures were added through the minimal oil to the finished first sub-stage PCR reactions. The PCR procedure included a pre-denaturation step at 95° C. for 10 minutes, 30 cycles of three-step amplification with each cycle consisting of denaturation at 94° C. for 30 second, annealing at 55° C. for 1 minute, and extension at 72° C. for 1 minute. A final extension step was at 72° C. for 5 minutes.

After the two-stage PCR reaction, 1.25 µl Qiagen Proteinase K (approximately 20 mg/ml) was added to the total 25 µl reaction. The Proteinase K digestion condition consisted of 70° C. for 10 minutes and 90° C. for 15 minutes.

Example 5

Analysis of Multiplex PCR Products

The multiplex PCR reaction products were analyzed on a 3% agarose gel.

Example 6

Ligase Detection Reaction and Hybridization to Universal Array

Ligation detection reaction was carried out in a 20 µl volumes containing 20 mM Tris-HCl pH 7.6, 10 mM $MgCl_2$, 100 mM KCl, 20 mM DTT, 1 mM NAD, 50 fmol wild type Tth ligase, 500 fmol each of LDR probes, and 5-10 ng each of the PCR amplicons. The Tth ligase may be diluted in a buffer containing 15 mM Tris-HCl pH 7.6, 7.5 mM $MgCl_2$, and 0.15 mg/ml BSA. Two probe mixes were prepared. One contained 48 discriminating probes and 48 common probes. The other contained 30 discriminating probes and 30 common probes. The reaction mixtures were pre-heated for 3 minutes at 95° C. and then cycled for 25 rounds of 95° C. for 30 seconds and 60° C. for four minutes.

The LDR reaction (20 µl) was diluted with equal volume of 2× hybridization buffer (600 mM MES pH 6.0, 20 mM $MgCl_2$, and 0.2% SDS), and denatured at 95° C. for 3 minutes then plunged on ice. The universal arrays were pre-equilibrated with 1× hybridization buffer at room temperature for at least 15 minutes. Coverwells (Grace Bio-Labs, Bend, Oreg.) were attached to arrays and filled with the 40 µl denatured LDR mixtures. The assembled arrays were incubated in a rotating hybridization oven for 60 minutes at 65° C. After hybridization, the arrays were washed in 300 mM Bicine pH 8.0, and 0.1% SDS for 10 minutes at 60° C. The fluorescent signals were measured using a ScanArray 5000 scanner (Perkin Elmer, Boston, Mass.).

At the end of the experiments, fluorescent signals on the arrays may be stripped by boiling 2 minutes in the solution contains 300 mM NaCl and 0.1% SDS. The stripped arrays maybe re-used for more than 10 times.

Example 7

Diethylenetriamine Treatment

To search for better catalysts (rather than hydroquinone) that can facilitate the conversion of unmethylated cytosine into uracil more efficiently, diethylenetriamine was used (Sigma Cat# D 1551) in the bisulfite treatment. Komiyama, M., et al., *Tetrahedron Letters,* 35: 8185-8188 (1994), which is hereby incorporated by reference in its entirety. Genomic DNA from CRC cell line HTB39 was stored in a final concentration of 20 mM Tricine pH 8.5 and 2 mM EDTA to prevent degradation. 2 µg genomic DNA in a total volume of 40 µl was denatured by adding one-tenth volume of 2M NaOH and incubated at 37° C. for 10 minutes. Then, 520 µl of freshly made 3M sodium bisulfite containing either 10, 20, or 40 mM diethylenetriamine at pH 5.0 was added. After pre-bubbling with argon for 20 minutes to remove oxygen, the mixtures was then incubated for 16 hours in a DNA thermal cycler (Perkin Elmer Cetus) with the cycles of 50° C. for 20 minutes followed by a denaturing step of 85° C. for 15 seconds. The bisulfite/diethylenetriamine treated DNAs were cleaned with Wizard DNA clean-up kit (Promega, Madison, Wis.). The eluted DNAs were incubated with one-tenth volume of 3N NaOH at room temperature for 5 minutes before ethanol precipitation. The DNA pellet was then resuspended in 20 µl deionized $H_2O$ and stored at 4° C. until PCR amplification.

Example 8

Figure 48:
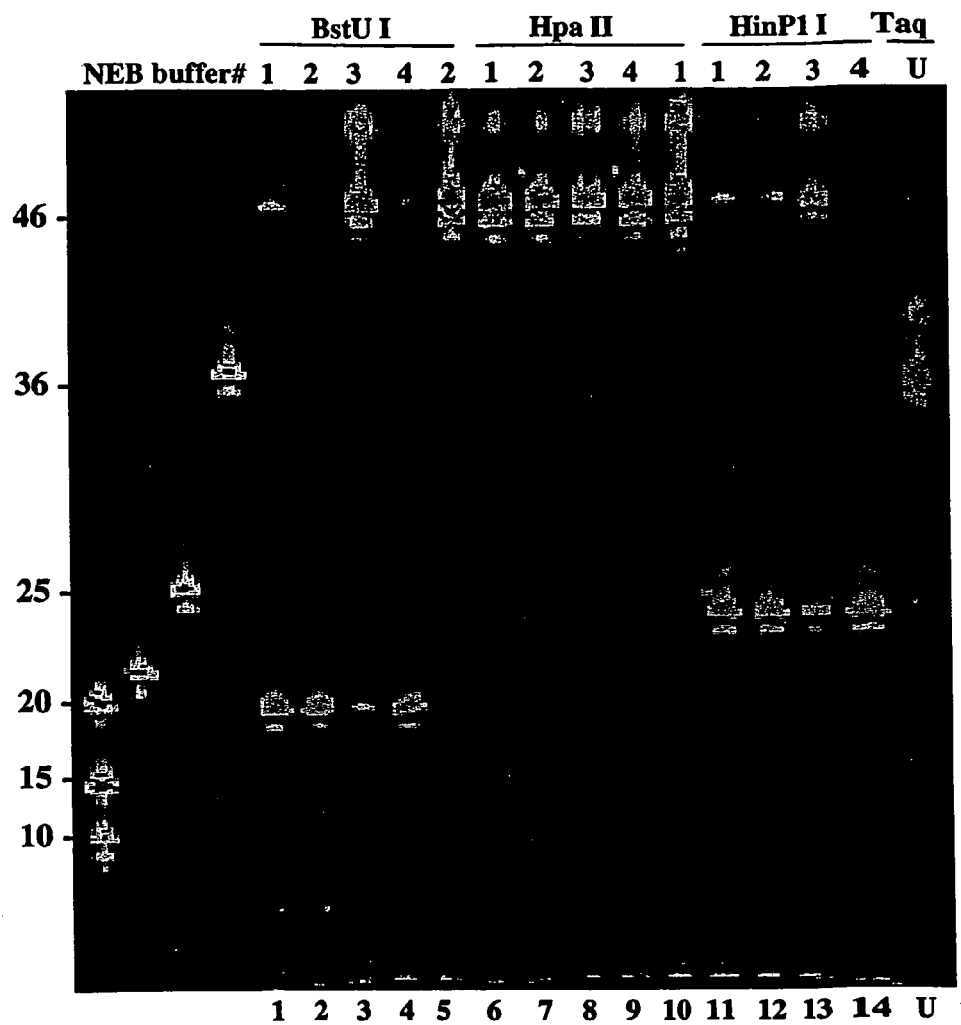
FIG. 48 is the demonstration of the nicking capability of restriction endonucleases (BstUI, Hpa II, HinP1 I, Taq I) on a methylated DNA substrate. One strand of the synthetic DNA is methylated at the cytosines of CpG dinucleotides (SEQ ID NO:310). The other strand is unmethylated and 5' labeled with fluorescence group Fam (SEQ ID NO:311). The restriction enzyme cutting sites of each endonuclease is indicated. New England Biolabs buffers 1, 2, 3, 4, and U were used in each reaction. Except in reactions 5 and 10, 10 U each of the indicated endonuclease was used in each reaction. The nicking position of each enzymes is indicated by the arrow heads.

BstUI, HpaII, HinP1I, TaqI Digestion of the In Vitro Methylated Synthetic Template To test the capability of restriction endonucleases nicking a methylated DNA, a synthetic DNA template (Integrated DNA Technologies, Coralville, Iowa) carrying the restriction sites of BstUI, HpaII, HinP1I, TaqI (New England Biolabs, Beverly, Mass.) was made. One strand of this synthetic DNA is methylated at the cytosines of CpG dinucleotides. The other strand is unmethylated and 5' labeled with fluorescence group Fam. New England Biolabs buffers 1, 2, 3, 4, and U were used to test the nicking characteristics of BstUI, HpaII, HinP1I, and TaqI. The heteroduplex synthetic DNA was made by incubating 6 pmol of each of synthetic single strand DNA with final concentration of 1× New England Biolabs (NEB) buffer (the NEB buffer number is indicated in the FIG. 48) in a total reaction volume of 15 µl for 1 minute at 95° C., then 15 minutes at 65° C. followed by 15 minutes at room temperature.

1 µl of the above heteroduplex DNA was further incubated with the corresponded 1× NEB buffer and 10 U of each restriction endonuclease (except reactions 5 and 10) in a total volume of 10 µl in each reaction. Reactions 1 to 5 (BstUI condition) were incubated at 65° C. for 1 hour, reactions 6 to 10 (HpaII condition) were incubated at 37° C. for 1 hour then inactivated at 65° C. for 20 minutes, reactions 11 to 14 (HinP1 I condition) were incubated at 37°

C. for 1 hour then inactivated at 65° C. for 20 minutes, reaction 15 (TaqI) was incubated at 65° C. for 1 hour then inactivated at 80° C. for 20 minutes. 1 μl of each the restriction digestion reaction was subjected to electrophoresis on a 15% acrylamide gel and detected with ABI 377 analyzer.

Examples 9

PCR Amplification With Universal Primers

Figure 10:
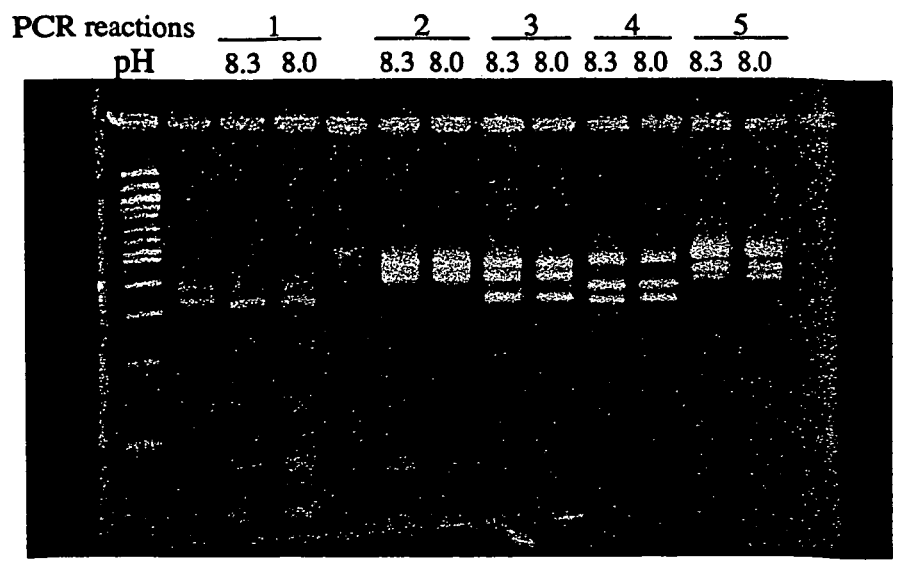
FIG. 10 shows the multiplex PCR products on a 3% non-denaturing agarose gel. Normal human lymphocyte genomic DNAs (Roche, Indianapolis, USA) were used for bisulfite treatment and served as templates for multiplex PCR amplifications. Each multiplex PCR reaction was carried out at two different buffer conditions (pH 8.3 and pH 8.0). The composition of the amplified promoter regions in each multiplex PCR reaction is indicated on the bottom panel.

In order to simultaneously determine methylation status among multiple genes, it is necessary to amplify the appropriate promoter regions after bisulfite treatment. FIG. 10 shows the multiplex PCR products under a series of buffer and primer conditions. Sodium bisulfite treated normal human lymphocyte genomic DNAs (Roche, Indianapolis, USA, prepared as in Example 2) were used as templates for multiplex PCR amplification under a variety of testing conditions. The gene-specific PCR primers (containing a universal sequence on their 5' ends) were used for the first stage multiplex PCR amplification, and a universal primer was used for the second stage PCR amplification. The detailed multiplex PCR thermal cycling condition is described in Example 3. The 100 base pair DNA marker XIV on the far left side of gel is used as a molecular size standard (Roche, Indianapolis, USA). Five different PCR primer combinations (indicated as PCR reactions # 1 to 5) were performed. Two PCR buffer conditions (pH 8.3 and pH 8.0) were tested for each multiplex PCR reaction. PCR reaction #1 includes 4 sets of multiplex PCR primers (p15Ex1, p16Ex1,p19Ex1,p21S2), and a primer mix was divided into two aliquots; one aliquot was used in the PCR reaction with pH 8.3, the other aliquot was used in the pH 8.0 PCR reaction. In PCR reaction #1, one dominant (around 317 b.p.), two weak bands (around 346 and 363 b.p.) and a vague fourth fragment (around 400 b.p.) were observed at both pH conditions. PCR reaction #2 includes 5 sets of multiplex PCR primers (p21S1,p27,p53, BRCA1, SNRPN), and a master primer mix was divided into two aliquots; one aliquot was used in the pH 8.3 PCR reaction, the other aliquot was used in the pH 8.0 PCR. In PCR reaction #2, two dominant bands were observed around 390 and 440 b.p., with a smearing of the rest of the PCR fragments observed in both pH conditions. PCR reaction #3 includes 3 sets of multiplex PCR primers (p 5Ex1, p21S1, SNRPN), a primer mix was divided into two aliquots; one aliquot was used in the pH 8.3 PCR reaction, the other aliquot was used in the pH 8.0 PCR. In PCR reaction #3, three distinct bands were observed in both pH conditions at around 317, 391, and 442 b.p. PCR reaction #4 includes 3 sets of multiplex PCR primers (p19Ex1,p21S2,p27). A primer mix was divided into two aliquots; one aliquot was used in the pH 8.3 PCR reaction, and the other aliquot was used in the pH 8.0 PCR. In PCR reaction #4, three distinct bands (around 346, 360, and 426 b.p.) were observed at both pH conditions. PCR reaction #5 includes 3 sets of multiplex PCR primers (p16Ex1,p53, BRCA1). A primer mix was divided into two aliquots; one aliquot was used in the pH 8.3 PCR reaction, and the other aliquot was used in the pH 8.0 PCR. In PCR reaction #5, three distinct bands (around 363, 418, and 459 b.p.) were observed in both pH conditions.

Figure 13:
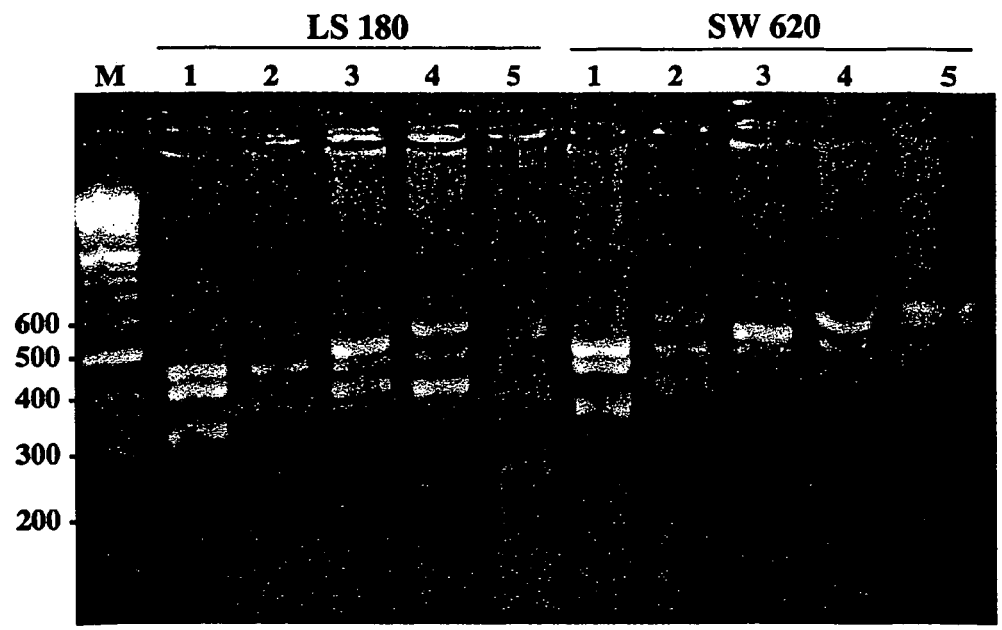
FIG. 13 shows the simultaneous PCR amplification of 16 candidate promoter regions (15 tumor suppressor genes and 1 imprinted gene) in LS180 and SW620 colorectal cell line genomic DNAs. Numbers 1 to 5 represent 5 individual multiplex PCR reactions. Letter M represents the 100 base pair DNA molecular weight marker XIV (Roche, Indianapolis, USA). The corresponding PCR fragments and their sizes are indicated on the lower panel. These PCR fragments were analyzed on a 3% denaturing agarose gel.

Among all 5 multiplex PCR reactions, there was no significant difference in PCR amplification efficiency between two pH buffer conditions. The size of each PCR fragment is shown in FIG. 13. The 1/10 th aliquots of each of the PCR reactions were electrophoresed on a 3% non-denaturing agarose gel. The PCR primer sequences are shown in Table 1. The composition of the amplified promoter regions in each multiplex PCR reaction is indicated on the bottom panel.

The multiplex amplification has been established to work with DNA isolated from both cell lines and tumor samples. Shown in FIG. 13 is the simultaneous PCR amplification of 15 candidate promoter regions in putative tumor suppressor genes in LS180 and SW620 colorectal cell lines. Tumor cell line genomic DNA was treated with sodium bisulfite and used as PCR amplification templates.

Five multiplex PCR reactions were performed in each bisulfite modified genomic DNA. The gene-specific PCR primers were used for the first stage multiplex PCR amplification, and a universal primer was used for the second stage PCR amplification. The detailed multiplex PCR thermal cycling condition is described in Example 3. Three distinct PCR fragments in each multiplex reaction were observed. The corresponding PCR products in each reaction and their sizes are indicated on the lower panel in FIG. 13. Numbers 1 to 5 represent 5 individual multiplex PCR reactions. Letter M represents the 100 base pair DNA molecular weight marker XWV (Roche, Indianapolis, USA). These PCR fragments were analyzed on a 3% denaturing agarose gel.

Example 10

LDR Analysis Following Multiplex PCR Amplification

The multiplex PCR reactions were pooled in equal volumes and subjected to the ligase detection reaction (details set forth in Example 6). A universal array was used to capture the ligase detection reaction products. A unique zip-code oligonucleotide sequence was covalently linked to individual addresses on the universal array. Each address on the universal array can capture a unique ligase detection reaction product by hybridizing to the complementary zip-code that is attached to each unlabeled common oligonucleotide LDR probe. The presence or absence of methyl cytosine can thus be identified based upon the particular fluorescent label attached to the LDR product, and hybridized to a given address on the array.

To validate the LDR/Universal array approach, the methylation status in the promoter regions of DNA isolated from cell lines was determined. Cy5 fluorescent labeled probes are used to detect unmethylated cytosines, while Cy3 fluorescent labeled probes are used to distinguish the methylated cytosines. The results of these experiments are shown in FIGS. 11, 12, 14, and 15 Each of the common probes is phosphorylated at its 5' end and has a unique zip-code complement sequence attached to its 3' end. The ligation products are captured on a Universal Array and the fluorescent signals are measured using a microarray scanner. Three universal array addresses were assigned to each promoter region under interrogation. Each address is double spotted to ensure the quality of array fabrication and oligonucleotide hybridization accuracy. The LDR/Universal Array approach has been fully described in Gerry, N. P., et al., *J. Mol. Biol.* 292: 251-262 (1999); Favis, R., et al., *Natural Biotechnology* 18: 561-564 (2000), which are hereby incorporated by reference in its entirety.

FIG. 11 shows the results achieved when the multiplex PCR products shown in FIG. 10 were subject to an LDR reaction with Cy5 labeled LDR probes. Only PCR reaction products produced at a pH of 8.0 were used as templates in the ligase detection reactions. The presence of Cy5 fluorescent signal at each promoter region indicates the corresponding PCR fragments (from FIG. 10) are unmethylated. That is, the unmethylated promoter regions of p15, p16, p19, and p21 were detected in normal human lymphocytes in reaction 1; the unmethylated promoter regions of SNRPN, p53, BRCA1, p21, and p27 were detected in normal human lymphocytes in reaction 2; the unmethylated promoter regions of SNRPN, p15, and p21 were detected in normal human lymphocytes in reaction 3; the unmethylated promoter regions of p19, p21, and p27 were detected in normal human lymphocytes in reaction 4; the unmethylated promoter regions of p53, p16, BRCA1, p21, and p27 were detected in normal human lymphocytes in reaction 5.

Figure 12:
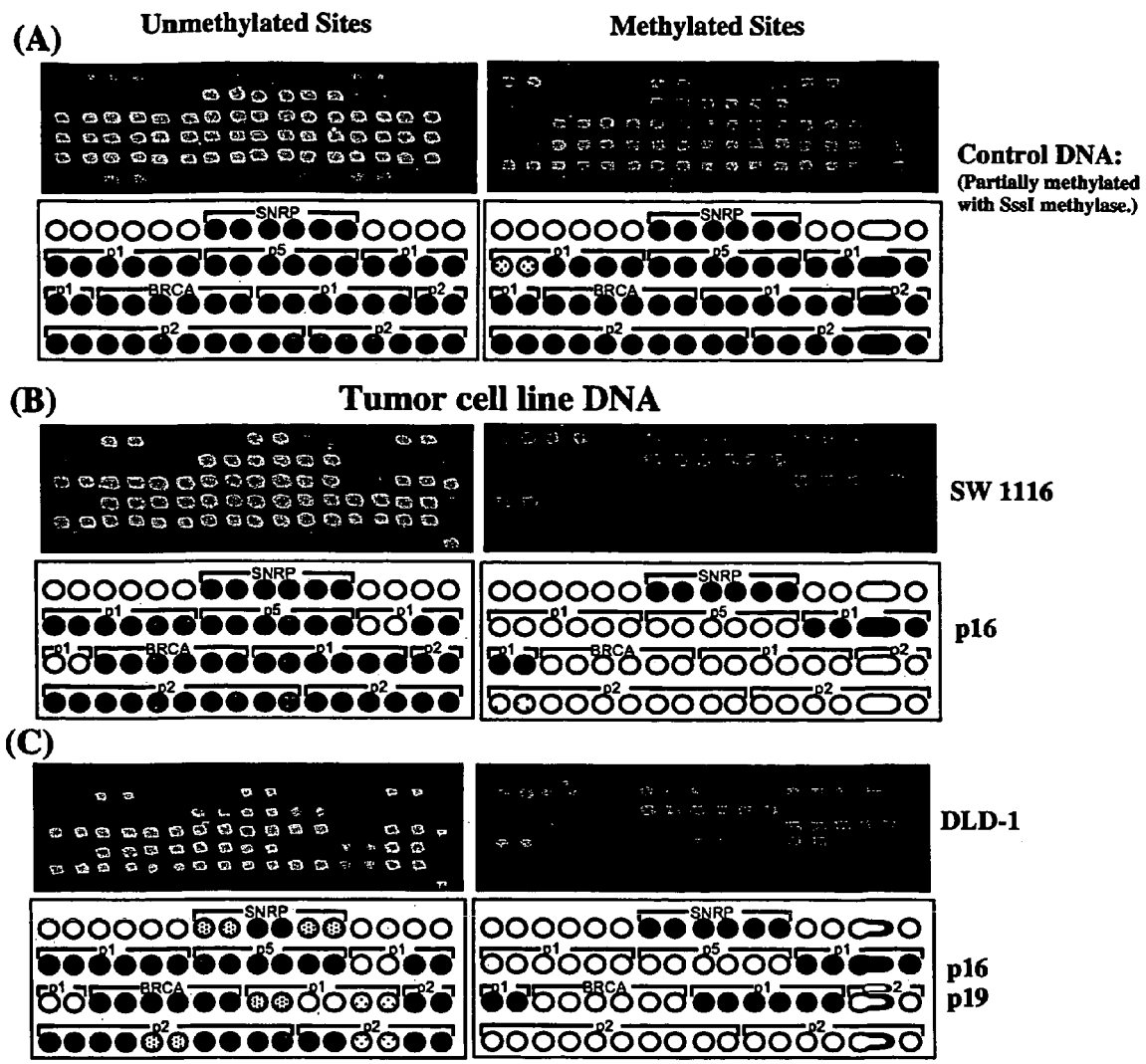
FIG. 12 show the universal array images of methylation profiles of selected promoter regions (SNRPN, p15, p16, p19, p21, p27, p53, and BRCA1) in normal and colorectal tumor cell line genomic DNAs. False color green represents the status of unmethylated promoter regions detected by Cy5 labeled LDR probes. False color red represents the status of methylated promoter regions detected by Cy3 labeled LDR probes.

The success of the bisulfite/PCR-PCR/LDR/Universal Array approach is also demonstrated in normal lymphocytes and colorectal tumor cell line genomic DNAs. Genomic DNAs were treated with sodium bisulfite (as described in Example 2) and subjected to multiplex PCR (as described in Example 3) and LDR/Universal Array assay (as described in Example 6). FIG. 12 shows the universal array images of methylation profiles for selected promoter regions (SNRPN, p15, p16, p19, p21, p27, p53, and BRCA1). False color green represents the status of unmethylated promoter regions detected by Cy5 labeled LDR probes. False color red represents the status of methylated promoter regions detected by Cy3 labeled LDR probes. Panel A indicates the candidate promoter regions are unmethylated in normal human lymphocyte genomic DNAs. Since SssI methylase can methylate all the promoter region that are being analyzed, an unmethylated result accurately reflects the methylation status of the target DNA. In panels B and C, the methylation profiles of two colorectal cancer cell line genomic DNAs were analyzed. Among all the eight genes that were analyzed in the colorectal cancer cell line SW1116 and DLD-1, only the p16 promoter region was methylated in cell line SW1116 (panel B) and both the p16 and p19 promoter regions were methylated in cell line DLD-1.

Figure 14:
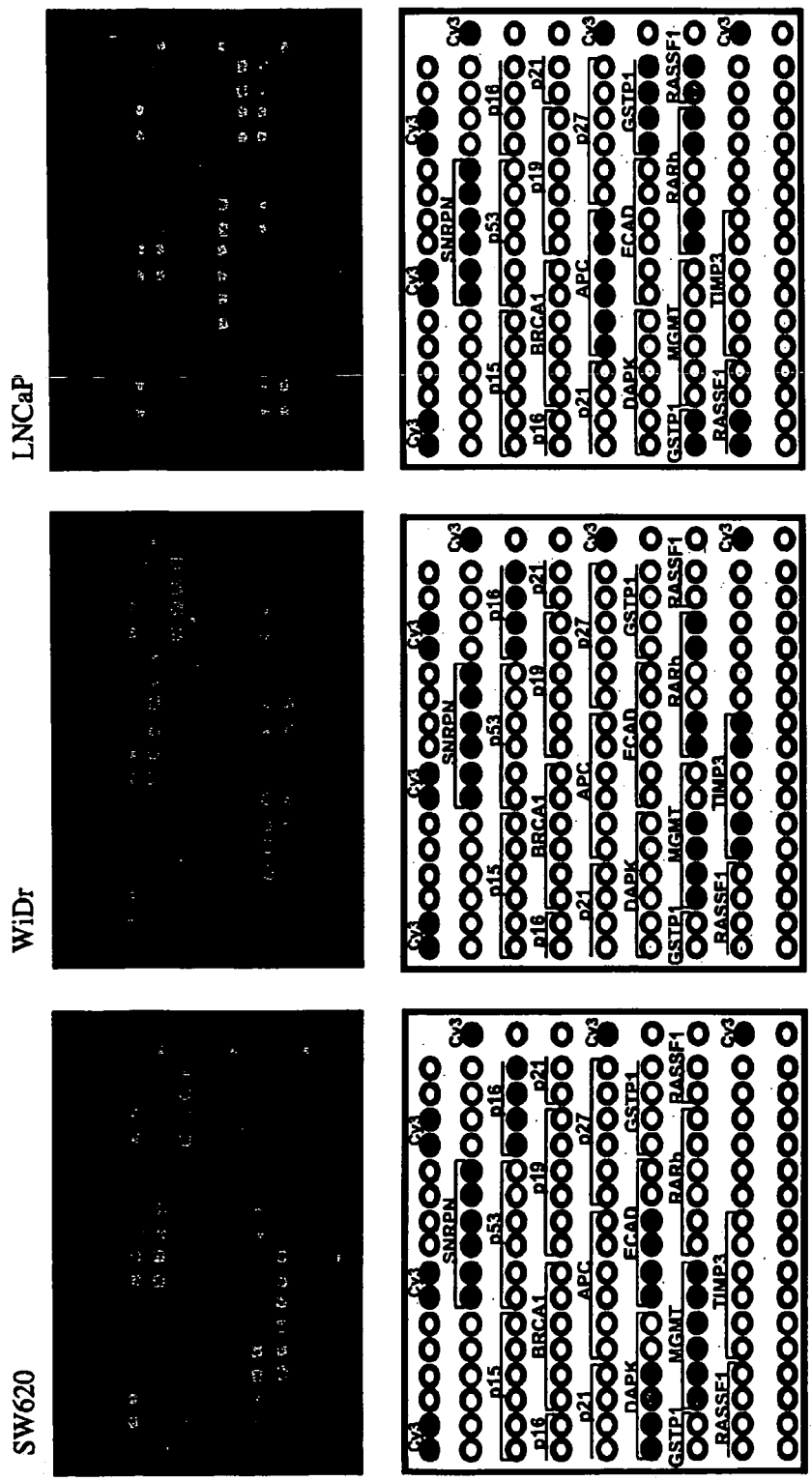
FIG. 14 presents the universal array images of the methylation status of the genomic DNAs of two colorectal cancer cell lines (SW620 and WiDr) and one prostate cancer cell line (LNCaP). Sixteen selected promoter regions (SNRPN, p15, p16, p19, p21, p27, p53, BRCA1, APC, DAPK, ECAD, GSTP1, MGMT, RARβ, RASSF1, and TIMP3) were analyzed for each cell line. False color red represents the methylated promoter regions detected by Cy3 labeled LDR probes. Cell line SW620 has SNRPN, p16, DAPK, ECAD, and MGMT promoters methylated. Cell line WiDr has SNRPN, p16, MGMT, RARβ, and TIMP3 promoters methylated. Cell line LNCaP has SNRPN, APC, GSTP1, RARβ, and RASSF1 promoters methylated.
Figure 15:
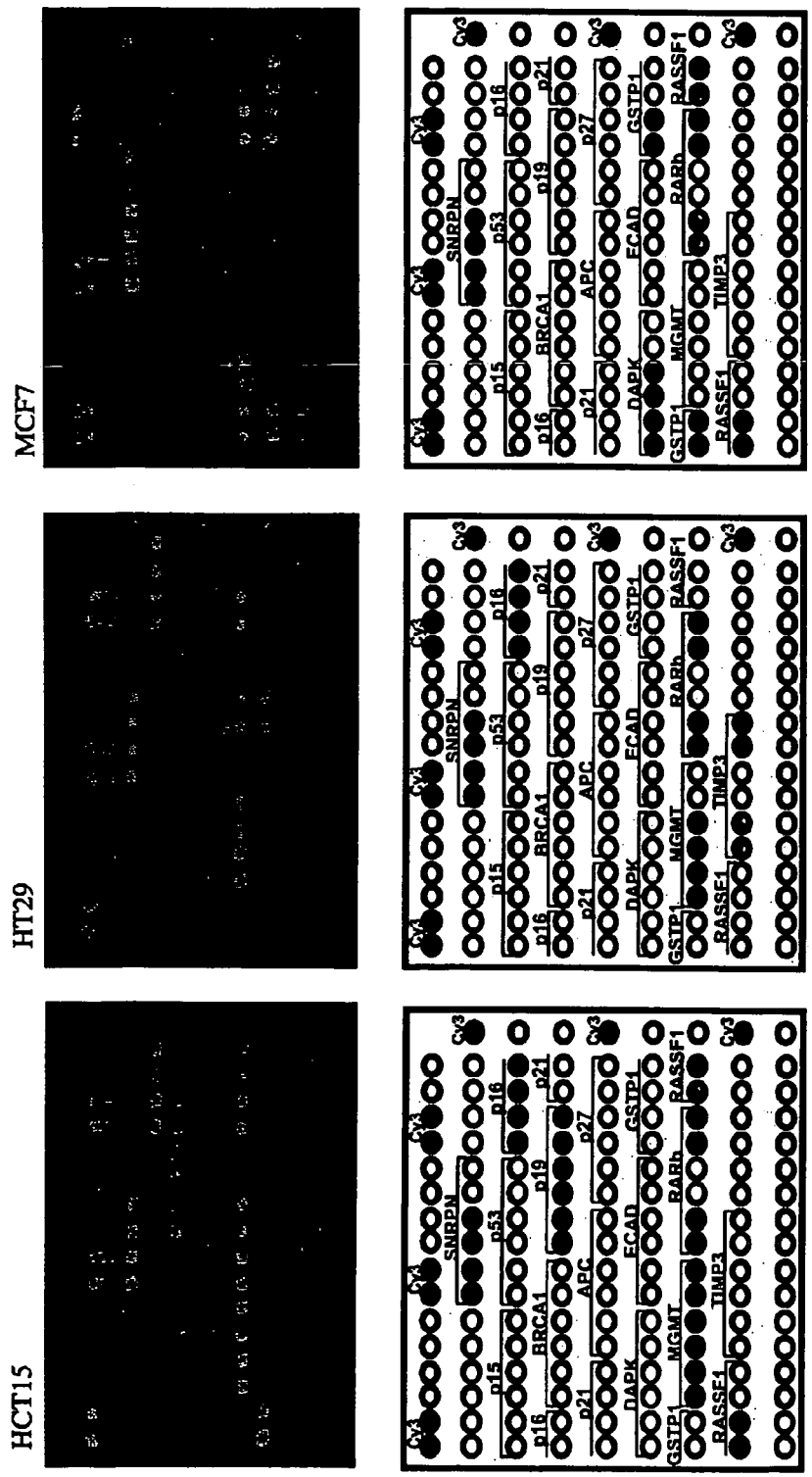
FIG. 15 presents the universal array images of the methylation status of the genomic DNAs of two colorectal cancer cell lines (HCT15 and HT29) and one breast cancer cell line (MCF7). Sixteen selected promoter regions (SNRPN, p15, p16, p19, p21, p27, p53, BRCA1, APC, DAPK, ECAD, GSTP1, MGMT, RARβ, RASSF1, and TIMP3) were analyzed for each cell line. False color red represents the methylated promoter regions detected by Cy3 labeled LDR probes. Cell line HCT15 has SNRPN, p16, p19, MGMT, and RASSF1 promoters methylated. Cell line HT29 has SNRPN, p16, MGMT, RARβ, and TIMP3 promoters methylated. Cell line MCF7 has SNRPN, DAPK, GSTP1, RARβ, and RASSF1 promoters methylated.
Figure 16:
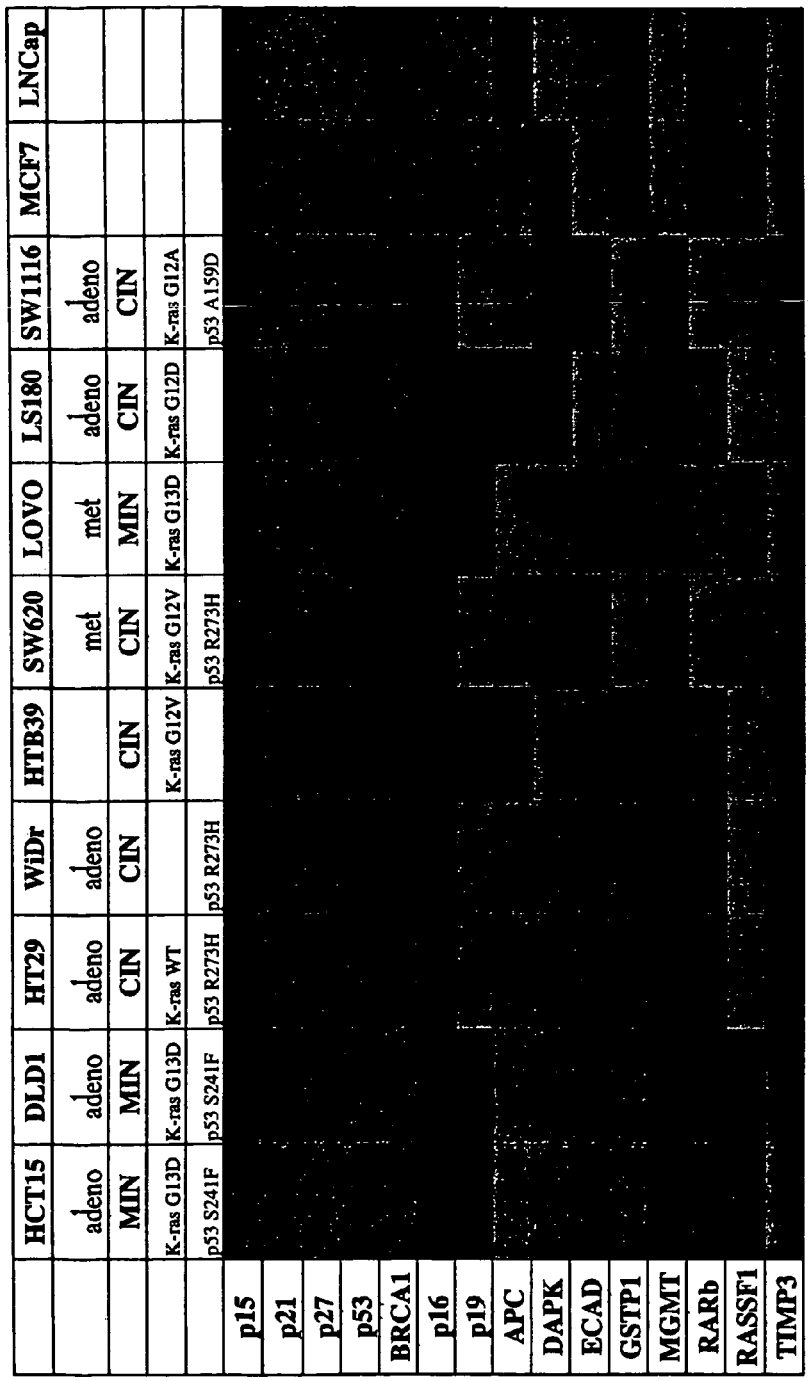
FIG. 16 presents a summary of the methylation status of the genomic DNAs of nine colorectal cancer cell lines (HCT15, DLD1, HT29, WiDr, HTB39, SW620, LOVO, LS180, and SW1116), one breast cancer cell line (MCF7), and one prostate cancer cell line (LNCaP). Sixteen selected promoter regions (SNRPN, p15, p16, p19, p21, p27, p53, BRCA1, APC, DAPK, ECAD, GSTP1, MGMT, RARβ, RASSF1, and TIMP3) were analyzed for each cell line. The corresponding mutation status of K-ras, p53 genes, the genome stability and the cell line origins are indicated on the top of the table. The unmethylated promoter regions are designated in green and the methylated promoter regions are designated in red. Note that cell lines HCT15/DLD1 and HT29/WiDr are derived from the same patient, respectively.

More candidate genes were analyzed for their promoter methylation status using the bisulfite/PCR-PCR/LDR/Universal Array approach. Sixteen selected promoter regions (SNRPN, p15, p16, p19, p21, p27, p53, BRCA1, APC, DAPK, ECAD, GSTP1, MGMT, RARβ, RASSF1, and TIMP3) that were analyzed for colorectal cancer (SW620, WiDr, HCT15, and HT29), prostate cancer (LNCaP) and breast cancer (MCF7) cell lines are shown in FIGS. 14 and 15. False color red in FIGS. 14 and 15 represents the methylated promoter regions detected by Cy3 labeled LDR probes. Cell line WiDr has SNRPN, p16, MGMT, RARβ, and TIMP3 promoters methylated. Cell line LNCaP has SNRPN, APC, GSTP1, RARβ, and RASSF1 promoters methylated. Cell line SW620 has SNRPN, p16, DAPK, ECAD, and MGMT promoters methylated. Cell line HCT15 has SNRPN, p16, p19, MGMT, and RASSF1 promoters methylated. Cell line HT29 has SNRPN, p16, MGMT, RARβ, and TIMP3 promoters methylated. Cell line MCF7 has SNRPN, DAPK, GSTP1, RARβ, and RASSF1 promoters methylated. A summary of the methylation status of the genomic DNAs of nine colorectal cancer cell lines (HCT15, DLD1, HT29, WiDr, HTB39, SW620, LOVO, LS180, and SW1116), one breast cancer cell line (MCF7) and one prostate cancer cell line (LNCaP) are shown in FIG. 16. The unmethylated promoter regions are designated in green and the methylated promoter regions are designated in red. Notice cell lines HCT15/DLD1 and HT29/WiDr are derived from the same patient. The fact that cell lines HCT15 and HT29 have identical methylation patterns as cell lines DLD1 and WiDr, respectively, indicates the bisulfite/PCR-PCR/LDR/Universal Array approach is robust and allows the identification of distinct methylation signature based on the cellular origins.

Figure 17:
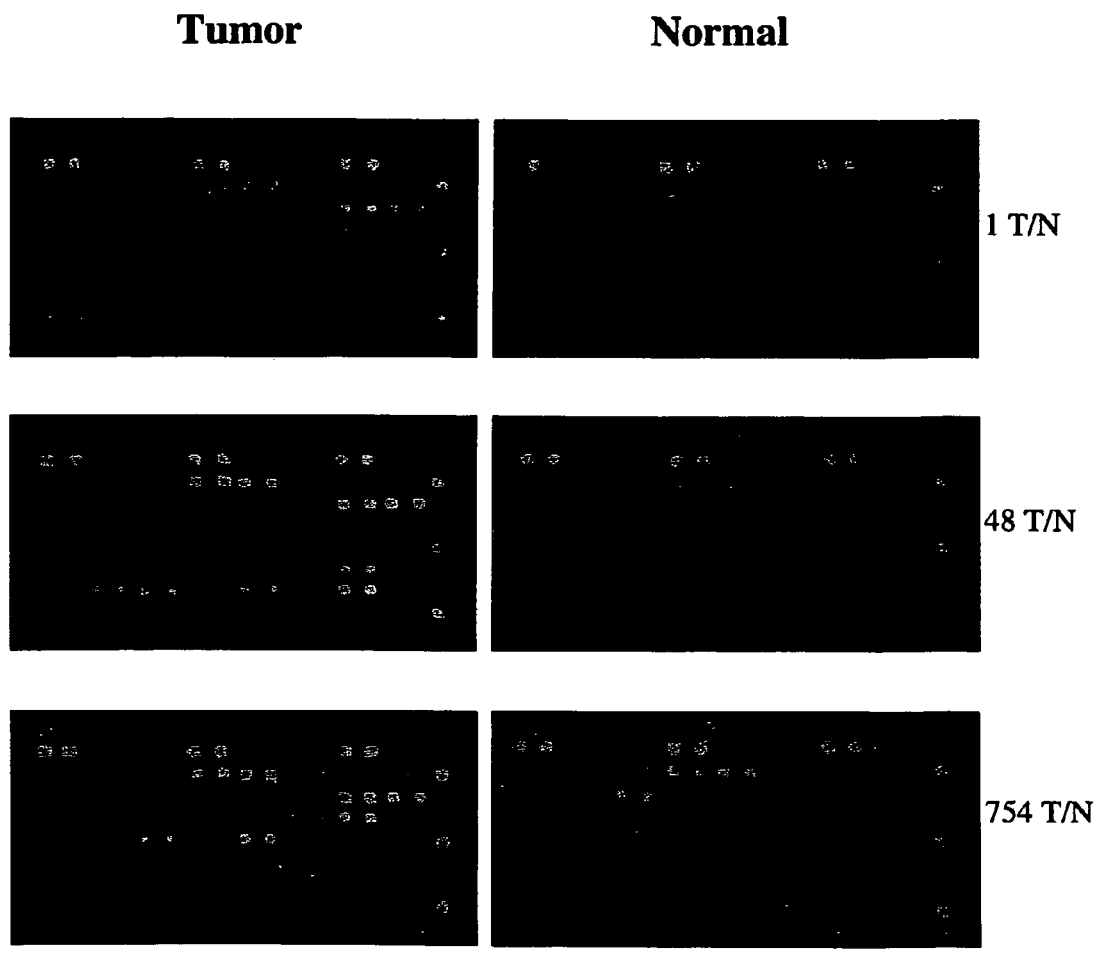
FIG. 17 presents the universal array images of the methylation status of the genomic DNAs extracted from three colorectal tumor and matched normal tissues. Sixteen selected promoter regions (SNRPN, p15, p16, p19, p21, p27, p53, BRCA1, APC, DAPK, ECAD, GSTP1, MGMT, RARβ, RASSF1, and TIMP3) were analyzed for each sample. False color red represents the methylated promoter regions detected by Cy3 labeled LDR probes. By comparing the tumor sample with its matched normal, anonymous tumor #1 has p16, p19, MGMT, RARβ, and RASSF1 promoters methylated. Anonymous tumor #48 has p16, GSTP1, MGMT, and RARβ promoters methylated. Anonymous tumor #754 has p16, p19, and APC promoters methylated.
Figure 18:
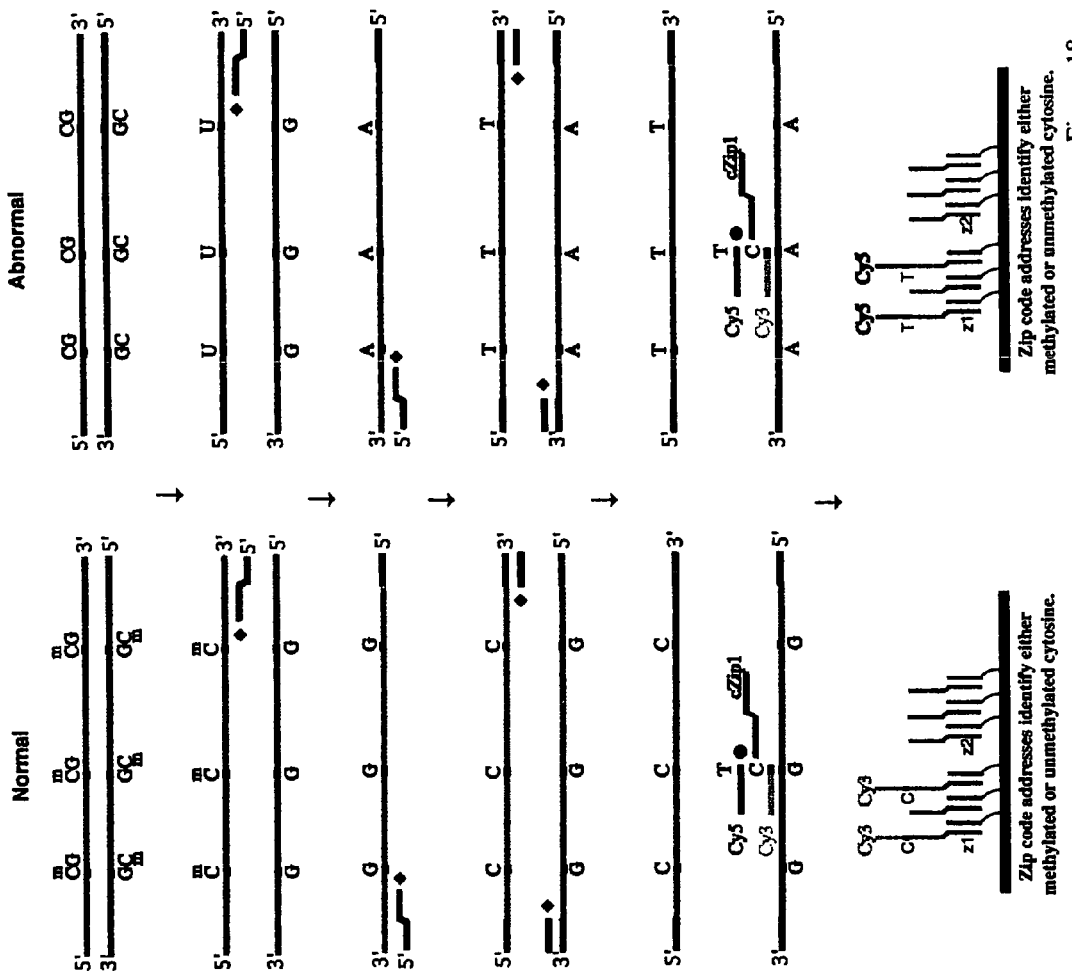
FIG. 18 is a schematic diagram illustrating the Bisulfite/PCR-PCR/LDR/Universal Array procedure for high-throughput detection of DNA hypomethylation in a given sample. This procedure consists of bisulfite treatment of genomic DNA, multiplex PCR with gene-specific/universal primers(A), multiplex LDR, and universal array approaches. In this scenario, the genomic DNA under normal conditions is methylated, while the genomic DNA under abnormal conditions (i.e. in a tumor) is hypomethylated.
Figure 19:
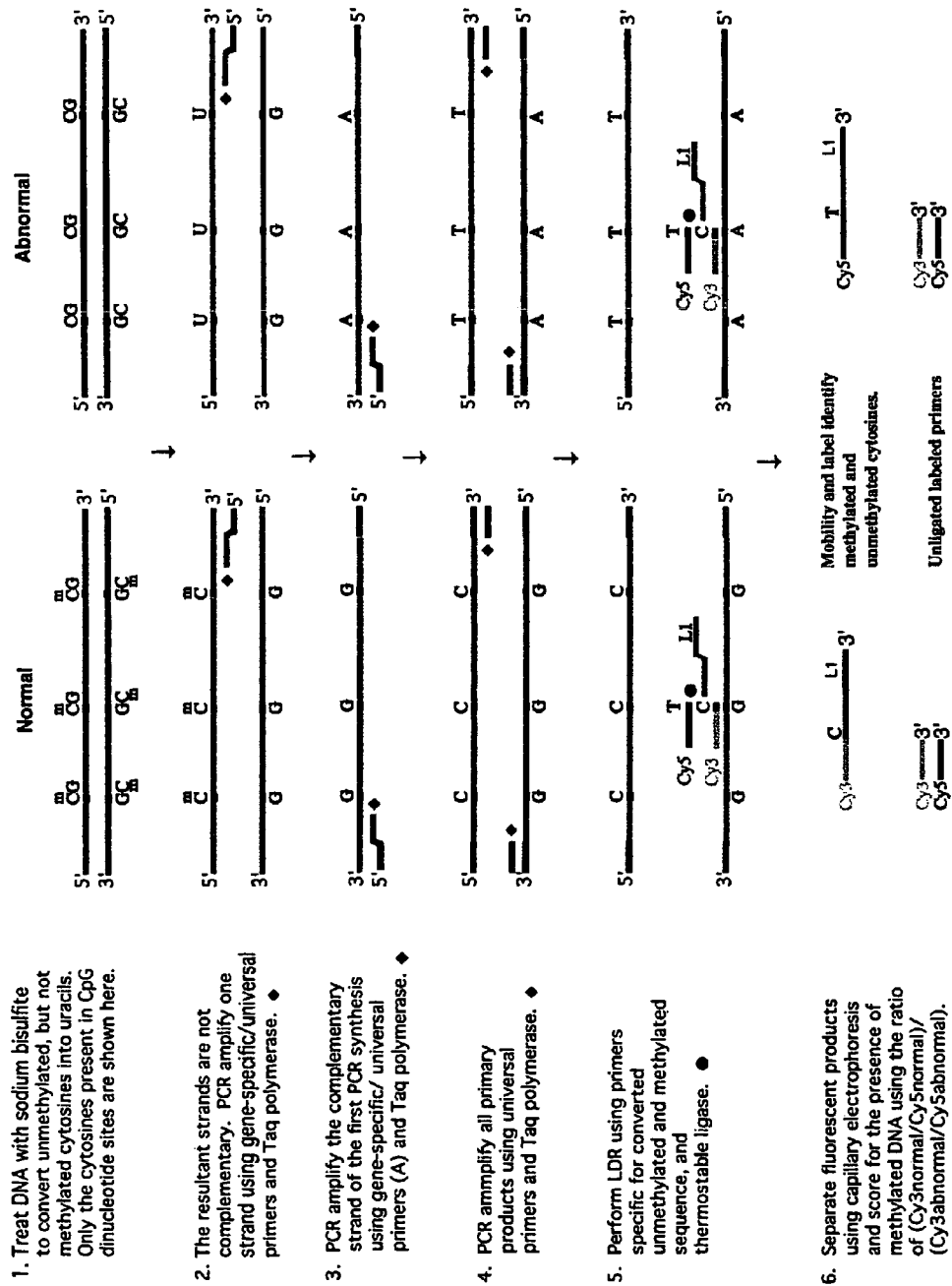
FIG. 19 is a schematic diagram illustrating the Bisulfite/PCR-PCR/LDR/capillary electrophoresis procedure for high-throughput detection of DNA hypomethylation in a given sample. This procedure consists of bisulfite treatment of genomic DNA, multiplex PCR with gene-specific/universal primers(A), multiplex LDR, and capillary electrophoresis approaches. In this scenario, the genomic DNA under normal conditions is methylated, while the genomic DNA under abnormal conditions (i.e. in a tumor) is hypomethylated.
Figure 20:
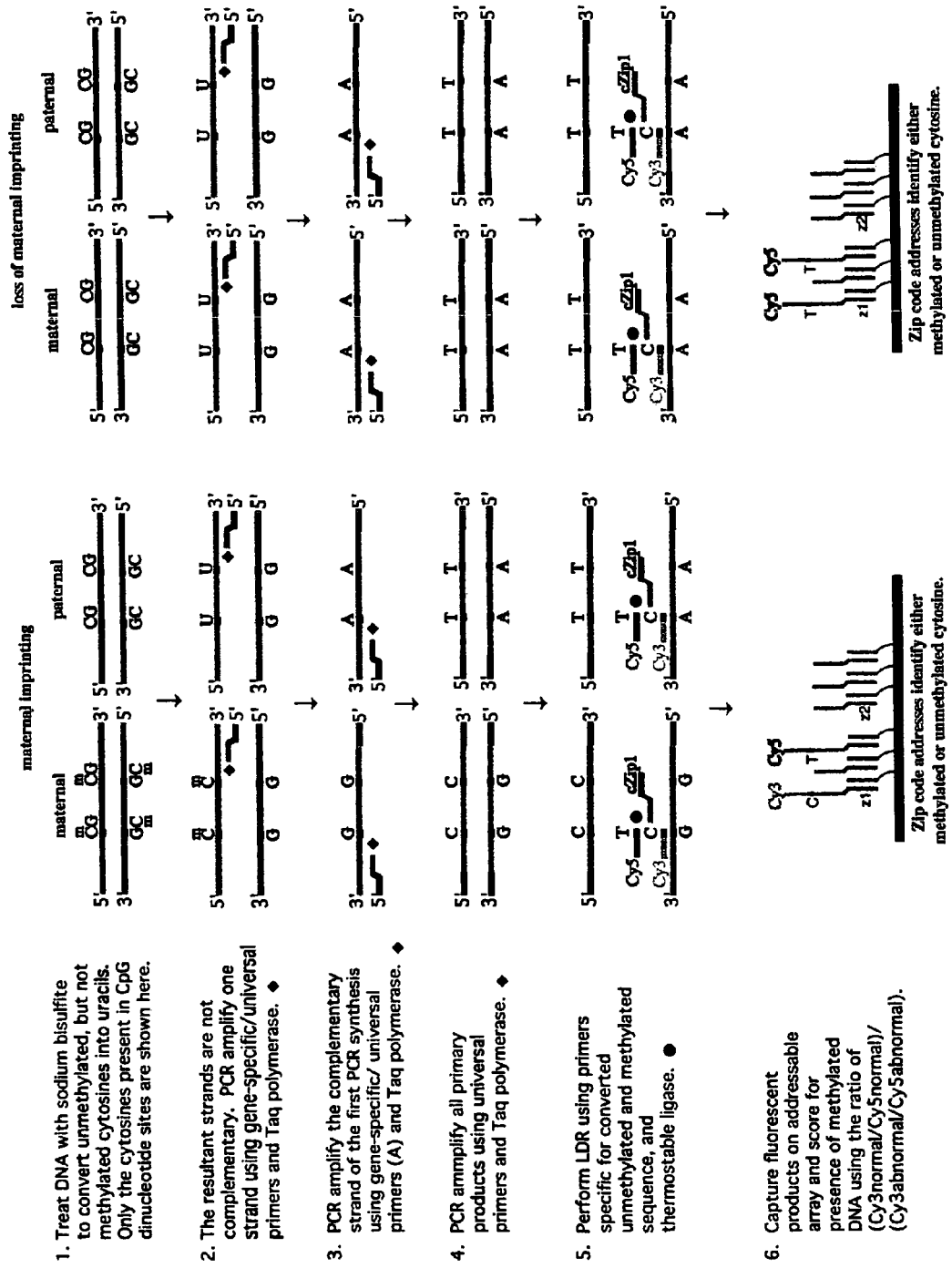
FIG. 20 is a schematic diagram illustrating the Bisulfite/PCR-PCR/LDR/Universal Array procedure for high-throughput detection of the loss of maternal imprinting in a given sample. This procedure consists of bisulfite treatment of genomic DNA, multiplex PCR with gene-specific/universal primers (A), multiplex LDR, and universal array approaches. The normal cellular state carries one copy of maternal allele (methylated) and one copy of paternal allele (unmethylated). In a disease stage, the cellular genomic content consists of one copy of hypomethylated maternal allele and the copy of paternal allele remains unmethylated.
Figure 21:
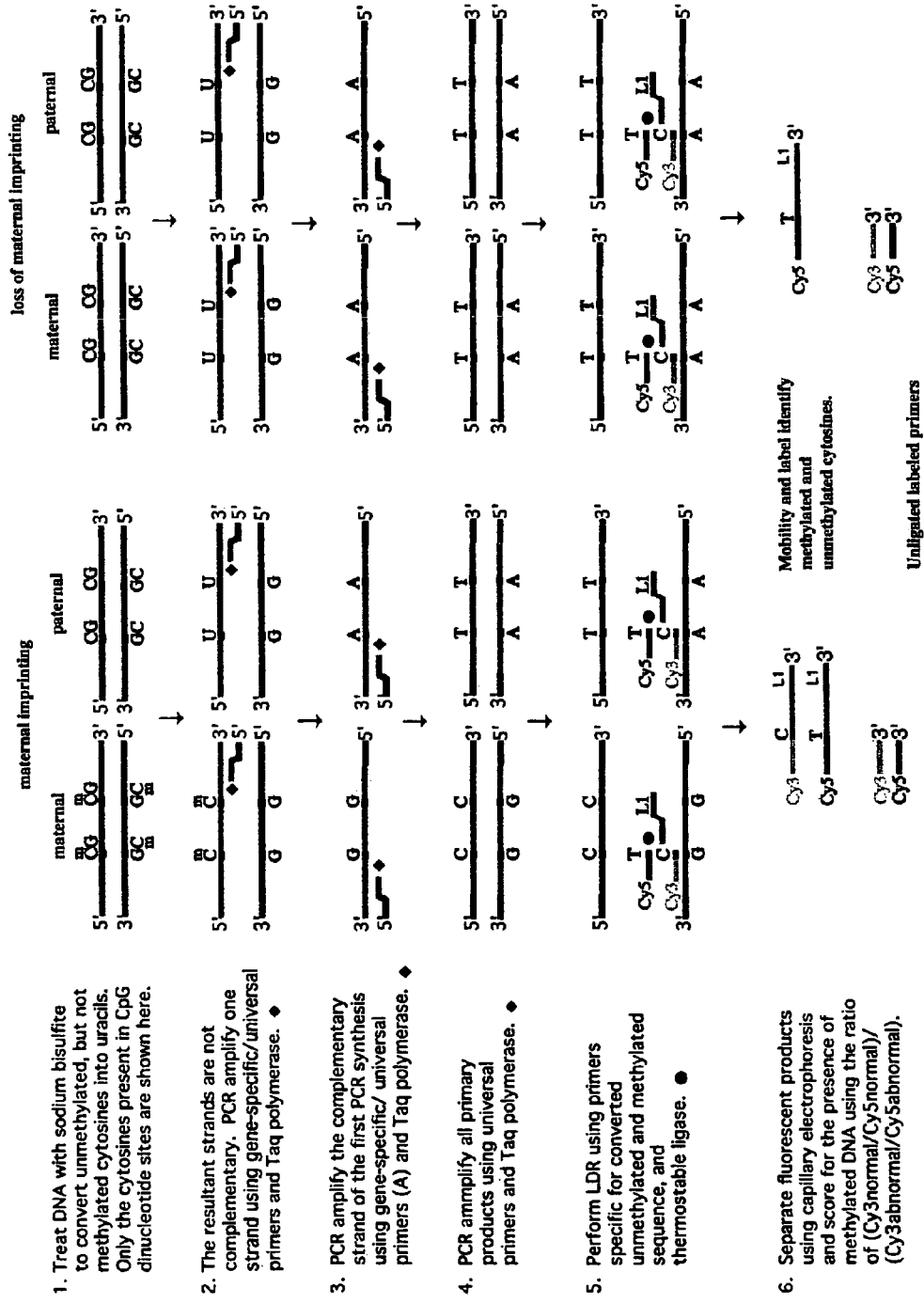
FIG. 21 is a schematic diagram illustrating the Bisulfite/PCR-PCR/LDR/capillary electrophoresis procedure for high-throughput detection of the loss of maternal imprinting in a given sample. This procedure consists of bisulfite treatment of genomic DNA, multiplex PCR with gene-specific/universal primers (A), multiplex LDR, and capillary electrophoresis approaches. The normal cellular state carries one copy of maternal allele (methylated) and one copy of paternal allele (unmethylated). In a disease stage, the cellular genomic content consists of one copy of hypomethylated maternal allele and the copy of paternal allele remains unmethylated.

The success of the bisulfite/PCR-PCR/LDR/Universal Array approach is further demonstrated in the genomic DNAs of three colorectal tumor and matched normal tissues. As shown in FIG. 17, sixteen selected promoter regions (SNRPN, p15, p16, p19, p21, p27, p53, BRCA1, APC, DAPK, ECAD, GSTP1, MGMT, RARβ, RASSF1, and TIMP3) were analyzed for each sample. False color red represents the methylated promoter regions detected by Cy3 labeled LDR probes. By comparing the tumor sample with its matched normal, anonymous tumor #1 has p16, p19, MGMT, RARβ, and RASSF1 promoters methylated. Anonymous tumor #48 has p16, GSTP1, MGMT, and RARE promoters methylated. Anonymous tumor #754 has p16, p19, and APC promoters methylated. Thus, it is demonstrated the bisulfite/PCR-PCR/LDR/Universal Array approach is robust on tumor samples as well.

Example 11

Figure 22:
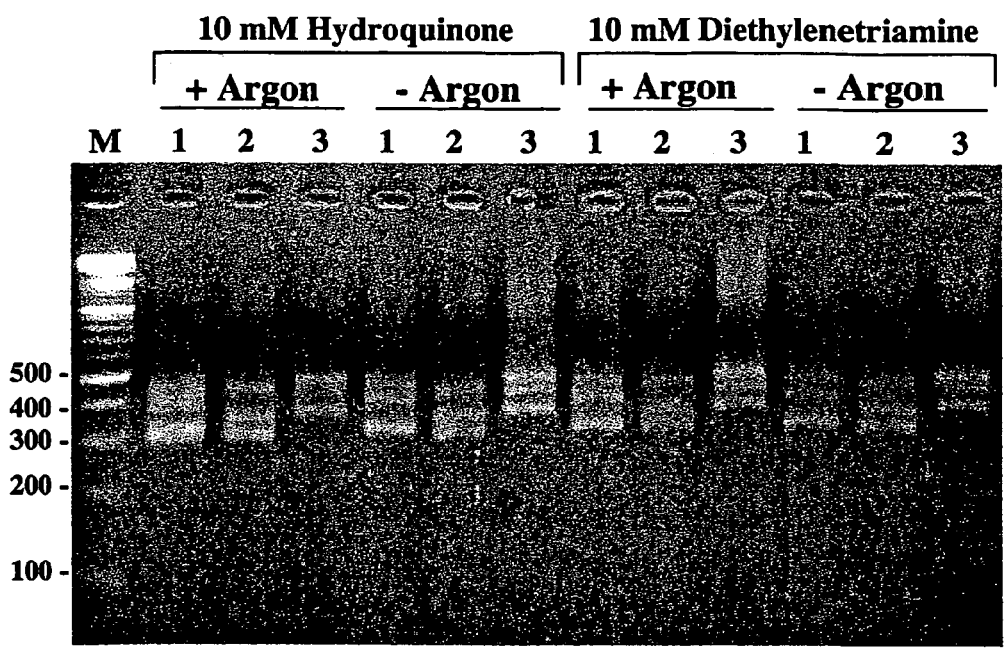
FIG. 22 shows the multiplex PCR reaction performed on colorectal cancer cell line (HTB39) genomic DNA treated with bisulfite, and catalyzed with either 10 mM hydroquinone or 10 mM diethylenetriamine in the presence or absence of argon degassed buffer. The PCR products were visualized on a 3% agarose gel. The composition of the amplified promoter regions in each multiplex PCR reaction is indicated on the bottom panel.
Figure 23:
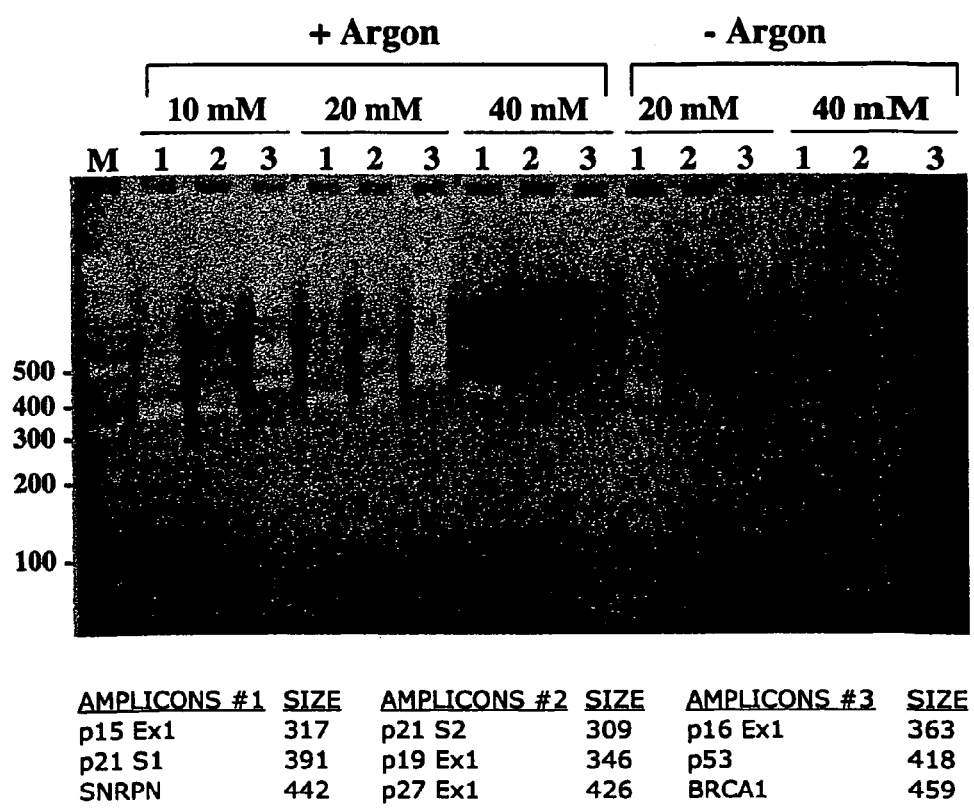
FIG. 23 shows the multiplex PCR reaction performed on colorectal cancer cell line (HTB39) genomic DNA treated with bisulfite, and catalyzed with 10 mM, 20 mM, and 40 mM of diethylenetriamine in the presence or absence of argon degassed solution. The PCR products were visualized on a 3% agarose gel. The composition of the amplified promoter regions in each multiplex PCR reaction is indicated on the bottom panel.

PCR Amplification of Colorectal Cancer Cell Line Genomic DNA Treated With Sodium Bisulfite Under Variety of Catalyst Conditions A variety of conditions were tested to optimize bisulfite deamination of unmethylated but not methylated cytosines. FIGS. 22 and 23 show the multiplex PCR reaction performed on colorectal cancer cell line (HTB39) genomic DNA treated with sodium bisulfite, and catalyzed with either 10 mM hydroquinone or a serious concentration of diethylenetriamine in the presence or absence of argon degassed buffer. Nine candidate gene promoter regions were simultaneously amplified in three PCR reactions in each catalyst condition. The composition and the size of the amplified promoter regions in each multiplex PCR reaction is indicated on the bottom panel of each figure. The PCR products were visualized on a 3% agarose gel.

In FIG. 22, the HTB39 genomic DNA was treated with bisulfite and catalyzed with either 10 mM hydroquinone or 10 mM diethylenetriamine. The catalyst-added bisulfite solution was divided into two aliquots; one aliquot was degassed with argon for 15 minutes at room temperature before mixing with the genomic DNA, the other aliquot was mixed with the genomic DNA without argon degassing. All of the mixtures were then incubated for 16-20 hours, preferable 16 hours, in a DNA thermal cycler (Perkin Elmer Cetus) with the cycles of 50° C. for 20 minutes followed by a denaturing step of 85° C. for 15 seconds.

In FIG. 23, the HTB39 genomic DNA was treated with sodium bisulfite and catalyzed with either 10, 20, or 40 mM diethylenetriaamine. The catalyst-added bisulfite solution was divided into two aliquots; one aliquot was degassed with argon for 15 minutes at room temperature before mixing with the genomic DNA. The other aliquot was mixed with the genomic DNA without argon degassing. All of the mixtures were then incubated for 16-20 hours, preferable 16 hours, in a DNA thermal cycler (Perkin Elmer Cetus) with the cycles of 50° C. for 20 minutes followed by a denaturing step of 85° C. for 15 seconds.

The bisulfite treated DNAs were cleaned with Wizard DNA clean-up kit (Promega, Madison, Wis.) or, alternatively, desalted using MICROCON centrifugal filter devices (Millipore, Bedford, Mass.). The eluted DNAs were incubated with one-tenth volume of 3N NaOH at room temperature for 5 minutes followed by ethanol precipitation. The DNA pellets were resuspended and subject to two-stage multiplex PCR amplification, as described in Examples 3 and 9. Proteinase K (QIAGEN, Valencia, Calif.) was added at the end of the second stage multiplex PCR reaction to inactivate the remaining thermostable polymerase. Before pooling the PCR products for further LDR/Universal array analysis, the existence of the proper size of PCR fragments was verified by gel or capillary electrophoresis.

As shown in FIG. 22, a similar PCR amplification efficiency was observed between 10 mM hydroquinone and 10 mM diethylenetriamine conditions in the presence and absence of the argon treatment. However, the lack of PCR products at 20 and 40 mM diethylenetriamine (argon minus) and 40 mM diethylenetriamine (argon plus) indicate a poor PCR amplification efficiency. This reduced PCR efficiency may result from the degradation of DNA template during bisulfite treatment.

The multiplex PCR reactions were pooled in equal volume and subjected to the ligase detection reaction (details set forth in Example 6). A universal array is used to capture the ligase detection reaction products. A unique zip-code oligonucleotide sequence has been covalently linked to individual addresses on the universal array. Each address on the universal array can capture a unique ligase detection reaction product by hybridizing to the complementary zip-code that is attached to each unlabeled common oligonucleotide LDR probe. The presence or absence of methyl cytosine can thus be identified based upon the particular fluorescent label attached to the LDR product, and hybridized to a given address on the array.

Figure 24:
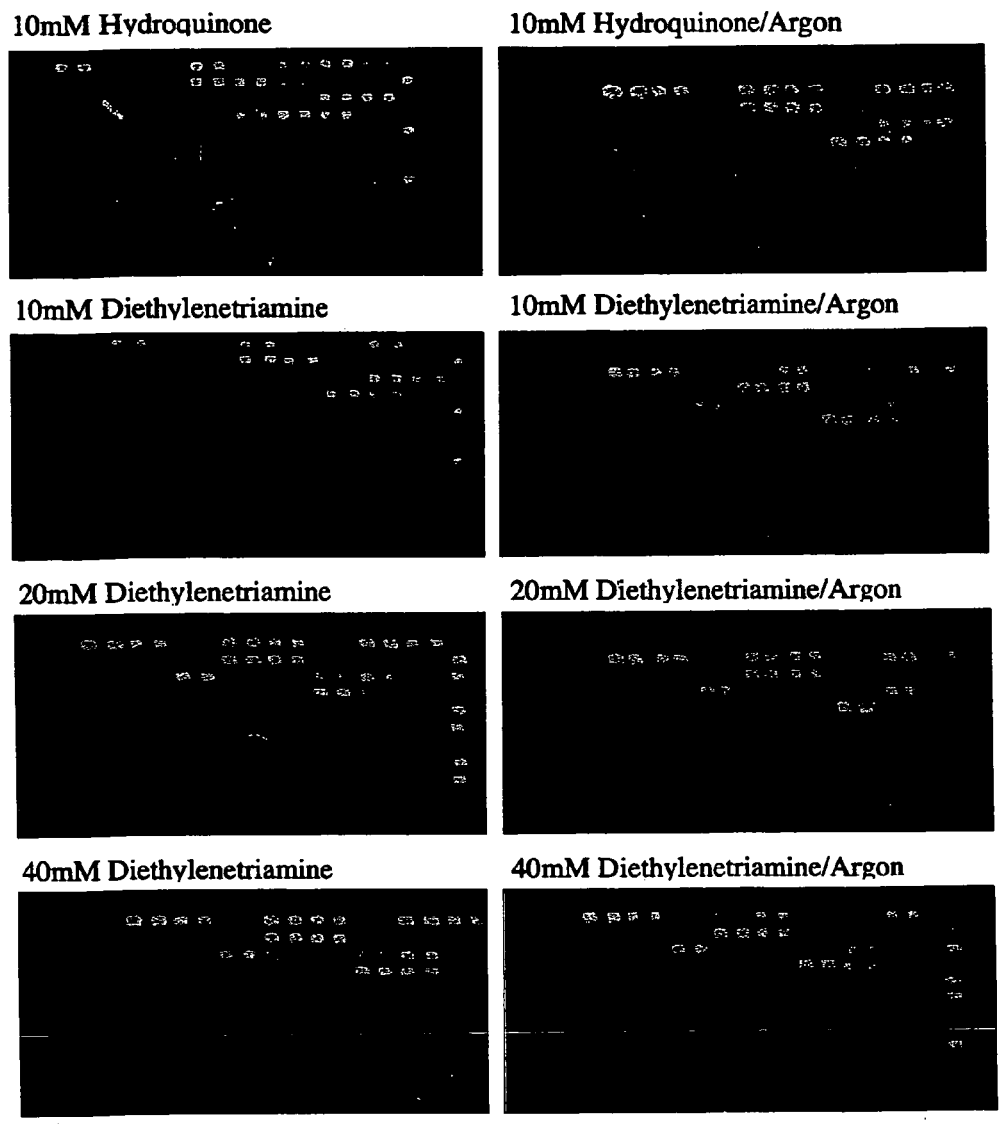
FIG. 24 presents the universal array images of the methylation status of the colorectal cell line (HTB39) genomic DNA in eight promoter regions (SNRPN, p15, p16, p19, p21, p27, p53, and BRCA1). The genomic DNA was bisulfite treated and catalyzed with either 10 mM hydroquinone or 10 mM, 20 mM, and 40 mM diethylenetriamine in the presence or absence of argon degassed solution. The DNA templates used in these LDR reactions are the same as those shown in FIGS. 22 and 23. The false color red represents the methylated promoter regions detected by Cy3 labeled LDR probes. Notice that SNRPN, p16, and p19 promoters are methylated in HTB39 cell line.
Figure 26:
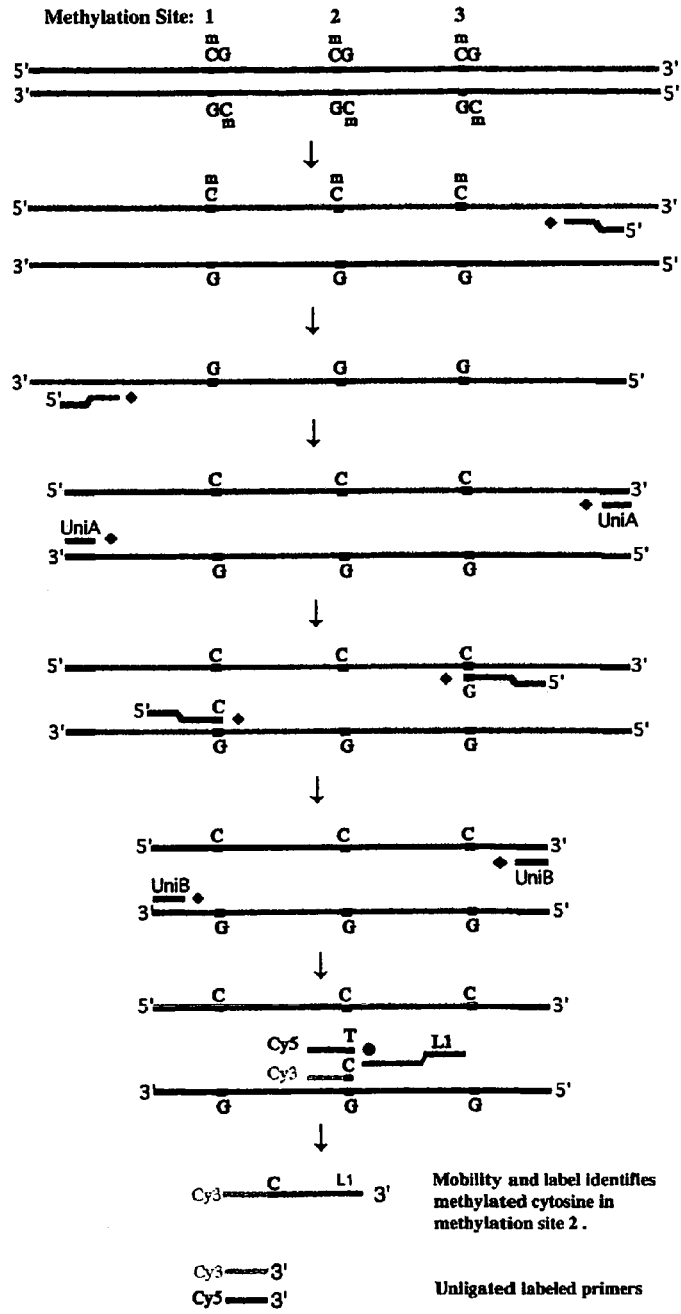
FIG. 26 is a schematic diagram illustrating the Bisulfite/PCR-PCR/MS-PCR-PCR/LDR/capillary electrophoresis procedure for high-throughput detection of promoter methylation status of low abundance methylation alleles in a given sample. This procedure consists of bisulfite treatment of genomic DNA, multiplex PCR with gene specific/universal primers (A), methylation specific multiplex PCR with methyl-specific/universal primers (B), multiplex LDR, and capillary electrophoresis approaches. The methyl-specific/universal PCR primer has the discriminating 3'OH base pairing to the cytosine of CpG dinucleotides (or pairing the guanine if it is on the opposite DNA strand) to ensure the selection of methylated alleles.

Based on the previous experiments (shown in FIG. 16), only two gene promoters (p16 and p19) are methylated among all eight promoter regions that were examined (SN-RPN, p15, p16, p19, p21, p27, p53, BRCA1). Indeed, the same results of both p16 and p19 methylation were also observed (FIG. 24) in the reactions catalyzed by either 10 mM hydroquinone or 10 mM diethylenetriamine (in both with and without argon degas). Non-specific methylation signals (in the addresses of p15 and BRCA1 genes on the Universal array) were accumulated in the reactions catalyzed with 20 and 40 mM diethylenetriamine (in both with and without argon degas). Therefore, it can be concluded that 10 mM diethylenetriamine catalyzes the bisulfite deamination reaction as efficient as 10 mM hydroquinone.

Example 12

Simultaneous Amplification with Gene-specific PCR Primers

Figure 31:
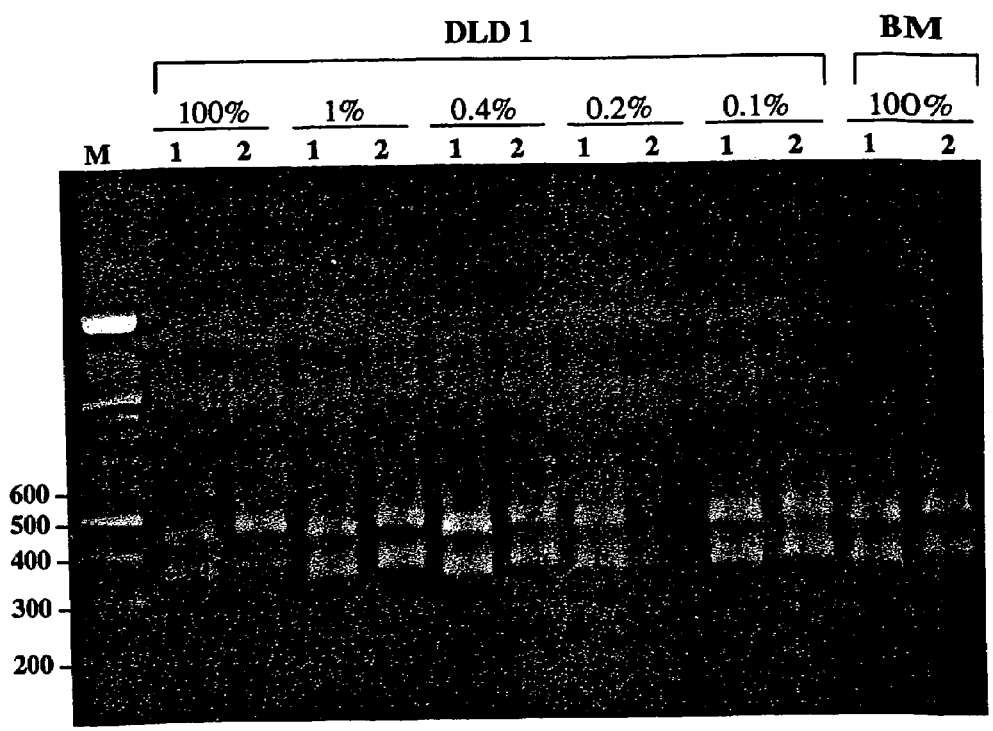
FIG. 31 demonstrates the first round of amplification of Bisulfite/PCR-PCR/MS-PCR-PCR/LDR/Universal Array approach simultaneously amplified 4 candidate gene promoter regions (SNRPN, BRCA1, p16, and p19) in colorectal cancer cell line (DLD1) and normal human lymphocyte (BM) genomic DNAs. The genomic DNA of DLD1 was mixed with a different amount of normal human lymphocyte DNA and the percentages are indicated. Two fragments were amplified in each PCR reaction (amplicon1: SNRPN and p19; amplicon2: BRCA1 and p16) and were validated on a 3% agarose gel as shown.

As shown in FIG. 31, all the target promoter regions are simultaneously amplified with gene-specific PCR primers followed by a first universal PCR primer (primer "A"), where its sequence is present on the 5' portion of each gene-specific PCR primer. The genomic DNA of colorectal cancer cell line (DLD1) was mixed with different amount of normal human lymphocyte DNA (BM) and the percentages are indicated. In these PCR amplifications, the annealing temperature of universal PCR reaction is 5° C. lower than the PCR condition of gene-specific amplification. This lowered annealing temperature ensures all of the first around full length PCR products are amplified at similar efficiency. Proteinase K (QIAGEN, Valencia, Calif.) is added at the end of the second round multiplex PCR reaction to inactivate the remaining thermostable polymerase.

The next step is a MS-PCR-PCR amplification, including a methylation specific PCR followed by a second universal PCR amplification with universal primers that differ from the ones used in previous step.

The methylation specific PCR primers were designed with a Tm at around 70° C. and are internal to the gene-specific primers used in the second step. MS-PCR amplification is then carried out in a multiplex format to increase the assay throughput. 1 μl of the PCR products (as shown in FIG. 31) was diluted in 50 fold and 1 μl of the diluent was used as the template for methyl-specific PCR. The methylation specific PCR primer sequences, universal primers A, B and concentrations were listed in the Table 7.

Table 7 shows the methyl-specific PCR primer sequences used in the Bisulfite/PCR-PCR/Ms-PCR-PCR procedure for the detection of promoter methylation status of low abundance methylation alleles in a given sample. The amount of each primer used per PCR reaction is listed on the right.

TABLE 7

| MSP 1st round Primers | Sequence (5' to 3') | Amount in PCR |
|---|---|---|
| Group 1 | | |
| SNRPNb FP (A) | CGCTGCCAACTACCGCACATCGTTGGGATTTTTGTA TTGTGGTAAATAAG (SEQ ID NO: 292) | 5 pmol |
| SNRPN RP (A) | CGCTGCCAACTACCGCACATCCCAATACGAACGAAC AAAATACCATC (SEQ ID NO: 293) | 5 pmol |
| p19 Ex1b FP (A) | CGCTGCCAACTACCGCACATCCCCAATCTACAATTA AAAAAACAAAAATAAC (SEQ ID NO: 294) | 2.5 pmol |
| p19 Ex1 RP (A) | CGCTGCCAACTACCGCACATCGGTTTTTTTTATTTG GTTTTTTAGGAAG (SEQ ID NO: 295) | 2.5 pmol |
| Group 2 | | |
| BRCA1 FP (A)/T | CGCTGCCAACTACCGCACATCGAGATTTTTATTAGG GTGGAAAGAGTG (SEQ ID NO: 296) | 5 pmol |
| BRCA1 RP (A)/G | CGCTGCCAACTACCGCACATCCCGTCCAAAAAATCT CAACGAACTC (SEQ ID NO: 297) | 5 pmol |

TABLE 7-continued

| | | |
|---|---|---|
| p16 Ex1b FP (A) | CGCTGCCAACTACCGCACATCGAAAAAAACTCTTCC GCCAACAC (SEQ ID NO: 298) | 2.5 pmol |
| p16 Ex1b RP (A) | CGCTGCCAACTACCGCACATCTGTTTGTTATTTTTT GTTTTTGTTGTAG (SEQ ID NO: 299) | 2.5 pmol |
| UniA | CGCTGCCAACTACCGCACATC (SEQ ID NO: 300) | |

| MSP 2nd round Primers | Sequence (5' to 3') | Amount in PCR |
|---|---|---|
| Group 1 | | |
| SNRPN MSP FP (B) | GGAGCACGCTATCCCGTTAGACGATTTTTGTATTGC GGTAAATAAGTACG (SEQ ID NO: 301) | 5 pmol |
| SNRPN MSP RP (B) | GGAGCACGCTATCCCGTTAGACAACAAAATACCATC GAAACAAAACG (SEQ ID NO: 302) | 5 pmol |
| p19 MSP FP (B) | GGAGCACGCTATCCCGTTAGACCAATCTACAATTAA AAAAACAAAAATAACG (SEQ ID NO: 303) | 2.5 pmol |
| p19 MSP RP (B) | GGAGCACGCTATCCCGTTAGACGGAAGCGGTTGTTG TTTTAGACG (SEQ ID NO: 304) | 2.5 pmol |
| Group 2 | | |
| BRCA1 MSP FP (B) | GGAGCACGCTATCCCGTTAGACGGGATTGGGATTTT TTTTTACG (SEQ ID NO: 305) | 5 pmol |
| BRCA1 MSP RP (B) | GGAGCACGCTATCCCGTTAGACGTCCAAAAAATCTC AACGAACTCAC (SEQ ID NO: 306) | 5 pmol |
| p16 MSP FP (B) | GGAGCACGCTATCCCGTTAGACAAACTCTTCCGCCA ACACCG (SEQ ID NO: 307) | 2.5 pmol |
| p16 MSP RP (B) | GGAGCACGCTATCCCGTTAGACTTATTTGGATCGGT TTTCGATCG (SEQ ID NO: 308) | 2.5 pmol |
| UniB | GGAGCACGCTATCCCGTTAGAC (SEQ ID NO: 309) | |

Figure 32:
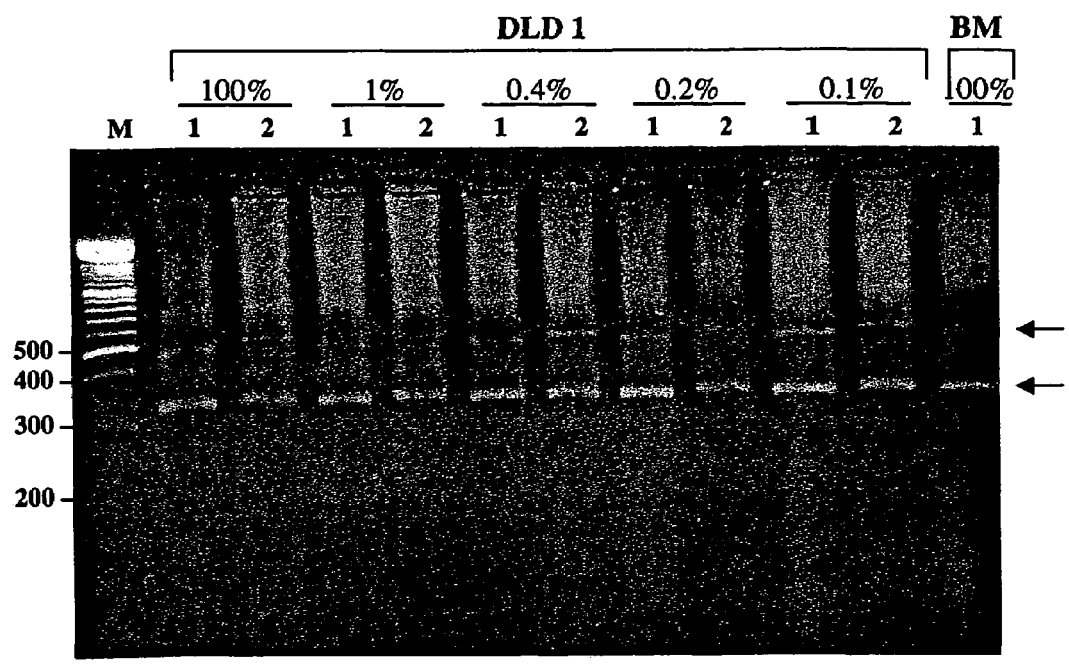
FIG. 32 demonstrates the second round of amplification (methyl-specific) of Bisulfite/PCR-PCR/MS-PCR-PCR/LDR/Universal Array approach simultaneously amplified 4 candidate gene promoter regions (SNRPN, BRCA1, p16, and p19) in colorectal cancer cell line (DLD1) and normal human lymphocyte (BM) genomic DNAs. The genomic DNA of DLD1 was mixed with different amount of normal human lymphocyte DNA and the percentages are indicated. Two fragments were amplified in each PCR reaction (amplicon1: SNRPN and p19; amplicon2: BRCA1 and p16) and were validated on a 3% agarose gel as shown.

After methylation-specific PCR amplification, the next step is to simultaneously amplify all target regions with a second universal PCR primer (primer "B") where its sequence has been attached to the 5' portion of each methylation, gene-specific PCR primer. In this round of PCR amplification, the annealing temperature of universal PCR reaction is 5° C. lower than the PCR condition of methylation specific amplification. This lowered annealing temperature ensures all of the full length PCR products are amplified at similar efficiency. Proteinase K (QIAGEN, Valencia, Calif.) is added at the end of the second round multiplex PCR reaction to inactivate the remaining thermostable polymerase. Before pooling the PCR products for further LDR analysis, the PCR fragments are verified by agarose gel electrophoresis and visualized via ethidium bromide staining as shown in FIG. 32.

Figure 33:
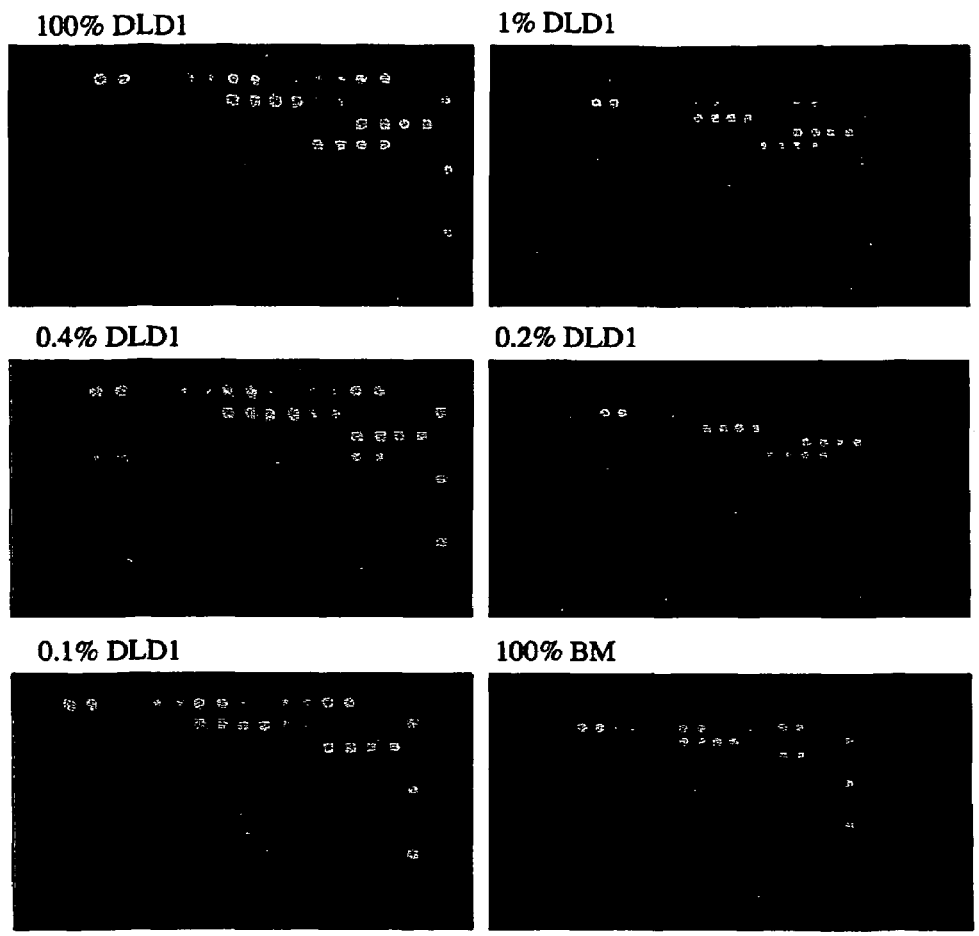
FIG. 33 presents the universal array images Bisulfite/PCR-PCR/MS-PCR-PCR/LDR/Universal Array approach. The methylation status in the promoter regions of SNRPN, BRCA1, p16, and p19 in various amount of colorectal cancer cell line (DLD1) mixing with normal human lymphocyte (BM) genomic DNAs. The DNA templates used in LDR reactions are the same as those shown in FIG. 32. False color red represents the methylated promoter regions detected by Cy3 labeled LDR probes. The p16 and p19 promoters are methylated in DLD1 cell line but not in normal human lymphocyte DNA (except one site at the p16 promoter). Notice that the Bisulfite/PCR-PCR/MS-PCR-PCR/LDR/Universal Array approach can detect up to 0.1% tumor DNA in a given sample.
Figure 38:
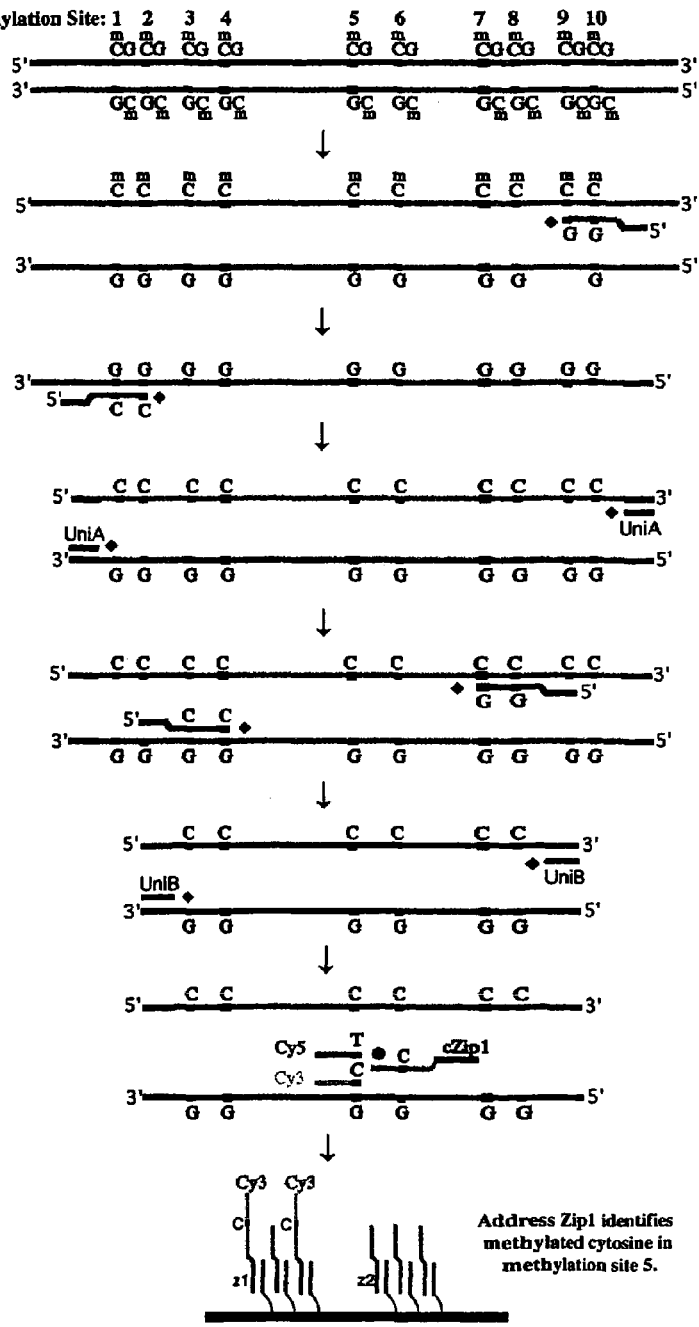
FIG. 38 is a schematic diagram illustrating the Bisulfite/ MS-PCR-PCR/MS-PCR-PCR/LDR/Universal Array procedure for high-throughput detection of promoter methylation status of low abundance methylation alleles in a given sample. This procedure consists of bisulfite treatment of genomic DNA, multiplex PCR with methyl-specific/universal primers (A), methylation specific multiplex PCR with methyl-specific/universal primers (B), multiplex LDR, and universal array approaches. The methyl-specific/universal PCR primer has the discriminating 3'OH base pairing to the cytosine of CpG dinucleotides (or pairing the guanine if it is on the opposite DNA strand) to ensure the selection of methylated alleles. Nucleotides G and C are used in the multiplex PCR primers and LDR probes (methylation sites 1, 3, 6, 8, and 10). The hybridization of such primers/probes with their DNA template results in the C:G Watson-Crick base pairings on methylated sequences, yet G:T wobble base pairings and C:A mismatches on un-methylated sequences occur. The designs of these primers/probes have the advantage of preferentially selecting fully methylated DNA sequences. Notice that the identification of a methylated cytosine at methylation site 5 requires the methylated cytosines at sites 2, 4, 7, and 9. Further, the methylated cytosines at methylation sites 1, 3, 6, 8, and 10 provide additional selective power for methylated alleles since these positions are located in the middle of oligonucleotide probes.

The next step is to provide LDR probes to interrogate the methylation status of the cytosines reside in the CpG dinucleotides. The same sets of LDR probes described previously (as shown in FIG. 12 and Table 3) were used for the detection of low abundant methylation alleles. FIG. 33 shows how Cy3 fluorescent labeled probes (False color red) are used to detect methylated cytosines. Each of the common probes is 5' end phosphorylated with a unique zip-code complement sequence attached to its 3' end. The LDR products are captured on a Universal Array and the fluorescence signals are measured using a microarray scanner. A different amount of colorectal cell line (DLD1) genomic DNA was mixed with normal human lymphocyte genomic DNA (BM). Based on the methylation signature of promoters of the SNRPN, p16, and p 19 genes in DLD1 cellular genomic DNA, this method has demonstrated the addition of a methylation-specific PCR amplification step improves detection sensitivity up to at least 1,000 fold.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method for identifying, in a sample, one or more target nucleic acid molecules differing from other nucleic acid molecules in the sample by one or more methylated cytosine residues, said method comprising:

providing a sample potentially containing one or more target nucleic acid molecules;

subjecting the sample to a bisulfite treatment to convert, in the nucleic acid molecules of the sample, unmethylated cytosine residues, but not methylated cytosine residues, into uracil residues;

providing one or more primary oligonucleotide primer sets, each set characterized by (a) a first oligonucleotide primer, having a target-specific portion and a 5' upstream secondary primer-specific portion, wherein the target-specific portion is suitable for hybridization on a first strand of the target nucleic acid molecule in which unmethylated cytosines have been converted to uracil, and (b) a second oligonucleotide primer, having a target-specific portion and a 5' upstream secondary primer-specific portion, wherein the target-specific portion is suitable for hybridization on a polymerase extension product of the first strand or on a second strand of the target nucleic acid molecule, either of which having unmethylated cytosines converted to uracil and wherein the first and second oligonucleotide primers of each set contain the same 5' upstream secondary primer-specific-portion;

providing a polymerase;

blending the sample, the primary oligonucleotide primer set, and the polymerase to form a primary polymerase chain reaction mixture;

subjecting the primary polymerase chain reaction mixture to two or more polymerase chain reaction cycles comprising a denaturation treatment, wherein hybridized nucleic acid sequences are separated, a hybridization treatment, wherein the target-specific portions of the primary oligonucleotide primer sets hybridize to the target nucleic acid molecules with unmethylated cytosines converted to uracil or to extension products of such modified target nucleic acid molecules, and an extension treatment, wherein the hybridized primary oligonucleotide primers are extended to form primary extension products complementary to the target nucleic acid molecules with unmethylated cytosines converted to uracil;

providing a secondary oligonucleotide primer set characterized by (a) a first secondary primer containing the 5' upstream portion of the first oligonucleotide primer of the primary oligonucleotide primer set, and (b) a second secondary primer containing the 5' upstream portion of the second oligonucleotide primer of the primary oligonucleotide primer set;

blending the primary extension products, the secondary oligonucleotide primer set, and the polymerase to form a secondary polymerase chain reaction mixture;

subjecting the secondary polymerase chain reaction mixture to two or more polymerase chain reaction cycles comprising a denaturation treatment, wherein hybridized nucleic acid sequences are separated, a hybridization treatment, wherein the secondary oligonucleotide primers hybridize to the primary extension products, and an extension treatment, wherein the hybridized secondary oligonucleotide primers are extended to form secondary extension products complementary to the primary extension products;

providing a plurality of oligonucleotide probe sets, each set characterized by (a) a first oligonucleotide probe, having a secondary extension product-specific portion and a detectable reporter label, and (b) a second oligonucleotide probe, having a secondary extension product-specific portion, wherein the oligonucleotide probes in a particular set are suitable for ligation together when hybridized on a complementary secondary extension product, but have a mismatch which interferes with such ligation when hybridized to any other nucleic acid molecule present in the sample;

providing a ligase;

blending the secondary extension products, the plurality of oligonucleotide probe sets, and the ligase to form a ligase detection reaction mixture;

subjecting the ligase detection reaction mixture to one or more ligase detection reaction cycles comprising a denaturation treatment, wherein any hybridized oligonucleotides are separated from the secondary extension product, and a hybridization treatment, wherein the oligonucleotide probe sets hybridize in a base-specific manner to their respective secondary extension products, if present, and ligate to one another to form a ligation product containing (a) the detectable reporter label and (b) the secondary extension product-specific portions connected together, wherein the oligonucleotide probe sets may hybridize to other nucleic acid molecules but do not ligate together due to a presence of one or more mismatches and individually separate during the denaturation treatment; and detecting the reporter labels of the ligation products, thereby indicating the presence of two or more methylated cytosine bases in the target nucleotide sequences in the sample.

2. The method according to claim 1, wherein the ligation products of the oligonucleotide probes in a particular set have a unique length so that they can be distinguished from other nucleic acid molecules in the ligase detection reaction mixture, said detecting comprising:

separating the ligation products by size or electrophoretic mobility and distinguishing the ligation products which differ in size.

3. The method according to claim 1, wherein the second oligonucleotide probe of each oligonucleotide probe set has an addressable array-specific portion, said detecting further comprising:

providing a solid support with different capture oligonucleotide probes immobilized at different particular sites, wherein the capture oligonucleotides are complementary to the addressable array-specific portions and contacting the ligase detection reaction mixture, after said subjecting it to one or more ligase detection reaction cycles, with the solid support under conditions effective to hybridize the ligation products to the capture oligonucleotide probes in a base-specific manner, thereby capturing the addressable array-specific portions to the solid support at the site with the complementary capture oligonucleotide.

4. The method according to claim 1, wherein the bisulfite treatment is catalyzed by hydroquinone and is carried out under cycling conditions to periodically dissociate both strands of nucleic acid molecules in the sample.

5. The method according to claim 4, wherein the cycling conditions comprise:

incubating at 50°C. for 20 minutes;
incubating at 85°C. for 15 seconds; and
repeating said incubating steps for 45 cycles.

6. The method according to claim 4 further comprising:

desalting, after the bisulfite treatment, to eliminate bisulfite and fragmented small pieces of nucleic acid molecules and to concentrate the bisulfite-treated sample.

7. The method according to claim 1, wherein the bisulfite treatment step is catalyzed by diethylenetriamine and is carried out under cycling conditions to periodically dissociate both strands of nucleic acid molecules in the sample.

8. The method according to claim 7, wherein the cycling conditions comprise:

incubating at 50°C. for 20 minutes;
incubating at 85°C. for 15 seconds; and
repeating said incubating steps for 45 cycles.

9. The method according to claim 7 further comprising:

desalting, after the bisulfite treatment, to eliminate bisulfite and fragmented small pieces of nucleic acid molecules and to concentrate the bisulfite-treated sample.

10. The method according to claim 1, wherein the oligonucleotide primers of the primary oligonucleotide primer sets contain degenerate positions or nucleotide analogues to permit hybridization of the first and second oligonucleotide primers of the primary oligonucleotide primer set to the target nucleic acid molecule independent of the target nucleic acid molecule's methylation status.

11. The method according to claim 10, wherein the nucleotide analogue is selected from the group consisting of 2-dimethylaminomethyleneamino-6-methoxyaminopurine (dK), 6H,8H-3,4-dihydro-pyrimido[4,5-c][1,2]oxazin-7-one (dP), 3-nitropyrrole, 5-nitroindole, and inosine.

12. The method according to claim 1, wherein the oligonucleotide probe sets contain degenerate positions or nucleotide analogues to permit hybridization to the secondary extension products independent of the target nucleic acid molecule's methylation status at CpG sites neighboring CpG sites where the presence of two or more methylated cytosine bases in the target nucleotide sequences in the sample is indicated.

13. The method according to claim 12, wherein the nucleotide analogue is selected from the group consisting of 2-dimethylaminomethyleneamino-6-methoxyaminopurine (dK), 6H,8H-3,4-dihydro-pyrimido[4,5-c][1,2]oxazin-7-one (dP), 3-nitropyrrole, 5-nitroindole, and inosine.

14. The method according to claim 1, wherein the primary oligonucleotide primer set preferentially hybridizes to the bisulfite-treated target nucleic acid molecule or to extension products of the first primer of the primary oligonucleotide probe set, which are methylated in the region of hybridization.

15. The method according to claim 14, wherein the oligonucleotide probe sets preferentially hybridize to the secondary extension products, where the target nucleic acid molecule is methylated in the region of hybridization.

16. The method according to claim 15, wherein a presence of low abundance methylated cytosine residues in the target nucleic acid molecule in the sample is distinguished from a presence of a majority of target nucleic acid molecule with unmethylated cytosine residues in the sample.

17. The method according to claim 16, wherein the presence of low abundance methylated cytosine residues in the target nucleic acid molecule is distinguished from a presence of a 100 to 10,000-fold excess of target nucleic acid molecule with unmethylated cytosine residues in the sample.

18. The method according to claim 14, wherein a presence of low abundance methylated cytosine residues in the target nucleic acid molecule in the sample is distinguished from a presence of a majority of target nucleic acid molecule with unmethylated cytosine residues in the sample.

19. The method according to claim 18, wherein the presence of low abundance methylated cytosine residues in the target nucleic acid molecule in the sample is distinguished from a presence of a 10 to 1,000-fold excess of target nucleic acid molecule with unmethylated cytosine residues in the sample.

20. The method according to claim 1, wherein the primary oligonucleotide primer set preferentially hybridizes to the bisulfite-treated target nucleic acid molecule or extension products of the first primer of the primary oligonucleotide probe set, which are unmethylated in the region of hybridization.

21. The method according to claim 1, wherein the oligonucleotide probe sets preferentially hybridize to the secondary extension product, where the target nucleic acid molecule is methylated in the region of hybridization.

22. The method according to claim 1, wherein the oligonucleotide probe sets preferentially hybridize to the secondary extension products where the target nucleic acid molecule is unmethylated in the region of hybridization.

23. The method according to claim 1, wherein multiple secondary extension products are pooled prior to said subjecting the ligase detection reaction mixture to one or more ligase detection reaction cycles.

24. The method according to claim 1, wherein the upstream secondary primer-specific portions of the primary oligonucleotide primers are identical or greater than 80% identical in sequence.

25. The method according to claim 1, wherein the upstream secondary primer-specific portions of the primary oligonucleotide primers are identical in sequence.

26. The method according to claim 1, wherein the method is used to distinguish a presence of low abundance methylated cytosine residues in the target nucleic acid molecule in the sample from a presence of a majority of target nucleic acid molecule with unmethylated cytosine residues in the sample.

27. A method according to claim 26, wherein the presence of low abundance methylated cytosine residues in the target nucleic acid molecule in the sample is distinguished in the presence of a 10 to 100-fold excess of target nuculeic acid molecule with unmethylated cytosine residues in the sample.

28. The method according to claim 1, wherein relative amounts of one or more of a plurality of target nucleic acid molecules, differing by one or more methylated cytosines in unknown amounts are quantified, said method further comprising:
    quantifying the amount of ligation products detected and
    comparing the amount of ligation products generated from target nucleic acid molecules in the sample which are methylated at defined sites with the amount of ligation products generated from target nucleic acid molecules in the sample which are unmethylated at defined sites within the sample, whereby a quantitative measure of the relative level of target nucleic acid molecules with methylated cytosine residues in the sample is determined.

29. The method according to claim 1, wherein relative amounts of one or more of a plurality of target nucleic acid molecules, differing by one or more methylated cytosines in unknown amounts are quantified, said method further comprising:
    providing a standard sample for comparison with the sample potentially containing one or more target nucleic acid molecules;
    quantifying the amount of ligation products generated from the standard sample and the sample potentially containing one or more target nucleic acid molecules; and
    comparing the ratio of the amount of ligation products generated from the methylated target nucleic acid molecule at defined sites within the standard sample with the amount of ligation products generated from target nucleic acid molecule with unmethylated cytosine residues at defined sites within the standard sample to a ratio of the amount of ligation products generated from target nucleic acid molecule with methylated cytosine residues at defined sites within the sample potentially containing one or more target nucleic acid molecules with the amount of ligation product sequences generated from unmethylated target nucleic acid molecule at defined sites within the sample potentially containing methylated target nucleic acid molecules to provide a quantitative measure of the relative level of target nucleic acid molecules with methylated cytosine residues at defined sites within the sample.

30. A method for identifying one or more target nucleic acids in a sample, differing by one or more methylated cytosine residues, said method comprising:
    providing a sample potentially containing one or more target nucleic acid molecules;
    subjecting the sample to a bisulfite treatment to convert, in the nucleic acid molecules of the sample, unmethylated cytosine residues, but not methylated cytosine residues, into uracil residues;
    providing one or more primary oligonucleotide primer sets, each set characterized by (a) a first oligonucleotide primer, having a target-specific portion and a 5' upstream secondary primer-specific portion, wherein the target-specific portion is suitable for hybridization on a first strand of the target nucleic acid molecule in which unmethylated cytosines have been converted to uracil, and (b) a second oligonucleotide primer, having a target-specific portion and a 5' upstream secondary primer-specific portion, wherein the target-specific portion is suitable for hybridization on a polymerase extension product of the first strand or on a second strand of the target nucleic acid molecule, either of which having unmethylated cytosines converted to uracil and wherein the first and second oligonucleotide primers of each set contain the same 5' upstream secondary primer-specific-portion;
    providing a polymerase;
    blending the sample, the primary oligonucleotide primer set, and the polymerase to form a primary polymerase chain reaction mixture;
    subjecting the primary polymerase chain reaction mixture to two or more polymerase chain reaction cycles comprising a denaturation treatment, wherein hybridized nucleic acid sequences are separated, a hybridization treatment, wherein the target-specific portions of the primary oligonucleotide primer sets hybridize to the target nucleic acid molecules with unmethylated cytosines converted to uracil or to extension products of such modified target nucleic acid molecules, and an extension treatment, wherein the hybridized primary oligonucleotide primers are extended to form primary extension products complementary to the target nucleic acid molecules with unmethylated cytosines converted to uracil;

providing a secondary oligonucleotide primer set characterized by (a) a first secondary primer containing the 5' upstream portion of the first oligonucleotide primer of the primary oligonucleotide primer set, and (b) a second secondary primer containing the 5' upstream portion of the second oligonucleotide primer of the primary oligonucleotide primer set;

blending the primary extension products, the secondary oligonucleotide primer set, and the polymerase to form a secondary polymerase chain reaction mixture;

subjecting the secondary polymerase chain reaction mixture to two or more polymerase chain reaction cycles comprising a denaturation treatment, wherein hybridized nucleic acid sequences are separated, a hybridization treatment, wherein the secondary oligonucleotide primers hybridize to the primary extension products, and an extension treatment, wherein the hybridized secondary oligonucleotide primers are extended to form secondary extension products complementary to the primary extension products;

providing one or more tertiary oligonucleotide primer sets, each set characterized by (a) a first oligonucleotide primer, having a target-specific portion and a 5' upstream quaternary primer-specific portion, where the target-specific portion is suitable for and preferentially hybridizes to the secondary extension products that arise when the target nucleic acid molecule is methylated in the region of hybridization, and (b) a second oligonucleotide primer, having a target-specific portion and a 5' upstream quaternary primer-specific portion, wherein the target-specific portion is suitable for and preferentially hybridizes to the secondary extension products that arise when the target nucleic acid molecule is methylated in the region of hybridization, to permit formation of a polymerase chain reaction product, but have a mismatch which interferes with formation of such a polymerase chain reaction product when hybridized to any other nucleic acid molecule present in the sample;

blending the secondary polymerase chain reaction mixture, the tertiary oligonucleotide primers, and the polymerase to form a tertiary polymerase chain reaction mixture;

subjecting the tertiary polymerase chain reaction mixture to two or more polymerase chain reaction cycles comprising a denaturation treatment, wherein hybridized nucleic acid sequences are separated, a hybridization treatment, wherein the target-specific portions of the tertiary oligonucleotide primers hybridize to the secondary extension products, and an extension treatment, wherein the hybridized tertiary oligonucleotide primers are extended to form tertiary extension products complementary to the target nucleic acid molecule to which a tertiary oligonucleotide primer is hybridized;

providing a quaternary oligonucleotide primer set characterized by (a) a first quaternary oligonucleotide primer containing the same sequence as the 5' upstream quaternary primer-specific portion of a first oligonucleotide primer of the tertiary oligonucleotide primer set, and (b) a second quaternary oligonucleotide primer containing the same sequence as the 5' upstream quaternary primer-specific portion of a second oligonucleotide primer of the tertiary oligonucleotide primer set, wherein a set of quaternary oligonucleotide primers may be used to amplify all of the tertiary extension products;

blending the tertiary extension products, the quaternary oligonucleotide primers, and the polymerase to form a quaternary polymerase chain reaction mixture;

subjecting the quaternary polymerase chain reaction mixture to two or more polymerase chain reaction cycles comprising a denaturation treatment, wherein hybridized nucleic acid sequences are separated, a hybridization treatment, wherein the quaternary oligonucleotide primers hybridize to the tertiary extension products, and an extension treatment, wherein the hybridized quaternary oligonucleotide primers are extended to form quaternary extension products complementary to the tertiary extension products;

providing a plurality of oligonucleotide probe sets, each set characterized by (a) a first oligonucleotide probe, having a quaternary extension product-specific portion and a detectable reporter label, and (b) a second oligonucleotide probe, having a quaternary extension product-specific portion, wherein the oligonucleotide probes in a particular set are suitable for ligation together when hybridized on a complementary quaternary extension product, but have a mismatch which interferes with such ligation when hybridized to any other nucleic acid molecule present in the sample;

providing a ligase;

blending the quaternary extension products, the plurality of oligonucleotide probe sets, and the ligase to form a ligase detection reaction mixture;

subjecting the ligase detection reaction mixture to one or more ligase detection reaction cycles comprising a denaturation treatment, wherein any hybridized oligonucleotides are separated from the quaternary extension product, and a hybridization treatment, wherein the oligonucleotide probe sets hybridize in a base-specific manner to their respective quaternary extension products, if present, and ligate to one another to form a ligation product containing (a) the detectable reporter label and (b) the quaternary extension product-specific portions connected together, wherein the oligonucleotide probe sets may hybridize to other nucleic acid molecules but do not ligate together due to a presence of one or more mismatches and individually separate during the denaturation treatment; and detecting the reporter labels of the ligation products, thereby indicating the presence of two or more methylated cytosine bases in the target nucleotide sequences in the sample.

31. The method according to claim 30, wherein the ligation product of the oligonucleotide probes in a particular set have a unique length so that they can be distinguished from other nucleic acid molecules in the ligase detection reaction mixture, said method further comprising:

separating the ligation products by size or electrophoretic mobility and distinguishing, after said detecting, the ligation products which differ in size.

32. The method according to claim 31, wherein the bisulfite treatment is catalyzed by hydroquinone and is carried out under cycling conditions to periodically dissociate both strands of nucleic acid molecules in the sample.

33. The method according to claim 32, wherein the cycling conditions comprise:

incubating at 50°C. for 20 minutes;
incubating at 85°C. for 15 seconds; and
repeating said incubating steps for 45 cycles.

34. The method according to claim 32 further comprising:
desalting, after the bisulfite treatment, to eliminate bisulfite and fragmented small pieces of nucleic acid molecules and to concentrate the bisulfite-treated sample.

35. The method according to claim 31, wherein the upstream secondary primer-specific portions of the primary oligonucleotide primers are identical or greater than 80% identical in sequence.

36. The method according to claim 30, wherein the second oligonucleotide probe of each oligonucleotide probe set has an addressable array-specific portion, said detecting further comprising:
providing a solid support with different capture oligonucleotide probes immobilized at different particular sites, wherein the capture oligonucleotides are complementary to the addressable array-specific portions and
contacting the ligase detection reaction mixture, after said subjecting it to one or more ligase detection reaction cycles, with the solid support under conditions effective to hybridize the ligation products to the capture oligonucleotide probes in a base-specific manner, thereby capturing the addressable array-specific portions to the solid support at the site with the complementary capture oligonucleotide.

37. The method according to claim 30, wherein the bisulfite treatment step is catalyzed by diethylenetriamine and is carried out under cycling conditions to periodically dissociate both strands of nucleic acid molecules in the sample.

38. The method according to claim 37, wherein the cycling conditions comprise:
incubating at 50°C. for 20 minutes;
incubating at 85°C. for 15 seconds; and
repeating said incubating steps for 45 cycles.

39. The method according to claim 37 further comprising:
desalting, after the bisulfite treatment, to eliminate bisulfite and fragmented small pieces of nucleic acid molecules and to concentrate the bisulfite-treated sample.

40. The method according to claim 30, wherein the oligonucleotide probes of the primary oligonucleotide primer sets contain degenerate positions or nucleotide analogues to permit hybridization of the first and second oligonucleotide primers of the primary oligonucleotide primer set to the target nucleic acid molecule, independent of the target nucleic acid molecule's methylation status.

41. The method according to claim 40, wherein the nucleotide analogue is selected from the group consisting of 2-dimethylaminomethyleneamino-6-methyoxyaminopurine (dK), 6H,8H-3,4-dihydro-pyrimido[4,5-c][1,2]oxazin-7-one (dP), 3-nitropyrrole, 5-nitroindole, and inosine.

42. The method according to claim 30, wherein the oligonucleotide probe sets contain degenerate positions or nucleotide analogues to permit hybridization to the secondary extension products independent of the target nucleic acid molecule's methylation status at CpG sites neighboring CpG sites where the presence of two or more methylated cytosine bases in the target nucleotide sequences in the sample is indicated.

43. The method according to claim 42, wherein the nucleotide analogue is selected from the group consisting of 2-dimethylaminomethyleneamino-6-methyoxyaminopurine (dK), 6H,8H-3,4-dihydro-pyrimido[4,5-c][1,2]oxazin-7-one (dP), 3-nitropyrrole, 5-nitroindole, and inosine.

44. The method according to claim 30, wherein the primary oligonucleotide primer set preferentially hybridizes to the bisulfite-treated target nucleic acid molecule or extension products of the first primer of the primary oligonucleotide probe set, which are methylated in the region of hybridization.

45. The method according to claim 44, wherein the oligonucleotide probe sets preferentially hybridize to the quaternary extension products, where the target nucleic acid molecule is methylated in the region of hybridization.

46. The method according to claim 44, wherein a presence of low abundance target nucleic acid molecules with methylated cytosine residues in the sample is distinguished from a presence of a majority of target nucleic acid molecules with unmethylated cytosine residues in the sample.

47. The method according to claim 46, wherein the presence of low abundance target nucleic acid molecules with methylated cytosine residues may be distinguished from a presence of a 100 to 10,000-fold excess of target nucleic acid molecules with unmethylated cytosine residues in the sample.

48. The method according to claim 30, wherein the oligonucleotide probe sets preferentially hybridize to the quaternary extension product, where the target nucleic acid molecule is methylated in the region of hybridization.

49. The method according to claim 30, wherein multiple secondary extension products are pooled prior to said subjecting the ligase detection reaction mixture to one or more ligase detection reaction cycles.

50. The method according to claim 30, wherein a presence of low abundance methylated target DNA in the sample is distinguished from a presence of a majority of target nucleic acid molecules with unmethylated cytosine residues in the sample.

51. The method according to claim 50, wherein the presence of low abundance target nucleic acid molecules with methylated cytosine residues in the sample is distinguished from a presence of a 10 to 1,000-fold excess of target nucleic acid molecules with unmethylated cytosine residues in the sample.

52. The method according to claim 30, wherein a presence of low abundance target nucleic acid molecules with methylated cytosine residues in the sample is distinguished from a presence of a majority of target nucleic acid molecules with unmethylated cytosine residues in the sample.

53. The method according to claim 52, wherein the presence of low abundance target nucleic acid molecules with methylated cytosine residues may be distinguished from a presence of a 10,000 to 1,000,000-fold excess of target nucleic acid molecules with unmethylated cytosine residues in the sample.

54. A method for identifying, in sample, one or more target nucleic acid molecules differing by one or more methylated cytosine residues, said method comprising:
providing a sample potentially containing one or more target nucleic acid molecules;
providing a restriction endonuclease that cleaves the one or more target nucleic acid molecules at an unmethylated cytosine residue, does not cleave the one or more target nucleic acid molecules at a methylated cytosine residue on both strands, and does not nick a heteroduplex comprising one strand containing a methylated cytosine residue and one strand containing an unmethylated cytosine residue;

blending the sample and the restriction endonuclease to form a primary restriction endonuclease reaction mixture;

subjecting the restriction endonuclease reaction mixture to enzymatic digestion conditions effective to cut the majority of the one or more target nucleic acid molecules at an unmethylated cytosine residue while leaving the one or more target nucleic acid molecules at a methylated cytosine residue intact;

providing a plurality of primary oligonucleotide primers having a target-specific portion suitable for hybridization on one strand of the target nucleic acid molecule upstream of one or more restriction sites;

providing one or more nucleotide analogues and additional nucleotides that may be incorporated into a polymerase extension product, does not interfere with cleavage of heteroduplexed extension products by the restriction endonuclease, and renders the extension product resistant to exonucleolytic digestion;

providing a polymerase;

blending the restriction endonuclease reaction mixture, the primary oligonucleotide primers, the one or more nucleotide analogues and additional nucleotides, and the polymerase to form a primary extension reaction mixture;

subjecting the primary extension reaction mixture to a primary extension reaction comprising a denaturation treatment, wherein hybridized nucleic acid molecules are separated, a hybridization treatment, wherein the target-specific portions of the primary oligonucleotide primers hybridize to the target nucleic acid molecules, and an extension treatment wherein the hybridized primary oligonucleotide primers are extended to form primary extension products, containing nucleotide analogues and additional nucleotides, which is complementary to the target nucleic acid molecule to which the primary oligonucleotide primers are hybridized;

blending the extension reaction mixture and the restriction endonuclease to form an extension/restriction reaction mixture;

subjecting the extension/restriction reaction mixture to enzymatic digestion conditions effective to cut both strands of the residual unmethylated nucleic acid molecules resulting from extension of primary oligonucleotide primers on unmethylated target nucleic acid molecules during said primary extension reaction, while neither nicking nor culling either strand of hemi-methylated target nucleic acid molecule resulting from extension of primary oligonucleotide primers on methylated target nucleic acid molecules during said primary extension reaction;

providing an exonuclease;

blending the extension/restriction reaction mixture and the exonuclease to form an exonuclease reaction mixture;

subjecting the exonuclease reaction mixture to enzymatic digestion under conditions effective to digest target nucleic acid molecules but not primary extension products resulting from primary oligonucleotide primers hybridized and extended on methylated target nucleic acid molecules;

providing a group of secondary oligonucleotide primer sets, each set characterized by (a) a first secondary oligonucleotide primer, having a target-specific portion and a 5' upstream tertiary primer-specific portion, and (b) a second secondary oligonucleotide primer, having a target-specific portion and a 5' upstream tertiary primer-specific portion, wherein the first oligonucleotide primers of each set contain the same 5' upstream tertiary primer-specific portion and the second oligonucleotide primers of each set contain the same 5' upstream tertiary primer-specific portion, wherein the secondary oligonucleotide primers in a particular set are suitable for hybridization on complementary strands of a corresponding target nucleic acid molecules;

blending the exonuclease reaction mixture, the secondary oligonucleotide primers, and the polymerase to form a secondary polymerase chain reaction mixture;

subjecting the secondary polymerase chain reaction mixture to two or more polymerase chain reaction cycles comprising a denaturation treatment, wherein hybridized nucleic acid molecules are separated, a hybridization treatment, wherein the target-specific portions of the secondary oligonucleotide primers hybridize to the target nucleic acid molecules or to extension products of the target nucleic acid molecules, and an extension treatment, wherein the hybridized secondary oligonucleotide primers are extended to form secondary extension products complementary to the target nucleic acid molecules to which the secondary oligonucleotide primer is hybridized;

providing a tertiary oligonucleotide primer set characterized by (a) a first tertiary primer containing the same sequence as the 5' upstream portion of a first secondary oligonucleotide primer, and (b) a second tertiary primer containing the same sequence as the 5' upstream portion of the second secondary oligonucleotide primer from the same secondary oligonucleotide primer set as the first secondary oligonucleotide primer contained by the first tertiary primer, wherein a set of tertiary oligonucleotide primers may be used to amplify all of the secondary extension products;

blending the secondary extension products, the tertiary oligonucleotide primers, and the polymerase to form a tertiary polymerase chain reaction mixture;

subjecting the tertiary polymerase chain reaction mixture to two or more polymerase chain reaction cycles comprising a denaturation treatment, wherein hybridized nucleic acid molecules are separated, a hybridization treatment, wherein the tertiary oligonucleotide primers hybridize to the secondary extension products, an extension treatment, wherein the hybridized tertiary oligonucleotide primers are extended to form tertiary extension products complementary to the secondary extension products;

providing a plurality of oligonucleotide probe sets, each set characterized by (a) a first oligonucleotide probe, having a tertiary extension product-specific portion and a detectable reporter label, and (b) a second oligonucleotide probe, having a tertiary extension product-specific portion, wherein the oligonucleotide probes in a particular set are suitable for ligation together when hybridized on a complementary tertiary extension product, but have a mismatch which interferes with such ligation when hybridized to any other nucleic acid molecule present in the sample;

providing a ligase;

blending the tertiary extension products, the plurality of oligonucleotide probe sets, and the ligase to form a ligase detection reaction mixture;

subjecting the ligase detection reaction mixture to one or more ligase detection reaction cycles comprising a denaturation treatment, wherein any hybridized oligonucleotides are separated from the tertiary extension product, and a hybridization treatment, wherein the oligonucleotide probe sets hybridize in a base-specific manner to their respective tertiary extension products, if present, and ligate to one another to form a ligation product containing (a) the detectable reporter label and (b) the tertiary extension product-specific portions connected together, wherein the oligonucleotide probe sets may hybridize to nucleic acid molecules other than their respective complementary tertiary extension products but do not ligate together due to a presence of one or more mismatches and individually separate during the denaturation treatment; and detecting the reporter labels of the ligation products, thereby indicating the presence of methylated cytosine bases in the target nucleic acid molecules in the sample.

55. The method according to claim 54, wherein the ligation products of the oligonucleotide probes in a particular set have a unique length so that they can be distinguished from other nucleic acid molecules in the ligase detection reaction mixture, said detecting comprising:

separating the ligation products by size or electrophoretic mobility and distinguishing the ligation products which differ in size.

56. The method according to claim 55, wherein the upstream secondary primer-specific portions of the primary oligonucleotide primers are identical or greater than 80% identical in sequence.

57. The method according to claim 54, wherein the second oligonucleotide probe of each oligonucleotide probe set has an addressable array-specific portion, said detecting further comprising:

providing a solid support with different capture oligonucleotide probes immobilized at different particular sites, wherein the capture oligonucleotides are complementary to the addressable array-specific portions and contacting the ligase detection reaction mixture, after said subjecting it to one or more ligase detection reaction cycles, with the solid support under conditions effective to hybridize the ligation products to the capture oligonucleotide probes in a base-specific manner, thereby capturing the addressable array-specific portions to the solid support at the site with the complementary capture oligonucleotide.

58. The method according to claim 54, wherein the restriction endonuclease is BstUI.

59. The method according to claim 54, wherein the nucleotide analogue is selected from the group consisting of alpha thiophosphate dATP and alpha thiophosphate TTP.

60. The method according to claim 54, wherein the exonuclease is selected from the group consisting of Exonuclease I, Exonuclease III, and other 3' exonucleases.

61. The method according to claim 54, wherein the primary oligonucleotide primer has a non-phosphorylated or blocked 5' end or contains analogue(s) that confer exonuclease resistance, and the exonuclease is selected from the group consisting of lambda Exonuclease and other 5' exonucleases.

62. The method according to claim 54, wherein a presence of low abundance target nucleic acid molecules with methylated cytosine residue is distinguished from a presence of a majority of target nucleic acid molecules with unmethylated cytosine residues.

63. The method according to claim 62, wherein the presence of low abundance target nucleic acid molecules with methylated cytosine residues is distinguished from a presence of a 1,000 to 100,000-fold excess of target nucleic acid molecules with unmethylated cytosine residues.

64. The method for identifying one or more target nucleic acid molecules differing by one or more methylated cytosine residues, said method comprising:

providing a sample potentially containing one or more target nucleic acid molecules;

providing a restriction endonuclease that cleaves the one or more target nucleic acid molecules at an unmethylated cytosine residue and does not cleave the one or more target nucleic acid molecules at a methylated cytosine residues on both strands, but does nick a heteroduplex comprising of one strand containing a methylated cytosine residue and one strand containing an unmethylated cytosine residue;

blending the sample and the restriction endonuclease to form a primary restriction endonuclease reaction mixture;

subjecting the restriction endonuclease reaction mixture to an enzymatic digestion procedure under conditions effective to cut the majority of the unmethylated cytosine residues while leaving the methylated cytosine residues intact;

providing a plurality of primary oligonucleotide primers having a target-specific portion suitable for hybridization on one strand of the target nucleic acid molecule upstream of one or more restriction sites;

providing a polymerase which can incorporate nucleotide analogue(s);

providing one or more nucleotide analogues and additional nucleotides that may be incorporated by a polymerase into an extension product, and does not interfere with cleavage of the heteroduplexed extension product by the restriction endonuclease, but which renders the extension product resistant to exonucleolytic digestion;

blending the restriction endonuclease reaction mixture, the primary oligonucleotide primers, the one or more nucleotide analogues and additional nucleotides, and the polymerase to form a primary extension reaction mixture;

subjecting the primary extension reaction mixture to a primary extension reaction comprising a denaturation treatment, wherein hybridized nucleic acid sequences are separated, a hybridization treatment, wherein the target-specific portions of the primary oligonucleotide primers hybridize to the target nucleic acid molecule, and an extension treatment wherein the hybridized primary oligonucleotide primers are extended to form primary extension products complementary to the target nucleic acid molecule to which the primary oligonucleotide primers are hybridized;

blending the primary extension reaction mixture, the one or more nucleotide analogues and additional nucleotides, and the restriction endonuclease to form a restriction/extension reaction mixture;

subjecting the restriction/extension reaction mixture to a restriction/extension cycle comprising an enzymatic digestion phase under conditions effective to cut both strands of the residual unmethylated cytosine residues resulting from extension of the primary oligonucleotide primers on unmethylated cytosine residues of target nucleic acid molecules, while nicking the unmethylated strand of hemi-methylated target nucleic acid molecules resulting from extension of primary oligonucleotide primers on methylated cytosine residues of target nucleic acid molecules, followed by an incubation effective to inactivate the restriction endonuclease but not denature the nicked primary extension products from their target nucleic acid molecules, wherein the nicked primary extension products re-extend at the nick, generating extension products, containing nucleotide analogues and additional nucleotides, which are complementary to the target nucleic acid molecules to which the primary oligonucleotide primers are hybridized;

providing an exonuclease;

blending the restriction/extension reaction mixture and the exonuclease to form an exonuclease reaction mixture;

subjecting the exonuclease reaction mixture to a enzymatic digestion process under conditions effective to digest target nucleic acid molecule but not the extension product containing nucleotide analogues resulting from oligonucleotide extension primers hybridized to and extended on methylated cytosine residues of target nucleic acid molecules;

providing a group of secondary oligonucleotide primer sets, each set characterized by (a) a first secondary oligonucleotide primer, having a target-specific portion and a 5' upstream tertiary primer-specific portion, and (b) a second secondary oligonucleotide primer, having a target-specific portion and a 5' upstream tertiary primer-specific portion, wherein the first oligonucleotide primers of each set contain the same 5' upstream tertiary primer-specific portion and the second oligonucleotide primers of each set in the group contain the same 5' upstream tertiary primer-specific portion;

blending the exonuclease reaction mixture, the secondary oligonucleotide primers, and the polymerase to form a secondary polymerase chain reaction mixture;

subjecting the secondary polymerase chain reaction mixture to two or more polymerase chain reaction cycles comprising a denaturation treatment, wherein hybridized nucleic acid sequences are separated, a hybridization treatment, wherein the target-specific portions of the secondary oligonucleotide primers hybridize to the target nucleic acid molecules in the exonuclease reaction mixture or to extension products thereof, and an extension treatment, wherein the hybridized secondary oligonucleotide primers are extended to form secondary extension products complementary to the target nucleic acid molecule sequence to which the secondary oligonucleotide primer is hybridized;

providing a tertiary oligonucleotide primer set characterized by (a) a first tertiary primer containing the same sequence as the 5' upstream portion of a first secondary oligonucleotide primer, and (b) a second secondary primer containing the same sequence as the 5' upstream portion of a second secondary oligonucleotide primer from the same secondary oligonucleotide primer set as the 5' upstream portion of the first secondary oligonucleotide primer contained by the first tertiary primer, wherein a set of tertiary oligonucleotide primers may be used to amplify all of the secondary extension products in the group;

blending the secondary extension products, the tertiary oligonucleotide primers, and the polymerase to form a tertiary polymerase chain reaction mixture;

subjecting the tertiary polymerase chain reaction mixture to two or more polymerase chain reaction cycles comprising a denaturation treatment, wherein hybridized nucleic acid sequences are separated, a hybridization treatment, wherein the tertiary oligonucleotide primers hybridize to the secondary extension products, an extension treatment, wherein the hybridized tertiary oligonucleotide primers are extended to form tertiary extension products complementary to the secondary extension products;

providing a plurality of oligonucleotide probe sets, each set characterized by (a) a first oligonucleotide probe, having a tertiary extension product-specific portion and a detectable reporter label, and (b) a second oligonucleotide probe, having a tertiary extension product-specific portion, wherein the oligonucleotide probes in a particular set are suitable for ligation together when hybridized on a complementary tertiary extension product, but have a mismatch which interferes with such ligation when hybridized to any other nucleic acid molecule present;

providing a ligase;

blending the tertiary extension products, the plurality of oligonucleotide probe sets, and the ligase to form a ligase detection reaction mixture;

subjecting the ligase detection reaction mixture to one or more ligase detection reaction cycles comprising a denaturation treatment, wherein any hybridized oligonucleotides are separated from the tertiary extension product, and a hybridization treatment, wherein the oligonucleotide probe sets hybridize in a base-specific manner to their respective tertiary extension products, if present, and ligate to one another to form a ligation product containing (a) the detectable reporter label and (b) the tertiary extension product-specific portions connected together, wherein the oligonucleotide probe sets may hybridize to target nucleic acid molecules other than their respective complementary tertiary extension products but do not ligate together due to a presence of one or more mismatches and individually separate during the denaturation treatment; and detecting the reporter labels of the ligation product, thereby indicating the presence of methylated cytosine bases in the target nucleic acid molecule in the sample.

65. The method according to claim 64, wherein the ligation products of the oligonucleotide probes in a particular set have a unique length so that they can be distinguished from other nucleic acid molecules in the ligase detection reaction mixture, said detecting comprising:

separating the ligation products by size or electrophoretic mobility and distinguishing the ligation products which differ in size.

66. The method according to claim 64, wherein the second oligonucleotide probe of each oligonucleotide probe set has an addressable array-specific portion, said detecting further comprising:

providing a solid support with different capture oligonucleotide probes immobilized at different particular sites, wherein the capture oligonucleotides are complementary to the addressable array-specific portions and contacting the ligase detection reaction mixture, after said subjecting it to one or more ligase detection reaction cycles, with the solid support under conditions effective to hybridize the ligation products to the capture oligonucleotide probes in a base-specific manner, thereby capturing the addressable array-specific portions to the solid support at the site with the complementary capture oligonucleotide.

67. The method according to claim 64, wherein the restriction endonuclease is selected from the group consisting of HinP1I, HhaI, AciI, and other endonucleases that contain CpG in their recognition sequence.

68. The method according to claim 64, wherein the nucleotide analogue is selected from the group consisting of alpha thiophosphate dATP and alpha thiophosphate TTP.

69. The method according to claim 64, wherein the exonuclease is selected from the goup consisting of Exonuclease I, Exonuclease III, and other 3' exonucleases.

70. The method according to claim 64, wherein the primary oligonucleotide primer has a non-phosphorylated or blocked 5' end or contains analogue(s) that confer exonuclease resistance, and the exonuclease is selected from the group consisting of lambda Exonuclease and other 5' exonucleases.

71. The method according to claim 64, wherein a presence of low abundance target nucleic acid molecules with methylated cytosine residues may be distinguished in a presence of a majority of target nucleic acid molecules with unmethylated cytosine residues.

72. The method according to claim 71, wherein a presence of low abundance target nucleic acid molecules with methylated cytosine residues is distinguished in a presence of a 1,000 to 100,000-fold excess of target nucleic acid molecules with unmethylated cytosine residues.

73. The method according to claim 64, wherein the upstream secondary primer-specific portions of the primary oligonucleotide primers are identical or greater than 80% identical in sequence.

74. The method for identifying one or more target nucleic acid molecules differing by one or more methylated cytosine residues, said method comprising:
   providing a sample potentially containing one or more target nucleic acid molecules with a plurality of sequence differences;
   providing a restriction endonuclease that cleaves unmethylated cytosine residues in the target nucleic acid molecules, and does not cleave target nucleic acid molecules which are methylated on both strands;
   blending the sample and the restriction endonuclease to form a primary restriction endonuclease reaction mixture;
   subjecting the restriction endonuclease reaction mixture to an enzymatic digestion processs under conditions effective to cut the majority of unmethylated cytosine residues target nucleic acid molecules while leaving the methylated cytosine residues target nucleic acid molecules intact;
   providing a plurality of primary oligonucleotide primers, having either a non-phosphorylated end, a blocked 5' end, or internal nucleotide or backbone analogue(s) that confer resistance to digestion by exonuclease(s), said primary oligonucleotide primers having a target-specific portion suitable for hybridization on one strand of the target nucleic acid molecules upstream of one or more restriction sites;
   providing a polymerase;
   providing one or more nucleotide analogues and additional nucleotides that may be incorporated by a polymerase into an extension product, and does not interfere with cleavage of the heteroduplexed extension product by the restriction endonuclease, but which renders the extension product resistant to exonucleolytic digestion;
   blending the restriction endonuclease reaction mixture, the primary oligonucleotide primers, the one or more nucleotide analogues and additional nucleotides, and the polymerase to form a primary extension reaction mixture;
   subjecting the primary extension reaction mixture to an extension reaction comprising a denaturation treatment, wherein hybridized nucleic acid molecules are separated, a hybridization treatment, wherein the target-specific portions of the primary oligonucleotide primers hybridize to the target nucleic acid molecules, and an extension treatment wherein the hybridized primary oligonucleotide primers are extended to form primary extension products complementary to the target nucleic acid molecule to which the primary oligonucleotide primers are hybridized;
   blending the primary extension reaction mixture and the restriction endonuclease to form a restriction/extension reaction mixture;
   subjecting the restriction/extension reaction mixture to a restriction/extension cycle comprising an incubation phase sufficient to cut both strands of residual unmethylated cytosine residues in the target nucleic acid molecules arising from extension of primary oligonucleotide extension primers on unmethylated cytosine residues in the target nucleic acid molecules, while either nicking or not cleaving the unmethylated strand of hemi-methylated target nucleic acid molecule arising from extension of oligonucleotide primers on a methylated target nucleic acid molecule, followed by an incubation sufficient to inactivate the restriction endonuclease but not denature the nicked extension products from their target sequences, wherein the nicked secondary extension products re-extend at the nick generating extension products complementary to the target nucleic acid molecule to which the primary oligonucleotide primers are hybridized;
   providing an exonuclease;
   blending the restriction/extension reaction mixture and the exonuclease to form an exonuclease reaction mixture;
   subjecting the exonuclease reaction mixture to enzymatic digestion conditions effective to digest target nucleic acid molecules but not extension products arising from the primary oligonucleotide primers hybridized and extended on methylated target nucleic acid molecules;
   providing a set of secondary oligonucleotide primers, each set characterized by (a) a first secondary oligonucleotide primer, having a target-specific portion and a 5' upstream tertiary primer-specific portion, and (b) a second secondary oligonucleotide primer, having a target-specific portion and a 5' upstream secondary primer-specific portion, wherein the first secondary oligonucleotide primers of each set contain the same 5' upstream tertiary primer-specific portion and the second secondary oligonucleotide primers of each set contain the same 5' upstream tertiary primer-specific portion;
   blending the exonuclease reaction mixture, the secondary oligonucleotide primers, and the polymerase to form a secondary polymerase chain reaction mixture;
   subjecting the secondary polymerase chain reaction mixture to two or more polymerase chain reaction cycles comprising a denaturation treatment, wherein hybridized nucleic acid molecules are separated, a hybridization treatment, wherein the target-specific portions of the secondary oligonucleotide primers hybridize to treated target nucleic acid molecules or to extension products of the target nucleic acid molecules, and an extension treatment, wherein the hybridized secondary oligonucleotide primers are extended to form secondary extension products complementary to the target nucleic acid molecule to which the secondary oligonucleotide primers is hybridized;

providing a tertiary oligonucleotide primer set characterized by (a) a first tertiary primer containing the same sequence as the 5' upstream portion of a first secondary oligonucleotide primer, and (b) a second tertiary primer containing the same sequence as the 5' upstream portion of a second secondary oligonucleotide primer from the same secondary oligonucleotide primer set as the first secondary oligonucleotide primer contained by the first tertiary oligonucleotide primer, wherein a set of tertiary oligonucleotide primers may be used to amplify all of the secondary extension products;

blending the secondary extension products, the tertiary oligonucleotide primers, and the polymerase to form a tertiary polymerase chain reaction mixture;

subjecting the tertiary polymerase chain reaction mixture to two or more polymerase chain reaction cycles comprising a denaturation treatment, wherein hybridized nucleic acid molecules are separated, a hybridization treatment, wherein the tertiary oligonucleotide primers hybridize to the secondary extension products, an extension treatment, wherein the hybridized tertiary oligonucleotide primers are extended to form tertiary extension products complementary to the secondary extension products;

providing a plurality of oligonucleotide probe sets, each set characterized by (a) a first oligonucleotide probe, having a tertiary extension product-specific portion and a detectable reporter label, and (b) a second oligonucleotide probe, having a tertiary extension product-specific portion, wherein the oligonucleotide probes in a particular set are suitable for ligation together when hybridized on a complementary tertiary extension product, but have a mismatch which interferes with such ligation when hybridized to any other nucleic acid molecule present in the sample;

providing a ligase;

blending the tertiary extension products, the plurality of oligonucleotide probe sets, and the ligase to form a ligase detection reaction mixture;

subjecting the ligase detection reaction mixture to one or more ligase detection reaction cycles comprising a denaturation treatment, wherein any hybridized oligonucleotides are separated from the tertiary extension product, and a hybridization treatment, wherein the oligonucleotide probe sets hybridize in a base-specific manner to their respective tertiary extension products, if present, and ligate to one another to form a ligation product containing (a) the detectable reporter label and (b) the tertiary extension product-specific portions connected together, wherein the oligonucleotide probe sets may hybridize to nucleic acid molecules other than their respective complementary tertiary extension products but do not ligate together due to a presence of one or more mismatches and individually separate during the denaturation treatment; and detecting the reporter labels of the ligation product, thereby indicating the presence of methylated cytosine bases in the target nucleic acid molecules in the sample.

75. The method according to claim 74, wherein the ligation products of the oligonucleotide probes in a particular set have a unique length so that they can be distinguished from other nucleic acids in the ligase detection reaction mixture, said method further comprising:

separating the ligation products by size or electrophoretic mobility and distinguishing, after said detecting, the ligation products which differ in size.

76. The method according to claim 74, wherein the second oligonucleotide probe of each oligonucleotide probe set has an addressable array-specific portion, said detecting further comprising:

providing a solid support with different capture oligonucleotide probes immobilized at different particular sites, wherein the capture oligonucleotides are complementary to the addressable array-specific portions and contacting the ligase detection reaction mixture, after said subjecting it to one or more ligase detection reaction cycles, with the solid support under conditions effective to hybridize the ligation products to the capture oligonucleotide probes in a base-specific manner, thereby capturing the addressable array-specific portions to the solid support at the site with the complementary capture oligonucleotide.

77. The method according to claim 74, wherein the restriction endonuclease does not nick hemi-methylated DNA, obviating the need to inactivate the endonuclease and re-extend nicked DNA with polymerase.

78. The method according to claim 74, wherein the restriction endonuclease is selected from the group consisting of BstUI, HpaII, HinPI, HhaI, AciI, and other endonucleases that contain CpG in their recognition sequence.

79. The method according to claim 74, wherein the primary oligonucleotide primer has a non-phosphorylated or blocked 5' end or contain analogue(s) that confer exonuclease resistance, and the exonuclease is selected from the group consisting of lambda Exonuclease and other 5' exonucleases.

80. The method according to claim 74, wherein a presence of low abundance target nucleic acid molecules with methylated cytosine residues may be distinguished in a presence of a majority of target nucleic acid molecules with unmethylated cytosine residues.

81. The method according to claim 80, wherein a presence of low abundance target nucleic acid molecules with methylated cytosine residues is distinguished in a presence of a 1,000 to 100,000-fold excess of target nucleic acid molecules with unmethylated cytosine residues.

82. The method according to claim 74, wherein the upstream secondary primer-specific portions of the primary oligonucleotide primers are identical or greater than 80% identical in sequence.

\* \* \* \* \*

SEQUENCE LISTING

<160> NUMBER OF SEQ ID NOS: 309

<210> SEQ ID NO 1
<211> LENGTH: 47
<212> TYPE: DNA
<213> ORGANISM: Artificial Sequence
<220> FEATURE:
<223> OTHER INFORMATION: Description of Artificial Sequence: primer

<400> SEQUENCE: 1
cgctgccaac taccgcacat cctttaccka ctaactcccc actctac                47

<210> SEQ ID NO 2
<211> LENGTH: 50
<212> TYPE: DNA
<213> ORGANISM: Artificial Sequence
<220> FEATURE:
<223> OTHER INFORMATION: Description of Artificial Sequence: primer

<400> SEQUENCE: 2
cgctgccaac taccgcacat cttttttttt tttaggagat ttgggtttag             50

<210> SEQ ID NO 3
<211> LENGTH: 48
<212> TYPE: DNA
<213> ORGANISM: Artificial Sequence
<220> FEATURE:
<223> OTHER INFORMATION: Description of Artificial Sequence: primer

<400> SEQUENCE: 3
cgctgccaac taccgcacat ccctcctaaa aataccaac tcattctc                48

<210> SEQ ID NO 4
<211> LENGTH: 51
<212> TYPE: DNA
<213> ORGANISM: Artificial Sequence
<220> FEATURE:
<223> OTHER INFORMATION: Description of Artificial Sequence: primer

<400> SEQUENCE: 4
cgctgccaac taccgcacat ctgatttrgg tagttgttta tattttagtt g           51

<210> SEQ ID NO 5
<211> LENGTH: 50
<212> TYPE: DNA
<213> ORGANISM: Artificial Sequence
<220> FEATURE:
<223> OTHER INFORMATION: Description of Artificial Sequence: primer

<400> SEQUENCE: 5
cgctgccaac taccgcacat cgttgggatt tttgtattgr ggtaaataag             50

<210> SEQ ID NO 6
<211> LENGTH: 47
<212> TYPE: DNA
<213> ORGANISM: Artificial Sequence
<220> FEATURE:
<223> OTHER INFORMATION: Description of Artificial Sequence: primer

<400> SEQUENCE: 6
cgctgccaac taccgcacat cccaatacka ackaacaaaa taccatc                47

<210> SEQ ID NO 7
<211> LENGTH: 45

<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 7
cgctgccaac taccgcacat ckacaaacaa caaaaaaccc ckaac          45

<210> SEQ ID NO 8
<211> LENGTH: 46
<212> TYPE: DNA
<213> ORGANISM: Artificial Sequence
<220> FEATURE:
<223> OTHER INFORMATION: Description of Artificial Sequence: primer

<400> SEQUENCE: 8
cgctgccaac taccgcacat cgrgtgatta gggattttg tatttg          46

<210> SEQ ID NO 9
<211> LENGTH: 52
<212> TYPE: DNA
<213> ORGANISM: Artificial Sequence
<220> FEATURE:
<223> OTHER INFORMATION: Description of Artificial Sequence: primer

<400> SEQUENCE: 9
cgctgccaac taccgcacat ccccaatcta caattaaaaa acaaaaata ac    52

<210> SEQ ID NO 10
<211> LENGTH: 49
<212> TYPE: DNA
<213> ORGANISM: Artificial Sequence
<220> FEATURE:
<223> OTHER INFORMATION: Description of Artificial Sequence: primer

<400> SEQUENCE: 10
cgctgccaac taccgcacat cggttttttt tatttggttt tttaggaag       49

<210> SEQ ID NO 11
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 11
cgctgccaac taccgcacat caccaccctc tcckcttacc taatc          45

<210> SEQ ID NO 12
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 12
cgctgccaac taccgcacat catrgggtrg aagaggtttt tgtag          45

<210> SEQ ID NO 13
<211> LENGTH: 44
<212> TYPE: DNA
<213> ORGANISM: Artificial Sequence
<220> FEATURE:
<223> OTHER INFORMATION: Description of Artificial Sequence: primer

<400> SEQUENCE: 13

```
cgctgccaac taccgcacat ckaaaaaaac tcttcckcca acac              44
```

<210> SEQ ID NO 14
<211> LENGTH: 49
<212> TYPE: DNA
<213> ORGANISM: Artificial Sequence
<220> FEATURE:
<223> OTHER INFORMATION: Description of Artificial Sequence: primer

<400> SEQUENCE: 14

```
cgctgccaac taccgcacat crgttrgtta tttttttgttt trgttgtag        49
```

<210> SEQ ID NO 15
<211> LENGTH: 56
<212> TYPE: DNA
<213> ORGANISM: Artificial Sequence
<220> FEATURE:
<223> OTHER INFORMATION: Description of Artificial Sequence: primer

<400> SEQUENCE: 15

```
cgctgccaac taccgcacat ctttggtttg tagaattttt tattttaaaa tgttag    56
```

<210> SEQ ID NO 16
<211> LENGTH: 49
<212> TYPE: DNA
<213> ORGANISM: Artificial Sequence
<220> FEATURE:
<223> OTHER INFORMATION: Description of Artificial Sequence: primer

<400> SEQUENCE: 16

```
cgctgccaac taccgcacat ctcaaattca atcaaaaact tacccaatc         49
```

<210> SEQ ID NO 17
<211> LENGTH: 48
<212> TYPE: DNA
<213> ORGANISM: Artificial Sequence
<220> FEATURE:
<223> OTHER INFORMATION: Description of Artificial Sequence: primer

<400> SEQUENCE: 17

```
cgctgccaac taccgcacat cgagattttt attagggrgg aaagagtg          48
```

<210> SEQ ID NO 18
<211> LENGTH: 46
<212> TYPE: DNA
<213> ORGANISM: Artificial Sequence
<220> FEATURE:
<223> OTHER INFORMATION: Description of Artificial Sequence: primer

<400> SEQUENCE: 18

```
cgctgccaac taccgcacat cccktccaaa aaatctcaac kaactc            46
```

<210> SEQ ID NO 19
<211> LENGTH: 47
<212> TYPE: DNA
<213> ORGANISM: Artificial Sequence
<220> FEATURE:
<223> OTHER INFORMATION: Description of Artificial Sequence: primer

<400> SEQUENCE: 19

```
cgctgccaac taccgcacat cctttaccga ctaactcccc actctac           47
```

<210> SEQ ID NO 20
<211> LENGTH: 50
<212> TYPE: DNA
<213> ORGANISM: Artificial Sequence
<220> FEATURE:
<223> OTHER INFORMATION: Description of Artificial Sequence: primer

<400> SEQUENCE: 20
cgctgccaac taccgcacat cttttttttt tttaggagat tgggtttag          50

<210> SEQ ID NO 21
<211> LENGTH: 48
<212> TYPE: DNA
<213> ORGANISM: Artificial Sequence
<220> FEATURE:
<223> OTHER INFORMATION: Description of Artificial Sequence: primer

<400> SEQUENCE: 21
cgctgccaac taccgcacat ccctcctaaa aataccaac tcattctc            48

<210> SEQ ID NO 22
<211> LENGTH: 51
<212> TYPE: DNA
<213> ORGANISM: Artificial Sequence
<220> FEATURE:
<223> OTHER INFORMATION: Description of Artificial Sequence: primer

<400> SEQUENCE: 22
cgctgccaac taccgcacat ctgattttgg tagttgttta tattttagtt g       51

<210> SEQ ID NO 23
<211> LENGTH: 49
<212> TYPE: DNA
<213> ORGANISM: Artificial Sequence
<220> FEATURE:
<223> OTHER INFORMATION: Description of Artificial Sequence: primer

<400> SEQUENCE: 23
cgctgccaac taccgcacat cacgaactac accaatacaa ccacatatc          49

<210> SEQ ID NO 24
<211> LENGTH: 56
<212> TYPE: DNA
<213> ORGANISM: Artificial Sequence
<220> FEATURE:
<223> OTHER INFORMATION: Description of Artificial Sequence: primer

<400> SEQUENCE: 24
cgctgccaac taccgcacat ctattgtttt tttgtgttgt aaaaattata gtaatt  56

<210> SEQ ID NO 25
<211> LENGTH: 50
<212> TYPE: DNA
<213> ORGANISM: Artificial Sequence
<220> FEATURE:
<223> OTHER INFORMATION: Description of Artificial Sequence: primer

<400> SEQUENCE: 25
cgctgccaac taccgcacat cgttgggatt tttgtattgt ggtaaataag         50

<210> SEQ ID NO 26
<211> LENGTH: 47
<212> TYPE: DNA
<213> ORGANISM: Artificial Sequence
<220> FEATURE:
<223> OTHER INFORMATION: Description of Artificial Sequence: primer

<400> SEQUENCE: 26
cgctgccaac taccgcacat cccaatacga acgaacaaaa taccatc            47

<210> SEQ ID NO 27
<211> LENGTH: 52
<212> TYPE: DNA
<213> ORGANISM: Artificial Sequence
<220> FEATURE:
<223> OTHER INFORMATION: Description of Artificial Sequence: primer

<400> SEQUENCE: 27
cgctgccaac taccgcacat ccccaatcta caattaaaaa aacaaaaata ac             52

<210> SEQ ID NO 28
<211> LENGTH: 49
<212> TYPE: DNA
<213> ORGANISM: Artificial Sequence
<220> FEATURE:
<223> OTHER INFORMATION: Description of Artificial Sequence: primer

<400> SEQUENCE: 28
cgctgccaac taccgcacat cggttttttt tatttggttt tttaggaag                 49

<210> SEQ ID NO 29
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 29
cgctgccaac taccgcacat caccaccctc tccgcttacc taatc                     45

<210> SEQ ID NO 30
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 30
cgctgccaac taccgcacat cattgggttg aagaggtttt tgtag                     45

<210> SEQ ID NO 31
<211> LENGTH: 44
<212> TYPE: DNA
<213> ORGANISM: Artificial Sequence
<220> FEATURE:
<223> OTHER INFORMATION: Description of Artificial Sequence: primer

<400> SEQUENCE: 31
cgctgccaac taccgcacat ctcacctacc gaccacaacc aatc                      44

<210> SEQ ID NO 32
<211> LENGTH: 47
<212> TYPE: DNA
<213> ORGANISM: Artificial Sequence
<220> FEATURE:
<223> OTHER INFORMATION: Description of Artificial Sequence: primer

<400> SEQUENCE: 32
cgctgccaac taccgcacat cttattgttt ttgttcgttt cgatttg                   47

<210> SEQ ID NO 33
<211> LENGTH: 44
<212> TYPE: DNA
<213> ORGANISM: Artificial Sequence
<220> FEATURE:
<223> OTHER INFORMATION: Description of Artificial Sequence: primer

```
<400> SEQUENCE: 33
cgctgccaac taccgcacat cgaaaaaaac tcttccgcca acac                    44

<210> SEQ ID NO 34
<211> LENGTH: 49
<212> TYPE: DNA
<213> ORGANISM: Artificial Sequence
<220> FEATURE:
<223> OTHER INFORMATION: Description of Artificial Sequence: primer

<400> SEQUENCE: 34
cgctgccaac taccgcacat ctgtttgtta tttttgttt ttgttgtag                49

<210> SEQ ID NO 35
<211> LENGTH: 56
<212> TYPE: DNA
<213> ORGANISM: Artificial Sequence
<220> FEATURE:
<223> OTHER INFORMATION: Description of Artificial Sequence: primer

<400> SEQUENCE: 35
cgctgccaac taccgcacat ctttggtttg tagaattttt tattttaaaa tgttag       56

<210> SEQ ID NO 36
<211> LENGTH: 49
<212> TYPE: DNA
<213> ORGANISM: Artificial Sequence
<220> FEATURE:
<223> OTHER INFORMATION: Description of Artificial Sequence: primer

<400> SEQUENCE: 36
cgctgccaac taccgcacat ctcaaattca atcaaaaact tacccaatc               49

<210> SEQ ID NO 37
<211> LENGTH: 48
<212> TYPE: DNA
<213> ORGANISM: Artificial Sequence
<220> FEATURE:
<223> OTHER INFORMATION: Description of Artificial Sequence: primer

<400> SEQUENCE: 37
cgctgccaac taccgcacat cgagattttt attagggtgg aaagagtg                48

<210> SEQ ID NO 38
<211> LENGTH: 46
<212> TYPE: DNA
<213> ORGANISM: Artificial Sequence
<220> FEATURE:
<223> OTHER INFORMATION: Description of Artificial Sequence: primer

<400> SEQUENCE: 38
cgctgccaac taccgcacat cccgtccaaa aaatctcaac gaactc                  46

<210> SEQ ID NO 39
<211> LENGTH: 43
<212> TYPE: DNA
<213> ORGANISM: Artificial Sequence
<220> FEATURE:
<223> OTHER INFORMATION: Description of Artificial Sequence: primer

<400> SEQUENCE: 39
cgctgccaac taccgcacat cccgacccta atcctccgac aac                     43

<210> SEQ ID NO 40
```

```
<211> LENGTH: 44
<212> TYPE: DNA
<213> ORGANISM: Artificial Sequence
<220> FEATURE:
<223> OTHER INFORMATION: Description of Artificial Sequence: primer

<400> SEQUENCE: 40
cgctgccaac taccgcacat ctttgattag gggagtggtt ttag                    44

<210> SEQ ID NO 41
<211> LENGTH: 46
<212> TYPE: DNA
<213> ORGANISM: Artificial Sequence
<220> FEATURE:
<223> OTHER INFORMATION: Description of Artificial Sequence: primer

<400> SEQUENCE: 41
cgctgccaac taccgcacat cgcgccctaa ctaaaaaaac aaaaac                  46

<210> SEQ ID NO 42
<211> LENGTH: 49
<212> TYPE: DNA
<213> ORGANISM: Artificial Sequence
<220> FEATURE:
<223> OTHER INFORMATION: Description of Artificial Sequence: primer

<400> SEQUENCE: 42
cgctgccaac taccgcacat ccgttagttc gtttgtaggg tttttattg               49

<210> SEQ ID NO 43
<211> LENGTH: 51
<212> TYPE: DNA
<213> ORGANISM: Artificial Sequence
<220> FEATURE:
<223> OTHER INFORMATION: Description of Artificial Sequence: primer

<400> SEQUENCE: 43
cgctgccaac taccgcacat ccgaattaac cccatactaa aaactctaaa c            51

<210> SEQ ID NO 44
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 44
cgctgccaac taccgcacat ctgttttgtg aagtgggtgt gtaag                   45

<210> SEQ ID NO 45
<211> LENGTH: 42
<212> TYPE: DNA
<213> ORGANISM: Artificial Sequence
<220> FEATURE:
<223> OTHER INFORMATION: Description of Artificial Sequence: primer

<400> SEQUENCE: 45
cgctgccaac taccgcacat cccgctctac cccgctacct aa                      42

<210> SEQ ID NO 46
<211> LENGTH: 47
<212> TYPE: DNA
<213> ORGANISM: Artificial Sequence
<220> FEATURE:
<223> OTHER INFORMATION: Description of Artificial Sequence: primer

<400> SEQUENCE: 46
```
cgctgccaac taccgcacat cgttggtttt ggtttgggtt agagata         47

<210> SEQ ID NO 47
<211> LENGTH: 47
<212> TYPE: DNA
<213> ORGANISM: Artificial Sequence
<220> FEATURE:
<223> OTHER INFORMATION: Description of Artificial Sequence: primer

<400> SEQUENCE: 47
cgctgccaac taccgcacat ccgacgacta cgctacccct taactac        47

<210> SEQ ID NO 48
<211> LENGTH: 46
<212> TYPE: DNA
<213> ORGANISM: Artificial Sequence
<220> FEATURE:
<223> OTHER INFORMATION: Description of Artificial Sequence: primer

<400> SEQUENCE: 48
cgctgccaac taccgcacat cttttcgtcg tttagtttgg attttg          46

<210> SEQ ID NO 49
<211> LENGTH: 48
<212> TYPE: DNA
<213> ORGANISM: Artificial Sequence
<220> FEATURE:
<223> OTHER INFORMATION: Description of Artificial Sequence: primer

<400> SEQUENCE: 49
cgctgccaac taccgcacat ctcccaaatt ctccttccaa ataaatac        48

<210> SEQ ID NO 50
<211> LENGTH: 50
<212> TYPE: DNA
<213> ORGANISM: Artificial Sequence
<220> FEATURE:
<223> OTHER INFORMATION: Description of Artificial Sequence: primer

<400> SEQUENCE: 50
cgctgccaac taccgcacat cttggttttt tttttgttta ttttaaaagt      50

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 51
cgctgccaac taccgcacat c                                      21

<210> SEQ ID NO 52
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 52
aggtaggttg grgrgtatgt ttaggc                                 26

<210> SEQ ID NO 53
<211> LENGTH: 24
<212> TYPE: DNA

<213> ORGANISM: Artificial Sequence
<220> FEATURE:
<223> OTHER INFORMATION: Description of Artificial Sequence: primer

<400> SEQUENCE: 53
gagrggtrgt rggagatgtt tgac                                          24

<210> SEQ ID NO 54
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 54
gtggtttttt ttaagagata gtttggggag c                                  31

<210> SEQ ID NO 55
<211> LENGTH: 50
<212> TYPE: DNA
<213> ORGANISM: Artificial Sequence
<220> FEATURE:
<223> OTHER INFORMATION: Description of Artificial Sequence: primer

<400> SEQUENCE: 55
ggggatgtgt grgaagtttg trgttgatgg ccgtgctggg gacaagtcaa              50

<210> SEQ ID NO 56
<211> LENGTH: 54
<212> TYPE: DNA
<213> ORGANISM: Artificial Sequence
<220> FEATURE:
<223> OTHER INFORMATION: Description of Artificial Sequence: primer

<400> SEQUENCE: 56
gtatttgttt gaggagrggt tagtgargrg ttgcaacggg ctggtcaacg tcaa          54

<210> SEQ ID NO 57
<211> LENGTH: 74
<212> TYPE: DNA
<213> ORGANISM: Artificial Sequence
<220> FEATURE:
<223> OTHER INFORMATION: Description of Artificial Sequence: primer

<400> SEQUENCE: 57
ggttattttt atttattaga tattttaagt ttttaggatt tggagtattg catcatgggg   60
gaaagcttcg tcaa                                                     74

<210> SEQ ID NO 58
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 58
ggargtagtr gagtttaaag trgttttggt c                                  31

<210> SEQ ID NO 59
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 59
tttttggrgt ttaagaatta grgggc                                       26

<210> SEQ ID NO 60
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 60
gtrgtttttt tgrggtttgg ggtttc                                       26

<210> SEQ ID NO 61
<211> LENGTH: 46
<212> TYPE: DNA
<213> ORGANISM: Artificial Sequence
<220> FEATURE:
<223> OTHER INFORMATION: Description of Artificial Sequence: primer

<400> SEQUENCE: 61
gtagggtgrg gargrgtrgr ggcatcgtcc ctttcgatgg gatcaa                  46

<210> SEQ ID NO 62
<211> LENGTH: 52
<212> TYPE: DNA
<213> ORGANISM: Artificial Sequence
<220> FEATURE:
<223> OTHER INFORMATION: Description of Artificial Sequence: primer

<400> SEQUENCE: 62
grgtttggat tgttttggg aaaaagrgca aggcacgtcc cagacgcatc aa            52

<210> SEQ ID NO 63
<211> LENGTH: 48
<212> TYPE: DNA
<213> ORGANISM: Artificial Sequence
<220> FEATURE:
<223> OTHER INFORMATION: Description of Artificial Sequence: primer

<400> SEQUENCE: 63
gtgtagtggt rgagrggtrg gtrggcacgg gagctgacga cgtgtcaa                48

<210> SEQ ID NO 64
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 64
ttgttttttt tttttrgta gtrgtrgagc                                    30

<210> SEQ ID NO 65
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 65
ggtrgrggtr gtggttagtt agttagtc                                     28

<210> SEQ ID NO 66
<211> LENGTH: 29
<212> TYPE: DNA

```
<213> ORGANISM: Artificial Sequence
<220> FEATURE:
<223> OTHER INFORMATION: Description of Artificial Sequence: primer

<400> SEQUENCE: 66
atrggttttr gatrgtaatt attrggtgc                                         29

<210> SEQ ID NO 67
<211> LENGTH: 55
<212> TYPE: DNA
<213> ORGANISM: Artificial Sequence
<220> FEATURE:
<223> OTHER INFORMATION: Description of Artificial Sequence: primer

<400> SEQUENCE: 67
gtargrggtt rgttttattt tttggtgatt agctggctgg cacgcaccag aatca            55

<210> SEQ ID NO 68
<211> LENGTH: 55
<212> TYPE: DNA
<213> ORGANISM: Artificial Sequence
<220> FEATURE:
<223> OTHER INFORMATION: Description of Artificial Sequence: primer

<400> SEQUENCE: 68
gaaggtttta tgttgttttt rgtrgtrggt tggctccgtc agaaagcgac aatca            55

<210> SEQ ID NO 69
<211> LENGTH: 55
<212> TYPE: DNA
<213> ORGANISM: Artificial Sequence
<220> FEATURE:
<223> OTHER INFORMATION: Description of Artificial Sequence: primer

<400> SEQUENCE: 69
gttgggtagr gttttrgttt ttagtagrgt tacgagggat acccgcaaac gatca            55

<210> SEQ ID NO 70
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 70
ttagggtrga gttrggtagt rgttgc                                            26

<210> SEQ ID NO 71
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 71
rgggtrgtar grgrgtrgaa ttc                                               23

<210> SEQ ID NO 72
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 72
gtargagggt tatagrggrg ggc                                               23
```

<210> SEQ ID NO 73
<211> LENGTH: 61
<212> TYPE: DNA
<213> ORGANISM: Artificial Sequence
<220> FEATURE:
<223> OTHER INFORMATION: Description of Artificial Sequence: primer

<400> SEQUENCE: 73
gtrgtttttt ggtattagag gtgagtagrg ttatttgtc cgtccatggc aagcgtgatc    60
a                                                                  61

<210> SEQ ID NO 74
<211> LENGTH: 60
<212> TYPE: DNA
<213> ORGANISM: Artificial Sequence
<220> FEATURE:
<223> OTHER INFORMATION: Description of Artificial Sequence: primer

<400> SEQUENCE: 74
ggagggttat taagaatttg rgtattatgt tttrgtggct gcaccccgttg aggcacatca   60

<210> SEQ ID NO 75
<211> LENGTH: 55
<212> TYPE: DNA
<213> ORGANISM: Artificial Sequence
<220> FEATURE:
<223> OTHER INFORMATION: Description of Artificial Sequence: primer

<400> SEQUENCE: 75
gtttttggrg ttgtttattt tttrgtgagt rtcaacatcg gctaacggtc catca         55

<210> SEQ ID NO 76
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 76 tttttagtt tttrgtttgr gttggtgc                                       28

<210> SEQ ID NO 77
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 77
ttagttgagt ttggtrgagt tttagtaggt tagtc                              35

<210> SEQ ID NO 78
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 78
ggttrgtttt aaggaggrgg gattc                                         25

<210> SEQ ID NO 79
<211> LENGTH: 65
<212> TYPE: DNA

<213> ORGANISM: Artificial Sequence
<220> FEATURE:
<223> OTHER INFORMATION: Description of Artificial Sequence: primer

<400> SEQUENCE: 79
gttggatata tttttttarg aagtgagtta taaatttggt tcgcacgcag tcctcctccg    60
tatca    65

<210> SEQ ID NO 80
<211> LENGTH: 50
<212> TYPE: DNA
<213> ORGANISM: Artificial Sequence
<220> FEATURE:
<223> OTHER INFORMATION: Description of Artificial Sequence: primer

<400> SEQUENCE: 80
ggtttrggaa tttrgcgtgt tgtaggggct cgcaggctgg ctcatcctaa    50

<210> SEQ ID NO 81
<211> LENGTH: 49
<212> TYPE: DNA
<213> ORGANISM: Artificial Sequence
<220> FEATURE:
<223> OTHER INFORMATION: Description of Artificial Sequence: primer

<400> SEQUENCE: 81
grgttrggtt tatrgrgtrg ttrggcgcat gaggggaaac gacgagatt    49

<210> SEQ ID NO 82
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 82
tattrgrgaa targtatttt rgrggatac    29

<210> SEQ ID NO 83
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 83
trgtgtgrgt aagtrgagrg rgtatc    26

<210> SEQ ID NO 84
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 84
ttttrgtttr ggggttttrg gtatatttc    29

<210> SEQ ID NO 85
<211> LENGTH: 53
<212> TYPE: DNA
<213> ORGANISM: Artificial Sequence
<220> FEATURE:
<223> OTHER INFORMATION: Description of Artificial Sequence: primer

<400> SEQUENCE: 85

```
gtagggatat argrgggtar gtttggttrg caccgtgaac gacagttgcg att          53
```

<210> SEQ ID NO 86
<211> LENGTH: 64
<212> TYPE: DNA
<213> ORGANISM: Artificial Sequence
<220> FEATURE:
<223> OTHER INFORMATION: Description of Artificial Sequence: primer

<400> SEQUENCE: 86

```
gatttargtt rgttatttat ttgtrgtaga aatatttgtg cgcaggtcgc tgcgtgtcct   60
gatt                                                               64
```

<210> SEQ ID NO 87
<211> LENGTH: 59
<212> TYPE: DNA
<213> ORGANISM: Artificial Sequence
<220> FEATURE:
<223> OTHER INFORMATION: Description of Artificial Sequence: primer

<400> SEQUENCE: 87

```
gattttrgtt attrgrgtat ttagagatat rgtgtcgcaa agcagacaca gggtcgatt    59
```

<210> SEQ ID NO 88
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 88

```
gttaaaagat atagatttrg argagttarg gttc                              34
```

<210> SEQ ID NO 89
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 89

```
aaaatrgaat aaaataaagr gttttargt agttc                              35
```

<210> SEQ ID NO 90
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 90

```
gggtgtttrg tttgtttggr gtttattc                                     28
```

<210> SEQ ID NO 91
<211> LENGTH: 50
<212> TYPE: DNA
<213> ORGANISM: Artificial Sequence
<220> FEATURE:
<223> OTHER INFORMATION: Description of Artificial Sequence: primer

<400> SEQUENCE: 91

```
gagttttagg agrgrgtagg ggttgrcatc gcacttcgct ttggctgatt              50
```

<210> SEQ ID NO 92

<211> LENGTH: 57
<212> TYPE: DNA
<213> ORGANISM: Artificial Sequence
<220> FEATURE:
<223> OTHER INFORMATION: Description of Artificial Sequence: primer

<400> SEQUENCE: 92
gaattttttt rggaagttta grgattgttt trgttgcggg aactcacgag gtcgtat        57

<210> SEQ ID NO 93
<211> LENGTH: 62
<212> TYPE: DNA
<213> ORGANISM: Artificial Sequence
<220> FEATURE:
<223> OTHER INFORMATION: Description of Artificial Sequence: primer

<400> SEQUENCE: 93
gttttaggtt agggttttrg ttagatattr gtargtttgc acggctcgat aggtcaagct    60
tt                                                                   62

<210> SEQ ID NO 94
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 94
taggrggatt atttgttttt atttgttatg gc                                  32

<210> SEQ ID NO 95
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 95
gggttttttt tttttatgtg tttaagattg gc                                  32

<210> SEQ ID NO 96
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 96
tgggtttrgg ggatattttg rgttc                                          25

<210> SEQ ID NO 97
<211> LENGTH: 59
<212> TYPE: DNA
<213> ORGANISM: Artificial Sequence
<220> FEATURE:
<223> OTHER INFORMATION: Description of Artificial Sequence: primer

<400> SEQUENCE: 97
gattgtttag ttttgtgtta ggagtttrgt aggggagacg caccgcaaca ggctgtcaa    59

<210> SEQ ID NO 98
<211> LENGTH: 69
<212> TYPE: DNA
<213> ORGANISM: Artificial Sequence
<220> FEATURE:
<223> OTHER INFORMATION: Description of Artificial Sequence: primer -continued

<400> SEQUENCE: 98
gttaaaagtt ttgagttttt taaaagttta gagttatcgt ttaggcatcg ctgcaagtac     60
cgcactcaa     69

<210> SEQ ID NO 99
<211> LENGTH: 50
<212> TYPE: DNA
<213> ORGANISM: Artificial Sequence
<220> FEATURE:
<223> OTHER INFORMATION: Description of Artificial Sequence: primer

<400> SEQUENCE: 99
gggttgggag rgtgttttt argargggct gggacgtgca gaccgttcaa     50

<210> SEQ ID NO 100
<211> LENGTH: 41
<212> TYPE: DNA
<213> ORGANISM: Artificial Sequence
<220> FEATURE:
<223> OTHER INFORMATION: Description of Artificial Sequence: primer

<400> SEQUENCE: 100
attttgattt trgtatagta attattgtga tgtaataagt c     41

<210> SEQ ID NO 101
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 101
gggggtagat tgggtggtta atttagagtt tc     32

<210> SEQ ID NO 102
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 102
tagrggtagt tttttggttt trgtggtaac     30

<210> SEQ ID NO 103
<211> LENGTH: 65
<212> TYPE: DNA
<213> ORGANISM: Artificial Sequence
<220> FEATURE:
<223> OTHER INFORMATION: Description of Artificial Sequence: primer

<400> SEQUENCE: 103
gtaattggaa gagtagaggt tagagggtag gtattttatg ggggaggctg ctgtcctttc     60
gatca     65

<210> SEQ ID NO 104
<211> LENGTH: 62
<212> TYPE: DNA
<213> ORGANISM: Artificial Sequence
<220> FEATURE:
<223> OTHER INFORMATION: Description of Artificial Sequence: primer

<400> SEQUENCE: 104

-continued

```
gagagargtt tggttttttt tgttttttttt attttttgac agcgtgttcg ttgcttgcat      60
ca                                                                      62
```

<210> SEQ ID NO 105
<211> LENGTH: 59
<212> TYPE: DNA
<213> ORGANISM: Artificial Sequence
<220> FEATURE:
<223> OTHER INFORMATION: Description of Artificial Sequence: primer

<400> SEQUENCE: 105

```
ggaaaagrgr gggaattata gataaattaa aattgatggc gatggtccac tcgcaatca        59
```

<210> SEQ ID NO 106
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 106

```
kacaaacttc kcacacatcc cca                                               23
```

<210> SEQ ID NO 107
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 107

```
actaacckct cctcaaacaa ataca                                             25
```

<210> SEQ ID NO 108
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 108

```
taaaaactta aaatatctaa taaataaaaa taacca                                 36
```

<210> SEQ ID NO 109
<211> LENGTH: 52
<212> TYPE: DNA
<213> ORGANISM: Artificial Sequence
<220> FEATURE:
<223> OTHER INFORMATION: Description of Artificial Sequence: primer

<400> SEQUENCE: 109

```
cctaaacata ckckccaacc tacctctaat ggccgtgctg gggacaagtc aa               52
```

<210> SEQ ID NO 110
<211> LENGTH: 49
<212> TYPE: DNA
<213> ORGANISM: Artificial Sequence
<220> FEATURE:
<223> OTHER INFORMATION: Description of Artificial Sequence: primer

<400> SEQUENCE: 110

```
tcaaacatct cckackacck ctccattgca acgggctggt caacgtcaa                   49
```

<210> SEQ ID NO 111
<211> LENGTH: 57

```
<212> TYPE: DNA
<213> ORGANISM: Artificial Sequence
<220> FEATURE:
<223> OTHER INFORMATION: Description of Artificial Sequence: primer

<400> SEQUENCE: 111
ctccccaaac tatctcttaa aaaaaaccac ckacatcatg ggggaaagct tcgtcaa         57

<210> SEQ ID NO 112
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 112
tcckckackc ktcckcaccc taca                                            24

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 113
ccaaaaacaa tccaaackca                                                 20

<210> SEQ ID NO 114
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 114
acckctckac cactacaca                                                  19

<210> SEQ ID NO 115
<211> LENGTH: 56
<212> TYPE: DNA
<213> ORGANISM: Artificial Sequence
<220> FEATURE:
<223> OTHER INFORMATION: Description of Artificial Sequence: primer

<400> SEQUENCE: 115
accaaaacka ctttaaactc kactacktcc kccatcgtcc ctttcgatgg gatcaa         56

<210> SEQ ID NO 116
<211> LENGTH: 49
<212> TYPE: DNA
<213> ORGANISM: Artificial Sequence
<220> FEATURE:
<223> OTHER INFORMATION: Description of Artificial Sequence: primer

<400> SEQUENCE: 116
ccckctaatt cttaaackcc aaaacaaggc acgtcccaga cgcatcaag                 49

<210> SEQ ID NO 117
<211> LENGTH: 46
<212> TYPE: DNA
<213> ORGANISM: Artificial Sequence
<220> FEATURE:
<223> OTHER INFORMATION: Description of Artificial Sequence: primer

<400> SEQUENCE: 117
```

```
aaaccccaaa cckcaaaaaa agcacgggag ctgacgacgt gtcaag              46
```

<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 118

```
aaataaaack aacckcktac a                                         21
```

<210> SEQ ID NO 119
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 119

```
ccktckacka aaacaacat aaaaccttca                                 30
```

<210> SEQ ID NO 120
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 120

```
ckctactaaa aackaaaack ctacccaaca                                30
```

<210> SEQ ID NO 121
<211> LENGTH: 54
<212> TYPE: DNA
<213> ORGANISM: Artificial Sequence
<220> FEATURE:
<223> OTHER INFORMATION: Description of Artificial Sequence: primer

<400> SEQUENCE: 121

```
ctckackact ackaaaaaaa aaaaacaaa gctggctggc acgcaccaga atca       54
```

<210> SEQ ID NO 122
<211> LENGTH: 58
<212> TYPE: DNA
<213> ORGANISM: Artificial Sequence
<220> FEATURE:
<223> OTHER INFORMATION: Description of Artificial Sequence: primer

<400> SEQUENCE: 122

```
actaactaac taaccackac ckckacckaa atcggctccg tcagaaagcg acaatcag  58
```

<210> SEQ ID NO 123
<211> LENGTH: 54
<212> TYPE: DNA
<213> ORGANISM: Artificial Sequence
<220> FEATURE:
<223> OTHER INFORMATION: Description of Artificial Sequence: primer

<400> SEQUENCE: 123

```
cacckaataa ttackatcka aaacckatcc acgagggata cccgcaaacg atca      54
```

<210> SEQ ID NO 124
<211> LENGTH: 24
<212> TYPE: DNA
<213> ORGANISM: Artificial Sequence

```
<220> FEATURE:
<223> OTHER INFORMATION: Description of Artificial Sequence: primer

<400> SEQUENCE: 124
cacctctaat accaaaaaac kaca                                          24

<210> SEQ ID NO 125
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 125
acataatack caaattctta ataaccctcc a                                  31

<210> SEQ ID NO 126
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 126
ctcackaaaa aataaacaac kccaaaaaca                                    30

<210> SEQ ID NO 127
<211> LENGTH: 49
<212> TYPE: DNA
<213> ORGANISM: Artificial Sequence
<220> FEATURE:
<223> OTHER INFORMATION: Description of Artificial Sequence: primer

<400> SEQUENCE: 127
caackactac ckaactckac cctaagtccg tccatggcaa gcgtgatca               49

<210> SEQ ID NO 128
<211> LENGTH: 50
<212> TYPE: DNA
<213> ORGANISM: Artificial Sequence
<220> FEATURE:
<223> OTHER INFORMATION: Description of Artificial Sequence: primer

<400> SEQUENCE: 128
aattckackc kcktackacc ckcckcggct gcacccgttg aggcacatca              50

<210> SEQ ID NO 129
<211> LENGTH: 47
<212> TYPE: DNA
<213> ORGANISM: Artificial Sequence
<220> FEATURE:
<223> OTHER INFORMATION: Description of Artificial Sequence: primer

<400> SEQUENCE: 129
ccckcckcta taaccctckt acttcaacat cggctaacgg tccatca                 47

<210> SEQ ID NO 130
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 130
cacttcktaa aaaatatat ccaaca                                         26
```

```
<210> SEQ ID NO 131
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 131
tacaacackc kaaattccka aacca                                           25

<210> SEQ ID NO 132
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 132
aackackcka taaacckaac kca                                             23

<210> SEQ ID NO 133
<211> LENGTH: 53
<212> TYPE: DNA
<213> ORGANISM: Artificial Sequence
<220> FEATURE:
<223> OTHER INFORMATION: Description of Artificial Sequence: primer

<400> SEQUENCE: 133
caccaackca aackaaaaac taaaaaaaac gcacgcagtc ctcctccgta tca            53

<210> SEQ ID NO 134
<211> LENGTH: 62
<212> TYPE: DNA
<213> ORGANISM: Artificial Sequence
<220> FEATURE:
<223> OTHER INFORMATION: Description of Artificial Sequence: primer

<400> SEQUENCE: 134
actaacctac taaaactcka ccaaactcaa ctaactckgg ctcgcaggct ggctcatcct     60
aa                                                                   62

<210> SEQ ID NO 135
<211> LENGTH: 51
<212> TYPE: DNA
<213> ORGANISM: Artificial Sequence
<220> FEATURE:
<223> OTHER INFORMATION: Description of Artificial Sequence: primer

<400> SEQUENCE: 135
aatccckcct ccttaaaack aaccckcgca tgaggggaaa cgacgagatt g              51

<210> SEQ ID NO 136
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 136
accaaackta ccckcktata tccctaca                                        28

<210> SEQ ID NO 137
<211> LENGTH: 30
<212> TYPE: DNA
<213> ORGANISM: Artificial Sequence
```

```
<220> FEATURE:
<223> OTHER INFORMATION: Description of Artificial Sequence:  primer

<400> SEQUENCE: 137
ctackacaaa taaataacka acktaaatca                                           30

<210> SEQ ID NO 138
<211> LENGTH: 27
<212> TYPE: DNA
<213> ORGANISM: Artificial Sequence
<220> FEATURE:
<223> OTHER INFORMATION: Description of Artificial Sequence:  primer

<400> SEQUENCE: 138
ctctaaatac kckaataack aaaatca                                              27

<210> SEQ ID NO 139
<211> LENGTH: 57
<212> TYPE: DNA
<213> ORGANISM: Artificial Sequence
<220> FEATURE:
<223> OTHER INFORMATION: Description of Artificial Sequence:  primer

<400> SEQUENCE: 139
tatcckckaa aatacktatt ckckaatata tacgcaccgt gaacgacagt tgcgatt            57

<210> SEQ ID NO 140
<211> LENGTH: 52
<212> TYPE: DNA
<213> ORGANISM: Artificial Sequence
<220> FEATURE:
<223> OTHER INFORMATION: Description of Artificial Sequence:  primer

<400> SEQUENCE: 140
atackckctc kacttackca cackatacgc aggtcgctgc gtgtcctgat tg                  52

<210> SEQ ID NO 141
<211> LENGTH: 55
<212> TYPE: DNA
<213> ORGANISM: Artificial Sequence
<220> FEATURE:
<223> OTHER INFORMATION: Description of Artificial Sequence:  primer

<400> SEQUENCE: 141
aaatatacck aaaaccccka aackaaaaac cgcaaagcag acacagggtc gattg              55

<210> SEQ ID NO 142
<211> LENGTH: 20
<212> TYPE: DNA
<213> ORGANISM: Artificial Sequence
<220> FEATURE:
<223> OTHER INFORMATION: Description of Artificial Sequence:  primer

<400> SEQUENCE: 142
ctackckctc ctaaaactca                                                      20

<210> SEQ ID NO 143
<211> LENGTH: 23
<212> TYPE: DNA
<213> ORGANISM: Artificial Sequence
<220> FEATURE:
<223> OTHER INFORMATION: Description of Artificial Sequence:  primer

<400> SEQUENCE: 143
kctaaacttc ckaaaaaaat tca                                                  23
```

<210> SEQ ID NO 144
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 144
aackaaaacc ctaacctaaa aca                                          23

<210> SEQ ID NO 145
<211> LENGTH: 54
<212> TYPE: DNA
<213> ORGANISM: Artificial Sequence
<220> FEATURE:
<223> OTHER INFORMATION: Description of Artificial Sequence: primer

<400> SEQUENCE: 145
aaccktaact cktckaaatc tatatctttc atcgcacttc gctttggctg attg        54

<210> SEQ ID NO 146
<211> LENGTH: 56
<212> TYPE: DNA
<213> ORGANISM: Artificial Sequence
<220> FEATURE:
<223> OTHER INFORMATION: Description of Artificial Sequence: primer

<400> SEQUENCE: 146
aactacktaa aaackcttta ttttattcka tttgcgggaa ctcacgaggt cgtatg      56

<210> SEQ ID NO 147
<211> LENGTH: 49
<212> TYPE: DNA
<213> ORGANISM: Artificial Sequence
<220> FEATURE:
<223> OTHER INFORMATION: Description of Artificial Sequence: primer

<400> SEQUENCE: 147
aataaackcc aaacaaacka aacacgcacg gctcgatagg tcaagcttt              49

<210> SEQ ID NO 148
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 148
ctackaaact cctaacacaa aactaaacaa tca                               33

<210> SEQ ID NO 149
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 149
ctctaaactt ttaaaaaact caaaactttt aaca                              34

<210> SEQ ID NO 150
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 150
cktaaaaaac ackctcccaa ccca                                    24

<210> SEQ ID NO 151
<211> LENGTH: 57
<212> TYPE: DNA
<213> ORGANISM: Artificial Sequence
<220> FEATURE:
<223> OTHER INFORMATION: Description of Artificial Sequence: primer

<400> SEQUENCE: 151
ccataacaaa taaaaacaaa taatcckcca ccagacgcac cgcaacaggc tgtcaag    57

<210> SEQ ID NO 152
<211> LENGTH: 59
<212> TYPE: DNA
<213> ORGANISM: Artificial Sequence
<220> FEATURE:
<223> OTHER INFORMATION: Description of Artificial Sequence: primer

<400> SEQUENCE: 152
ccaatcttaa acacataaaa aaaaaaaacc caatcatcgc tgcaagtacc gcactcaag    59

<210> SEQ ID NO 153
<211> LENGTH: 50
<212> TYPE: DNA
<213> ORGANISM: Artificial Sequence
<220> FEATURE:
<223> OTHER INFORMATION: Description of Artificial Sequence: primer

<400> SEQUENCE: 153
aackcaaaat atcccckaaa cccaacggct gggacgtgca gaccgttcaa         50

<210> SEQ ID NO 154
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 154
ctaccctcta acctctactc ttccaattac a                            31

<210> SEQ ID NO 155
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 155
aaaaaaacaa aaaaaaccaa acktctctca                              30

<210> SEQ ID NO 156
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 156
atctataatt ccckckcttt tcca                                    24

<210> SEQ ID NO 157

```
<211> LENGTH: 67
<212> TYPE: DNA
<213> ORGANISM: Artificial Sequence
<220> FEATURE:
<223> OTHER INFORMATION: Description of Artificial Sequence: primer

<400> SEQUENCE: 157
acttattaca tcacaataat tactatacka aaatcaaaat ckcgggaggc tgctgtcctt    60
tcgatca                                                             67

<210> SEQ ID NO 158
<211> LENGTH: 58
<212> TYPE: DNA
<213> ORGANISM: Artificial Sequence
<220> FEATURE:
<223> OTHER INFORMATION: Description of Artificial Sequence: primer

<400> SEQUENCE: 158
aaactctaaa ttaaccaccc aatctacccc ckaaacagcg tgttcgttgc ttgcatca     58

<210> SEQ ID NO 159
<211> LENGTH: 51
<212> TYPE: DNA
<213> ORGANISM: Artificial Sequence
<220> FEATURE:
<223> OTHER INFORMATION: Description of Artificial Sequence: primer

<400> SEQUENCE: 159
ttaccackaa aaccaaaaaa ctacckcatg gcgatggtcc actcgcaatc a             51

<210> SEQ ID NO 160
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 160
tttttggtat tttgtgttaa ttttttttgtt ttgt                              34

<210> SEQ ID NO 161
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 161
tgtgttttat tgtggagtgt gggtt                                         25

<210> SEQ ID NO 162
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 162
gatgtggatt agggtgtttt ttatttttt                                     28

<210> SEQ ID NO 163
<211> LENGTH: 33
<212> TYPE: DNA
<213> ORGANISM: Artificial Sequence
<220> FEATURE:
<223> OTHER INFORMATION: Description of Artificial Sequence: primer
```

<400> SEQUENCE: 163
tttcggtatt ttgtgttaat tttttttgttt tgc    33

<210> SEQ ID NO 164
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 164
tgtgttttat tgcggagtgc gggtc    25

<210> SEQ ID NO 165
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 165
gatgcggatt agggcgtttt ttattttc    28

<210> SEQ ID NO 166
<211> LENGTH: 61
<212> TYPE: DNA
<213> ORGANISM: Artificial Sequence
<220> FEATURE:
<223> OTHER INFORMATION: Description of Artificial Sequence: primer

<400> SEQUENCE: 166 ggatttttt cgatttttta ttatgcgtgt taattgtgca ccgtgaacga cagttgcgat    60
t    61

<210> SEQ ID NO 167
<211> LENGTH: 57
<212> TYPE: DNA
<213> ORGANISM: Artificial Sequence
<220> FEATURE:
<223> OTHER INFORMATION: Description of Artificial Sequence: primer

<400> SEQUENCE: 167
gggaagtgga gagagaagta gttgtgtaat ttgcgcaggt cgctgcgtgt cctgatt    57

<210> SEQ ID NO 168
<211> LENGTH: 49
<212> TYPE: DNA
<213> ORGANISM: Artificial Sequence
<220> FEATURE:
<223> OTHER INFORMATION: Description of Artificial Sequence: primer

<400> SEQUENCE: 168
gttgggagtt tgttgattgg ttgggcgcaa agcagacaca gggtcgatt    49

<210> SEQ ID NO 169
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 169 gtttttgtt taaaaggcgg taaggagtt    29

<210> SEQ ID NO 170
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 170
ttttgttttt tttgtggagg ggattt                                26

<210> SEQ ID NO 171
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 171
ttttcggtgt tggtgtttat ggtt                                  24

<210> SEQ ID NO 172
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 172
gtttttcgtt taaaaggcgg taaggagtc                             29

<210> SEQ ID NO 173
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 173
ttttgttttt ttcgcggagg ggattc                                26

<210> SEQ ID NO 174
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 174
ttttcggcgt tggcgtttat ggtc                                  24

<210> SEQ ID NO 175
<211> LENGTH: 54
<212> TYPE: DNA
<213> ORGANISM: Artificial Sequence
<220> FEATURE:
<223> OTHER INFORMATION: Description of Artificial Sequence: primer

<400> SEQUENCE: 175
gagaggttgt ttcggagtgt gaggaggata cgatttcgac tcaagcggct cttt    54

<210> SEQ ID NO 176
<211> LENGTH: 52
<212> TYPE: DNA
<213> ORGANISM: Artificial Sequence
<220> FEATURE:
<223> OTHER INFORMATION: Description of Artificial Sequence: primer

<400> SEQUENCE: 176
ggtaattcgt agcggtaggg tttggggtcg caatggtagg tgagcaagca ga            52

<210> SEQ ID NO 177
<211> LENGTH: 51
<212> TYPE: DNA
<213> ORGANISM: Artificial Sequence
<220> FEATURE:
<223> OTHER INFORMATION: Description of Artificial Sequence: primer

<400> SEQUENCE: 177
ggttttcgat agcgtttcgg agggatcgtc cccgttacct aggcgatcag a             51

<210> SEQ ID NO 178
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 178
ttaggagttt gaggttgtag tgagttgtga tt                                  32

<210> SEQ ID NO 179
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 179
gttgggattt gaatttagtg gaattagaat t                                   31

<210> SEQ ID NO 180
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 180
gagggttatt gtgtttatgt gaggtt                                         26

<210> SEQ ID NO 181
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 181
ttaggagttc gaggttgtag tgagttgtga tc                                  32

<210> SEQ ID NO 182
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 182
gttgggattc gaatttagtg gaattagaat c                                   31

<210> SEQ ID NO 183

```
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 183
gagggttatc gcgtttatgc gaggtc                                          26

<210> SEQ ID NO 184
<211> LENGTH: 71
<212> TYPE: DNA
<213> ORGANISM: Artificial Sequence
<220> FEATURE:
<223> OTHER INFORMATION: Description of Artificial Sequence: primer

<400> SEQUENCE: 184
gtattattgt attttagttt gggtgaaaga gtgagtttta tttttaaatg ggtccacagt     60
accgctgcag a                                                         71

<210> SEQ ID NO 185
<211> LENGTH: 74
<212> TYPE: DNA
<213> ORGANISM: Artificial Sequence
<220> FEATURE:
<223> OTHER INFORMATION: Description of Artificial Sequence: primer

<400> SEQUENCE: 185
gtgtaggttt tataatttat ttagatttta gtaattttag gttagagggt ccgtgggaga     60
ttaggtggct caga                                                      74

<210> SEQ ID NO 186
<211> LENGTH: 47
<212> TYPE: DNA
<213> ORGANISM: Artificial Sequence
<220> FEATURE:
<223> OTHER INFORMATION: Description of Artificial Sequence: primer

<400> SEQUENCE: 186
gggtgggcgg gtcgttagtt tcggggaatg gaggtgggaa cgagaca                  47

<210> SEQ ID NO 187
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 187
tttagggaat ttttttttgt gatgtttt                                       28

<210> SEQ ID NO 188
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 188
gatttgggaa agagggaaag gttttttt                                       28

<210> SEQ ID NO 189
<211> LENGTH: 28
<212> TYPE: DNA
<213> ORGANISM: Artificial Sequence
```

```
<220> FEATURE:
<223> OTHER INFORMATION: Description of Artificial Sequence:  primer

<400> SEQUENCE: 189
gggagtttgt gggattttttt agaagagt                                    28

<210> SEQ ID NO 190
<211> LENGTH: 28
<212> TYPE: DNA
<213> ORGANISM: Artificial Sequence
<220> FEATURE:
<223> OTHER INFORMATION: Description of Artificial Sequence:  primer

<400> SEQUENCE: 190
tttagggaat ttttttcgc gatgtttc                                      28

<210> SEQ ID NO 191
<211> LENGTH: 28
<212> TYPE: DNA
<213> ORGANISM: Artificial Sequence
<220> FEATURE:
<223> OTHER INFORMATION: Description of Artificial Sequence:  primer

<400> SEQUENCE: 191
gatttgggaa agagggaaag gttttttc                                     28

<210> SEQ ID NO 192
<211> LENGTH: 27
<212> TYPE: DNA
<213> ORGANISM: Artificial Sequence
<220> FEATURE:
<223> OTHER INFORMATION: Description of Artificial Sequence:  primer

<400> SEQUENCE: 192
ggagttcgcg ggattttta gaagagc                                       27

<210> SEQ ID NO 193
<211> LENGTH: 52
<212> TYPE: DNA
<213> ORGANISM: Artificial Sequence
<220> FEATURE:
<223> OTHER INFORMATION: Description of Artificial Sequence:  primer

<400> SEQUENCE: 193
ggcgcgttag ttcgttgcgt atatttcgcg tggctgactc gctgcgatga ca          52

<210> SEQ ID NO 194
<211> LENGTH: 47
<212> TYPE: DNA
<213> ORGANISM: Artificial Sequence
<220> FEATURE:
<223> OTHER INFORMATION: Description of Artificial Sequence:  primer

<400> SEQUENCE: 194
ggttagttgt gtggtgattt tggttgcgca ccatcaggtt agggaca                47

<210> SEQ ID NO 195
<211> LENGTH: 50
<212> TYPE: DNA
<213> ORGANISM: Artificial Sequence
<220> FEATURE:
<223> OTHER INFORMATION: Description of Artificial Sequence:  primer

<400> SEQUENCE: 195
ggtcggcgtc gtgatttagt attggggcac cgatatggag accgcagaca             50
```

<210> SEQ ID NO 196
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 196
tgggtttagt gtagttgttt tgagtaggat t                          31

<210> SEQ ID NO 197
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 197 gattttgtg tgtttttagg attattt                                27

<210> SEQ ID NO 198
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 198
agttttaggt ggaagttggg aaggt                                 25

<210> SEQ ID NO 199
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 199
cgggtttagc gtagtcgttt cgagtaggat c                          31

<210> SEQ ID NO 200
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 200
gattttcgcg cgttttagg attattc                                27

<210> SEQ ID NO 201
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 201
gttttaggcg gaagttggga aggc                                  24

<210> SEQ ID NO 202
<211> LENGTH: 51
<212> TYPE: DNA
<213> ORGANISM: Artificial Sequence
<220> FEATURE:
<223> OTHER INFORMATION: Description of Artificial Sequence: primer

<400> SEQUENCE: 202
gggattttta ttaagcgggc gtcgtttcat cgacaaggta acgcgtggac a    51

<210> SEQ ID NO 203
<211> LENGTH: 53
<212> TYPE: DNA
<213> ORGANISM: Artificial Sequence
<220> FEATURE:
<223> OTHER INFORMATION: Description of Artificial Sequence: primer

<400> SEQUENCE: 203
gggtacgtgg taggtcgttt gtacgttcgt gagcgcaagg tcagagcacg aca    53

<210> SEQ ID NO 204
<211> LENGTH: 51
<212> TYPE: DNA
<213> ORGANISM: Artificial Sequence
<220> FEATURE:
<223> OTHER INFORMATION: Description of Artificial Sequence: primer

<400> SEQUENCE: 204
gttgtttggt ttgtattggt tgaagggaag ccgcagcacg attccgtgac a    51

<210> SEQ ID NO 205
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 205
gaaagaaaat gttggtttgt gtgttt    26

<210> SEQ ID NO 206
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 206
atgttagatt agttgggtta tttgaaggtt agtagttt    38

<210> SEQ ID NO 207
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 207
atgtgagttg tttgaggatt gggatgtt    28

<210> SEQ ID NO 208
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 208
gaaagaaaac gtcggtttgt gcgttc    26

<210> SEQ ID NO 209

```
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 209
atgttagatt agttgggtta tttgaaggtt agtagttc                               38

<210> SEQ ID NO 210
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 210
atgcgagttg tttgaggatt gggatgtc                                         28

<210> SEQ ID NO 211
<211> LENGTH: 59
<212> TYPE: DNA
<213> ORGANISM: Artificial Sequence
<220> FEATURE:
<223> OTHER INFORMATION: Description of Artificial Sequence: primer

<400> SEQUENCE: 211
gttgtttgtt ttttggttg tttgttttg tagggtgaga agcgtccaag ccagaacga         59

<210> SEQ ID NO 212
<211> LENGTH: 65
<212> TYPE: DNA
<213> ORGANISM: Artificial Sequence
<220> FEATURE:
<223> OTHER INFORMATION: Description of Artificial Sequence: primer

<400> SEQUENCE: 212
gggtagggtt tattgaaagt ttatttgtat atattaggta acatccaagg tccgacacgc      60
aacga                                                                  65

<210> SEQ ID NO 213
<211> LENGTH: 50
<212> TYPE: DNA
<213> ORGANISM: Artificial Sequence
<220> FEATURE:
<223> OTHER INFORMATION: Description of Artificial Sequence: primer

<400> SEQUENCE: 213
gagaatgtga gtgatttgag tagggtttcg acgattcgca tcaacgcaag                 50

<210> SEQ ID NO 214
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 214
ggtttgtgtt tgttagtgtt taaagttagt                                       30

<210> SEQ ID NO 215
<211> LENGTH: 24
<212> TYPE: DNA
<213> ORGANISM: Artificial Sequence
<220> FEATURE:
<223> OTHER INFORMATION: Description of Artificial Sequence: primer
```

```
<400> SEQUENCE: 215
ggtgtgttgg aagggttgt attt                                              24

<210> SEQ ID NO 216
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 216
tgtgtaattt tatatggtag ttggttttg gtt                                    33

<210> SEQ ID NO 217
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 217
gttcgcgttt gttagcgttt aaagttagc                                        29

<210> SEQ ID NO 218
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 218
ggcgcgttgg aagggtcgt attc                                              24

<210> SEQ ID NO 219
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 219
cgtgtaattt tatacggtag ttggttttg gtc                                    33

<210> SEQ ID NO 220
<211> LENGTH: 54
<212> TYPE: DNA
<213> ORGANISM: Artificial Sequence
<220> FEATURE:
<223> OTHER INFORMATION: Description of Artificial Sequence: primer

<400> SEQUENCE: 220
gaagtacggg tttaatcggg ttatgtcggg aacggggaag gttgagcgtg acag            54

<210> SEQ ID NO 221
<211> LENGTH: 49
<212> TYPE: DNA
<213> ORGANISM: Artificial Sequence
<220> FEATURE:
<223> OTHER INFORMATION: Description of Artificial Sequence: primer

<400> SEQUENCE: 221
ggttggagcg tgttaacgcg ttgcgcactg cacacgaaac ggcacacag                  49

<210> SEQ ID NO 222
```

-continued

```
<210> SEQ ID NO 222
<211> LENGTH: 52
<212> TYPE: DNA
<213> ORGANISM: Artificial Sequence
<220> FEATURE:
<223> OTHER INFORMATION: Description of Artificial Sequence: primer

<400> SEQUENCE: 222
gtggttatcg tttttagttc gcggggttta ccgacatcct gggattgcat gg            52

<210> SEQ ID NO 223
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 223
ggttagggtg tagatgagaa ggggtat                                        27

<210> SEQ ID NO 224
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 224
gtgtgtttta gtttatttat ttgtgtgttt at                                  32

<210> SEQ ID NO 225
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 225
tttggttttg ttttttttt ggagggtt                                        28

<210> SEQ ID NO 226
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 226
ggttagggcg tagacgagaa ggggtac                                        27

<210> SEQ ID NO 227
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 227
gcgcgtttta gtttatttat tcgcgtgttt ac                                  32

<210> SEQ ID NO 228
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 228
```
ttcggtttcg ttttttttttt ggagggtc                                    28

<210> SEQ ID NO 229
<211> LENGTH: 51
<212> TYPE: DNA
<213> ORGANISM: Artificial Sequence
<220> FEATURE:
<223> OTHER INFORMATION: Description of Artificial Sequence: primer

<400> SEQUENCE: 229
gagggttttg ttttgaggat ttagtggact ccgcattgcc agagctgatg g           51

<210> SEQ ID NO 230
<211> LENGTH: 60
<212> TYPE: DNA
<213> ORGANISM: Artificial Sequence
<220> FEATURE:
<223> OTHER INFORMATION: Description of Artificial Sequence: primer

<400> SEQUENCE: 230
ggtggtatta tttttataa ggatttgaat gatttgcgat ggcttcctta cccagattcg   60

<210> SEQ ID NO 231
<211> LENGTH: 56
<212> TYPE: DNA
<213> ORGANISM: Artificial Sequence
<220> FEATURE:
<223> OTHER INFORMATION: Description of Artificial Sequence: primer

<400> SEQUENCE: 231
gatgaggtaa tgtggttttg ttattggttt gacgcattcg atggacagga cattcg      56

<210> SEQ ID NO 232
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 232
tgttaatttt tttgttttgc ggattttttt c                                 31

<210> SEQ ID NO 233
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 233
gggattgggg tcgtgagggt atattttc                                     28

<210> SEQ ID NO 234
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 234
agagagaagt agttgtgtaa ttcgttggat gc                                32

<210> SEQ ID NO 235
<211> LENGTH: 68
<212> TYPE: DNA

```
<213> ORGANISM: Artificial Sequence
<220> FEATURE:
<223> OTHER INFORMATION: Description of Artificial Sequence: primer

<400> SEQUENCE: 235 gatttttat tatgcgtgtt aattgttatt aattttttg tttggcaccg tgaacgacag    60
ttgcgatt                                                           68

<210> SEQ ID NO 236
<211> LENGTH: 54
<212> TYPE: DNA
<213> ORGANISM: Artificial Sequence
<220> FEATURE:
<223> OTHER INFORMATION: Description of Artificial Sequence: primer

<400> SEQUENCE: 236
gaggggtacg gggttagggt taggtaggtt cgcaggtcgc tgcgtgtcct gatt        54

<210> SEQ ID NO 237
<211> LENGTH: 53
<212> TYPE: DNA
<213> ORGANISM: Artificial Sequence
<220> FEATURE:
<223> OTHER INFORMATION: Description of Artificial Sequence: primer

<400> SEQUENCE: 237
ggattagggc gtttttatt ttcgtcgggc gcaaagcaga cacagggtcg att          53

<210> SEQ ID NO 238
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 238
aggcggtaag gagtcgagag gttgtttc                                     28

<210> SEQ ID NO 239
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 239
ggtcggcgtt tgggagggat ttgc                                         24

<210> SEQ ID NO 240
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 240
gcgttggcgt ttatggtcgg ttttc                                        25

<210> SEQ ID NO 241
<211> LENGTH: 52
<212> TYPE: DNA
<213> ORGANISM: Artificial Sequence
<220> FEATURE:
<223> OTHER INFORMATION: Description of Artificial Sequence: primer

<400> SEQUENCE: 241
```

```
ggagtgtgag gaggatagtc ggatcgagaa gcaagccaag gtatggcttt gc         52

<210> SEQ ID NO 242
<211> LENGTH: 63
<212> TYPE: DNA
<213> ORGANISM: Artificial Sequence
<220> FEATURE:
<223> OTHER INFORMATION: Description of Artificial Sequence: primer

<400> SEQUENCE: 242 gtttttatt tattttttag ttgtgttttc gtcgtcgttt tcggctgttc gtaggcaaga   60
ggt                                                                63

<210> SEQ ID NO 243
<211> LENGTH: 48
<212> TYPE: DNA
<213> ORGANISM: Artificial Sequence
<220> FEATURE:
<223> OTHER INFORMATION: Description of Artificial Sequence: primer

<400> SEQUENCE: 243
gatagcgttt cggagggatc ggggtagggc acatgggcac ttgcaggt               48

<210> SEQ ID NO 244
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 244
ggggttagag gatcgtttga gtttaggagt tc                                32

<210> SEQ ID NO 245
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 245
gttatcggcg gggttgggat tc                                           22

<210> SEQ ID NO 246
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 246
gtttatgcga ggtcgggtgg gc                                           22

<210> SEQ ID NO 247
<211> LENGTH: 67
<212> TYPE: DNA
<213> ORGANISM: Artificial Sequence
<220> FEATURE:
<223> OTHER INFORMATION: Description of Artificial Sequence: primer

<400> SEQUENCE: 247
gaggttgtag tgagttgtga tcgtattatt gtattttagt ttgttcgggg agtccggtcc  60
agatcct                                                            67
```

<210> SEQ ID NO 248
<211> LENGTH: 68
<212> TYPE: DNA
<213> ORGANISM: Artificial Sequence
<220> FEATURE:
<223> OTHER INFORMATION: Description of Artificial Sequence: primer

<400> SEQUENCE: 248
gaatttagtg gaattagaat cgtgtaggtt ttataattta tttaggctcg tgtgtagctg    60
ccgttcct                                                             68

<210> SEQ ID NO 249
<211> LENGTH: 50
<212> TYPE: DNA
<213> ORGANISM: Artificial Sequence
<220> FEATURE:
<223> OTHER INFORMATION: Description of Artificial Sequence: primer

<400> SEQUENCE: 249
gggtcgttag tttcgttttg gggaggggtc aagcgctgag gtggtccatc               50

<210> SEQ ID NO 250
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 250
cgcgatgttt cggcgcgtta gttc                                           24

<210> SEQ ID NO 251
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 251
ggcgatttcg gggattttag ggc                                            23

<210> SEQ ID NO 252
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 252
gcggggcggg attatttta taaggttc                                        28

<210> SEQ ID NO 253
<211> LENGTH: 56
<212> TYPE: DNA
<213> ORGANISM: Artificial Sequence
<220> FEATURE:
<223> OTHER INFORMATION: Description of Artificial Sequence: primer

<400> SEQUENCE: 253
gttgcgtata tttcgttgcg gttttttttt tgcgtggctg actcgctgcg atgaca         56

<210> SEQ ID NO 254
<211> LENGTH: 48
<212> TYPE: DNA
<213> ORGANISM: Artificial Sequence

```
<220> FEATURE:
<223> OTHER INFORMATION: Description of Artificial Sequence: primer

<400> SEQUENCE: 254
gtttttttgc ggtcgacgtt cgggttgcgc accatcaggt tagggaca                    48

<210> SEQ ID NO 255
<211> LENGTH: 48
<212> TYPE: DNA
<213> ORGANISM: Artificial Sequence
<220> FEATURE:
<223> OTHER INFORMATION: Description of Artificial Sequence: primer

<400> SEQUENCE: 255
ggaggtcgcg aggttttcgt tggagcaccg atatggagac cgcagaca                    48

<210> SEQ ID NO 256
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 256
gtttcgagta ggatcgggat ttttattaag c                                      31

<210> SEQ ID NO 257
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 257
tttttaggat tattcgggta cgtggtaggt c                                      31

<210> SEQ ID NO 258
<211> LENGTH: 37
<212> TYPE: DNA
<213> ORGANISM: Artificial Sequence
<220> FEATURE:
<223> OTHER INFORMATION: Description of Artificial Sequence: primer

<400> SEQUENCE: 258
cgggttattt ggtaaattaa ggtatagagt tttaggc                                37

<210> SEQ ID NO 259
<211> LENGTH: 48
<212> TYPE: DNA
<213> ORGANISM: Artificial Sequence
<220> FEATURE:
<223> OTHER INFORMATION: Description of Artificial Sequence: primer

<400> SEQUENCE: 259
gggcgtcgtt ttacgatttt cgcgcatcga caaggtaacg cgtggaca                    48

<210> SEQ ID NO 260
<211> LENGTH: 57
<212> TYPE: DNA
<213> ORGANISM: Artificial Sequence
<220> FEATURE:
<223> OTHER INFORMATION: Description of Artificial Sequence: primer

<400> SEQUENCE: 260
gtttgtacgt tcgcggatta tttttgtgat aggtgagcgc aaggtcagag cacgaca          57
```

<210> SEQ ID NO 261
<211> LENGTH: 48
<212> TYPE: DNA
<213> ORGANISM: Artificial Sequence
<220> FEATURE:
<223> OTHER INFORMATION: Description of Artificial Sequence: primer

<400> SEQUENCE: 261
ggaagttggg aaggcgtcgt tcggaagccg cagcacgatt ccgtgaca        48

<210> SEQ ID NO 262
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 262
aataggaaag aaaacgtcgg tttgtgc        27

<210> SEQ ID NO 263
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 263
tatttgaagg ttagtagttc gggtagggtt tatc        34

<210> SEQ ID NO 264
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 264
agcgattcga gtagggtttg tttgggtatc        30

<210> SEQ ID NO 265
<211> LENGTH: 58
<212> TYPE: DNA
<213> ORGANISM: Artificial Sequence
<220> FEATURE:
<223> OTHER INFORMATION: Description of Artificial Sequence: primer

<400> SEQUENCE: 265
gttcgttgtt tgtttttttg gttgtttgtt tttgtgagaa gcgtccaagc cagaacga        58

<210> SEQ ID NO 266
<211> LENGTH: 72
<212> TYPE: DNA
<213> ORGANISM: Artificial Sequence
<220> FEATURE:
<223> OTHER INFORMATION: Description of Artificial Sequence: primer

<400> SEQUENCE: 266
gaaagtttat tcgtatatat taggtaattt aatttttat tttgtgtgca tccaaggtcc        60
gacacgcaac ga        72

<210> SEQ ID NO 267
<211> LENGTH: 51
<212> TYPE: DNA
<213> ORGANISM: Artificial Sequence

```
<220> FEATURE:
<223> OTHER INFORMATION: Description of Artificial Sequence: primer

<400> SEQUENCE: 267
gtcggggtag gattcggaac gtattcgttc gacgattcgc atcaacgcaa g          51

<210> SEQ ID NO 268
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 268
tttcgttcgg ttcgcgtttg ttagc                                       25

<210> SEQ ID NO 269
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 269
ttgggcgcgt tgggaagggt c                                           21

<210> SEQ ID NO 270
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 270
atacggtagt tggtttttgg tcgtggttat c                                31

<210> SEQ ID NO 271
<211> LENGTH: 58
<212> TYPE: DNA
<213> ORGANISM: Artificial Sequence
<220> FEATURE:
<223> OTHER INFORMATION: Description of Artificial Sequence: primer

<400> SEQUENCE: 271
gtttaaagtt agcgaagtac gggtttaatc gggtaacggg gaaggttgag cgtgacag   58

<210> SEQ ID NO 272
<211> LENGTH: 51
<212> TYPE: DNA
<213> ORGANISM: Artificial Sequence
<220> FEATURE:
<223> OTHER INFORMATION: Description of Artificial Sequence: primer

<400> SEQUENCE: 272
gtattcggtt ggagcgtgtt aacgcgtcac tgcacacgaa acggcacaca g          51

<210> SEQ ID NO 273
<211> LENGTH: 53
<212> TYPE: DNA
<213> ORGANISM: Artificial Sequence
<220> FEATURE:
<223> OTHER INFORMATION: Description of Artificial Sequence: primer

<400> SEQUENCE: 273
gtttttagtt cgcggggttc gttacgtatt accgacatcc tgggattgca tgg        53
```

```
<210> SEQ ID NO 274
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 274
gtagacgaga aggggtacga gggtttc                                              27

<210> SEQ ID NO 275
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 275
tttcgtttcg ttattttttg ttttcggttt c                                         31

<210> SEQ ID NO 276
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 276
cggttttgtt attggtttga gggggc                                               26

<210> SEQ ID NO 277
<211> LENGTH: 57
<212> TYPE: DNA
<213> ORGANISM: Artificial Sequence
<220> FEATURE:
<223> OTHER INFORMATION: Description of Artificial Sequence: primer

<400> SEQUENCE: 277
gtttcgagga tttagcggta agtatcggtt tcgggctacg acgcatgtaa acgttcg             57

<210> SEQ ID NO 278
<211> LENGTH: 56
<212> TYPE: DNA
<213> ORGANISM: Artificial Sequence
<220> FEATURE:
<223> OTHER INFORMATION: Description of Artificial Sequence: primer

<400> SEQUENCE: 278 gtttttttt tggagggtcg atgaggtaat gcgtcccaag ttgcggctca ctttcg               56

<210> SEQ ID NO 279
<211> LENGTH: 52
<212> TYPE: DNA
<213> ORGANISM: Artificial Sequence
<220> FEATURE:
<223> OTHER INFORMATION: Description of Artificial Sequence: primer

<400> SEQUENCE: 279
gggttttaat agttcgaggc ggggttttcg tgcgcacact cactgtcctt cg                  52

<210> SEQ ID NO 280
<211> LENGTH: 30
<212> TYPE: DNA
<213> ORGANISM: Artificial Sequence
<220> FEATURE:
<223> OTHER INFORMATION: Description of Artificial Sequence: primer
```

<400> SEQUENCE: 280
cgtcgttcgt tgtttgtttt ttttttttc 30

<210> SEQ ID NO 281
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 281
ttattcgatt tcgggtcgcg gtc 23

<210> SEQ ID NO 282
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 282
tatttggatc ggttttcgat cgtaattatt c 31

<210> SEQ ID NO 283
<211> LENGTH: 50
<212> TYPE: DNA
<213> ORGANISM: Artificial Sequence
<220> FEATURE:
<223> OTHER INFORMATION: Description of Artificial Sequence: primer

<400> SEQUENCE: 283
gtagtcgtcg agcgtacgcg gttcgtgctg gctggcacgc accagaatca 50

<210> SEQ ID NO 284
<211> LENGTH: 64
<212> TYPE: DNA
<213> ORGANISM: Artificial Sequence
<220> FEATURE:
<223> OTHER INFORMATION: Description of Artificial Sequence: primer

<400> SEQUENCE: 284
gtggttagtt agttagtcga aggttttatg ttgttttcg ggctccgtca gaaagcgaca 60
atca 64

<210> SEQ ID NO 285
<211> LENGTH: 51
<212> TYPE: DNA
<213> ORGANISM: Artificial Sequence
<220> FEATURE:
<223> OTHER INFORMATION: Description of Artificial Sequence: primer

<400> SEQUENCE: 285
ggtgcgttgg gtagcgtttt cgttttacg agggataccc gcaaacgatc a 51

<210> SEQ ID NO 286
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 286
atgttttcgt cgttttagg gtcgagttc 29

<210> SEQ ID NO 287
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 287
tttcgtgagt cgcgggatgt gaattac                                27

<210> SEQ ID NO 288
<211> LENGTH: 40
<212> TYPE: DNA
<213> ORGANISM: Artificial Sequence
<220> FEATURE:
<223> OTHER INFORMATION: Description of Artificial Sequence: primer

<400> SEQUENCE: 288
gttgttgttt tagacgttgg ttttttagta gtattagtac                   40

<210> SEQ ID NO 289
<211> LENGTH: 55
<212> TYPE: DNA
<213> ORGANISM: Artificial Sequence
<220> FEATURE:
<223> OTHER INFORMATION: Description of Artificial Sequence: primer

<400> SEQUENCE: 289
ggtagtcgtt gcgtcgtttt ttggtattag agtccgtcca tggcaagcgt gatca   55

<210> SEQ ID NO 290
<211> LENGTH: 50
<212> TYPE: DNA
<213> ORGANISM: Artificial Sequence
<220> FEATURE:
<223> OTHER INFORMATION: Description of Artificial Sequence: primer

<400> SEQUENCE: 290
gaaaattttt attcgcggcg ggtcgtggct gcacccgttg aggcacatca         50

<210> SEQ ID NO 291
<211> LENGTH: 48
<212> TYPE: DNA
<213> ORGANISM: Artificial Sequence
<220> FEATURE:
<223> OTHER INFORMATION: Description of Artificial Sequence: primer

<400> SEQUENCE: 291
gagggttata gcggcgggcg tttttcaaca tcggctaacg gtccatca           48

<210> SEQ ID NO 292
<211> LENGTH: 50
<212> TYPE: DNA
<213> ORGANISM: Artificial Sequence
<220> FEATURE:
<223> OTHER INFORMATION: Description of Artificial Sequence: primer

<400> SEQUENCE: 292
cgctgccaac taccgcacat cgttgggatt tttgtattgt ggtaaataag         50

<210> SEQ ID NO 293
<211> LENGTH: 47
<212> TYPE: DNA
<213> ORGANISM: Artificial Sequence
<220> FEATURE:
<223> OTHER INFORMATION: Description of Artificial Sequence: primer

<400> SEQUENCE: 293
cgctgccaac taccgcacat cccaatacga acgaacaaaa taccatc                47

<210> SEQ ID NO 294
<211> LENGTH: 52
<212> TYPE: DNA
<213> ORGANISM: Artificial Sequence
<220> FEATURE:
<223> OTHER INFORMATION: Description of Artificial Sequence: primer

<400> SEQUENCE: 294
cgctgccaac taccgcacat ccccaatcta caattaaaaa aacaaaaata ac          52

<210> SEQ ID NO 295
<211> LENGTH: 49
<212> TYPE: DNA
<213> ORGANISM: Artificial Sequence
<220> FEATURE:
<223> OTHER INFORMATION: Description of Artificial Sequence: primer

<400> SEQUENCE: 295
cgctgccaac taccgcacat cggttttttt tatttggttt tttaggaag              49

<210> SEQ ID NO 296
<211> LENGTH: 48
<212> TYPE: DNA
<213> ORGANISM: Artificial Sequence
<220> FEATURE:
<223> OTHER INFORMATION: Description of Artificial Sequence: primer

<400> SEQUENCE: 296
cgctgccaac taccgcacat cgagattttt attagggtgg aaagagtg               48

<210> SEQ ID NO 297
<211> LENGTH: 46
<212> TYPE: DNA
<213> ORGANISM: Artificial Sequence
<220> FEATURE:
<223> OTHER INFORMATION: Description of Artificial Sequence: primer

<400> SEQUENCE: 297
cgctgccaac taccgcacat cccgtccaaa aaatctcaac gaactc                 46

<210> SEQ ID NO 298
<211> LENGTH: 44
<212> TYPE: DNA
<213> ORGANISM: Artificial Sequence
<220> FEATURE:
<223> OTHER INFORMATION: Description of Artificial Sequence: primer

<400> SEQUENCE: 298
cgctgccaac taccgcacat cgaaaaaaac tcttccgcca acac                   44

<210> SEQ ID NO 299
<211> LENGTH: 49
<212> TYPE: DNA
<213> ORGANISM: Artificial Sequence
<220> FEATURE:
<223> OTHER INFORMATION: Description of Artificial Sequence: primer

<400> SEQUENCE: 299
cgctgccaac taccgcacat ctgtttgtta tttttttgttt tgttgtag              49

<210> SEQ ID NO 300

<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 300
cgctgccaac taccgcacat c                                             21

<210> SEQ ID NO 301
<211> LENGTH: 50
<212> TYPE: DNA
<213> ORGANISM: Artificial Sequence
<220> FEATURE:
<223> OTHER INFORMATION: Description of Artificial Sequence: primer

<400> SEQUENCE: 301
ggagcacgct atcccgttag acgattttttg tattgcggta aataagtacg              50

<210> SEQ ID NO 302
<211> LENGTH: 47
<212> TYPE: DNA
<213> ORGANISM: Artificial Sequence
<220> FEATURE:
<223> OTHER INFORMATION: Description of Artificial Sequence: primer

<400> SEQUENCE: 302
ggagcacgct atcccgttag acaacaaaat accatcgaaa caaaacg                  47

<210> SEQ ID NO 303
<211> LENGTH: 52
<212> TYPE: DNA
<213> ORGANISM: Artificial Sequence
<220> FEATURE:
<223> OTHER INFORMATION: Description of Artificial Sequence: primer

<400> SEQUENCE: 303
ggagcacgct atcccgttag accaatctac aattaaaaaa acaaaaataa cg            52

<210> SEQ ID NO 304
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 304
ggagcacgct atcccgttag acggaagcgg ttgttgtttt agacg                    45

<210> SEQ ID NO 305
<211> LENGTH: 44
<212> TYPE: DNA
<213> ORGANISM: Artificial Sequence
<220> FEATURE:
<223> OTHER INFORMATION: Description of Artificial Sequence: primer

<400> SEQUENCE: 305
ggagcacgct atcccgttag acgggattgg gattttttttt tacg                    44

<210> SEQ ID NO 306
<211> LENGTH: 47
<212> TYPE: DNA
<213> ORGANISM: Artificial Sequence
<220> FEATURE:
<223> OTHER INFORMATION: Description of Artificial Sequence: primer

<400> SEQUENCE: 306

```
ggagcacgct atcccgttag acgtccaaaa aatctcaacg aactcac            47

<210> SEQ ID NO 307
<211> LENGTH: 42
<212> TYPE: DNA
<213> ORGANISM: Artificial Sequence
<220> FEATURE:
<223> OTHER INFORMATION: Description of Artificial Sequence: primer

<400> SEQUENCE: 307
ggagcacgct atcccgttag acaaactctt ccgccaacac cg                 42

<210> SEQ ID NO 308
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 308
ggagcacgct atcccgttag acttatttgg atcggttttc gatcg              45

<210> SEQ ID NO 309
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 309
ggagcacgct atcccgttag ac                                       22
```